US009409976B2

(12) United States Patent
Teng et al.

(10) Patent No.: US 9,409,976 B2
(45) Date of Patent: Aug. 9, 2016

(54) CDIM BINDING PROTEINS AND USES THEREOF

(71) Applicants: Nelson N. H. Teng, Hillsborough, CA (US); Neelima M. Bhat, Los Altos, CA (US); Marcia M. Bieber, Los Altos, CA (US); Bruce A. Keyt, Hillsborough, CA (US)

(72) Inventors: Nelson N. H. Teng, Hillsborough, CA (US); Neelima M. Bhat, Los Altos, CA (US); Marcia M. Bieber, Los Altos, CA (US); Bruce A. Keyt, Hillsborough, CA (US)

(73) Assignee: IGM BIOSCIENCES, INC., Santa Clara, CA (US)

( * ) Notice: Subject to any disclaimer, the term of this patent is extended or adjusted under 35 U.S.C. 154(b) by 2 days.

(21) Appl. No.: 13/763,398

(22) Filed: Feb. 8, 2013

(65) Prior Publication Data

US 2014/0044739 A1 Feb. 13, 2014

Related U.S. Application Data

(60) Provisional application No. 61/633,330, filed on Feb. 8, 2012.

(51) Int. Cl.
*C07K 16/18* (2006.01)
*C07K 16/28* (2006.01)
*C07K 16/30* (2006.01)

(52) U.S. Cl.
CPC .......... *C07K 16/18* (2013.01); *C07K 16/28* (2013.01); *C07K 16/3061* (2013.01); *C07K 2317/33* (2013.01); *C07K 2317/734* (2013.01); *C07K 2317/92* (2013.01)

(58) Field of Classification Search
CPC ..... C07K 16/18; C07K 16/28; C07K 16/3061
See application file for complete search history.

(56) References Cited

U.S. PATENT DOCUMENTS

| | | | |
|---|---|---|---|
| 4,399,216 A | 8/1983 | Axel et al. | |
| 4,740,461 A | 4/1988 | Kaufman | |
| 4,816,567 A | 3/1989 | Cabilly et al. | |
| 4,831,175 A | 5/1989 | Gansow et al. | |
| 4,912,040 A | 3/1990 | Kaufman et al. | |
| 4,959,455 A | 9/1990 | Clark et al. | |
| 5,099,069 A | 3/1992 | Gansow et al. | |
| 5,124,471 A | 6/1992 | Gansow et al. | |
| 5,246,692 A | 9/1993 | Gansow et al. | |
| 5,286,850 A | 2/1994 | Gansoh et al. | |
| 5,417,972 A * | 5/1995 | Bhat et al. | 424/137.1 |
| 5,434,287 A | 7/1995 | Gansow et al. | |
| 5,460,785 A | 10/1995 | Rhodes et al. | |
| 5,521,184 A | 5/1996 | Zimmermann | |
| 5,591,828 A * | 1/1997 | Bosslet | C07K 16/3007 435/188.5 |
| 5,593,676 A | 1/1997 | Bhat et al. | |
| 6,083,903 A | 7/2000 | Adams et al. | |
| 6,235,883 B1 * | 5/2001 | Jakobovits et al. | 530/388.22 |
| 6,441,163 B1 | 8/2002 | Chari et al. | |
| 6,645,974 B2 | 11/2003 | Hutchinson et al. | |
| 6,660,744 B1 | 12/2003 | Hirst et al. | |
| 6,680,335 B2 | 1/2004 | Tang | |
| 7,485,297 B2 * | 2/2009 | Wood et al. | 424/130.1 |
| 7,718,777 B2 * | 5/2010 | Hoogenboom et al. | 530/388.2 |
| 7,867,494 B2 * | 1/2011 | Liu et al. | 424/133.1 |
| 7,988,971 B2 * | 8/2011 | Dimitrov et al. | 424/147.1 |
| 8,377,435 B2 * | 2/2013 | Bhat et al. | 424/130.1 |
| 2002/0028178 A1 | 3/2002 | Hanna et al. | |
| 2002/0090366 A1 | 7/2002 | Browning et al. | |
| 2004/0121951 A1 | 6/2004 | Rhee | |
| 2005/0112130 A1 | 5/2005 | Bhat et al. | |
| 2010/0322849 A1 * | 12/2010 | Bhat et al. | 424/1.11 |

FOREIGN PATENT DOCUMENTS

| | | |
|---|---|---|
| EP | 404097 A2 | 12/1990 |
| EP | 712307 B1 | 5/1996 |
| WO | WO9311161 A1 | 6/1993 |
| WO | WO9503770 A1 | 2/1995 |
| WO | WO9707784 A2 | 3/1997 |
| WO | WO02096948 A2 | 12/2002 |
| WO | WO2005044998 A2 | 5/2005 |

OTHER PUBLICATIONS

Bieber et al., Pediatr Blood Cancer 2007; 48:380-83.*
Almagro & Fransson, Frontiers in Bioscience 2008; 13:1619-33.*
PJ Carter, Nat Rev Immunol, 2006; 6:343-357.*
De Genst et al., Dev Comp Immunol 2006; 30:187-98.*
Thornton et al., Nature, "News and Views", 354:105-106 (1991).*
Beauner et al., (1985) J. Nuc. Med. 26:1172-79.
Bhat et al., 42nd Annual Meeting of the American Society of Hematology, San Francisco, CA Dec. 1-5, 2000.
Hamann et al, (2002) Bioconjug. Chem. 13:40-46.
Li e al. (1999) Int. J. Mol. Med. 3:647-653.
Mandler et al. (2002) J. Natl. Cancer Inst. 92:1549-1951.
Murray, J. (1985) Nuc. Med. 26:3328.
Roelke ,(1989) Transfusion Med. Rev. 2:140-166.
Silberstein et al. (1996) Blood Cells, Molecules, and Diseases 22:126-138.
Silberstein et al., (1991) Blood 78:2372-2386.

(Continued)

*Primary Examiner* — Jessica H Roark
(74) *Attorney, Agent, or Firm* — Chao Hadidi Stark & Barker LLP; Birgit Millauer

(57) ABSTRACT

The present disclosure relates to Cell Death Inducing Molecule ("CDIM") binding proteins and pharmaceutical compositions thereof. Particularly, the disclosure provides CDIM binding proteins that are useful in the selective depleting and killing of B cells, including neoplastic B cells as well as neoplastic cells that are not of B-cell origin that express CDIM-like antigens. In addition, the disclosure encompasses polynucleotides encoding the disclosed antigen binding proteins, and expression systems for producing the same. Further the present disclosure encompasses methods of treating patients with B cell proliferative- and mediated diseases by administering the CDIM binding proteins as well as diagnostic assays for identifying proteins that bind to CDIM. The disclosure further contemplates diagnostic assays for identifying patient populations that can be treated with the CDIM binding proteins.

23 Claims, 56 Drawing Sheets

(56) References Cited

OTHER PUBLICATIONS

Stevenson et al., (1989) Br. J. Haematol. 72:9-15.
Weng et al., (1992) Eur. J. Immunol. 22:1075-1082.
Nicolaou et al., (1994) Angewandte Chem Journal, vol. 33 No. 2, pp. 183-186.
Bhat et al., (1997) Clin. Immunology and Immunopathology 84:283-289.
Bhat et al., (2005) Human Antibodies 13:63-68.
Bhat et al., (2001) Crit. Rev. Oncol. Hematol. 39:59-68.
Binz and Pluckthun (2005) Engineered Proteins as specific binding reagents, Curr. Opin. Biotechnol. 16:459-469.
Bowie et al., 1991, a Method to Identify Protein Sequences that Fold into a Known Three- Dimensional Structure, Science 253:164-170.
Browning, J.L. (2006) B cells move to centre stage: novel opportunities for autoimmune disease treatment, Nature (Reviews) 5:564-576.
Zhou et al., (2007) J. Autoimmun. 29(4):219-228.
Roelcke, (1989) Transfusion Med. Rev. 2:140-166.
Silman and Burshteyn, (2000) Cytometry 40(4), 316-26.
Skerra, A. (2000) J. Mol. Recog. 13:167-18.
Hamann et al. (2002) Bioconjug. Chem. 13:40-46.
Hazra et al., 1994, Linking Radiosilver to Monoclonal Antibodies Reduced by Ascorbic Acid, Cell Biophys. 24-25:1-7.
Hinton et al., 2006, An Engineered Human IgG1 Antibody with Longer Serum Half-Life, J. Immunol. 176:346-356.
Holt et al, (2003) Domain antibodies: proteins for therapy, Trends Biotechnol. 21:484-490.
Jumaa et al. (2005) B Cell Signaling and Tumorigenesis, Annu. Rev. Immunol. 23:415-445.
Li et al., (1999) Int. J. Mol. Med. 3:647-653.
Liedtke et al. (2012) Phase I trial of a novel human monoclonal antibody mAb216 in patients with relapsed or refractory B-cell acute lymphoblastic leukemia, Haematologica 97(1):30-37.
Liu et al. (1996) Eradication of large colon tumor xenografts by targeted delivery of Maytansinoids, Proc. Natl. Acad. Sci. USA 93:8618-8623.
Mandler et al. (2002) J. Natl. Cancer Inst., 92:1549-1951.
Muyldermans et al. (2001) Reviews in Molecular Biotechnology 74:277-302.
Vorauer-Uhl et al. (2010) J. Immunol. Methods 359:21-27.
Witzig, T.E. (2001) Cancer Chemother. Pharmacol. 48 Suppl 1:91-95.
Agnew (1994) Chem. Intl. Ed. Engl., 33, 183-186.
Ben-Bassat, H. et al. (2002) J. Pharmacol. Exp. Ther. 303, 163-171.
Bhat et al., Clin. Immunology and Immunopathology 1997, 84:283-289.
Bhat et al., Scand. J. Immunol., 2000, 51:134-140.
Bhat, et al., "Rapid cytotoxicity of human B lymphocytes induced by VH4-34 (VH4.21) gene-encoded monoclonal antibodies", Clinical and Experimental Immunology, vol. 105, No. 1, 1996, pp. 183-190, XP009103512, ISSN: 0009-9104.
Bhat, et al., (1993) J. Immunol. 151, 5011-5021.
Bhat, et al., (1997) Clin. Exp. Immunol. 108:151 —159.
Bhat, et al., (2005) Human Antibodies 13, 63-68.
Bi, G. Q., et al., (1995) J. Cell Biol. 131, 1747-1758.
Buskens, C. et al., Digestive Disease Week Abstracts and Itinerary Planner, 2003, abstract No. 850.
Carey et al., J. Immunol. 2001 166:1618-1626.
Carraguillo et al., (1985) J. Nuc. Med. 26, 67.
Carter, S. K. et al., Chemotherapy of Cancer; Second edition; John Wiley & Sons: New York, 1981; appendix C.
Chen et al., Mol. Immuol. 1998, 35:195-205.
Clackson et al., (1991) Nature, 352, 624-628.
Clark et al., PNAS (USA) 82:pp. 1766-1770 (1985).
Cohen, Int. J. Radiat. Oncol. Biol. Phys. 1987, 13:251-8.
Cook, G. P., et al., (1994) Nat. Genet. 7, 162-168.
Granger, B. L., et al., (1990) J. Biol. Chem. 265, 12036;-12043.
Grillot-Courvalin, C., et al., (1992) Eur. J. Immunol. 22, 1781-1788;.
Holliger et al., (1993) Proc. Natl. Acad. Sci. USA 90, 6444-6448.
Hurwitz, R., et al., (1979) Int. J. Cancer 23, 174-180.
Ishigami et al., "Anti-IgM antibody-induced cell death in a human B lymphoma cell line, B104, represents a novel programmed cell death", Journal of Immunology (Baltimore, MD: 1950) Jan. 15, 1992, vol. 148, No. 2, 15 Jan. 1992, pp. 360-368, XP002489104, ISSN: 0022-1767.
Janeway et al., Immunobiology 5, 2001, Garland Science, Figure 9.3, 12.2, and 13.1.
Jones et al., (1986) Nature 321, 522-525.
Kaiser, Science, 2006, 313, 1370.
Klausner, R. D., (1992) J. Cell Biol. 116, 1071 -1080.
Kohler et al., Nature 256, p. 495-497 (1975).
Kraj P, et al., (1995) J. Immunol. 154, 6406-6420.
Krontiris and Capizzi, Internal Medicine, 4th Edition, Editor-in-chief Jay Stein, Elsevier Science, 1994 Chapters 71-72, pp. 699-729.
Mahon, T M and O'Neill, L A (1995) J. Biol. Chem. 270, 28557-28564.
Martinez, I., et al. (2000) J. Cell. Biol. 148, 1141-1149.
McNeil, P. L. (2002) J. Cell Sci. 115, 873-879.
McNeil, P. L., and R. A. Steinhardt (2003) Ann. Rev. Cell Dev. Biol. 19:697-731.
Miyake, K., and P. L. McNeil (1995) J. Cell Biol. 131, 1737-.1745.
Morrison et al., (1984) Proc. Natl. Acad. Sci. USA, 81, 6851-6855.
Murray et al., Cancer Res. 1985; 45:2376-81.
National Cancer Institute (Dictionary of Cancer Terms, www.cancer.gov, phase I trial, Mar. 26, 2009).
Pascual, V., (1992) J. Immunol. 149, 2337-2344.
Pascual, V., et al., (1991) J. Immunol. 146, 4385-4391.
Peitersz et al. (1987) Immunol. Cell Biol. 65, 111-125.
Reddy, A., et al., (2001) Cell 106, 157-169.
Rosenfield, C., A. et al., (1977) Nature 267, 841-843.
Reichmann et al., (1988) Nature 332, 323-329.
Rodriguez, A., et al., (1997) J. Cell. Biol. 137, 93-104.

\* cited by examiner

FIGURE 1A

Heavy Chain Variable Region of IGM1 and IGM23 (SEQ ID NO:1)

```
        FR1                          CDRH1        FR2              CDRH2              FR3
QVQLQQWGAGLLKPSETLSLTCAVYGGS  FSGYYWS  WIRQPPGKGLEWIG  EINHSGSTNYNPSLKS  RVTISVDTSKNQFSLKLSSVTAADTAVYYCAR
    CDRH3          JH
GRMAWGASVN  FDYWGQGTLVTVSS
```

Heavy Chain Variable region of IGM2 and IGM24 (SEQ ID NO:2)

```
QVQLQQWGAGLLKPSETLSLTCAVYGGS  FSGYYWS  WIRQPPGKGLEWIG  EINHSGSTNYNPSLKS  RVTISVDTSKNQFSLKLSSVTAADTAVYYCAR
GRRAWGASVN  FDYWGQGTLVTVSS
```

Heavy Chain Variable region of IGM3 and IGM25 (SEQ ID NO:3)

```
QVQLQQWGAGLLKPSETLSLTCAVYGGS  FSGYYWS  WIRQPPGKGLEWIG  EINHSGSTNYNPSLKS  RVTISVDTSKNQFSLKLSSVTAADTAVYYCAR
GRMARGASVN  FDYWGQGTLVTVSS
```

Heavy Chain Variable region of IGM4 and IGM26 (SEQ ID NO:4)

```
QVQLQQWGAGLLKPSETLSLTCAVYGGS  FSGYYWS  WIRQPPGKGLEWIG  EINHSGSTNYNPSLKS  RVTISVDTSKNQFSLKLSSVTAADTAVYYCAR
GRRARGASVN  FDYWGQGTLVTVSS
```

Heavy Chain Variable region of IGM5 and IGM27 (SEQ ID NO:5)

```
QVQLQQWGAGLLKPSETLSLTCAVYGGS  FSGYYWS  WIRQPPGKGLEWIG  EINHSGSTNYNPSLKS  RVTISVDTSKNQFSLKLSSVTAADTAVYYCAR
RGMAWGASVN  FDYWGQGTLVTVSS
```

Heavy Chain Variable region of IGM6 and IGM28 (SEQ ID NO:6)

```
QVQLQQWGAGLLKPSETLSLTCAVYGGS  FSGYYWS  WIRQPPGKGLEWIG  EINHSGSTNYNPSLKS  RVTISVDTSKNQFSLKLSSVTAADTAVYYCAR
RRMAWGASVN  FDYWGQGTLVTVSS
```

FIGURE 1B

Heavy Chain Variable region of IGM7 and IGM29 (SEQ ID NO:7)

QVQLQQWGAGLLKPSETLSLTCAVYGGS FSGYYWS WIRQPPGKGLEWIG EINHSGSTNYNPSLKS RVTISVDTSKNQFSLKLSSVTAADTAVYYCAR
RGMARGASVN FDYWGQGTLVTVSS

Heavy Chain Variable region of IGM8 and IGM30 (SEQ ID NO:8)

QVQLQQWGAGLLKPSETLSLTCAVYGGS FSGYYWS WIRQPPGKGLEWIG EINHSGSTNYNPSLKS RVTISVDTSKNQFSLKLSSVTAADTAVYYCAR
RGRARGASVN FDYWGQGTLVTVSS

Heavy Chain Variable region of IGM9 and IGM31 (SEQ ID NO:9)

QVQLQQWGAGLLKPSETLSLTCAVYGGS FSGYYWS WIRQPPGKGLEWIG EINHSGSTNYNPSLKS RVTISVDTSKNQFSLKLSSVTAADTAVYYCAR
RRGARGASVN FDYWGQGTLVTVSS

Heavy Chain Variable region of IGM10 and IGM32 (SEQ ID NO:10)

QVQLQQWGAGLLKPSETLSLTCAVYGGS FSGYYWS WIRQPPGKGLEWIG EINHSGSTNYNPSLKS RVTISVDTSKNQFSLKLSSVTAADTAVYYCAR
AGRAWGASVN FDYWGQGTLVTVSS

Heavy Chain Variable region of IGM11 and IGM33 (SEQ ID NO:11)

QVQLQQWGAGLLKPSETLSLTCAVYGGS FSGYYWS WIRQPPGKGLEWIG EINHSGSTNYNPSLKS RVTISVDTSKNQFSLKLSSVTAADTAVYYCAR
RGRAWGASVN FDYWGQGTLVTVSS

Heavy Chain Variable region of IGM12 and IGM34 (SEQ ID NO:12)

QVQLQQWGAGLLKPSETLSLTCAVYGGS FSGYYWS WIRQPPGKGLEWIG EINHSGSTNYNPSLKS RVTISVDTSKNQFSLKLSSVTAADTAVYYCAR
ARTAWGSSI FDYWGQGTLVTVSS

FIGURE 1C

Heavy Chain Variable region of IGM13 and IGM35 (SEQ ID NO:13)

QVQLQQWGAGLLKPSETLSLTCAVYGGS FSGYYWS WIRQPPGKGLEWIG EINHSGSTNYNPSLKS RVTISVDTSKNQFSLKLSSVTAADTAVYYCAR
ARRAWGSSI FDYWGQGTLVTVSS

Heavy Chain Variable region of IGM14 and IGM36 (SEQ ID NO:14)

QVQLQQWGAGLLKPSETLSLTCAVYGGS FSGYYWS WIRQPPGKGLEWIG EINHSGSTNYNPSLKS RVTISVDTSKNQFSLKLSSVTAADTAVYYCAR
ARTARGSSI FDYWGQGTLVTVSS

Heavy Chain Variable region of IGM15 and IGM37 (SEQ ID NO:15)

QVQLQQWGAGLLKPSETLSLTCAVYGGS FSGYYWS WIRQPPGKGLEWIG EINHSGSTNYNPSLKS RVTISVDTSKNQFSLKLSSVTAADTAVYYCAR
ARRARGSSI FDYWGQGTLVTVSS

Heavy Chain Variable region of IGM16 and IGM38 (SEQ ID NO:16)

QVQLQQWGAGLLKPSETLSLTCAVYGGS FSGYYWS WIRQPPGKGLEWIG EINHSGSTNYNPSLKS RVTISVDTSKNQFSLKLSSVTAADTAVYYCAR
RATAWGSSI FDYWGQGTLVTVSS

Heavy Chain Variable region of IGM17 and IGM39 (SEQ ID NO:17)

QVQLQQWGAGLLKPSETLSLTCAVYGGS FSGYYWS WIRQPPGKGLEWIG EINHSGSTNYNPSLKS RVTISVDTSKNQFSLKLSSVTAADTAVYYCAR
RRTAWGSSI FDYWGQGTLVTVSS

Heavy Chain Variable region of IGM18 and IGM40 (SEQ ID NO:18)

QVQLQQWGAGLLKPSETLSLTCAVYGGS FSGYYWS WIRQPPGKGLEWIG EINHSGSTNYNPSLKS RVTISVDTSKNQFSLKLSSVTAADTAVYYCAR
RATARGSSI FDYWGQGTLVTVSS

FIGURE 1D

Heavy Chain Variable region of IGM19 and IGM41 (SEQ ID NO:19)

QVQLQQWGAGLLKPSETLSLTCAVYGGS  FSGYYWS  WIRQPPGKGLEWIG  EINHSGSTNYNPSLKS  RVTISVDTSKNQFSLKLSSVTAADTAVYYCAR
RARARGSSI   FDYWGQGTLVTVSS

Heavy Chain Variable region of IGM20 and IGM42 (SEQ ID NO:20)

QVQLQQWGAGLLKPSETLSLTCAVYGGS  FSGYYWS  WIRQPPGKGLEWIG  EINHSGSTNYNPSLKS  RVTISVDTSKNQFSLKLSSVTAADTAVYYCAR
RRTARGSSI   FDYWGQGTLVTVSS

Heavy Chain Variable region of IGM21 and IGM43 (SEQ ID NO:21)

QVQLQQWGAGLLKPSETLSLTCAVYGGS  FSGYYWS  WIRQPPGKGLEWIG  EINHSGSTNYNPSLKS  RVTISVDTSKNQFSLKLSSVTAADTAVYYCAR
GARAWGSSI   FDYWGQGTLVTVSS

Heavy Chain Variable region of IGM22 and IGM44 (SEQ ID NO:22)

QVQLQQWGAGLLKPSETLSLTCAVYGGS  FSGYYWS  WIRQPPGKGLEWIG  EINHSGSTNYNPSLKS  RVTISVDTSKNQFSLKLSSVTAADTAVYYCAR
RARAWGSSI   FDYWGQGTLVTVSS

FIGURE 1E

Light Chain Variable region of IGM1 through IGM22 (SEQ ID NO:23) (used with lambda light chain constant region)

```
       FR1                        CDRL1                  FR2            CDRL2            FR3
DIQMTQSPSTLSASVGDRVTITC   TGTSSDVGGYNYVS   WYQQHPGKAPKLMIY   GVSNRFS   GSKSGNTASLTISGLAAEDEADYYC

CDRL3            JL
SSYTSSSTL   VVFGGGTKLTVLG
```

Light Chain Variable region of IGM23 through IGM44 (SEQ ID NO:24) (used with kappa light chain constant region)

```
       FR1                        CDRL1                  FR2            CDRL2            FR3
DIQMTQSPSSLSASVGDRVTITC   RASQSISSYLN      WYQQKPGKAPKLLIY   AASSLQS   GVPSRFSGSGSGTDFTLTISSLQPEDFATYYC

CDRL3            JL
QQSYSTP   ITFGQGTRLEIKR
```

FIGURE 1F

Constant Region for IGM Heavy Chain (SEQ ID NO:25)

GSASAPTLFPLVSCENSPSDTSSVAVGCLAQDFLPDSITFSWKYKNNSDISSTRGFPSVLRGGKYAATSQVLLPSKDVMQGTDEHVCKVQHPNGNKEKNVPLPVIA
ELPPKVSVFVPPRDGFFGNPRKSKLICQATGFSPRQIQVSWLREGKQVGSGVTTDQVQAEAKESGPTTYKVTSTLTIKESDWLGQSMFTCRVDHRGLTFQQNASSMC
VPDQDTAIRVFAIPPSFASIFLTKSTKLTCLVTDLTTYDSVTISWTRQNGEAVKTHTNISESHPNATFSAVGEASICEDDWNSGERFTCTVTHTDLPSPLKQTISRP
KGVALHRPDVYLLPPAREQLNLRESATITCLVTGFSPADVFVQWMQRGQPLSPEKYVTSAPMPEPQAPGRYFAHSILTVSEEWNTGETYTCVAHDALPNRVTERTV
DKSTGKPTLYNVSLVMSDTAGTCY

Constant Region for IGλ Light Chain (SEQ ID NO:26)

QPKAAPSVTL FPPSSEELQA NKATLVCLIS DFYPGAVTVA WKADSSPVKA GVETTTPSKQS NNKYAASSYL SLTPEQWKSH RSYSCQVTHE
GSTVEKTVAP TECS

Constant Region for IGκ Light Chain (SEQ ID NO:27)

TVAAPSVFIF PPSDEQLKSG TASVVCLLNN FYPREAKVQW KVDNALQSGN SQESVTEQDS KDSTYSLSST LTLSKADYEK HKVYACEVTH
QGLSSPVTKS FNRGEC

FIGURE 2A

IGM1:

SEQ ID NO:28
HEAVY CHAIN
QVQLQQWGAGLLKPSETLSLTCAVYGGSFSGYYWSWIRQPPGKGLEWIGEINHSGSTNYNPSLKSRVTISVDTSKNQFSLKLSSVTAADTAVYYCARGRMAWGASVNFDYWGQGTLVTV
SSGSASAPTLFPLVSCENSPSDTSSVAVGCLAQDFLPDSITFSWKYKNNSDISSTRGFPSVLRGGKYAATSQVLLPSKDVMQGTDEHVCKVQHPNGNKEKNVPLPVIAELPPKVSVFV
PPRDGFFGNPRKSKLICQATGFSPRQIQVSWLREGKQVGSGVTDQVQAEAKESGPTTYKVTSTLTIKESDWLSQSMFTCRVDHRGLTFQQNASSMCVPDQDTAIRVFAIPPSFASIFL
TKSTKLTCLVTDLTTYDSVTISWTRQNGEAVKTHTNISESHPNATFSAVGEASICEDDWNSGERFTCTVTHTDLPSPLKQTISRPKGVALHRPDVYLLPPAREQLNLRESATITCLVTG
FSPADVFVQWMQRGQPLSPEKYVTSAPMPEPQAPGRYFAHSILTVSEEEWNTGETYTCVVAHEALPNRVTERTVDKSTGKPTLYNVSLVMSDTAGTCY

SEQ ID NO:50
LIGHT CHAIN
DIQMTQSPSTLSASVGDRVTITCTGTSSDVGGYNYVSWYQQHPGKAPKLMIYGVSNRFSGSKSGNTASLTISGLAAEDEADYCCSSYTSSSTLVVFGGGTKLTVLG
QPKAAPSVTLFPPSSEELQANKATLVCLISDFYPGAVTVAWKADSSPVKAGVETTTPSKQSNNKYAASSYLSLTPEQWKSHRSYSCQVTHEGSTVEKTVAPTECS

IGM2:

SEQ ID NO:29
HEAVY CHAIN
QVQLQQWGAGLLKPSETLSLTCAVYGGSFSGYYWSWIRQPPGKGLEWIGEINHSGSTNYNPSLKSRVTISVDTSKNQFSLKLSSVTAADTAVYYCARGRRAWGASVNFDYWGQGTLVTV
SSGSASAPTLFPLVSCENSPSDTSSVAVGCLAQDFLPDSITFSWKYKNNSDISSTRGFPSVLRGGKYAATSQVLLPSKDVMQGTDEHVCKVQHPNGNKEKNVPLPVIAELPPKVSVFV
PPRDGFFGNPRKSKLICQATGFSPRQIQVSWLREGKQVGSGVTDQVQAEAKESGPTTYKVTSTLTIKESDWLSQSMFTCRVDHRGLTFQQNASSMCVPDQDTAIRVFAIPPSFASIFL
TKSTKLTCLVTDLTTYDSVTISWTRQNGEAVKTHTNISESHPNATFSAVGEASICEDDWNSGERFTCTVTHTDLPSPLKQTISRPKGVALHRPDVYLLPPAREQLNLRESATITCLVTG
FSPADVFVQWMQRGQPLSPEKYVTSAPMPEPQAPGRYFAHSILTVSEEEWNTGETYTCVVAHEALPNRVTERTVDKSTGKPTLYNVSLVMSDTAGTCY

SEQ ID NO:50
LIGHT CHAIN
DIQMTQSPSTLSASVGDRVTITCTGTSSDVGGYNYVSWYQQHPGKAPKLMIYGVSNRFSGSKSGNTASLTISGLAAEDEADYCCSSYTSSSTLVVFGGGTKLTVLG
QPKAAPSVTLFPPSSEELQANKATLVCLISDFYPGAVTVAWKADSSPVKAGVETTTPSKQSNNKYAASSYLSLTPEQWKSHRSYSCQVTHEGSTVEKTVAPTECS

FIGURE 2B

IGM3:

SEQ ID NO:30
HEAVY CHAIN
QVQLQQWGAGLLKPSETLSLTCAVYGGSFSGYYWSWIRQPPGKGLEWIGEINHSGSTNYNPSLKSRVTISVDTSKNQFSLKLSSVTAADTAVYYCARGRMARGASVNFDYWGQGTLVTV
SSGSASAPTLFPLVSCENSPSDTSSVAVGCLAQDFLPDSITFSWKYKNNSDISSTRGFPSVLRGGKYAATSQVLLPSKDVMQGTDEHVVCKVQHPNGNKEKNVPLPVIAELPPKVSVFV
PPRDGFFGNPRKSKLICQATGFSPRQIQVSWLREGKQVGSGVTTDQVQAEAKESGPTTYKVTSLTIKESDWLSQSMFTCRVDHRGLTFQQNASSMCVPDQTAIRVFAIPPSFASIFL
TKSTKLTCLVTDLTTYDSVTISWTRQNGEAVKTHTNISESHPNATFSAVGEASICEDDWNSGERFTCTVTHTDLPSPLKQTISRPKGVALHRPDVYLLPPAREQLNLRESATITCLVTG
FSPADVFVQWMQRGQPLSPEKYVTSAPMPEPQAPGRYFAHSILTVSEEEWNTGETYTCVVAHEALPNRVTERTVDKSTGKPTLYNVSLVMSDTAGTCY

SEQ ID NO:50
LIGHT CHAIN
DIQMTQSPSTLSASVGDRVTITCTGTSSDVGGYNYVSWYQQHPGKAPKLMIYGVSNRFSGSKSGNTASLTISGLAAEDEADYCSSYTSSSTLVVFGGGTKLTVLG
QPKAAPSVTLFPPSSEELQANKATLVCLISDFYPGAVTVAWKADSSPVKAGVETTPSKQSNNKYAASSYLSLTPEQWKSHRSYSCQVTHEGSTVEKTVAPTECS

IGM4:

SEQ ID NO:31
HEAVY CHAIN
QVQLQQWGAGLLKPSETLSLTCAVYGGSFSGYYWSWIRQPPGKGLEWIGEINHSGSTNYNPSLKSRVTISVDTSKNQFSLKLSSVTAADTAVYYCARGRRARGASVNFDYWGQGTLVTV
SSGSASAPTLFPLVSCENSPSDTSSVAVGCLAQDFLPDSITFSWKYKNNSDISSTRGFPSVLRGGKYAATSQVLLPSKDVMQGTDEHVVCKVQHPNGNKEKNVPLPVIAELPPKVSVFV
PPRDGFFGNPRKSKLICQATGFSPRQIQVSWLREGKQVGSGVTTDQVQAEAKESGPTTYKVTSLTIKESDWLSQSMFTCRVDHRGLTFQQNASSMCVPDQTAIRVFAIPPSFASIFL
TKSTKLICLVTDLTTYDSVTISWTRQNGEAVKTHTNISESHPNATFSAVGEASICEDDWNSGERFTCTVTHTDLPSPLKQTISRPKGVALHRPDVYLLPPAREQLNLRESATITCLVTG
FSPADVFVQWMQRGQPLSPEKYVTSAPMPEPQAPGRYFAHSILTVSEEEWNTGETYTCVVAHEALPNRVTERTVDKSTGKPTLYNVSLVMSDTAGTCY

SEQ ID NO:50
LIGHT CHAIN
DIQMTQSPSTLSASVGDRVTITCTGTSSDVGGYNYVSWYQQHPGKAPKLMIYGVSNRFSGSKSGNTASLTISGLAAEDEADYCSSYTSSSTLVVFGGGTKLTVLG
QPKAAPSVTLFPPSSEELQANKATLVCLISDFYPGAVTVAWKADSSPVKAGVETTPSKQSNNKYAASSYLSLTPEQWKSHRSYSCQVTHEGSTVEKTVAPTECS

FIGURE 2C

IGM5:

SEQ ID NO:32
HEAVY CHAIN
QVQLQQWGAGLLKPSETLSLTCAVYGGSFSGYYWSWIRQPPGKGLEWIGEINHSGSTNYNPSLKSRVTISVDTSKNQFSLKLSSVTAADTAVYYCARRGMAWGASVNFDYWGQGTLVTV
SSGSASAPTLFPLVSCENSPSDTSSVAVGCLAQDFLPDSITFSWKYKNNSDISSTRGFPSVLRGGKYAATSQVLLPSKDVMQGTDEHVCKVQHPNGNKEKNVPLPVIAELPPKVSVFV
PPRDGFFGNPRKSKLICQATGFSPRQIQVSWLREGKQVGSGVTTDQVQAEAKESGPTTYKVTSTLTIKESDWLSQSMFTCRVDHRGLTFQQNASSMCVPDQDTAIRVFAIPPSFASIFL
TKSTKLTCLVTDLTTYDSVTISWTRQNGEAVKTHTNISESHPNATFSAVGEASICEDDWNSGERFTCTVTHTDLPSPLKQTISRPKGVALHRPDVYLLPPAREQLNLRESATITCLVTG
FSPADVFVQWMQRGQPLSPEKYVTSAPMPEPQAPGRYFAHSILTVSEEEWNTGETYTCVVAHEALPNRVTERTVDKSTGKPTLYNVSLVMSDTAGTCY

SEQ ID NO:50
LIGHT CHAIN
DIQMTQSPSTLSASVGDRVTITCTGTSSDVGGYNYVSWYQQHPGKAPKLMIYGVSNRFSGSKSGNTASLTISGLAAEDEADYCCSSYTSSSTLVFGGGTKLTVLG
QPKAAPSVTLFPPSSEELQANKATLVCLISDFYPGAVTVAWKADSSPVKAGVETTPSKQSNNKYAASSYLSLTPEQWKSHRSYSCQVTHEGSTVEKTVAPTECS

IGM6:

SEQ ID NO:33
HEAVY CHAIN
QVQLQQWGAGLLKPSETLSLTCAVYGGSFSGYYWSWIRQPPGKGLEWIGEINHSGSTNYNPSLKSRVTISVDTSKNQFSLKLSSVTAADTAVYYCARRRMAWGASVNFDYWGQGTLVTV
SSGSASAPTLFPLVSCENSPSDTSSVAVGCLAQDFLPDSITFSWKYKNNSDISSTRGFPSVLRGGKYAATSQVLLPSKDVMQGTDEHVCKVQHPNGNKEKNVPLPVIAELPPKVSVFV
PPRDGFFGNPRKSKLICQATGFSPRQIQVSWLREGKQVGSGVTTDQVQAEAKESGPTTYKVTSTLTIKESDWLSQSMFTCRVDHRGLTFQQNASSMCVPDQDTAIRVFAIPPSFASIFL
TKSTKLTCLVTDLTTYDSVTISWTRQNGEAVKTHTNISESHPNATFSAVGEASICEDDWNSGERFTCTVTHTDLPSPLKQTISRPKGVALHRPDVYLLPPAREQLNLRESATITCLVTG
FSPADVFVQWMQRGQPLSPEKYVTSAPMPEPQAPGRYFAHSILTVSEEEWNTGETYTCVVAHEALPNRVTERTVDKSTGKPTLYNVSLVMSDTAGTCY

SEQ ID NO:50
LIGHT CHAIN
DIQMTQSPSTLSASVGDRVTITCTGTSSDVGGYNYVSWYQQHPGKAPKLMIYGVSNRFSGSKSGNTASLTISGLAAEDEADYCCSSYTSSSTLVFGGGTKLTVLG
QPKAAPSVTLFPPSSEELQANKATLVCLISDFYPGAVTVAWKADSSPVKAGVETTPSKQSNNKYAASSYLSLTPEQWKSHRSYSCQVTHEGSTVEKTVAPTECS

FIGURE 2D

IGM7:

SEQ ID NO:34
HEAVY CHAIN
QVQLQQWGAGLLKPSETLSLTCAVYGGSFSGYYWSWIRQPPGKGLEWIGEINHSGSTNYNPSLKSRVTISVDTSKNQFSLKLSSVTAADTAVYYCARRGMARGASVNFDYWGQGTLVTV
SSGSASAPTLFPLVSCENSPSDTSSVAVGCLAQDFLPDSITFSWKYKNNSDISSTRGFPSVLRGGKYAATSQVLLPSKDVMQGTDEHVCKVQHPNGNKEKNVPLPVIAELPPKVSVFV
PPRDGFFGNPRKSKLICQATGFSPRQIQVSWLREGKQVGSGVTTDQVQAEAKESGPTTYKVTSTLTIKESDWLSQSMFTCRVDHRGLTFQQNASSMCVPDQTAIRVFAIPPSFASIFL
TKSTKLTCLVTDLTTYDSVTISWTRQNGEAVKTHTNISESHPNATFSAVGEASICEDDWNSGERFTCTVTHTDLPSPLKQTISRPKGVALHRPDVYLLPPAREQLNLRESATITCLVTG
FSPADVFVQWMQRGQPLSPEKYVTSAPMPEPQAPGRYFAHSILTVSEEEWNTGETYTCVVAHEALPNRVTERTVDKSTGKPTLYNVSLVMSDTAGTCY

SEQ ID NO:50
LIGHT CHAIN
DIQMTQSPSTLSASVGDRVTITCTGTSSDVGGYNYVSWYQQHPGKAPKLMIYGVSNRFSGSKSGNTASLTISGLAAEDEADYYCSSYTSSSTLVVFGGGTKLTVLG
QPKAAPSVTLFPPSSEELQANKATLVCLISDFYPGAVTVAWKADSSPVKAGVETTPSKQSNNKYAASSYLSLTPEQWKSHRSYSCQVTHEGSTVEKTVAPTECS

IGM8:

SEQ ID NO:35
HEAVY CHAIN
QVQLQQWGAGLLKPSETLSLTCAVYGGSFSGYYWSWIRQPPGKGLEWIGEINHSGSTNYNPSLKSRVTISVDTSKNQFSLKLSSVTAADTAVYYCARRGRARGASVNFDYWGQGTLVTV
SSGSASAPTLFPLVSCENSPSDTSSVAVGCLAQDFLPDSITFSWKYKNNSDISSTRGFPSVLRGGKYAATSQVLLPSKDVMQGIDEHVCKVQHPNGNKEKNVPLPVIAELPPKVSVFV
PPRDGFFGNPRKSKLICQATGFSPRQIQVSWLREGKQVGSGVTTDQVQAEAKESGPTTYKVTSTLTIKESDWLSQSMFTCRVDHRGLTFQQNASSMCVPDQTAIRVFAIPPSFASIFL
TKSTKLTCLVTDLTTYDSVTISWTRQNGEAVKTHTNISESHPNATFSAVGEASICEDDWNSGERFTCTVTHTDLPSPLKQTISRPLKQTISRPKGVALHRPDVYLLPPAREQLNLRESATITCLVTG
FSPADVFVQWMQRGQPLSPEKYVTSAPMPEPQAPGRYFAHSILTVSEEEWNTGETYTCVVAHEALPNRVTERTVDKSTGKPTLYNVSLVMSDTAGTCY

SEQ ID NO:50
LIGHT CHAIN
DIQMTQSPSTLSASVGDRVTITCTGTSSDVGGYNYVSWYQQHPGKAPKLMIYGVSNRFSGSKSGNTASLTISGLAAEDEADYCSSYTSSSTLVVFGGGTKLTVLG
QPKAAPSVTLFPPSSEELQANKATLVCLISDFYPGAVTVAWKADSSPVKAGVETTPSKQSNNKYAASSYLSLTPEQWKSHRSYSCQVTHEGSTVEKTVAPTECS

FIGURE 2E

*IGM9:*

SEQ ID NO:36
HEAVY CHAIN
QVQLQQWGAGLLKPSETLSLTCAVYGGSFSGYYWSWIRQPPGKGLEWIGEINHSGSTNYNPSLKSRVTISVDTSKNQFSLKLSSVTAADTAVYYCARRRGARGASVNFDYWGQGTLVTV
SSGSASAPTLFPLVSCENSPSDTSSVAVGCLAQDFLPDSITFSWKYKNNSDISSTRGFPSVLRGGKYAATSQVLLPSKDVMQGTDEHVVCKVQHPNGNKEKNVPLPVIAELPPKVSVFV
PPRDGFFGNPRKSKLICQATGFSPRQIQVSWLREGKQVGSGVTDQVQAEAKESGPTTYKVTSTLTIKESDWLSQSMFTCRVDHRGLTFQQNASSMCVEDQDTAIRVFAIPPSFASIFL
TKSTKLTCLVTDLTTYDSVTISWTRQNGEAVKTHTNISESHPNATFSAVGEASICEDDWNSGERFTCTVTHTDLPSPLKQTISRPKGVALHRPDVYLLPPAREQLNLRESATITCLVTG
FSPADVFVQWMQRGQPLSPEKYVTSAPMPEPQAPGRYFAHSILTVSEEEWNTGETYTCVVAHEALPNRVTERTVDKSTGKPTLYNVSLVMSDTAGTCY

SEQ ID NO:50
LIGHT CHAIN
DIQMTQSPSTLSASVGDRVTITCTGTSSDVGGYNYVSWYQQHPGKAPKLMIYGVSNRFSGSKSGNTASLTISGLAAEDEADYCSSYTSSSTLVFEGGTKLTVLG
QPKAAPSVTLFPPSSEELQANKATLVCLISDFYPGAVTVAWKADSSPVKAGVETTTPSKQSNNKYAASSYLSLTPEQWKSHRSYSCQVTHEGSTVEKTVAPTECS

*IGM10:*

SEQ ID NO:37
HEAVY CHAIN
QVQLQQWGAGLLKPSETLSLTCAVYGGSFSGYYWSWIRQPPGKGLEWIGEINHSGSTNYNPSLKSRVTISVDTSKNQFSLKLSSVTAADTAVYYCARAGRAWGASVNFDYWGQGTLVTV
SSGSASAPTLFPLVSCENSPSDTSSVAVGCLAQDFLPDSITFSWKYKNNSDISSTRGFPSVLRGGKYAATSQVLLPSKDVMQGTDEHVVCKVQHPNGNKEKNVPLPVIAELPPKVSVFV
PPRDGFFGNPRKSKLICQATGFSPRQIQVSWLREGKQVGSGVTDQVQAEAKESGPTTYKVTSTLTIKESDWLSQSMFTCRVDHRGLTFQQNASSMCVEDQDTAIRVFAIPPSFASIFL
TKSTKLTCLVTDLTTYDSVTISWTRQNGEAVKTHTNISESHPNATFSAVGEASICEDDWNSGERFTCTVTHTDLPSPLKQTISRPKGVALHRPDVYLLPPAREQLNLRESATITCLVTG
FSPADVFVQWMQRGQPLSPEKYVTSAPMPEPQAPGRYFAHSILTVSEEEWNTGETYTCVVAHEALPNRVTERTVDKSTGKPTLYNVSLVMSDTAGTCY

SEQ ID NO:50
LIGHT CHAIN
DIQMTQSPSTLSASVGDRVTITCTGTSSDVGGYNYVSWYQQHPGKAPKLMIYGVSNRFSGSKSGNTASLTISGLAAEDEADYCSSYTSSSTLVFEGGTKLTVLG
QPKAAPSVTLFPPSSEELQANKATLVCLISDFYPGAVTVAWKADSSPVKAGVETTTPSKQSNNKYAASSYLSLTPEQWKSHRSYSCQVTHEGSTVEKTVAPTECS

FIGURE 2F

*IGM11:*

SEQ ID NO:38
HEAVY CHAIN
QVQLQQWGAGLLKPSETLSLTCAVYGGSFSGYYWSWIRQPPGKGLEWIGEINHSGSTNYNPSLKSRVTISVDTSKNQFSLKLSSVTAADTAVYYCARRGRAWGASVNFDYWGQGTLVTV
SSGSASAPTLFPLVSCENSPSDTSSVAVGCLAQDFLPDSITFSWKYKNNSDISSTRGFPSVLRGGKYAATSQVLLPSKDVMQGTDEHVVCKVQHPNGNKEKNVPLPVIAELPPKVSVFV
PPRDGFFGNPRKSKLICQATGFSPRQIQVSWLREGKQVGSGVTTDQVQAEAKESGPTTYKVTSTLTIKESDWLSQSMFTCRVDHRGLTFQQNASSMCVPDQDTAIRVFAIPPSFASIFL
TKSTKLTCLVTDLTTYDSVTISWTRQNGEAVKTHTNISESHPNATFSAVGEASICEDDWNSGERFTCTVTHTDLPSPLKQTISRPKGVALHRPDVYLLPPAREQLNLRESATITCLVTG
FSPADVFVQWMQRGQPLSPEKYVTSAPMEPQAPGRYFAHSILTVSEEEWNTGETYTCVVAHEALPNRVTERTVDKSTGKPTLYNVSLVMSDTAGTCY

SEQ ID NO:50
LIGHT CHAIN
DIQMTQSPSTLSASVGDRVTITCTGTSSDVGGYNYVSWYQQHPGKAPKLMIYGVSNRFSGSKSGNTASLTISGLAAEDEADYYCSSYTSSSTLVVFGGGTKLTVLG
QPKAAPSVTLFPPSSEELQANKATLVCLISDFYPGAVTVAWKADSSPVKAGVETTPSKQSNNKYAASSYLSLTPEQWKSHRSYSCQVTHEGSTVEKTVAPTECS

*IGM12:*

SEQ ID NO:39
HEAVY CHAIN
QVQLQQWGAGLLKPSETLSLTCAVYGGSFSGYYWSWIRQPPGKGLEWIGEINHSGSTNYNPSLKSRVTISVDTSKNQFSLKLSSVTAADTAVYYCARARTAWGSSIFDYWGQGTLVTVS
SGSASAPTLFPLVSCENSPSDTSSVAVGCLAQDFLPDSITFSWKYKNNSDISSTRGFPSVLRGGKYAATSQVLLPSKDVMQGTDEHVVCKVQHPNGNKEKNVPLPVIAELPPKVSVFVP
PRDGFFGNPRKSKLICQATGFSPRQIQVSWLREGKQVGSGVTTDQVQAEAKESGPTTYKVTSTLTIKESDWLSQSMFTCRVDHRGLTFQQNASSMCVPDQDTAIRVFAIPPSFASIFLT
KSTKLTCLVTDLTTYDSVTISWTRQNGEAVKTHTNISESHPNATFSAVGEASICEDDWNSGERFTCTVTHTDLPSPLKQTISRPKGVALHRPDVYLLPPAREQLNLRESATITCLVTGF
SPADVFVQWMQRGQPLSPEKYVTSAPMEPQAPGRYFAHSILTVSEEEWNTGETYTCVVAHEALPNRVTERTVDKSTGKPTLYNVSLVMSDTAGTCY

SEQ ID NO:50
LIGHT CHAIN
DIQMTQSPSTLSASVGDRVTITCTGTSSDVGGYNYVSWYQQHPGKAPKLMIYGVSNRFSGSKSGNTASLTISGLAAEDEADYYCSSYTSSSTLVVFGGGTKLTVLG
QPKAAPSVTLFPPSSEELQANKATLVCLISDFYPGAVTVAWKADSSPVKAGVETTPSKQSNNKYAASSYLSLTPEQWKSHRSYSCQVTHEGSTVEKTVAPTECS

FIGURE 2G

IGM13:

SEQ ID NO:41
HEAVY CHAIN
QVQLQQWGAGLLKPSETLSLTCAVYGGSFSGYYWSWIRQPPGKGLEWIGEINHSGSTNYNPSLKSRVTISVDTSKNQFSLKLSSVTAADTAVYYCARARRAWGSSIFDYWGQGTLVTVS
SGSASAPTLFPLVSCENSPSDTSSVAVGCLAQDFLPDSITFSWKYKNNSDISSTRGFPSVLRGGKYAATSQVLLPSKDVMQGTDEHVCKVQHPNGNKEKNVPLPVIAELPPKVSVFVP
PRDGFFGNPRKSKLICQATGFSPRQIQVSWLREGKQVGSGVTTDQVQAEAKESGPTTYKVTSTLTIKESDWLSQSMFTCRVDHRGLTFQQNASSMCVPDQDTAIRVFAIPPSFASIFLT
KSTKLTCLVTDLTTYDSVTISWTRQNGEAVKTHTNISESHPNATFSAVGEASICEDDWNSGERFTCTVTHDLPSPLKQTISRPKGVALHRPDVYLLPPAREQLNLRESATITCLVTGF
SPADVFVQWMQRGQPLSPEKYVTSAPMPEPQAPGRYFAHSILTVSEEEWNTGETYTCVVAHEALPNRVTERTVDKSTGKPTLYNVSLVMSDTAGTCY

SEQ ID NO:50
LIGHT CHAIN
DIQMTQSPSTLSASVGDRVTITCTGTSSDVGGYNYVSWYQQHPGKAPKLMIYGVSNRFSGSKSGNTASLTISGLAAEDEADYYCSSYTSSSTLVFGGGTKLTVLG
QPKAAPSVTLFPPSSEELQANKATLVCLISDFYPGAVTVAWKADSSPVKAGVETTPSKQSNNKYAASSYLSLTPEQWKSHRSYSCQVTHEGSIVEKTVAPTECS

IGM14:

SEQ ID NO:41
HEAVY CHAIN
QVQLQQWGAGLLKPSETLSLTCAVYGGSFSGYYWSWIRQPPGKGLEWIGEINHSGSTNYNPSLKSRVTISVDTSKNQFSLKLSSVTAADTAVYYCARARTARGSSIFDYWGQGTLVTVS
SGSASAPTLFPLVSCENSPSDTSSVAVGCLAQDFLPDSITFSWKYKNNSDISSTRGFPSVLRGGKYAATSQVLLPSKDVMQGTDEHVCKVQHENGNKEKNVPLPVIAELPPKVSVFVP
PRDGFFGNPRKSKLICQATGFSPRQIQVSWLREGKQVGSGVTTDQVQAEAKESGPTTYKVTSTLTIKESDWLSQSMFTCRVDHRGLTFQQNASSMCVPDQDTAIRVFAIPPSFASIFLT
KSTKLTCLVTDLTTYDSVTISWTRQNGEAVKTHTNISESHPNATFSAVGEASICEDDWNSGERFTCTVTHDLPSPLKQTISRPKGVALHRPDVYLLPPAREQLNLRESATITCLVTGF
SPADVFVQWMQRGQPLSPEKYVTSAPMPEPQAPGRYFAHSILTVSEEEWNTGETYTCVVAHEALPNRVTERTVDKSTGKPTLYNVSLVMSDTAGTCY

SEQ ID NO:50
LIGHT CHAIN
DIQMTQSPSTLSASVGDRVTITCTGTSSDVGGYNYVSWYQQHPGKAPKLMIYGVSNRFSGSKSGNTASLTISGLAAEDEADYYCSSYTSSSTLVFGGGTKLTVLG
QPKAAPSVTLFPPSSEELQANKATLVCLISDFYPGAVTVAWKADSSPVKAGVETTPSKQSNNKYAASSYLSLTPEQWKSHRSYSCQVTHEGSTVEKTVAPTECS

FIGURE 2H

IGM15:

SEQ ID NO:42
HEAVY CHAIN
QVQLQQWGAGLLKPSETLSLTCAVYGGSFSGYYWSWIRQPPGKGLEWIGEINHSGSTNYNPSLKSRVTISVDTSKNQFSLKLSSVTAADTAVYYCARARARGSSIFDYWGQGTLVTVS
SGSASAPTLFPLVSCENSPSDTSSVAVGCLAQDFLPDSITFSWKYKNNSDISSTRGFPSVLRGGKYAATSQVLLPSKDVMQGTDEHVVCKVQHPNGNKENVPLPVIAELPPKVSVFVP
PRDGFFGNPRKSKLICQATGFSPRQIQVSWLREGKQVGSGVTTDQVQAEAKESGPTTYKVTSTLTIKESDWLSQSMFTCRVDHRGLTFQQNASSMCVPDQTAIRVFAIPPSFASIFLT
KSTKLTCLVTDLTTYDSVTISWTRQNGEAVKTHTNISESHPNATFSAVGEASICEDDWNSGERFTCTVTHTDLPSPLKQTISRPKGVALHRPDVYLLPPAREQLNLRESATITCLVTGF
SPADVFVQWMQRGQPLSPEKYVTSAPMPEPQAPGRYFAHSILTVSEEEWNTGETYTCVVAHEALPNRVTERTVDKSTGKPTLYNVSLVMSDTAGTCY

SEQ ID NO:50
LIGHT CHAIN
DIQMTQSPSTLSASVGDRVTITCTGTSSDVGGYNYVSWYQQHPGKAPKLMIYGVSNRFSGSKSGNTASLTISGLAAEDEADYCCSSYTSSSTLVVFGGGTKLTVLG
QPKAAPSVTLFPPSSEELQANKATLVCLISDFYPGAVTVAWKADSSPVKAGVETTTPSKQSNNKYAASSYLSLTPEQWKSHRSYSCQVTHEGSTVEKTVAPTECS

IGM16:

SEQ ID NO:43
HEAVY CHAIN
QVQLQQWGAGLLKPSETLSLTCAVYGGSFSGYYWSWIRQPPGKGLEWIGEINHSGSTNYNPSLKSRVTISVDTSKNQFSLKLSSVTAADTAVYYCARRATAWGSSIFDYWGQGTLVTVS
SGSASAPTLFPLVSCENSPSDTSSVAVGCLAQDFLPDSITFSWKYKNNSDISSTRGFPSVLRGGKYAATSQVLLPSKDVMQGTDEHVVCKVQHPNGNKEKNVPLPVIAELPPKVSVFVP
PRDGFFGNPRKSKLICQATGFSPRQIQVSWLREGKQVGSGVTTDQVQAEAKESGPTTYKVTSTLTIKESDWLSQSMFTCRVDHRGLTFQQNASSMCVPDQTAIRVFAIPPSFASIFLT
KSTKLTCLVTDLTTYDSVTISWTRQNGEAVKTHTNISESHPNATFSAVGEASICEDDWNSGERFTCTVTHTDLPSPLKQTISRPKGVALHRPDVYLLPPAREQLNLRESATITCLVTGF
SPADVFVQWMQRGQPLSPEKYVTSAPMPEPQAPGRYFAHSILTVSEEEWNTGETYTCVVAHEALPNRVTERTVDKSTGKPTLYNVSLVMSDTAGTCY

SEQ ID NO:50
LIGHT CHAIN
DIQMTQSPSTLSASVGDRVTITCTGTSSDVGGYNYVSWYQQHPGKAPKLMIYGVSNRFSGSKSGNTASLTISGLAAEDEADYCCSSYTSSSTLVVFGGGTKLTVLG
QPKAAPSVTLFPPSSEELQANKATLVCLISDFYPGAVTVAWKADSSPVKAGVETTTPSKQSNNKYAASSYLSLTPEQWKSHRSYSCQVTHEGSTVEKTVAPTECS

FIGURE 2I

IGM17:

SEQ ID NO:44
HEAVY CHAIN
QVQLQQWGAGLLKPSETLSLTCAVYGGSFSGYYWSWIRQPPGKGLEWIGEINHSGSTNYNPSLKSRVTISVDTSKNQFSLKLSSVTAADTAVYYCARRRTAWGSSIFDYWGQGTLVTVS
SGSASAPTLFPLVSCENSPSDTSSVAVGCLAQDFLPDSITFSWKYKNNSDISSTRGFPSVLRGGKYAATSQVLLPSKDVMQGTDEHVVCKVQHPNGNKEKNVPLPVIAELPPKVSVFVP
PRDGFFGNPRKSKLICQATGFSPRQIQVSWLREGKQVGSGVTTDQVQAEAKESGPTTYKVTSTLTIKESDWLSQSMFTCRVDHRGLTFQQNASSMCVPDQDTAIRVFAIPPSFASIFLT
KSTKLTCLVTDLTTYDSVTISWTRQNGEAVKTHTNISESHPNATFSAVGEASICEDDWNSGERFTCTVTHTDLPSPLKQTISRPKGVALHRPDVYLLPPAREQLNLRESATITCLVTGF
SPADVFVQWMQRGQPLSPEKYVTSAPMPEPQAPGRYFAHSILTVSEEEWNTGETYTCVVAHEALPNRVTERTVDKSTGKPTLYNVSLVMSDTAGTCY

SEQ ID NO:50
LIGHT CHAIN
DIQMTQSPSTLSASVGDRVTITCTGTSSDVGGYNYVSWYQQHPGKAPKLMIYGVSNRFSGSKSGNTASLTISGLAAEDEADYCSSYTSSSTLVFGGGTKLTVLG
QPKAAPSVTLFPPSSEELQANKATLVCLISDFYPGAVTVAWKADSSPVKAGVETTPSKQSNNKYAASSYLSLTPEQWKSHRSYSCQVTHEGSTVEKTVAPTECS

IGM18:

SEQ ID NO:45
HEAVY CHAIN
QVQLQQWGAGLLKPSETLSLTCAVYGGSFSGYYWSWIRQPPGKGLEWIGEINHSGSTNYNPSLKSRVTISVDTSKNQFSLKLSSVTAADTAVYYCARRATARGSSIFDYWGQGTLVTVS
SGSASAPTLFPLVSCENSPSDTSSVAVGCLAQDFLPDSITFSWKYKNNSDISSTRGFPSVLRGGKYAATSQVLLPSKDVMQGTDEHVVCKVQHPNGNKEKNVPLPVIAELPPKVSVFVP
PRDGFFGNPRKSKLICQATGFSPRQIQVSWLREGKQVGSGVTTDQVQAEAKESGPTTYKVTSTLTIKESDWLSQSMFTCRVDHRGLTFQQNASSMCVPDQDTAIRVFAIPPSFASIFLT
KSTKLTCLVTDLTTYDSVTISWTRQNGEAVKTHTNISESHPNATFSAVGEASICEDDWNSGERFTCTVTHTDLPSPLKQTISRPKGVALHRPDVYLLPPAREQLNLRESATITCLVTGF
SPADVFVQWMQRGQPLSPEKYVTSAPMPEPQAPGRYFAHSILTVSEEEWNTGETYTCVVAHEALPNRVTERTVDKSTGKPTLYNVSLVMSDTAGTCY

SEQ ID NO:50
LIGHT CHAIN
DIQMTQSPSTLSASVGDRVTITCTGTSSDVGGYNYVSWYQQHPGKAPKLMIYGVSNRFSGSKSGNTASLTISGLAAEDEADYCSSYTSSSTLVFGGGTKLTVLG
QPKAAPSVTLFPPSSEELQANKATLVCLISDFYPGAVTVAWKADSSPVKAGVETTPSKQSNNKYAASSYLSLTPEQWKSHRSYSCQVTHEGSTVEKTVAPTECS

FIGURE 2J

IGM19:

SEQ ID NO:46
HEAVY CHAIN
QVQLQQWGAGLLKPSETLSLTCAVYGGSFSGYYWSWIRQPPGKGLEWIGEINHSGSTNYNPSLKSRVTISVDTSKNQFSLKLSSVTAADTAVYYCARRARARGSSIFDYWGQGTLVTVS
SGSASAPTLFPLVSCENSPSDTSSVAVGCLAQDFLPDSITFSWKYKNNSDISSTRGFPSVLRGGKYAATSQVLLPSKDVMQGTDEHVVCKVQHPNGNKEKNVPLPVIAELPPKVSVFVP
PRDGFFGNPRKSKLICQATGFSPRQIQVSWLREGKQVGSGVTTDQVQAEAKESGPTTYKVTSTLTIKESDWLSQSMFTCRVDHRGLTFQQNASSMCVPDQTAIRVFAIPPSFASIFLT
KSTKLTCLVTDLTTYDSVTISWTRQNGEAVKTHTNISESHPNATFSAVGEASICEDDWNSGERFTCTVTHTDLPSPLKQTISRPKGVALHRPDVYLLPAREQLNLRESATITCLVTGF
SPADVFVQWMQRGQPLSPEKYVTSAPMPEPQAPGRYFAHSILTVSEEEWNTGETYTCVVAHEALPNRVTERTVDKSTGKPTLYNVSLVMSDTAGTCY

SEQ ID NO:50
LIGHT CHAIN
DIQMTQSPSTLSASVGDRVTITCTGTSSDVGGYNYVSWYQQHPGKAPKLMIYGVSNRFSGSKSGNTASLTISGLAAEDEADYYCSSYTSSSTLVVFGGGTKLTVLG
QPKAAPSVTLFPPSSEELQANKATLVCLISDFYPGAVTVAWKADSSPVKAGVETTTPSKQSNNKYAASSYLSLTPEQWKSHRSYSCQVTHEGSTVEKTVAPTECS

IGM20:

SEQ ID NO:47
HEAVY CHAIN
QVQLQQWGAGLLKPSETLSLTCAVYGGSFSGYYWSWIRQPPGKGLEWIGEINHSGSTNYNPSLKSRVTISVDTSKNQFSLKLSSVTAADTAVYYCARRRTARGSSIFDYWGQGTLVTVS
SGSASAPTLFPLVSCENSPSDTSSVAVGCLAQDFLPDSITFSWKYKNNSDISSTRGFPSVLRGGKYAATSQVLLPSKDVMQGTDEHVVCKVQHPNGNKEKNVPLPVIAELPPKVSVFVP
PRDGFFGNPRKSKLICQATGFSPRQIQVSWLREGKQVGSGVTTDQVQAEAKESGPTTYKVTSLTLTIKESDWLSQSMFTCRVDHRGLTFQQNASSMCVPDQTAIRVFAIPPSFASIFLT
KSTKLTCLVTDLTTYDSVTISWTRQNGEAVKTHTNISESHPNATFSAVGEASICEDDWNSGERFTCTVTHTDLPSPLKQTISRPKGVALHRPDVYLLPAREQLNLRESATITCLVTGF
SPADVFVQWMQRGQPLSPEKYVTSAPMPEPQAPGRYFAHSILTVSEEEWNTGETYTCVVAHEALPNRVTERTVDKSTGKPTLYNVSLVMSDTAGTCY

SEQ ID NO:50
LIGHT CHAIN
DIQMTQSPSTLSASVGDRVTITCTGTSSDVGGYNYVSWYQQHPGKAPKLMIYGVSNRFSGSKSGNTASLTISGLAAEDEADYYCSSYTSSSTLVVFGGGTKLTVLG
QPKAAPSVTLFPPSSEELQANKATLVCLISDFYPGAVTVAWKADSSPVKAGVETTTPSKQSNNKYAASSYLSLTPEQWKSHRSYSCQVTHEGSTVEKTVAPTECS

FIGURE 2K

IGM21:

SEQ ID NO:48
HEAVY CHAIN
QVQLQQWGAGLLKPSETLSLTCAVYGGSFSGYYWSWIRQPPGKGLEWIGEINHSGSTNYNPSLKSRVTISVDTSKNQFSLKLSSVTAADTAVYYCARGARAWGSSIFDYWGQGTLVTVS
SGSASAPTLFPLVSCENSPSDTSSVAVGCLAQDFLPDSITFSWKYKNNSDISSTRGFPSVLRGGKYAATSQVLLPSKDVMQGTDEHVVCKVQHPNGNKEKNVPLPVIAELPPKVSVFVP
PRDGFFGNPRKSKLICQATGFSPRQIQVSWLREGKQVGSVTTDQVQAEAKESGPTTYKVTSLTIKESDWLSQSMFTCRVDHRGLTFQQNASSMCVPDQDTAIRVFAIPPSFASIFLT
KSTKLTCLVTDLTTYDSVTISWTRQNGEAVKTHTNISESHPNATFSAVGEASICEDDWNSGERFTCTVTHTDLPSPLKQTISRPKGVALHRPDVYLLPPAREQLNLRESATITCLVTGF
SPADVFVQWMQRGQPLSPEKYVTSAPMPEPQAPGRYFAHSILTVSEEEWNTGETYTCVVAHEALPNRVTERTVDKSTGKPTLYNVSLVMSDTAGTCY

SEQ ID NO:50
LIGHT CHAIN
DIQMTQSPSTLSASVGDRVTITCTGTSSDVGGYNYVSWYQQHPGKAPKLMIYGVSNRFSGSKSGNTASLTISGLAAEDEADYCCSYTSSSTLVFGGGTKLTVLG
QPKAAPSVTLFPPSSEELQANKATLVCLISDFYPGAVTVAWKADSSPVKAGVETTPSKQSNNKYAASSYLSLTPEQWKSHRSYSCQVTHEGSTVEKTVAPTECS

IGM22:

SEQ ID NO:49
HEAVY CHAIN
QVQLQQWGAGLLKPSETLSLTCAVYGGSFSGYYWSWIRQPPGKGLEWIGEINHSGSTNYNPSLKSRVTISVDTSKNQFSLKLSSVTAADTAVYYCARRARAWGSSIFDYWGQGTLVTVS
SGSASAPTLFPLVSCENSPSDTSSVAVGCLAQDFLPDSITFSWKYKNNSDISSTRGFPSVLRGGKYAATSQVLLPSKDVMQGTDEHVVCKVQHPNGNKEKNVPLPVIAELPPKVSVFVP
PRDGFFGNPRKSKLICQATGFSPRQIQVSWLREGKQVGSVTTDQVQAEAKESGPTTYKVTSLTIKESDWLSQSMFTCRVDHRGLTFQQNASSMCVPDQDTAIRVFAIPPSFASIFLT
KSTKLTCLVTDLTTYDSVTISWTRQNGEAVKTHTNISESHPNATFSAVGEASICEDDWNSGERFTCTVTHTDLPSPLKQTISRPKGVALHRPDVYLLPPAREQLNLRESATITCLVTGF
SPADVFVQWMQRGQPLSPEKYVTSAPMPEPQAPGRYFAHSILTVSEEEWNTGETYTCVVAHEALPNRVTERTVDKSTGKPTLYNVSLVMSDTAGTCY

SEQ ID NO:50
LIGHT CHAIN
DIQMTQSPSTLSASVGDRVTITCTGTSSDVGGYNYVSWYQQHPGKAPKLMIYGVSNRFSGSKSGNTASLTISGLAAEDEADYCCSYTSSSTLVFGGGTKLTVLG
QPKAAPSVTLFPPSSEELQANKATLVCLISDFYPGAVTVAWKADSSPVKAGVETTPSKQSNNKYAASSYLSLTPEQWKSHRSYSCQVTHEGSTVEKTVAPTECS

FIGURE 2L

IGM23:

SEQ ID NO:28
HEAVY CHAIN
QVQLQQWGAGLLKPSETLSLTCAVYGGSFSGYYWSWIRQPPGKGLEWIGEINHSGSTNYNPSLKSRVTISVDTSKNQFSLKLSSVTAADTAVYYCARGRMAWGASVNFDYWGQGTLVTV
SSGSASAPTLFPLVSCENSPSDTSSVAVGCLAQDFLPDSITFSWKYKNNSDISSTRGFPSVLRGGKYAATSQVLLPSKDVMQGTDEHVVCKVQHPNGNKEKNVPLPVIAELPPKVSVFV
PPRDGFFGNPRKSKLICQATGFSPRQIQVSWLREGKQVGSGVTTDQVQAEAKESGPTTYKVTSTLTIKESDWLSQSMFTCRVDHRGLTFQQNASSMCVPDQDTAIRVFAIPPSFASIFL
TKSTKLTCLVTDLTTYDSVTISWTRQNGEAVKTHTNISESHPNATFSAVGEASICEDDWNSGERFTCTVTHTDLPSPLKQTISRPKGVALHRPDVLLPPAREQLNLRESATITCLVTG
FSPADVFVQWMQRGQPLSPEKYVTSAPMPEPQAPGRYFAHSILTVSEEEWNTGETYTCVVAHEALPNRVTERTVDKSTGKPTLYNVSLVMSDTAGTCY

SEQ ID NO:51
LIGHT CHAIN
DIQMTQSPSSLSASVGDRVTITCRASQSISSYLNWYQQKPGKAPKLLIYAASSLQSGVPSRFSGSGSGTDFTLTISSLQPEDFATYCQQSYSTPITFGQGTRLEIKRTVAAPSVFIFP
PSDEQLKSGTASVVCLLNNFYPREAKVQWKVDNALQSGNSQESVTEQDSKDSTYSLSSTLTLSKADYEKHKVYACEVTHQGLSSPVTKSFNRGEC

IGM24:

SEQ ID NO:29
HEAVY CHAIN
QVQLQQWGAGLLKPSETLSLTCAVYGGSFSGYYWSWIRQPPGKGLEWIGEINHSGSTNYNPSLKSRVTISVDTSKNQFSLKLSSVTAADTAVYYCARGRRAWGASVNFDYWGQGTLVTV
SSGSASAPTLFPLVSCENSPSDTSSVAVGCLAQDFLPDSITFSWKYKNNSDISSTRGFPSVLRGGKYAATSQVLLPSKDVMQGTDEHVVCKVQHPNGNKEKNVPLPVIAELPPKVSVFV
PPRDGFFGNPRKSKLICQATGFSPRQIQVSWLREGKQVGSGVTTDQVQAEAKESGPTTYKVTSTLTIKESDWLSQSMFTCRVDHRGLTFQQNASSMCVPDQDTAIRVFAIPPSFASIFL
TKSTKLTCLVTDLTTYDSVTISWTRQNGEAVKTHTNISESHPNATFSAVGEASICEDDWNSGERFTCTVTHTDLPSPLKQTISRPKGVALHRPDVYLLPPAREQLNLRESATITCLVTG
FSPADVFVQWMQRGQPLSPEKYVTSAPMPEPQAPGRYFAHSILTVSEEEWNTGETYTCVVAHEALPNRVTERTVDKSTGKPTLYNVSLVMSDTAGTCY

SEQ ID NO:51
LIGHT CHAIN
DIQMTQSPSSLSASVGDRVTITCRASQSISSYLNWYQQKPGKAPKLLIYAASSLQSGVPSRFSGSGSGTDFTLTISSLQPEDFATYCQQSYSTPITFGQGTRLEIKRTVAAPSVFIFP
PSDEQLKSGTASVVCLLNNFYPREAKVQWKVDNALQSGNSQESVTEQDSKDSTYSLSSTLTLSKADYEKHKVYACEVTHQGLSSPVTKSFNRGEC

FIGURE 2M

IGM25:

SEQ ID NO:30
HEAVY CHAIN
QVQLQQWGAGLLKPSETLSLTCAVYGGSFSGYYWSWIRQPPGKGLEWIGEINHSGSTNYNPSLKSRVTISVDTSKNQFSLKLSSVTAADTAVYYCARGRMARGASVNFDYWGQGTLVTV
SSGSASAPTLFPLVSCENSPSDTSSVAVGCLAQDFLPDSITFSWKYKNNSDISSTRGFPSVLRGGKYAATSQVLLPSKDVMQGTDEHVVCKVQHPNGNKEKNVPLPVIAELPPKVSVFV
PPRDGFFGNPRKSKLICQATGFSPRQIQVSWLREGKQVGSGVTTDQVQAEAKESGPTTYKVTSLTIKESDWLSQSMFTCRVDHRGLTFQQNASSMCVPDQTAIRVFAIPPSFASIFL
TKSTKLTCLVTDLTTYDSVTISWTRQNGEAVKTHTNISESHPNATFSAVGEASICEDDWNSGERFTCTVTHTDLPSPLKQTISRPKGVALHRPDVLLPAREQLNLRESATITCLVTG
FSPADVFVQWMQRGQPLSPEKYVTSAPMPEPQAPGRYFAHSILTVSEEEWNTGETYTCVVAHEALPNRVTERTVDKSTGKPTLYNVSLVMSDTAGTCY

SEQ ID NO:51
LIGHT CHAIN
DIQMTQSPSSLSASVGDRVTITCRASQSISSYLNWYQQKPGKAPKLLIYAASSLQSGVPSRFSGSGSGTDFTLTISSLQPEDFATYYCQQSYSTPITFGQGTRLEIKRTVAAPSVFIFP
PSDEQLKSGTASVVCLLNNFYPREAKVQWKVDNALQSGNSQESVTEQDSKDSTYSLSSTLTLSKADYEKHKVYACEVTHQGLSSPVTKSFNRGEC

IGM26:

SEQ ID NO:31
HEAVY CHAIN
QVQLQQWGAGLLKPSETLSLTCAVYGGSFSGYYWSWIRQPPGKGLEWIGEINHSGSTNYNPSLKSRVTISVDTSKNQFSLKLSSVTAADTAVYYCARGRRARGASVNFDYWGQGTLVTV
SSGSASAPTLFPLVSCENSPSDTSSVAVGCLAQDFLPDSITFSWKYKNNSDISSTRGFPSVLRGGKYAATSQVLLPSKDVMQGTDEHVVCKVQHPNGNKEKNVPLPVIAELPPKVSVFV
PPRDGFFGNPRKSKLICQATGFSPRQIQVSWLREGKQVGSGVTTDQVQAEAKESGPTTYKVTSLTIKESDWLSQSMFTCRVDHRGLTFQQNASSMCVPDQTAIRVFAIPPSFASIFL
TKSTKLTCLVTDLTTYDSVTISWTRQNGEAVKTHTNISESHPNATFSAVGEASICEDDWNSGERFTCTVTHTDLPSPLKQTISRPKGVALHRPDVYLLPAREQLNLRESATITCLVTG
FSPADVFVQWMQRGQPLSPEKYVTSAPMPEPQAPGRYFAHSILTVSEEEWNTGETYTCVVAHEALPNRVTERTVDKSTGKPTLYNVSLVMSDTAGTCY

SEQ ID NO:51
LIGHT CHAIN
DIQMTQSPSSLSASVGDRVTITCRASQSISSYLNWYQQKPGKAPKLLIYAASSLQSGVPSRFSGSGSGTDFTLTISSLQPEDFATYYCQQSYSTPITFGQGTRLEIKRTVAAPSVFIFP
PSDEQLKSGTASVVCLLNNFYPREAKVQWKVDNALQSGNSQESVTEQDSKDSTYSLSSTLTLSKADYEKHKVYACEVTHQGLSSPVTKSFNRGEC

FIGURE 2N

*IGM27:*

**SEQ ID NO:32
HEAVY CHAIN**
QVQLQQWGAGLLKPSETLSLTCAVYGGSFSGYYWSWIRQPPGKGLEWIGEINHSGSTNYNPSLKSRVTISVDTSKNQFSLKLSSVTAADTAVYYCARRGMAWGASVNFDYWGQGTLVTV
SSGSASAPTLFPLVSCENSPSDTSSVAVGCLAQDFLPDSITFSWKYKNNSDISSTRGFPSVLRGGKYAATSQVLLPSKDVMQGTDEHVCKVQHPNGNKEKNVPLPVIAELPPKVSVFV
PPRDGFFGNPRKSKLICQATGFSPRQIQVSWLREGKQVGSGVTTDQVQAEAKESGPTTYKVTSTLTIKESDWLSQSMFTCRVDHRGLTFQQNASSMCVPDQDTAIRVFAIPPSFASIFL
TKSTKLTCLVTDLTTYDSVTISWTRQNGEAVKTHTNISESHPNATFSAVGEASICEDDWNSGERFTCTVTHTDLPSPLKQTISRPKGVALHRPDVYLLPPAREQLNLRESATITCLVTG
FSPADVFVQWMQRGQPLSPEKYVTSAPMPEPQAPGRYFAHSILTVSEEEWNTGETYTCVVAHEALPNRVTERTVDKSTGKPTLYNVSLVMSDTAGTCY

**SEQ ID NO:51
LIGHT CHAIN**
DIQMTQSPSSLSASVGDRVTITCRASQSISSYLNWYQQKPGKAPKLLIYAASSLQSGVPSRFSGSGSGTDFTLTISSLQPEDFATYYCQQSYSTPITFGQGTRLEIKRTVAAPSVFIFP
PSDEQLKSGTASVVCLLNNFYPREAKVQWKVDNALQSGNSQESVTEQDSKDSTYSLSSTLTLSKADYEKHKVYACEVTHQGLSSPVTKSFNRGEC

*IGM28:*

**SEQ ID NO:33
HEAVY CHAIN**
QVQLQQWGAGLLKPSETLSLTCAVYGGSFSGYYWSWIRQPPGKGLEWIGEINHSGSTNYNPSLKSRVTISVDTSKNQFSLKLSSVTAADTAVYYCARRRMAWGASVNFDYWGQGTLVTV
SSGSASAPTLFPLVSCENSPSDTSSVAVGCLAQDFLPDSITFSWKYKNNSDISSTRGFPSVLRGGKYAATSQVLLPSKDVMQGTDEHVCKVQHPNGNKEKNVPLPVIAELPPKVSVFV
PPRDGFFGNPRKSKLICQATGFSPRQIQVSWLREGKQVGSGVTTDQVQAEAKESGPTTYKVTSTLTIKESDWLSQSMFTCRVDHRGLTFQQNASSMCVPDQDTAIRVFAIPPSFASIFL
TKSTKLTCLVTDLTTYDSVTISWTRQNGEAVKTHTNISESHPNATFSAVGEASICEDDWNSGERFTCTVTHTDLPSPLKQTISRPKGVALHRPDVYLLPPAREQLNLRESATITCLVTG
FSPADVFVQWMQRGQPLSPEKYVTSAPMPEPQAPGRYFAHSILTVSEEEWNTGETYTCVVAHEALPNRVTERTVDKSTGKPTLYNVSLVMSDTAGTCY

**SEQ ID NO:51
LIGHT CHAIN**
DIQMTQSPSSLSASVGDRVTITCRASQSISSYLNWYQQKPGKAPKLLIYAASSLQSGVPSRFSGSGSGTDFTLTISSLQPEDFATYYCQQSYSTPITFGQGTRLEIKRTVAAPSVFIFP
PSDEQLKSGTASVVCLLNNFYPREAKVQWKVDNALQSGNSQESVTEQDSKDSTYSLSSTLTLSKADYEKHKVYACEVTHQGLSSPVTKSFNRGEC

FIGURE 20

IGM29:

SEQ ID NO:34
HEAVY CHAIN
QVQLQQWGAGLLKPSETLSLTCAVYGGSFSGYYWSWIRQPPGCKGLEWIGEINHSGSTNYNPSLKSRVTISVDTSKNQFSLKLSSVTAADTAVYYCARRGMARGASVNFDYWGQGTLVTV
SSGSASAPTLFPLVSCENSPSDTSSVAVGCLAQDFLPDSITFSWKYKNNSDISSTRGFPSVLRGGKYAATSQVLLPSKDVMQGTDEHVCKVQHPNGNKEKNVPLPVIAELPPKVSVFV
PPRDGFFGNPRKSKLICQATGFSPRQIQVSWLREGKQVGSGVTTDQVQAEAKESGPTTYKVTSTLTIKESDWLSQSMFTCRVDHRGLTFQQNASSMCVPDQTAIRVFAIPPSFASIFL
TKSTKLTCLVTDLTTYDSVTISWTRQNGEAVKTHTNISESHPNATFSAVGEASICEDDWNSGERFTCVTHTDLPSPLKQTISRPKGVALHRPDVYLLPPAREQLNLRESATITCLVTG
FSPADVFVQWMQRGQPLSPEKYVTSAPMPEPQAPGRYFAHSILTVSEEEWNTGETYTCVVAHEALPNRVTERTVDKSTGKPTLYNVSLVMSDTAGTCY

SEQ ID NO:51
LIGHT CHAIN
DIQMTQSPSSLSASVGDRVTITCRASQSISSYLNWYQQKPGKAPKLLIYAASSLQSGVPSRFSGSGSGTDFTLTISSLQPEDFATYYCQQSYSTPITFGQGTRLEIKRTVAAPSVFIFP
PSDEQLKSGTASVVCLLNNFYPREAKVQWKVDNALQSGNSQESVTEQDSKDSTYSLSSTLTLSKADYEKHKVYACEVTHQGLSSPVTKSFNRGEC

IGM30:

SEQ ID NO:35
HEAVY CHAIN
QVQLQQWGAGLLKPSETLSLTCAVYGGSFSGYYWSWIRQPPGCKGLEWIGEINHSGSTNYNPSLKSRVTISVDTSKNQFSLKLSSVTAADTAVYYCARRGRARGASVNFDYWGQGTLVTV
SSGSASAPTLFPLVSCENSPSDTSSVAVGCLAQDFLPDSITFSWKYKNNSDISSTRGFPSVLRGGKYAATSQVLLPSKDVMQGTDEHVCKVQHPNGNKEKNVPLPVIAELPPKVSVFV
PPRDGFFGNPRKSKLICQATGFSPRQIQVSWLREGKQVGSGVTTDQVQAEAKESGPTTYKVTSTLTIKESDWLSQSMFTCRVDHRGLTFQQNASSMCVPDQTAIRVFAIPPSFASIFL
TKSTKLICLVTDLTTYDSVTISWTRQNGEAVKTHTNISESHPNATFSAVGEASICEDDWNSGERFTCVTHTDLPSPLKQTISRPKGVALHRPDVYLLPPAREQLNLRESATITCLVTG
FSPADVFVQWMQRGQPLSPEKYVTSAPMPEPQAPGRYFAHSILTVSEEEWNTGETYTCVVAHEALPNRVTERTVDKSTGKPTLYNVSLVMSDTAGTCY

SEQ ID NO:51
LIGHT CHAIN
DIQMTQSPSSLSASVGDRVTITCRASQSISSYLNWYQQKPGKAPKLLIYAASSLQSGVPSRFSGSGSGTDFTLTISSLQPEDFATYYCQQSYSTPITFGQGTRLEIKRTVAAPSVFIFP
PSDEQLKSGTASVVCLLNNFYPREAKVQWKVDNALQSGNSQESVTEQDSKDSTYSLSSTLTLSKADYEKHKVYACEVTHQGLSSPVTKSFNRGEC

FIGURE 2P

IGM31:

SEQ ID NO:36
HEAVY CHAIN
QVQLQQWGAGLLKPSETLSLTCAVYGGSFSGYYWSWIRQPPGKGLEWIGEINHSGSTNYNPSLKSRVTISVDTSKNQFSLKLSSVTAADTAVYYCARRRGARGASVNFDYWGQGTLVTV
SSGSASAPTLFPLVSCENSPSDTSSVAVGCLAQDFLPDSITFSWKYKNNSDISSTRGFPSVLRGGKYAATSQVLLPSKDVMQGTDEHVCKVQHPNGNKEKNVPLPVIAELPPKVSVFV
PPRDGFFGNPRKSKLICQATGFSPRQIQVSWLREGKQVGSGVTTDQVQAEAKESGPTTYKVTSTLTIKESDWLSQSMFTCRVDHRGLTFQQNASSMCVPDQDTAIRVFAIPPSFASIFL
TKSTKLITCLVTDLTTYDSVTISWTRQNGEAVKTHTNISESHPNATFSAVGEASICEDDWNSGERFTCTVTHTDLPSPLKQTISRPKGVALHRPDVYLLPPAREQLNLRESATITCLVTG
FSPADVFVQWMQRGQPLSPEKYVTSAPMPEPQAPGRYFAHSILTVSEEEWNTGETYTCVVAHEALPNRVTERTVDKSTGKPTLYNVSLVMSDTAGTCY

SEQ ID NO:51
LIGHT CHAIN
DIQMTQSPSSLSASVGDRVTITCRASQSISSYLNWYQQKPGKAPKLLIYAASSLQSGVPSRFSGSGSGTDFTLTISSLQPEDFATYYCQQSYSTPITFGQGTRLEIKRTVAAPSVFIFP
PSDEQLKSGTASVVCLLNNFYPREAKVQWKVDNALQSGNSQESVTEQDSKDSTYSLSSTLTLSKADYEKHKVYACEVTHQGLSSPVTKSFNRGEC

IGM32:

SEQ ID NO:37
HEAVY CHAIN
QVQLQQWGAGLLKPSETLSLTCAVYGGSFSGYYWSWIRQPPGKGLEWIGEINHSGSTNYNPSLKSRVTISVDTSKNQFSLKLSSVTAADTAVYYCARAGRAWGASVNFDYWGQGTLVTV
SSGSASAPTLFPLVSCENSPSDTSSVAVGCLAQDFLPDSITFSWKYKNNSDISSTRGFPSVLRGGKYAATSQVLLPSKDVMQGTDEHVCKVQHPNGNKEKNVPLPVIAELPPKVSVFV
PPRDGFFGNPRKSKLICQATGFSPRQIQVSWLREGKQVGSGVTTDQVQAEAKESGPTTYKVTSTLTIKESDWLSQSMFTCRVDHRGLTFQQNASSMCVPDQDTAIRVFAIPPSFASIFL
TKSTKLITCLVTDLTTYDSVTISWTRQNGEAVKTHTNISESHPNATFSAVGEASICEDDWNSGERFTCTVTHTDLPSPLKQTISRPKGVALHRPDVYLLPPAREQLNLRESATITCLVTG
FSPADVFVQWMQRGQPLSPEKYVTSAPMPEPQAPGRYFAHSILTVSEEEWNTGETYTCVVAHEALPNRVTERTVDKSTGKPTLYNVSLVMSDTAGTCY

SEQ ID NO:51
LIGHT CHAIN
DIQMTQSPSSLSASVGDRVTITCRASQSISSYLNWYQQKPGKAPKLLIYAASSLQSGVPSRFSGSGSGTDFTLTISSLQPEDFATYYCQQSYSTPITFGQGTRLEIKRTVAAPSVFIFP
PSDEQLKSGTASVVCLLNNFYPREAKVQWKVDNALQSGNSQESVTEQDSKDSTYSLSSTLTLSKADYEKHKVYACEVTHQGLSSPVTKSFNRGEC

FIGURE 2Q

IGM33:

SEQ ID NO:38
HEAVY CHAIN
QVQLQQWGAGLLKPSETLSLTCAVYGGSFSGYYWSWIRQPPGKGLEWIGEINHSGSTNYNPSLKSRVTISVDTSKNQFSLKLSSVTAADTAVYYCARRGRAWGASVNFDYWGQGTLVTV
SSGSASAPTLFPLVSCENSPSDTSSVAVGCLAQDFLPDSITFSWKYKNNSDISSTRGFPSVLRGGKYAATSQVLLPSKDVMQGTDEHVCKVQHPNGNKEKNVPLPVIAELPPKVSVFV
PPRDGFFGNPRKSKLICQATGFSPRQIQVSWLREGKQVGSGVTTDQVQAEAKESGPTTYKVTSLTIKESDWLSQSMFTCRVDHRGLTFQQNASSMCVPDQTAIRVFAIPPSFASIFL
TKSTKLTCLVTDLTTYDSVTISWTRQNGEAVKTHTNISESHPNATFSAVGEASICEDDWNSGERFTCTVTHTDLPSPLKQTISRPKGVALHRPDVYLLPPAREQLNLRESATITCLVTG
FSPADVFVQWMQRGQPLSPEKYVTSAPMPEPQAPGRYFAHSILTVSEEEWNTGETYTCVVAHEALPNRVTERTVDKSTGKPTLYNVSLVMSDTAGTCY

SEQ ID NO:51
LIGHT CHAIN
DIQMTQSPSSLSASVGDRVTITCRASQSISSYLNWYQQKPGKAPKLLIYAASSLQSGVPSRFSGSGSGTDFTLTISSLQPEDFATYYCQQSYSTPITFGQGTRLEIKRTVAAPSVFIFP
PSDEQLKSGTASVVCLLNNFYPREAKVQWKVDNALQSGNSQESVTEQDSKDSTYSLSSTLTLSKADYEKHKVYACEVTHQGLSSPVTKSFNRGEC

IGM34:

SEQ ID NO:39
HEAVY CHAIN
QVQLQQWGAGLLKPSETLSLTCAVYGGSFSGYYWSWIRQPPGKGLEWIGEINHSGSTNYNPSLKSRVTISVDTSKNQFSLKLSSVTAADTAVYYCARARTAWGSSIFDYWGQGTLVTVS
SGSASAPTLFPLVSCENSPSDTSSVAVGCLAQDFLPDSITFSWKYKNNSDISSTRGFPSVLRGGKYAATSQVLLPSKDVMQGTDEHVCKVQHPNGNKEKNVPLPVIAELPPKVSVFVP
PRDGFFGNPRKSKLICQATGFSPRQIQVSWLREGKQVGSGVTTDQVQAEAKESGPTTYKVTSLTIKESDWLSQSMFTCRVDHRGLTFQQNASSMCVPDQTAIRVFAIPPSFASIFLT
KSTKLTCLVTDLTTYDSVTISWTRQNGEAVKTHTNISESHPNATFSAVGEASICEDDWNSGERFTCTVTHTDLPSPLKQTISRPKGVALHRPDVYLLPPAREQLNLRESATITCLVTGF
SPADVFVQWMQRGQPLSPEKYVTSAPMPEPQAPGRYFAHSILTVSEEEWNTGETYTCVVAHEALPNRVTERTVDKSTGKPTLYNVSLVMSDTAGTCY

SEQ ID NO:51
LIGHT CHAIN
DIQMTQSPSSLSASVGDRVTITCRASQSISSYLNWYQQKPGKAPKLLIYAASSLQSGVPSRFSGSGSGTDFTLTISSLQPEDFATYYCQQSYSTPITFGQGTRLEIKRTVAAPSVFIFP
PSDEQLKSGTASVVCLLNNFYPREAKVQWKVDNALQSGNSQESVTEQDSKDSTYSLSSTLTLSKADYEKHKVYACEVTHQGLSSPVTKSFNRGEC

FIGURE 2R

IGM35:

SEQ ID NO:40
HEAVY CHAIN
QVQLQQWGAGLLKPSETLSLTCAVYGGSFSGYYWSWIRQPPGKGLEWIGEINHSGSTNYNPSLKSRVTISVDTSKNQFSLKLSSVTAADTAVYYCARARRAWGSSIFDYWGQGTLVTVS
SGSASAPTLFPLVSCENSPSDTSSVAVGCLAQDFLPDSITFSWKYKNNSDISSTRGFPSVLRGGKYAATSQVLLPSKDVMQGTDEHVCKVQHPNGNKEKNVPLPVIAELPPKVSVFVP
PRDGFFGNPRKSKLICQATGFSPRQIQVSWLREGKQVGSGVTTDQVQAEAKESGPTTYKVTSTLTIKESDWLSQSMFTCRVDHRGLTFQQNASSMCVPDQDTAIRVFAIPPSFASIFLT
KSTKLTCLVTDLTTYDSVTISWTRQNGEAVKTHTNISESHPNATFSAVGEASICEDDWNSGERFTCTVTHTDLPSPLKQTISRPKGVALHRPDVYLLPPAREQLNLRESATITCLVTGF
SPADVFVQWMQRGQPLSPEKYVTSAPMPEPQAPGRYFAHSILTVSEEEWNTGETYTCVVAHEALPNRVTERTVDKSTGKPTLYNVSLVMSDTAGTCY

SEQ ID NO:51
LIGHT CHAIN
DIQMTQSPSSLSASVGDRVTITCRASQSISSYLNWYQQKPGKAPKLLIYAASSLQSGVPSRFSGSGSGTDFTLTISSLQPEDFATYYCQQSYSTPITFGQGTRLEIKRTVAAPSVFIFP
PSDEQLKSGTASVVCLLNNFYPREAKVQWKVDNALQSGNSQESVTEQDSKDSTYSLSSTLTLSKADYEKHKVYACEVTHQGLSSPVTKSFNRGEC

IGM36:

SEQ ID NO:41
HEAVY CHAIN
QVQLQQWGAGLLKPSETLSLTCAVYGGSFSGYYWSWIRQPPGKGLEWIGEINHSGSTNYNPSLKSRVTISVDTSKNQFSLKLSSVTAADTAVYYCARARTARGSSIFDYWGQGTLVTVS
SGSASAPTLFPLVSCENSPSDTSSVAVGCLAQDFLPDSITFSWKYKNNSDISSTRGFPSVLRGGKYAATSQVLLPSKDVMQGTDEHVCKVQHPNGNKEKNVPLPVIAELPPKVSVFVP
PRDGFFGNPRKSKLICQATGFSPRQIQVSWLREGKQVGSGVTTDQVQAEAKESGPTTYKVTSTLTIKESDWLSQSMFTCRVDHRGLTFQQNASSMCVPDQDTAIRVFAIPPSFASIFLT
KSTKLTCLVTDLTTYDSVTISWTRQNGEAVKTHTNISESHPNATFSAVGEASICEDDWNSGERFTCTVTHTDLPSPLKQTISRPKGVALHRPDVYLLPPAREQLNLRESATITCLVTGF
SPADVFVQWMQRGQPLSPEKYVTSAPMPEPQAPGRYFAHSILTVSEEEWNTGETYTCVVAHEALPNRVTERTVDKSTGKPTLYNVSLVMSDTAGTCY

SEQ ID NO:51
LIGHT CHAIN
DIQMTQSPSSLSASVGDRVTITCRASQSISSYLNWYQQKPGKAPKLLIYAASSLQSGVPSRFSGSGSGTDFTLTISSLQPEDFATYYCQQSYSTPITFGQGTRLEIKRTVAAPSVFIFP
PSDEQLKSGTASVVCLLNNFYPREAKVQWKVDNALQSGNSQESVTEQDSKDSTYSLSSTLTLSKADYEKHKVYACEVTHQGLSSPVTKSFNRGEC

FIGURE 2S

IGM37:

SEQ ID NO:42
HEAVY CHAIN
QVQLQQWGAGLLKPSETLSLTCAVYGGSFSGYYWSWIRQPPGKGLEWIGEINHSGSTNYNPSLKSRVTISVDTSKNQFSLKLSSVTAADTAVYYCARARRARGSSIFDYWGQGTLVTVS
SGSASAPTLFPLVSCENSPSDTSSVAVGCLAQDFLPDSITFSWKYKNNSDISSTRGFPSVLRGGKYAATSQVLLPSKDVMQGTDEHVVCKVQHPNGNKEKNVPLPVIAELPPKVSVFVP
PRDGFFGNPRKSKLICQATGFSPRQIQVSWLREGKQVGSGVTTDQVQAEAKESGPTTYKVTSTLTIKESDWLSQSMFTCRVDHRGLTFQQNASSMCVPDQDTAIRVFAIPPSFASIFLT
KSTKLTCLVTDLTTYDSVTISWTRQNGEAVKTHTNISESHPNATFSAVGEASICEDDWNSGERFTCTVTHTDLPSPLKQTISRPKGVALHRPDVYLLPPAREQLNLRESATITCLVTGF
SPADVFVQWMQRGQPLSPEKYVTSAPMPEPQAPGRYFAHSILTVSEEEWNTGETYTCVVAHEALPNRVTERTVDKSTGKPTLYNVSLVMSDTAGTCY

SEQ ID NO:51
LIGHT CHAIN
DIQMTQSPSSLSASVGDRVTITCRASQSISSYLNWYQQKPGKAPKLLIYAASSLQSGVPSRFSGSGSGTDFTLTISSLQPEDFATYYCQQSYSTPITFGQGTRLEIKRTVAAPSVFIFP
PSDEQLKSGTASVVCLLNNFYPREAKVQWKVDNALQSGNSQESVTEQDSKDSTYSLSSTLTLSKADYEKHKVYACEVTHQGLSSPVTKSFNRGEC

IGM38:

SEQ ID NO:43
HEAVY CHAIN
QVQLQQWGAGLLKPSETLSLTCAVYGGSFSGYYWSWIRQPPGKGLEWIGEINHSGSTNYNPSLKSRVTISVDTSKNQFSLKLSSVTAADTAVYYCARRATAWGSSIFDYWGQGTLVTVS
SGSASAPTLFPLVSCENSPSDTSSVAVGCLAQDFLPDSITFSWKYKNNSDISSTRGFPSVLRGGKYAATSQVLLPSKDVMQGTDEHVVCKVQHPNGNKENVPLPVIAELPPKVSVFVP
PRDGFFGNPRKSKLICQATGFSPRQIQVSWLREGKQVGSGVTTDQVQAEAKESGPTTYKVTSTLTIKESDWLSQSMFTCRVDHRGLTFQQNASSMCVPDQDTAIRVFAIPPSFASIFLT
KSTKLTCLVTDLTTYDSVTISWTRQNGEAVKTHTNISESHPNATFSAVGEASICEDDWNSGERFICTVTHTDLPSPLKQTISRPKGVALHRPDVYLLPPAREQLNLRESATITCLVTGF
SPADVFVQWMQRGQPLSPEKYVTSAPMPEPQAPGRYFAHSILTVSEEEWNTGETYTCVVAHEALPNVTERTVDKSTGKPTLYNVSLVMSDTAGTCY

SEQ ID NO:51
LIGHT CHAIN
DIQMTQSPSSLSASVGDRVTITCRASQSISSYLNWYQQKPGKAPKLLIYAASSLQSGVPSRFSGSGSGTDFTLTISSLQPEDFATYYCQQSYSTPITFGQGTRLEIKRTVAAPSVFIFP
PSDEQLKSGTASVVCLLNNFYPREAKVQWKVDNALQSGNSQESVTEQDSKDSTYSLSSTLTLSKADYEKHKVYACEVTHQGLSSPVTKSFNRGEC

FIGURE 2T

IGM39:

SEQ ID NO:44
HEAVY CHAIN
QVQLQQWGAGLLKPSETLSLTCAVYGGSFSGYYWSWIRQPPGKGLEWIGEINHSGSTNYNPSLKSRVTISVDTSKNQFSLKLSSVTAADTAVYYCARRTAWGSSIFDYWGQGTLVTVS
SGSASAPTLFPLVSCENSPSDTSSVAVGCLAQDFLPDSITFSWKYKNNSDISSTRGFPSVLRGGKYAATSQVLLPSKDVMQGTDEHVVCKVQHPNGNKEKNVPLPVIAELPPKVSVFVP
PRDGFFGNPRKSKLICQATGFSPRQIQVSWLREGKQVGSGVTTDQVQAEAKESGPTTYKVTSTLTIKESDWLSQSMFTCRVDHRGLTFQQNASSMCVPDQDTAIRVFAIPPSFASIFLT
KSTKLTCLVTDLTTYDSVTISWTRQNGEAVKTHTNISESHPNATFSAVGEASICEDDWNSGERFTCTVTHTDLPSPLKQTISRPKGVALHRPDVYLLPPAREQLNLRESATITCLVTGF
SPADVFVQWMQRGQPLSPEKYVTSAPMPEPQAPGRYFAHSILTVSEEEWNTGETYTCVVAHEALPNRVTERTVDKSTGKPTLYNVSLVMSDTAGTCY

SEQ ID NO:51
LIGHT CHAIN
DIQMTQSPSSLSASVGDRVTITCRASQSISSYLNWYQQKPGKAPKLLIYAASSLQSGVPSRFSGSGSGTDFTLTISSLQPEDFATYYCQQSYSTPITFGQGTRLEIKRTVAAPSVFIFP
PSDEQLKSGTASVVCLLNNFYPREAKVQWKVDNALQSGNSQESVTEQDSKDSTYSLSSTLTLSKADYEKHKVYACEVTHQGLSSPVTKSFNRGEC

IGM40:

SEQ ID NO:45
HEAVY CHAIN
QVQLQQWGAGLLKPSETLSLTCAVYGGSFSGYYWSWIRQPPGKGLEWIGEINHSGSTNYNPSLKSRVTISVDTSKNQFSLKLSSVTAADTAVYYCARRATARGSSIFDYWGQGTLVTVS
SGSASAPTLFPLVSCENSPSDTSSVAVGCLAQDFLPDSITFSWKYKNNSDISSTRGFPSVLRGGKYAATSQVLLPSKDVMQGTDEHVVCKVQHPNGNKEKNVPLPVIAELPPKVSVFVP
PRDGFFGNPRKSKLICQATGFSPRQIQVSWLREGKQVGSGVTTDQVQAEAKESGPTTYKVTSTLTIKESDWLSQSMFTCRVDHRGLTFQQNASSMCVPDQDTAIRVFAIPPSFASIFLT
KSTKLTCLVTDLTTYDSVTISWTRQNGEAVKTHTNISESHPNATFSAVGEASICEDDWNSGERFTCTVTHTDLPSPLKQTISRPKGVALHRPDVYLLPPAREQLNLRESATITCLVTGF
SPADVFVQWMQRGQPLSPEKYVTSAPMPEPQAPGRYFAHSILTVSEEEWNTGETYTCVVAHEALPNRVTERTVDKSTGKPTLYNVSLVMSDTAGTCY

SEQ ID NO:51
LIGHT CHAIN
DIQMTQSPSSLSASVGDRVTITCRASQSISSYLNWYQQKPGKAPKLLIYAASSLQSGVPSRFSGSGSGTDFTLTISSLQPEDFATYYCQQSYSTPITFGQGTRLEIKRTVAAPSVFIFP
PSDEQLKSGTASVVCLLNNFYPREAKVQWKVDNALQSGNSQESVTEQDSKDSTYSLSSTLTLSKADYEKHKVYACEVTHQGLSSPVTKSFNRGEC

FIGURE 2U

IGM41:

SEQ ID NO:46
HEAVY CHAIN
QVQLQQWGAGLLKPSETLSLTCAVYGGSFSGYYWSWIRQPPGKGLEWIGEINHSGSTNYNPSLKSRVTISVDTSKNQFSLKLSSVTAADTAVYYCARRARARGSSIFDYWGQGTLVTVS
SGSASAPTLFPLVSCENSPSDTSSVAVGCLAQDFLPDSITFSWKYKNNSDISSTRGFPSVLRGGKYAATSQVLLPSKDVMQGTDEHVCKVQHPNGNKEKNVPLPVIAELPPKVSVFVP
PRDGFFGNPRKSKLICQATGFSPRQIQVSWLREGKQVGSGVTTDQVQAEAKESGPTTYKVTSTLTIKESDWLSQSMFTCRVDHRGLTFQQNASSMCVPDQDTAIRVFAIPPSFASIFLT
KSTKLITCLVTDLTTYDSVTISWTRQNGEAVKTHTNISESHPNATFSAVGEASICEDDWNSGERFTCVTHTDLPSPLKQTISRPKGVALHRPDVYLLPPAREQLNLRESATITCLVTGF
SPADVFVQWMQRGQPLSPEKYVTSAPMPEPQAPGRYFAHSILTVSEEEWNTGETYTCVVAHEALPNRVTERTVDKSTGKPTLYNVSLVMSDTAGTCY

SEQ ID NO:51
LIGHT CHAIN
DIQMTQSPSSLSASVGDRVTITCRASQSISSYLNWYQQKPGKAPKLLIYAASSLQSGVPSRFSGSGSGTDFTLTISSLQPEDFATYYCQQSYSTPITFGQGTRLEIKRTVAAPSVFIFP
PSDEQLKSGTASVVCLLNNFYPREAKVQWKVDNALQSGNSQESVTEQDSKDSTYSLSSTLTLSKADYEKHKVYACEVTHQGLSSPVTKSFNRGEC

IGM42:

SEQ ID NO:47
HEAVY CHAIN
QVQLQQWGAGLLKPSETLSLTCAVYGGSFSGYYWSWIRQPPGKGLEWIGEINHSGSTNYNPSLKSRVTISVDTSKNQFSLKLSSVTAADTAVYYCARRRTARGSSIFDYWGQGTLVTVS
SGSASAPTLFPLVSCENSPSDTSSVAVGCLAQDFLPDSITFSWKYKNNSDISSTRGFPSVLRGGKYAATSQVLLPSKDVMQGTDEHVCKVQHPNGNKEKNVPLPVIAELPPKVSVFVP
PRDGFFGNPRKSKLICQATGFSPRQIQVSWLREGKQVGSGVTTDQVQAEAKESGPTTYKVTSTLTIKESDWLSQSMFTCRVDHRGLTFQQNASSMCVPDQDTAIRVFAIPPSFASIFLT
KSTKLITCLVTDLTTYDSVTISWTRQNGEAVKTHTNISESHPNATFSAVGEASICEDDWNSGERFTCVTHTDLPSPLKQTISRPKGVALHRPDVYLLPPAREQLNLRESATITCLVTGF
SPADVFVQWMQRGQPLSPEKYVTSAPMPEPQAPGRYFAHSILTVSEEEWNTGETYTCVVAHEALPNRVTERTVDKSTGKPTLYNVSLVMSDTAGTCY

SEQ ID NO:51
LIGHT CHAIN
DIQMTQSPSSLSASVGDRVTITCRASQSISSYLNWYQQKPGKAPKLLIYAASSLQSGVPSRFSGSGSGTDFTLTISSLQPEDFATYYCQQSYSTPITFGQGTRLEIKRTVAAPSVFIFP
PSDEQLKSGTASVVCLLNNFYPREAKVQWKVDNALQSGNSQESVTEQDSKDSTYSLSSTLTLSKADYEKHKVYACEVTHQGLSSPVTKSFNRGEC

FIGURE 2V

IGM43:

SEQ ID NO:48
HEAVY CHAIN
QVQLQQWGAGLLKPSETLSLTCAVYGGSFSGYYWSWIRQPPGKGLEWIGEINHSGSTNYNPSLKSRVTISVDTSKNQFSLKLSSVTAADTAVYYCARGARAWGSSIFDYWGQGTLVTVS
SGSASAPTLFPLVSCENSPSDTSSVAVGCLAQDFLPDSITFSWKYKNNSDISSTRGFPSVLRGGKYAATSQVLLPSKDVMQGTDEHVCCKVQHPNGNKEKNVPLPVIAELPPKVSVFVP
PRDGFFGNPRKSKLICQATGFSPRQIQVSWLREGKQVGSGVTTDQVQAEAKESGPTTYKVTSTLTIKESDWLSQSMFTCRVDHRGLTFQQNASSMCVPDQDTAIRVFAIPPSFASIFLT
KSTKLTCLVTDLTTYDSVTISWTRQNGEAVKTHTNISESHPNATFSAVGEASICEDDWNSGERFTCTVTHTDLPSPLKQTISRPKGVALHRPDVYLLPPAREQLNLRESATITCLVTGF
SPADVFVQWMQRGQPLSPEKYVTSAFMPEPQAPGRYFAHSILTVSEEEWNTGETYTCVVAHEALPNRVTERTVDKSTGKPTLYNVSLVMSDTAGTCY

SEQ ID NO:51
LIGHT CHAIN
DIQMTQSPSSLSASVGDRVTITCRASQSISSYLNWYQQKPGKAPKLLIYAASSLQSGVPSRFSGSGSGTDFTLTISSLQPEDFATYYCQQSYSTPITFGQGTRLEIKRTVAAPSVFIFP
PSDEQLKSGTASVVCLLNNFYPREAKVQWKVDNALQSGNSQESVTEQDSKDSTYSLSSTLTLSKADYEKHKVYACEVTHQGLSSPVTKSFNRGEC

IGM44:

SEQ ID NO:49
HEAVY CHAIN
QVQLQQWGAGLLKPSETLSLTCAVYGGSFSGYYWSWIRQPPGKGLEWIGEINHSGSTNYNPSLKSRVTISVDTSKNQFSLKLSSVTAADTAVYYCARRARAWGSSIFDYWGQGTLVTVS
SGSASAPTLFPLVSCENSPSDTSSVAVGCLAQDFLPDSITFSWKYKNNSDISSTRGFPSVLRGGKYAATSQVLLPSKDVMQGTDEHVCCKVQHPNGNKEKNVPLPVIAELPPKVSVFVP
PRDGFFGNPRKSKLICQATGFSPRQIQVSWLREGKQVGSGVTTDQVQAEAKESGPTTYKVTSTLTIKESDWLSQSMFTCRVDHRGLTFQQNASSMCVPDQDTAIRVFAIPPSFASIFLT
KSTKLTCLVTDLTTYDSVTISWTRQNGEAVKTHTNISESHPNATFSAVGEASICEDDWNSGERFTCTVTHTDLPSPLKQTISRPKGVALHRPDVYLLPPAREQLNLRESATITCLVTGF
SPADVFVQWMQRGQPLSPEKYVTSAFMPEPQAPGRYFAHSILTVSEEEWNTGETYTCVVAHEALPNRVTERTVDKSTGKPTLYNVSLVMSDTAGTCY

SEQ ID NO:51
LIGHT CHAIN
DIQMTQSPSSLSASVGDRVTITCRASQSISSYLNWYQQKPGKAPKLLIYAASSLQSGVPSRFSGSGSGTDFTLTISSLQPEDFATYYCQQSYSTPITFGQGTRLEIKRTVAAPSVFIFP
PSDEQLKSGTASVVCLLNNFYPREAKVQWKVDNALQSGNSQESVTEQDSKDSTYSLSSTLTLSKADYEKHKVYACEVTHQGLSSPVTKSFNRGEC

CDR3 Variants of H1 through H22

| | | | | |
|---|---|---|---|---|
| H1 | GRMAWGASVN (SEQ ID NO:78) | | H2 | ARTAWGSSI (SEQ ID NO:79) |
| H3 | GRRAWGASVN (SEQ ID NO:80) | | H14 | ARRAWGSSI (SEQ ID NO:91) |
| H5 | GRMARGASVN (SEQ ID NO:82) | | H4 | ARTARGSSI (SEQ ID NO:81) |
| H6 | GRRARGASVN (SEQ ID NO:83) | | H15 | ARRARGSSI (SEQ ID NO:92) |
| H7 | RGMAWGASVN (SEQ ID NO:84) | | H16 | RATAWGSSI (SEQ ID NO:93) |
| H8 | RRMAWGASVN (SEQ ID NO:85) | | H17 | RRTAWGSSI (SEQ ID NO:94) |
| H9 | RGMARGASVN (SEQ ID NO:86) | | H18 | RATARGSSI (SEQ ID NO:95) |
| H10 | RGRARGASVN (SEQ ID NO:87) | | H19 | RARARGSSI (SEQ ID NO:96) |
| H11 | RRGARGASVN (SEQ ID NO:88) | | H20 | RRTARGSSI (SEQ ID NO:97) |
| H12 | AGRAWGASVN (SEQ ID NO:89) | | H21 | GARAWGSSI (SEQ ID NO:98) |
| H13 | RGRAWGASVN (SEQ ID NO:90) | | H22 | RARAWGSSI (SEQ ID NO:99) |

SEQ ID NO:52
HEAVY CHAIN OF IGM1 AND IGM23

CAGGTGCAGCTCCAGCAGTGGGAGCAGGACTCTTGAGACTTTGAGCCTCACATGCGCTGTCTATGGCGGATCTTTCTCCGGCTACTATTGTCCTGATACGACAGCC
CCCAGGCAAAGGACTCGAGTGGATTGGGAGATCAACCACTCTGGTAGCACTAACTATATCCAAGCCTGAAGTCCCGTGAAGTTGATACATCCAAGAACCAATTTCCC
TGAAACTGAGCTCAGTGACTGCCGCCGACACTGCCGTCTACTACTGTGCTCTGTGAGAATAGCCCTGGAGTGGCCTTCCTGAATTTCGACTACTGGGACAGGTACCCTGTCACTGTC
TCTTCAGGTTCCGCATCCGCCCCAACCCTTTCCCCTGCGTCTCCTGTGAGAATACAGCAGCACCGGGCTTCCCATCAGTCCTGACATCAGCAGAACGCTGACATCAGCAGAAC
CACTTTCTCCTGGAAATACAAGAACGACTGACATCAGCAGCACCCTGGCAAAGTCCAGACATCAGCAGTCAGAACGGCACTCCACAGCACCTCACAGCAGTCTGGCTGCCTCCAAAGTCAGCGCTCTTCGTC
TCATGCAGGGCACAGACAGAACGTGTTGGCAAAGTCCAAGTCCAAGGCCAGCTCATCTGCCAGGCCACGACTCATCTGCCAGGTTTCAGTCCCGGCAGATTCAGGTGTCCTGCTGCGCAGGGGAAGCAGGTGGGTC
CCACCCCGACGGCTTCTTCGGCAACCCCGCAAGTTGGCAGGCTGAGGCCAAAGAGTCTGGGCCCACGACAGTCCCATCTGCCAGGCCACGACTCATGGCTCTGCCAGGCCACGACTGGTCAGCCAGAGCATGTTCACCT
GCCGTGTCACCAGGACCAGTGACCTTCAGCAGAATGCGTCCTCCAGTCAGCAGAGGCCCAGACTCCCCATCCCCCATCCTTTGCCAGCATCTTCCTC
GCCGTGATCACAGGGCCTGACCTTCAGCAGAATGCGTCCTCCAGTCAGCAGAGGCCCAGACGTGACCATCTCCTGACCGGATAATGCCCAGAAATGCCACAACCCACAAACATCCGAAGC
ACCAAGTTGACCAAGTTGACCTTCAGCGCCGTGACTGCCACAGATGCGGAATAGCGGCAGCACTGGAATAGCGGGAGTTCACGTGACCGTGAAGCTGAAAACCCACACCAACAATCGCCACTGAAGC
CCACCAATGCCACCAAGTTGACCTTCAGCGCCGTGACTGCCTGCCAGGCCCGATGTCTACTTGCTGCCCAGGGGAGAGCAGCCCCAATGCCGTGAACCTGCGGAGTCAGCCACCATCACGTGCCTGGTGACGGGC
AGACCATCTCCCGCGACGTCTTGTGAAGATCGAGATGCAGAGGGGGATGAACACGGGAGAATGAACACCGGGAGAATGAACACCTCTGCGAGCCTTGTCCCAGGGCCCGATGTCTACTTGCTGCCCAGGGGAGAGCAGCCCCAATGCCGTGAACCTGCGGAGTCAGCCACCATCACGTGCCTGGTGACGGGC
TTCTCTCCCGGGACGTCTTCGTGAAGATCGAGATGCAGAGGGGGATGAACACGGGAGAATGAACACCCTCAGAGGTCACCAGCTGCCCAACAGGGTCACCGAGGTCACCGGTACCCGAGGAGACCGTGACAAGTCCACCGGTA
CAGCAATCTGACCGTGTCCAAGAACGACGTGTCCCTGACCGTGTCCAAGAACGACAAGGGAATTGAACAGAGGTGGATCATGTCCCTGGTCATGTCCCTGGTCATGTCCCTGGACACCTGGCACCTGCTAC
AACCCACCCTGTACAACGTGTCCCTGGTCATGTCCCTGGACACCTGGCACCTGCTAC

SEQ ID NO:53
HEAVY CHAIN OF IGM2 AND IGM24

CAGGTGCAGCTCCAGCAGTGGGAGCAGGACTCTTGAAACCCCTCTGAGACTTTGAGCCTCACATGCGCTGTCTATGGCGGATCTTTCTCCGGCTACTATTGTCCTGATACGACAGCC
CCCAGGCAAAGGACTCGAGTGGATTGGGAGATCAACCACTCTGGTAGCACTAACTATATCCAAGCCTGAAGTCCCGTGAAGTTGATACATCCAAGAACCAATTTCCC
TGAAACTGAGCTCAGTGACTGCCGCCGACACTGCCGTCTACTACTGTGCTCTGTGAGAATAGCCCTGGAGTGGCCTTCCTGAATTTCGACTACTGGGACAGGTACCCTGTCACTGTC
TCTTCAGGTTCCGCATCCGCCCCAACCCTTTCCCCTGCGTCTCCTGTGAGAATACAGCAGCACCGGGCTTCCCATCAGTCCTGACATCAGCAGAACGCTGACATCAGCAGAAC
CACTTTCTCCTGGAAATACAAGAACGACTGACATCAGCAGCACCCTGGCAAAGTCCAGACATCAGCAGTCAGAACGGCACTCCACAGCACCTCACAGCAGTCTGGCTGCCTCCAAAGTCAGCGCTCTTCGTC
TCATGCAGGGCACAGACAGAACGTGTTGGCAAAGTCCAAGTCCAAGGCCAGCTCATCTGCCAGGCCACGACTCATCTGCCAGGTTTCAGTCCCGGCAGATTCAGGTGTCCTGCTGCGCAGGGGAAGCAGGTGGGTC
CCACCCCGACGGCTTCTTCGGCAACCCCGCAAGTTGGCAGGCTGAGGCCAAAGAGTCTGGGCCCACGACAGTCCCATCTGCCAGGCCACGACTGGTCAGCCAGAGCATGTTCACCT
GCCGTGTCACCAGGACCAGTGACCTTCAGCAGAATGCGTCCTCCAGTCAGCAGAGGCCCAGACTCCCCATCCCCCATCCTTTGCCAGCATCTTCCTC
GCCGTGATCACAGGGCCTGACCTTCAGCAGAATGCGTCCTCCAGTCAGCAGAGGCCCAGACGTGACCATCTCCTGACCGGATAATGCCCAGAAATGCCACAACCCACAAACATCCGAGAG
ACCAAGTCCACCAAGTTGACCTTCAGCGCCGTGACTGCCTCCAGGATGCTCACGTGACCGTGAAGCTGAAAACCCACACCAACAATCGCCACTGAAGC
CCACCAATGCCACCAAGTTGACCTTCAGCGCCGTGACTGCCTGCCAGGCCCGATGTCTACTTGCTGCCCAGGGGAGAGCAGCCCCAATGCCGTGAACCTGCGGAGTCAGCCACCATCACGTGCCTGGTGACGGGC
AGACCATCTCCCGCGACGTCTTGTGAAGATCGAGATGCAGAGGGGGATGAACACCTCAGAGGTCACCAGCTGCCCAACAGGGTCACCGAGGTCACCGGTACCCGAGGAGACCGTGACAAGTCCACCGGTA
TTCTCTCCCGGGACGTCTTCGTGAAGATCGAGATGCAGAGGGGGATGAACACCCTCAGAGGTCACCAGCTGCCCAACAGGGTCACCGAGGTCACCGGTACCCGAGGAGACCGTGACAAGTCCACCGGTA
CAGCAATCTGACCGTGTCCAAGAACGACGTGTCCCTGGTCATGTCCCTGGTCATGTCCCTGGTCATGTCCCTGGACACCTGGCACCTGCTAC
AACCCACCCTGTACAACGTGTCCCTGGTCATGTCCCTGGACACCTGGCACCTGCTAC

FIGURE 4B

SEQ ID NO:54
HEAVY CHAIN OF IGM3 AND IGM25
CAGTGCAGCTCCAGCAGTGGGAGCAGGAGACTCTTGAAACCCTCTGAGACTTTGAGCCTCACATGCGCTGTCTATGGCGGATCTTTCTCCGGCTACTATTGGTCCTGATACGACAGCC
CCCAGGCAAAGGACTGGAGTCGATTGGGAGAATCAACCACTCTGGTAGCACTACTGTCCGTGTAACTAATATTCCAAGCCTGAAGTCCCGTGTAACAATTAGTGTTGATACATCCAAGAACCAATTTCCC
TGAAACTGAGCTCAGTGACTGCCGCCGACACTGCCCCCAACCCTTTTCCCCTCGTCTGTCTGTAGAATAGCCCGTCGGATACGAGCAGCGTGGCCGTTGCTGCCTCGCACAGGACTTCCTTCCCGACTCAT
CACTTTCTCCTGGAAATACAAGAGACAACTCTGACATCAGCAGCAGCACCCGGGGCTTCCATCAGTCCTGAGAGGACTTCCATCAGTCCTGAGAGGGGAAGTACGCAGCACCCACACTCAGTGCCTCTTCTCCAAGTGCTCCTTCCAAGGACG
TCATGCAGGGCACAGACAGACAACACGTGGTTCGGCAACCCCGCAAGTCTGACAAACCCCGCAAGTCTCGGCAACCCCGCAAGTCTGACAATTGCTGAGCTGTCTCCGGCAGATTCAGGTGTCTCAGGTGTCTCAGGGGAAGTGAGCGTCTTGTC
CCACCCCGCGACGGCTTCTTCGGCAACCCCGACGGCTTCTTCGGCAACCCCGACCAGTTCAGCTCTCCCCCCCGACGCCGACACTGCCGAGGGCGACGCTACAAGTCTGGCCGACGCTACAAGTCTGGCCAACCGTCTACAAGAGTCTGGGCCAACCGTCTACAAGAGTCTGGGCCAACCGTCAGCCAGGTGCTCAGCCAGCATGTTCACCT
TGGGCGTCACCACGGACCAGGTGCAGCCTGACCTTCCAGCAGATGCGTCCTCCAGCAGAATGCTGCCACCTGGCGACCGACGTGACCTGGCCGGTCCCGTTCAAGAGAGCGACTGGCTCAGCCAGCATCCCCCATCCTTTGCCAGCATCTCCTC
GCCGGTGGATCACAGGGCCTGACCTTCCAGCGCCCAAGCTGCCCGGTCACAGCTTGACCTGCTGGTCACAGAGTCACCATTCCTGACCGCCAGAATGCCATCCGGGTCTTCGCCCATCCCCCAGAATGCCATCCGGGTCTTCGCCACCGTTCACGTGACCGAAGCTGTGAAAACCACACCAACATCTCCGAGAG
ACAAGTCCACCAAGTTGACCTGCCTGGTCACAGATCACAGAGACCTGGATCACAGAGTTCACGTGACCTCGGAAGTGGTTCACGTGACCGAACCTGCGGCCACATCACGTGCCTGGTGACGGGGC
CCACCCCAATGCTCCGGCCCAAGGGTGCCCCAAGTTCTCCCGGCCTGCCCAAGCTGAACTCACGCGCCCAATGCCTGAGCCCTGAGCCCCAATGCCCTGAGCCCCCAGGCCGTGACCTGGACCGTGGACCAAGTCCACCGGTA
AGACCATCTCCCGGGGACGTCTTCGTGCAGTGGATGGAACACGGGAAGAGGAATGGAACACGGGCAGCCCTGAGGGCAGCCCTACACCCTGAGGGCAGCCCTACACCCTGCCCACCAGGGGGATATGTGACCAGGGGGATATGTGACCGCCCCCAATGCCTGAGCCCTGAGCCCCAATGCCCTGAGCCCCCAGGCCGTGACTTCGCCCA
TTCTCTCCCGGGACGTCTTGCGTCCGAAGAGAATGGAACACGGGACGTCTCCCATGAGGGCCCATGAGGGCCCATGAGGCCCTACACGCCCCATGAGGCCCTACACGCCCCATGAGGCCCCTGCCCAACAGGGTCACCGAGAGACCGTGGACAAGTCCACCGGTA
AACCCACCCTGTACAACGTGTCCCTGCTCATGTCCGACACAGCTGGCACCTGCTAC

SEQ ID NO:55
HEAVY CHAIN OF IGM4 AND IGM26
CAGGTGCAGCTCCAGCAGTGGGAGCAGGAGACTCTTGAAACCCTCTGAGACTTTGAGCCTCACATGCGCTGTCTATGGCGGATCTTTCTCCGGCTACTATTGGTCCTGATACGACAGCC
CCCAGGCAAAGGACTGGAGTCGATTGGGAGAATCAACCACTCTGGTAGCACTACTATAATCCAAGCCTGAAGTCCCGTGTAACTAATATTCCAAGCCTGAAGTCCCGTGTAACAATTAGTGTTGATACATCCAAGAACCAATTTCCC
TGAAACTGAGCTCAGTGACTGCCGCCGACACTGCCCCCAACCCTTTTCCCCTCGTCTACTGTCTGTCTCCGTGTAGAAGGGCCAGGGGCCGTTCGTGAATTTCGACTACTGGGGACAGGTACCCTGGTCACTGTC
TCTTCAGGTTCCTGATCCGCCATCCGCCACTGCTTTCCCCCTCGTCGATCAGCAGCAGCCGGCGTCGGATATCGACCAGGCTGGCCGTCCGACAGCAGCCGCCACCTGCCACCTCAGGGTGCGTGCCTCTCCCAAGGACG
CACTTTCTCCTGGAAATACAAGAGACAACTCTGACATCAGCAGCAACACCCGGGGCTTCCACTCAGTCCTGACAAGTGCTGTGTGCAAGTGCTGTGTGCAAACCCCGCAAGTCTGATTGCTGAGCTGCCTGCCTCCCAAAGTGAGCGTCTTCGTC
TCATGCAGGGCACAGACAGACAACACGTGGTTCGGCAACCCCGCAAGTCTGACAATTCAGTGTCTGATCAGGATGTCCCGCCAGATTCAGGTGCCAGATTCAGTGCCAGCTGGCCAGCACTTACACCACTACACCCGCCAGATCCCCCATCCTTTTGCCAGCATCTCCTT
CACCACCGCGACGGCTTCTTCGGCAACCCCGACGCCGCAGGTCAGGTCAGCGGCAAACCCCTGAGGCCAAGAGTCTGGGCCAACCCTACAGGAGTCTGGCCAACCCTACACGAGTCACCATACCCCCATCAAGCTGCACCATCTCCGACCACCAGGAGAGCCAGCCAGCCAGGAAGAGGAAGGACGGGTC
GCCGTCAGCGGATCACAGGGCCTGACCTTCAGCGCCCTGACCGTGACCCCCTGACCGTGACCCCCTGACCGTGACCCAAGAGACCACAAGAGACCATCTCCCCCCATCCTTGCCAGCGCATCTTCCTGCCAGCGTCATCTTTGCCAGCATCTTCCT
ACCAAGTCCACCAAGTTGACCTGCCTGGTCACAGACCGTGACAGCGGGCTGGATGTGCACAGCCAGCGGTCCGCCAGGGGGCCCAGCCATCGGAAGTCATCGGGGAGAAGCTGTGAAAACCACACCAACATCTCCGAGAG
ACAATCATCTCCCGGGGACGTCTTCGCCAAGGGTGCCCCAAGGGTGCCTTTCAGCGCCCACTTTCAGCGCCCCACTTTCAGGCCCCAGCCATCGGGGAGCAGCTGACCATGCCCAATGGACCCACCCCCAGGCCCCAGCCGGTACCGAGCCCCACCTGCTGCTGGTCACCGTGGTGACGGGGC
AGACCATCTCCCGGGGACGTCTTCGCCATCCGCTTCGTCCCCCGGGACGTCTTCGCCATCCGCTTCGTCCCCCGGGACGTCTTCGCCATCCGCCCCCCAGAGGGCCCGATGTCTACTTGCTGCTGCCGAGAGGCCCGATGTCTACTTGCTGCCCGAGAAGTGACCAGCGACCGCCCCATCACGTGCCTGGTGACGTCGC
TTCTCTCCCGGGACGTCTTCGTCCGAAGAGAATGGAACACGGGAACCAGCTGACCATGACCCATGAGGGCCCATGAGGCCCTACACGCTGCCCACCAGGGTCACCGAGAGAGACCGTGGACAAGTCCACCGGTA
CAGCATCCTGACCGTGTCCAACGGAATGGAACACGGGAACCTGCCATGCCAACGGAACCAGCCCTGCCCCAACGTGTGCAACACAGGGACTGGAACGTGAACGGATGTGAACGGATGTGCCCAAACAGGGACTGGAACAGCTGCTAC
AACCCACCCTGTACAACGTGTCCCTGCTCATGTCCGACACAGCTGGCACCTGCTAC

FIGURE 4C

SEQ ID NO:56
HEAVY CHAIN OF IGM5 AND IGM27
CAGGTGCAGCTCCAGCAGTCGGGAGCAGTGGGAGCAGGACTTGAAACCCTCTGAGACTTTGAGCCTCACATGCGCTGTCTTATGCCGGATCTTTCTCCGGCTACTATTGGTCCTGGATACGACAGCC
CCCAGGCAAAGGACTCGAGTGGATTGGGGAAATCAACCACTCTGTAGCACTACTATAATCCAAGCCTGAAGTCCCGTTCCGTGTAACATTAGTGTTGATACATCCAAGAACCAATTTCCC
TGAAACTGAGCTCAGTGACTGCCGCCGACACTGCCGTCTCACTGTCTCGTGAGAATAGCCGTCGGACTGCAGCAGCGTGGCCGTTGGCCGTTGGCTGCTCGCACAGGACTTCCTTCCCGACTCCAT
TCTTCAGGTTCCGCATCCGCCCAACCCTTTCCCCTCGTCTCTGTGAGAATAGCCGTCGGACACCCGGGCTTCCACTAGTCCTGAGAGGGGCAAGTACGCAGCAGCGTGCCTCTTCCAGGACG
CACTTTCTCCTGGAAATACAAGAACAACTCTGACATCAGCAGACCCGGGCTTCCACAGTCCTGAGAGGGGCAAGTACGCAGCAGCTCAGCGTGTGCTCCAAAGTGAGCGTCTTCGTC
TCATGCAGGGCACAGACAGAACGAACACGTGGTGCAAAGTTGCAAGTCAAGCTCATCTGCCAGGCCAAGTCCCCGCAGATTCAGTGTCCTGGCTGCTGCCGAGGGAAGCAGGTGGGGTC
CCACCCCGCGACAGGCTTCTTCGGCAACCCCGCAAGTGCGGCAAAGTCTGGGCCAGAGTCTGCCCTCCCATGTGTCCCGATCAAGAACACAGCCATCCCCCCATCCTTTGCCAGCATCTTCCTC
TGGCGTCACCACGACCAGTCGGCCAGGTGCAGCTGAGGCAAGAGTCTGGGCCAGAGTCTGCCCTCCCATGTGTCCCGATCAAGAACACAGCCATCCCCCCATCCTTTGCCAGCATCTTCCTC
GCCGTCGGATCACAGGGCCTCACCTTCCGGTCACAGAGATCGCTGACCACTATGACAGCGTGACTGACCATCCTGGAGATAGCGGGAGAGGTTCACGTGACCGTGAACCTGCCCACCATCACGTGCCTGGTGACGGGC
ACAAGCCACCAAGTTGACCTCCCGTCCCTGGTCACAGATGCCTGACCACCTATGACAGCGTGACTGACCATCCTGGAGATAGCGGGAGAGGTTCACGTGACCGTGAACCTGCCCACCATCACGTGCCTGGTGACGGGC
CCACCCAATGCCACTTTCAGCGCCGTGGTGCCCTGACGCCCAGGCCCGACATCTGTACTTGCTGCCACCAGGGGCAGCTCTGAGATGTGACCACGCGCCCCAATGCCTGAACCTGGGAGTCGGAGTCTGAGCGCCCAGGCCCGTACTTCGCCCA
AGACCATCTCCCGCGGAGACTCTTCGTGACTGGATGCAGAGAGGACGGAACAGGGGAGAATGGAACACGGGAGAAGAGGACGGAACAGGGGAGAATGGAACAC
TTCTCTCCCCGGAGACTCTTCGTGACTGGATGCAGAGAGGACGGAACAGGGGAGAATGGAACACCTGTGGTGGCCCATGAGGCCTGGTGGCCCATGAGGCCTGTGGGGCCCATGAGGCCCTGACCTACACCTGTGCTGTGCCCAAGAGGCCCTGCCCAACAGGGTCACCGAGAGAGCCTGACAAGTCACCGGTA
CAGCATCCTGACCGTGTCCAACGTGTCCAACGGGTCACCATGGCCCATGAGGCCCTGACCTACACCTGTGCTGTGCCCAAGAGGCCCTGCCCAACAGGGTCACCGAGAGAGCCTGACAAGTCACCGGTA
AACCCACCCTGTACAACGTGTCCCTGGTCATGTCCGACACAGCTGGCACCTGCTAC

SEQ ID NO:57
HEAVY CHAIN OF IGM6 AND IGM28
CAGGTGCAGCTCCAGCAGTCGGGAGCAGTGGGAGCAGGACTCTTGAGACTTTGAGCCTCACATGCGCTGTCTTATGGCGGATCTTTCTCCGGCTACTATTGGTCCTGGATACGACAGCC
CCCAGGCAAAGGACTCGAGTGGATTGGGGAAATCAACCACTCTGTAGCACTACTATAATCAACGCCTGAAGTCCCGTGTAACATTAGTGTTGATACATCCAAGAACCAATTTCCC
TGAAACTGAGCTCAGTGACTGCCGCCGACACTGCCGTCTCACTGTCTCCCGTGAGAATAGCCCGTCGGACAATGCCCGTTGCCCGTTGGCCGTTCCGTGTAACATTAGTGTTGATACATCCAAGAACCAATTTCCC
TCTTCAGGTTCCGCATCCGCCCAACCCTTTCCCCTCGTCTCTGTGAGAATAGCCCGTCGGACAATGCCCGTTGCCCGTTGGCCGTTCCACTGAGCAGCCCACCTCAGGTGCTGCTGCCCTGCCCTTCCAAGGACG
CACTTTCTCCTGGAAATACAAGAGAACAACTCTGACATCAGCAGCACCCCGGGCTTCCACAGTCCTGAGCTTGCCTCTTCCAGTGAGTCGCTCCCAAGTGAGCGTCTTCGTC
TCATGCAGGGCACAGACAGAACACGTGGTGCAAAGTTGCAAACCCCCGCAAGTCAAGCCGTCCCAGGCCACAGTCCTGAGCTTGCCTCTTCCAGTGAGTCGCTCCCAAGTGAGCGTCTTCGTC
CCACCCCGCGACAGCGCTTCTTCGGCAACCCCGCAAGTGCGGCAAAGTCTGGCCAACCCCCGCAAGTCAAGCCGTCCCAGGCCACAGTCCTGAGCTTGCCTCTTCCAGTGAGTCGCTCCCAAGTGAGCGTCTTCGTC
GCCGCGTGGATCACAGGGCCTGACCTGCACAGAGATCGCTGACCACTATGACAGCGTGACTGACCATCCTGGAGATAGCGGGAGAGGTTCACGTGACCGTGAACCTGCCACCATCACGTGCCTGGTGACGGGC
ACCAAGTTCACCAAGCCCACCTGCACAGAGATCGCTGACCACTATGACAGCGTGACTGACCATCCTGGAGATAGCGGGAGAGGTTCACGTGACCGTGAACCTGCCACCATCACGTGCCTGGTGACGGGC
CCACCCAATGCCACCATCTCCCGGAGTCTTCCGCCAGGGGCAGCAGCTCTGAAGGGGGCAGCAGCTCGTGGAGGCCCATCAGCGCCCCAATGCCTGAGCCCCAATGCCTGAACCTGGGAGTCGGAGTCTGAGCGCCCAGGCCCGTACTTCGCCCA
AGACCATCTCCCGGAGTCTTCCGCCAGGGGCAGCAGCTCTGAAGGGGGCAGCAGCTCGTGGAGGCCCATCAGCGCCCCAATGCCTGAGCCCCAATGCCTGAACCTGGGAGTCGGAGTCTGAGCGCCCAGGCCCGTACTTCGCCCA
TTCTCTCCCCGGAGACTCTGTCCGAAGAGAATGGAACCTACACCTGTGTGGCCCATGAGGCCCTGACCTGGCCTGACCCTGACCTACACCTGTGCTGTGCCCAAGAGGCCCTGCCCAACAGGGTCACCGAGAGACCTGACAAGTCACCGGTA
CAGCATCCTGACCGTGTCCAACGTGTCCAACGTGCCCATGGCCCATGAGGCCCTGACCTGGCCTGACCCTGACCTACACCTGTGCTGTGCCCAAGAGGCCCTGCCCAACAGGGTCACCGAGAGACCTGACAAGTCACCGGTA
AACCCACCCTGTACAACGTGTCCCTGGTCATGTCCGACACAGCTGGCACCTGCTAC

FIGURE 4D

SEQ ID NO:58
HEAVY CHAIN OF IGM7 AND IGM29
CAGGTGCAGCTCCAGCAGTCGGGAGCAGGACTCTTGAAACCCTCTGGTAGTGAGACTTTGAGCCTCACATGCGCTGTCTATGGCGGATCTTTCTCCGGCTACTATTGGTCCTGGATACGACAGCC
CCCAGGCAAAGGACTCGAGTGATTGGGGAAATCAACCACTCTGGTAGCACTAATATAATCCAAGCCTGAAGTCCCGTGTAACATTAGTGTTGATACATCCAAGAACCAATTTTCCC
TGAAACTGAGCTCAGTGACTGCCGCGACACTGTTCCCCAACCCTTTCCCCATCGCCGTCTACTACTGTGCTCGCGTGAATAGCCCGTGCGATACCAAGCAGCGGCCTTCCGTGTAGCAGCAGCA
TCTTCAGGTTCCGATCCGCATCCCGCCCAACCCTTTCCCCACCCTTTCCCCGTCTACATAGCAGACACCCAAGCTCCTGAACATAGCCCGTGGCCGTTGCCGTGGCCGTGGCAGCACCTCACAGGT
CACTTTCTCCTGGAAATACAAGACACGAACACTCTGACATCTGCAAAGTCCAGACTGGTGTGCAAAGTCCAGAGAGTCTGGCAACCCCCAAGCTGTGGCAACCCCCAAGCT
TCATGCAGGGCACAGACCGGGCTTCTTCGGCAACCCCGGCAAGTCGTGTGCAACCCCCAAGCTCATCGGCCAAGCTCATCCGCCCCACGACCTCATCGCCCCACGACCTCCAGGGTGTC
CCACCCCGACGACCACCAGGTCCAGGCTCAGCGTCGACAGGCTCCAGAGCTGCGAACCCCGAAGCTCTGGGCAACCTACAAGGTGACCAGCACACTGCCCACCATCCCCCATCCTTTGCCAGCATCTCCTC
TGGCGCTACCACCGACCAGGGCCCTGACCTCCAGCAGGGGCCCTTCCCCGATCAGCAGTCGTGCCAGAGCCGTCCCCGATCAGCAGTCGTGCCAGAGCCGTTCCAGACCTGGGCCCTTGCCAGCATCTCCGAGAG
CACAGCCAATGCCACTTCAGCCCGTCTGGCCCTGACCCGTGGAGGATGAGGATGACTGCGAAATAGCCGGAGTTCAGTGCACTGCGGCGACCATCCGCCCCACCATCCCCCCACCATCCC
AGACCATCTCCGGCCCAGGGGGTGCCCTGCAGTGGATGTCAGAGGGGCAGCTCTGTGCAGACCCCGGAGTGCGGGAGCCCGGAGTCGGACCACATACTGTGCCGTGCCGGTACTTCCGCCA
TTCTCTCCCGGACGCTCGTCCGAAGAGGAATGGAACACGGGACGACCTACAACCCTGTTGCCCCACGACCCTGCCCAACACGGTCACCGAGACCCTGAGCCTGACAAGTCCACCGGTA
CAGCATCCTGACCCGTCGTCCGAAGAGGAATGGAACACGGGACGACCTACAACCCTGTTGCCCCACGACCCTGCCCAACACGGTCACCGAGACCCTGAGCCTGACAAGTCCACCGGTA
AACCCACCCTGTACAACGTGTCCCTGTCATGTCCGTGCACAGCTGGCACCTGCTAC

SEQ ID NO:59
HEAVY CHAIN OF IGM8 AND IGM30
CAGGTGCAGCTCCAGCAGTGGGGAGCAGGACTCTTGAAACCCTCTGGTGAGACTTTGAGCCTCACATGCGCTGTCTATGGCGGATCTTCTCCGGCTACTATTGGTCCTGGATACGACAGCC
CCCAGGCAAAGGACTCGAGTGATTGGGGAAATCAACCACTCTGGTAGCACTAATACTATAATCCAAGCCTGAAGTCCGGTGTAACATTAGTGTTGATACATCCAAGAACCAATTTTCCC
TGAAACTGAGCTCAGTGACTGCCGCGACACTCGTTCCCCCTCTACTACTGTGCTCGGGGAAGGGCCGTTCGTGAATTCGACTACTGGGGACAGGGTACCCTGGTCACTGTC
TCTTCAGGTTCCGATCCGCATCCCGCCCAACCCCTTTCCCCCTCGTCTGCTGCTGGCACCTCCAACAGCGGCCCTGCCGTGCCCTGCGCCTTCCCTGCCCACTCAT
CACTTTCTCCTGGAAATACAAGACACGAACACTCTGACATCTGCAAAGTCCAGAACTGGTGTCAAAGTCCAGACTGGTGTGGAAAGAACGTGCCTCTTCAGTGCTGCCTCCAAAGTGACCGTCTCGTC
CCACCCCGACGACCGGCGCTTCTGCAACCCCGCAAGTCCACGGACCCTCAGGCCAAGCTCACCGAGATTCAGTGTCCGGCAGATTCAGGTGTCCTGCGCGAGGGGAAGCAGTGGGGTC
TGGCGTCACCACGACCAGGTGACCTTCCAGCAGGAGTCGCTCCCTCAGCAGACACCAGCGGGCCTTGCCATCCCGGTCTTGCCACCATCCTTTTGCCAGCATCTCCTC
ACCAAGTCACCAGTTGACCTGCCTGCCGCGTCACAGACCTGGAATACGCCCGCAGAATGGGAGCTGTGAAAACCCACACAGATCTCCGAGAG
CCACCCCATGCCACCTTCAGCCCGTCCGCAGCATCTGCGAGGATGACTGGAATAGCCCGGAAGTTCAGTGAACCTGAACCTGACCTGCCCACTGTTC
AGACCATCTCCGGCGAGGGGTGCCCTGCAGTGGATGGGGAGAGGGGAGACCGGGGAGAATGGAACACTGTGAACCTGCGGGAGTCAGCTGAACCTGAAGGC
TTCTCTCCCCGGACCGTCTGTCGATGGATGAGGAATGGAAACACGGGACGACCTACAAGGCCCATAGGCGGAGTATGTGACCAGCGCCCCATGGAGCTGAAGCCCTGAGCCTCGAAGCC
CAGCATCCTGACCGTCGCGAAGAGGAATGGAAACACGGGACGACCTACAACTGGCCGTCGTGGCCCAACAGGTCACCGAGACCTCAGCGGCCTGACAAGTCCACCGGTA
AACCCACCCTGTACAACGTGTCCCTGTCATGTCCGTGCACAGCTGGCACCTGCTAC

FIGURE 4E

SEQ ID NO:60
HEAVY CHAIN OF IGM9 AND IGM31

CAGGTGCAGCTCCAGCAGTCGGGAGCAGGACTCTTGAAACCCTCTGAGACTTTGAGCCTCACATGCGCTGCTGTCTATGGCGGATCTTTCTCCGGCTACTATTGGTCCTGGATACGACAGCC
CCAGGCAAAGGACTCGAGTGGATTGGGAGAAATCAACCACTCTGTAGCACTACATATAATCAAGCCTGAAGTCCCGTGAACAATTAGTGTTGATACATCCAAGAACCAATTTTCCC
TGAAACTGAGCTGACTGCGCCGACACTGCCTTCCGTGTAGAGGGCGCTTCCGTGAATTCGACTACTGGGACAGGGTACCCTGGTCACTGTC
TCTTCAGTTCCGCATCCGCCCCAACCCTTTTCCCCCTCGTCTCCTGTGAGAATAGCCGTGGACAGCAGGGACAGGGCCGTTGGCTGCTCGCACAGAGGACTTCCTTCCCGACTCCAT
CACTTTCTCCTGGAAATACAAGAACAACTCTGACATCAGCAGCACCCGGGGCTTCCATCAGTCTGAGAGGGGCAAGTACGCAGCCACCTCACAGGTGCTGCTGCCTTCAAGGACG
TCATGCAGGGCACAGACGAACACGTGGTGCAAAGTGCAACAAAGAAAAGAACGTGCCTCTTCCAGTGATTGCTGAGCTGCCTCAAAGTGAGCGCTTCGTC
CCACCCCGCGACGGCTTCTTCGGACCAGGTGTGCAACCCCCGAAGCTCATCTGCCAAGCTCAAGAGTCTTGGGCACCAGGCCAAAGAGTCTGGGCACTCACAAGGTGCCTGGCTCAGCCAGATGAGCTGTGCCTCAGCCAGAGCATGTCACCT
TGGGCGTCACCACGGATCACAGGGGCCTGACCTTCAGCAGAGATGCGTCTTCCGATCAGTCACAGAGATCATCAAAGAGAGCCGCATCCCCCCATCCTTTGCCAGCATCTCCTC
GCCGCTGGATCACAGGGGCCTGACCTTCAGCAGAGATGCGTCTTCCGATCGTGTCCCGGCCACTGACCATCAAAGAGAGCCGCATCCCCCCATCCTTTGCCAGCATCTCCTC
ACCAAGTCCACCAATGCCACTGACCTGCCTGTCACAGACGTGACCACCTGACCATCTCCTGACCCGCCAGAATGGCGAAGCTGAAAACCACACATCCCCAC
CACCCAATGCCACTTTCAGCCCGGCCAAGGGGTGCCCTGGGTGCCCTGGCCTGGCCAGGCCAGGCCACAGCCCCTGACCCCCAGGCCCAAGAAAAACCACACATCCCCAC
AGACCATCTCCCGGCCCAAGGGGTGCCCTGGATGCCAGTGGCAGCAGGCCCAGCGGAGGTTCAGCTGCAGCAGCCCTGAGCCCCAGGCCCCCATCACGTGCCTGGTGACGGGC
TTCCTCCCCCGACGCTCTTCGTGCCAGATGGAACACGGGAGGGTCCAGACCCAGCCGTCGTCCCATGAGGGCCCCGCAACAGGGTCACCGTAGAGGACCGTGACAAGTCCACCGGTA
CAGACCTGACCGTGTCCAAGAGGGAATGGAACACGGGAGGGTCACCCAGGCCGTGCCCTGCAACAGGGTCACCGTAGAGGACCGTGACAAGTCCACCGGTA
AACCCACCCCTGTACACGTGTCCCTGGTCATGTCCGACACAGCTGGCACCTGCTAC

SEQ ID NO:61
HEAVY CHAIN OF IGM10 AND IGM32

CAGGTGCAGCTCCAGCAGTCGGGAGCAGGACTCTTGAAACCCTCTGAGACTTTGAGCCTCACATGCGCTGCTGTCTATGGCGGATCTTTCTCCGGCTACTATTGGTCCTGGATACGACAGCC
CCAGGCAAAGGACTCGAGTGGATTGGGAGAAATCAACCACTCTGTAGCACTACATATAATCAAGCCTGAAGTCCCGTGAACAATTAGTGTTGATACATCCAAGAACCAATTTTCCC
TGAAACTGAGCTCAGTGACTGCGCCGACACTGCCTTCCGTGTAGAGGGCGCTTCCGTGAATTCGACTACTGGGACAGGGTACCCTGGTCACTGTC
TCTTCAGTTCCGCATCCGCCCCAACCCTTTTCCCCCTCGTCTCCTGTGAGAATAGCCGTGGACAGCAGGGACAGGGCCGTTGGCTGCTCGCACAGAGGACTTCCTTCCCGACTCCAT
CACTTTCTCCTGGAAATACAAGAACAACTCTGACATCAGCAGCACCCGGGGCTTCCAAAGTCAGCTCAAGCTCAAGCTCAAGCTCAAGTCCCCTCTTCCAGATTGCCTGATTGCTGAGCTGTCCCAAAGTGAGCGTCTTCGTC
CCACCCCGCGACGGCTTCTTCGGACCAGGTGTGCAACCCCCGAAGCTCAAGCTGCCAAGGCTGAAGCCCAAAGAGTCTGGGCACCAGGCCAAAGAGTCTGGGCACTGACCAGGTTTCAGTGCCAGATTCAGGTGTCCTGCCTGCGGAGGAAGCAGGTGGGGTC
TGGGCGTCACCACGGGATCACAGGGGCCTGAGCCCAAGCTGACCTTCAGCAGAGATGCGTCCTGGTCCCCGATCGTGTCCCCGAGCCACTGACCAGGAGCACTGACCATCAAAGCCCAGAAGCTGCCTCAGCCAGCAGCATGTCAGCT
GCCGCCGGATCAACCAGGGCCTGAGGCCAAAGCTGACCTTCCTGGTCACAGACGTGACCACCTGACCATCCTGGACCGTGACCGTGAACCTGCCACCGTGAACCTGCCGGAGTTCAGCTGCAGCCAGCCAGGCCCCCATCAACCCACCAT
CCACCCCATCCCCGCGCACTTTCAGCCCGGCCAGTGGGGTGCCCTGCAGTGCCCTGGCAGTGGCCTGGGGAGCCCAGCCCCCAGCGCCCCATCGCACCTCAGCACCTGCCTGGTGACGGGC
TTCCTCTCCCCGCGACGTCTTCGTGCCAAGATGGAACACGGGAGGTCAGCCCTGAGCCCCAATGCTGCCCCCATGAGGGCCCCGCAACAGGGTCACCGTAGAGGACCGTGACAAGTCCACCGGTA
CAGCATCCTGACCGTGTCCAAGAGGGAATGGAACACGGGAGGTCAGCCCTGAGCCCCAATGCTGCCCCCATGAGGGCCCCGCAACAGGGTCACCGTAGAGGACCGTGACAAGTCCACCGGTA
AACCCACCCCTGTACACGTGTCCCTGGTCATGTCCGACACAGCTGGCACCTGCTAC

FIGURE 4F

SEQ ID NO:62
HEAVY CHAIN OF IGM11 AND IGM33

CAGGTCAGCTCCAGCAGTGGGAGCAGGACTCTTGAAACCCTCTGAGACTTTGAGCCTCACATGCGCTGTCTATGCGGATCTTTCTCCGGCTACTATTGGTCCTGATACGACAGCC
CCCAGGCAAAGGACTCGAGTGGATTGGGGAAATCAACACTCTGGTAGCACTAATATAATCCAAGCCTGTAAGTCCCGTGAATTAGTGTTGATACATCCAAGAACCAATTTCCC
TGAAACTGAGCTCAGTGACTGCCGCCGACACCCTTTCCCCCTCTACTACTGTCTCCTGTGAGAATAGCCCGTCGGATACGAGCAGCGTGGCCGTTCGTGAATTTCGACTACTGGGACAGGGTACCCTGTCACTGTC
TCTTCAGGTTCCGCATCCGCCCAACCCTTTCCCCCTCGACATCAGCAGCACCCGGGCTTCCCATCAGTTCTGAGAATAGCCCGTCGGATACGAGCAGCGTGGCCAAGTACGCAGCCACCTCACAGGTGCTGCTGCCTTCCAAGGACG
CACTTTCTCCTGGAAATACAAGACGAACACGTGGTGTGCAAAGTCCAAGGCAACAAAGAAAAGAACCTGCCTCTTCCAGTGATTGCTAGGGTCAAGTACGCAGCCACCTCACAGGTGCTGCTGCCTTCCAAGGACG
TCATGCAGGGCACAGACGAACACGTGGTGTGCAAAGTCCAAGGCAACAAAGAAAAGAACCTGCCTCTTCCAGTGATTGTCAGTGTCTTCAGTCTCCGGGAAGGGAAGGCAGGTGGGTC
CCACCCGGACGGCTTCTTCGGCAACCCCGCAAGTCATCTGCCAGGCCACGGGTTTCAGTCCCAGGGTCCACGGCACTGCTAAAGAGAGCGACTTGGCCAGGCCAGAGACATGTTCACCT
TGGGCCACCAGCAGGTCAGCAGGGTCTGGGCCCAAAGAGTCTGCCAAGGCCTACAAGGTCCTGCCCGATCACGAACAGCAGCCATCCGGGTCTTCCGCCATCCCCATCCTTTGCCAGCATCTCCTC
GCCGGTGGATCACAGGGGCCTGACCTTCCAGCAGAATGCGTTCCCATGTGTCCCGAAGCTGTGACCAGCATCTCCTGGAGGATGCGTGACCAGCATCAGCAGAGTGGAGAGGTCAGGTGGTCACCGCTGCTGTGCAGCCCTGAACATCTCCGAGAG
ACCAAGTGCACCAAGTTGACCTGCCTGGTCACAGCGCCCGCAGCATCTCGCACAGCAGTTCAGCGCACCTGAACCTGCGGAGTCGCCCACATCACCGTGCCTGGTGACGGGC
AGACCATCTCCCGGACAGCGTCTTCAGCCCCCAAGGGGTCCTGCCAGTCGCAGTGCCTCGAGGGGCAGCGCTTGGTCCCGTGCACCGCAGGCCAATGCCTGAGCCCCAGGCCCGGTACTTCGCCCA
TTCTCTCCCGGACCGTGTCCGAAGAGGAATGGAACACGGGGAGACCTACACCTGCGTGGTGGCCATGAGCCTGCCAACAGGGTCACCGAGAGGACCGTGGACAAGTCCACCGGTA
AACCCACCCTGTACAACGTGTCCCTGCATGTCCGACACAGCTGGCCACCTGCTAC

SEQ ID NO:63
HEAVY CHAIN OF IGM12 AND IGM34

CAGGTGCAGCTCCAGCAGTGGGAGCAGTGGGAGCAGGACTCTTGAAACCCTCTGAGACTTTGAGCCTCACATGCGCTGTCTGTGTCTATGGCGGATCTTTCTCCGGCTACTATTGGTCCTGATACGACAGCC
CCCAGGCAAAGGACTCGAGTGGATTGGGAGAATCAACACTCTGGTAGCACTAATATATCAACCTGAAGTCCCGTGAAGTCTAACATTAGTGTTGATACATCCAAGAACCAATTTCCC
TGAAACTGAGCTCAGTGACTGCCGCCGACACCCTGTCCGTCTAGAACCGTCCATCTTCGACTACTGGGACAGGGTACCCTGTCACTGTCTCT
TCAGGTTCCGCATCCGCCCAACCCTTTCCCCCTCGTCTCCTGTGAGAATAGCCCGTCCCATCAGTCTCGTGGCCTGCCTGCCACCTCACAGGTGCTGCCTTCCCGACTCCATCAC
TTTCTCCTGGAAATACAAGACGAACACGTGGTGTGCAAAGTCCAAGTCCAGCGCCACCCCAACGCAACAAAGAAAAGAACCTGCCTCTTCCAGTGATTGCTGAGCGTGTCCTCCCAAAGTGAGCGTTCGTCCCA
TGCAGGGCACAGACGACGGCTTCTTCGGCAACCCCGCAAGCTGTCAAACCCCGCAAGCCCAAGTCCAGCGCCACCCTACAAGGTGGGCCAGCCATACCTGCGTGCTGCGGAGGGAAGCAGGTGGGTCTGG
CGTCACCAGCAGGTCAGCCTGACCTTCCAGCAGAATGCGTTCTCCAGCCACACCGTGACCACAGCCATCCGGGTCTTCGCCATCTTCTCACC
GCGTGGATCACGAGGGCTGACCTTCCAGCAGAATGCGTTCCCATGTGTCTCCGACCGTCCTGGAAAACCCACACCACAATCTCCGAGAGCA
AAGTCACCAAGTTCAGCCGCGCGTGGGTGAGGCACATCGACGAGATAGCCGCGGAGGTCAGCACCACCTGCCGCACTGCCCACCCCACTGAAGCAGA
CCAATGCCACTTTCAGCCCCCAAGGGGTCCTGCAGTGATGACAGGGGCAGCGCTTGTGACCAGCCCGTGAACCTGCGGGAGTCGGGGAGTATGTGACCAGCCCCAATGCCTGAGCCCTGGTGACGGGCTTC
CCATCTCCCGGACCGTGTCCGAAGAGGAATGAACACGGGGAGACCTACACCTGCGTGGTGGCCATGAGCCCTGCCAACAGGGTCACCGAGAGGACCGTGGACAAGTCCACCGGTAAAC
CCACCCTGTACAACGTGTCCCTGTGCATGTCCGACACAGCTGGCCACCTGCTAC

FIGURE 4G

SEQ ID NO:64
HEAVY CHAIN OF IGM13 AND IGM35
CAGGTGCAGCTCCAGCAGTGGGAGCAGCAGACTCTTGAAACCCTCTGAGACTTTGAGCCTCACATGCGCTCTTGAGCCTCTGTCTATGGCGGATCTTTCTCCGGCTACTATTGGTCCTGGATACGAGAGCC
CCCAGGCAAAGGACTCGAGTGATTGGGAGAAATCAACACTCTGGTAGCACTACTATAATCAAGCCTGAAGTCCCGTGTAACAATTAGTGTTGATACATCCAAGAACCAATTTCCC
TGAAACTGAGCTCAGTGACTCGCCGCCAACTGCCCTGTACTACTGTGCTCCTGTGAGAATAGCCGTGGGAAGCTCCATCTTCGACTACTGGGACAGGGTACCCTGGTCACTGTCTCT
TCAGGTTCCGCATCCGCCCAACCCTTTCCCCCTGCTCTGTCCGTCGTCCTGTGAGAATACCAGCAGCGGGCAAGTGGCCGTTGGCGTCCCCAGGGACTTCCTGCCTTCCACTCCATCAC
TTTCCTGGAAATACAAGACAACTCTGACATCAGCACCGGCTTCCCATCAGTCTGACCAGGGGCAACTGTCCTCTCTCCACAGTGCTGCTGCTCTCCAAGGACGTCA
TGCAGGGCACAGACGAACACGTGGTGTGCAACCCCGCAAGTCCAGCACCCCAACGGCAACAAAGAAACGTGCCTCTTCCAGTGATTGCTGAGCTGAGTCCTCGTCCA
CCCCGCGACGGCTTCTTCGGCAACCTCAGCCCCGCAAGTCTGCCAGCCAAAGAGTCTCGGGCCAACGAAGTGCAAGGTCTGGGCCTCCAGCAGTGTTCACCTGCC
CGTGACCACCGACCCAGGTGCAGGCTGAAGCCTGACCTTGTCCCCGATCAAGAACAACAGCCATCCTGACCCGAGAATGGCCAAGCTGTGAAACCCACCAACATCTCCAGAGCCA
GGGTGGATCACAGGGCCTGACCTGCTGGTCAGACATGACAGCCTCGATCAGCCCAGCACCATCCTGACCCTTGACCCGGAGAGGTTCACGTGCACCGGAGTCGGAGTC CTGAGCCTGACGGGCTTC
AAGTCCACCAAGTTGACCTGCCTGGTCACGACCTGAGGCCCAGCATCGCGAGGATAGCCGGGAGAGGTTCACGTGCACCTGAGCCTGACGGGCTTC
CCCAATGCCACTTTCAGCGCCTGGTCAGGGTGGCCTGCACTGACAGCCCCTGATGTCACTTGCCACAGCCCCTACACCTGTGATCACGTGCCTGGTGACGGGCTTC
TCTCCCCGGACGTCTTCGTCGAAGAGGAATGAACACGACAGCCCCTACACCTGTGATCACCTCGTGATCACGTGCCTGGTGACGGGCTTC
CATCCTGACCGTGTACACGTGTCCCTGGTCAGTGGAATGAACACGGACACCAGCCTGCTAC
CACCCTGTACAACGTGTCCCTGGTCAGTGGAATGAACACGGACACCAGCCTGCTAC

SEQ ID NO:65
HEAVY CHAIN OF IGM14 AND IGM36
CAGGTGCAGCTCCAGCAGTGGGAGCAGCAGACTCTTGAAACCCTCTGAGACTTTGAGCCTCACATGCGCTCTTGAGCCTCTCATGCGCTGATCTTTCTCCGGCTACTATTGGTCCTGGATACGAGAGCC
CCAGGCAAAGGACTCGAGTGATTGGGAGAAATCAACACTCTGGTAGCACTACTATAATCAAGCCTGAAGTCCCGTGTAACAATTAGTGTTGATACATCCAAGAACCAATTTCCC
TGAAACTGAGCTCAGTGACTCGCCGCCAACTGCCCTGTACTACTGTGCTCCTGTGAGAATAGCCGTGGGAAGCTCCATCTTCGACTACTGGGACAGGGTACCCTGGTCACTGTCTCT
TCAGGTTCCGCATCCGCCCAACCCTTTCCCCCTGCTCTGTCCGTCGTCCTGTGAGAATACCAGCAGCGGGCAAGTGGCCGTTGGCGTCCCCAGGGACTTCCTGCCTTCCACTCCATCAC
TTTCCTGGAAATACAAGACAACTCTGACATCAGCACCGGCTTCCCATCAGTCTGACCAGGGGCAACTGTCCTCTCTCCACAGTGCTGCTGCTCTCCAAGGACGTCA
TGCAGGGCACAGACGAACACGTGGTGTGCAACCCCGCAAGTCCAGCACCCCAACGGCAACAAAGAAACGTGCCTCTTCCAGTGATTGCTGAGCTGAGTCCTCGTCCA
CCCCGCGACGGCTTCTTCGGCAACCTCAGCCCCGCAAGTCTGCCAGCCAAAGAGTCTCGGGCCAACGAAGTGCAAGGTCTGGGCCTCCAGCAGTGTTCACCTGCC
CGTGACCACCGACCCAGGTGCAGGCTGAAGCCTGACCTTGTCCCCGATCAAGAACAACAGCCATCCTGACCCGAGAATGGCCAAGCTGTGAAACCCACCAACATCTCCAGAGCCA
GGGTGGATCACAGGGCCTGACCTGCTGGTCAGACATGACAGCCTCGATCAGCCCAGCACCATCCTGACCCTTGACCCGGAGAGGTTCACGTGCACCGGAGTCGGAGTC CTGAGCCTGACGGGCTTC
AAGTCCACCAAGTTGACCTGCCTGGTCACGACCTGAGGCCCAGCATCGCGAGGATAGCCGGGAGAGGTTCACGTGCACCTGAGCCTGACGGGCTTC
CCCAATGCCACTTTCAGCGCCTGGTCAGGGTGGCCTGCACTGACAGCCCCTGATGTCACTTGCCACAGCCCCTACACCTGTGATCACGTGCCTGGTGACGGGCTTC
TCTCCCCGGACGTCTTCGTCGAAGAGGAATGAACACGACAGCCCCTACACCTGTGATCACCTCGTGATCACGTGCCTGGTGACGGGCTTC
CATCCTGACCGTGTACACGTGTCCCTGGTCAGTGGAATGAACACGGACACCAGCCTGCTAC
CACCCTGTACAACGTGTCCCTGGTCAGTGGAATGAACACGGACACCAGCCTGCTAC

FIGURE 4H

SEQ ID NO:66
HEAVY CHAIN OF IGM15 AND IGM37

CAGGTGCAGCTCCAGCAGTGGGGAGCAGGACTCTTGAAACCCTCTGAGACTTTGAGCCTCACATGCGCTGTCTATGCGGATCTTCTCCGGCTACTATTGTCCTGATACGACAGCC
CCAGGCAAAGGACTCGAGTGATTGGGGAAATCAACCACTCTGGTAGCACTAACTATATCCAAGCCTGTAAGTCCCGTGAAGTTGATACATCCAAGAACCAATTTTCCC
TGAAACTGAGCTCAGTGACTGCCGCCGACACTGCGTCTACTGTCCTCGTCTGAGAAGAGCTAGGGAGGAAGCTCCATCTTCGACTACTGGGACAGGTACCCTGGTCACTGTCTCT
TCAGGTTCCGAATACAAGAACAACTCTGACATCAGCAGCCTGAAGGCTTCCTGCCCGTTGCCTCGCACAGGACTTCCTTCCCGACTCCATCAC
TTTCTCTGGAAATACAAGACAGTCCTGACATCAGCAGCCTGAAAGAAAAGAACGTGCCTCTTCCAGTGATTGCTGATTGCTGAGTCCCAAAGTGAGCGTCTTCGTCCA
TGCAGGGCACAGACAGGAACAACGTGGTGCAACCCCCAGTCATCTGCCAGGCCACGGGTTTCAGTCCGGCAGATTCAGGTGTCTCAGCTGCTGCGGAGGGAAGCAGGTGGGTCTGG
CGTCACCACGACGACCAGGTCAGGCTGAGGCCAAAGAGTCTGGGCCTGACCAAGTGACCAGCACACAGCCATCCCGGTCTTCGCCATCCTTTGCCAGCATCTTCCTCACC
GCGTGGATCACAGGGGCCTGACCTTCCAGCAGAATGCGTCTCCATGTGTGTCCAGGAATGGCGAAGCTGTGAAAACCCACACAACATCTCCGAGAGCCA
AGTCCACCAAGTTGACCTGCCTGGTCACAGACCTGCAGCAATATCCTGGACCCCCGGAGATGGGAGAGGTTCACGTGCCACTGTCACGTGACGGGCTTC
CCCAATGCCACTTTCAGCGCCGTGGGCCCTGACCCATGCCCAGCATCTGCCACCGCCCGATGTCTACTTGCTGCCACAGAGAAGATATGTGACACGCACCTACAACCTGTGTGCC
TCTCCCGGACGTCTTCGTCCAGTGGATCAGAGAGGGGCCAGCCTTGTGCCAGACCCTACACCTGCTCGTGTGCCATGAGGGCCTGCCCAACAGGGTCACCGAGAGACCTGGACAAGTCCACCGTAAAC
CATCCTGACCGTGTCCCTGTCATCTGTCCGACACAGCTGGCCACCTGCTAC

SEQ ID NO:67
HEAVY CHAIN OF IGM16 AND IGM38

CAGGTGCAGCTCCAGCAGTGGGGAGCAGGACTCTTGAAACCCTCACATGCGCTGTCTATGCGCGATCTCTTTCCGGCTACTATTGGTCGTGATACGACAGCC
CCAGGCAAAGGACTCGAGTGATTGGGGAAATCAACCGCTGGTAGCACTATAATCAAGCCTGAAGTCCCGTGAAGTTGATACATCCAAGAACCAATTTTCCC
TGAAACTGAGCTCAGTGACTGCCGCCGACACTGCCGGTCTACTGTCCTCGTGAGACAACCGCTTGGGAAGCTCCATCTCGACTACTGGGACAGGTACCCTGGTCACTGTCTCT
TCAGGTTCCGCATCCGCCCAACCTTTCCCCGCTGTGCCCGATCAGCAGACCCGGTGACAGCTCGCCGTTGGCCTCGCACAGGACTTCCTTCCCGACTCCATCAC
TTTCTCTGGAAATACAAGACAGAACAACTCTGACATCAGCAGCCTGAAAGAAAAGAACGTGCCTCTTCCAGTGATTGCTGATTGCTGAGTCCCAAAGTGAGCGTCTTCGTCCA
TGCAGGGCACAGACAGCTCTTCGGCAACCCCCCAGTCAAGTCCAAGATCCAAGGTGACGCCCCAGGACCCGAAGGTTCAGTCCCGCACGACTGAACCATCAAAAGAGAGCAGCAGGTGGGTCTGG
CGTCACCACGACGACAGCTGCAGGTCAGGCTGAGGCCAAAGAGTGTGGCCTCCATGTGTCCCCACGACACAGCATCCGGGTCTTCGCCATCCTTGCCAGCATCTTCCTCACC
AAGTCCACCAAGTTGACCTGCCTGGTCACAGACCCTCTGACCAGTCACCAGGACCCGCGAAATGGGGGAGAGGTCACGTCACCGTGACCCACTGAAGCAGA
CCCATCAAGTCCATCTTCAGCGCCGTGGGCCCTGACCCATCTGCGAGGATGACTGGAATAGCGGAGAAGTATGTGACCAGCGCCCAATGCCTGAACCTGCGAGTGCCCATCACGTGCCCATCAC
TCTCCCGCGGAGTCTTCGTCGAAGAATGGACGGCCACCTACACCTGCTACCAACCCACAGACTGCCCCGCGACCCGCTGGTACTTCGCCCACAG
CATCCTGACCGTGTCCCTGTCATGAGGCCCATGAGGGCCCATGAGGCCTGCCCAACAGGGTCACCGAGGACCCCGTGACAAGTCCACCGTAAAC
CCACCCTGTACAACGTGTCCCTGTCATGTCCGACACAGCTGGCACCTGCTAC

FIGURE 4I

SEQ ID NO:68
HEAVY CHAIN OF IGM17 AND IGM39
CAGGTGCAGCTCCAGCAGTGGGGAGCAGGACTCTTGAAACCCTCTGAGACTTTGAGCCTCACATGCGCTGTCTATTGGTCCTGGATACGACAGCC
CCCAGGCAAGGACTGGAGTTGGATTGGGGAAATCAACACCACTCTGGTAGCACTACTATAATCCAAGCCTGTGAAGTCCCGTGTAACAATTAGTGTTGATACATCCAAGAACCAATTTCCC
TGAAACTGAGCTCAGTGACTGCCGCCGACACTGCCTCCCCCTCGTCTCCTGTGAGAATAGCCGTCGGATAGCCCGTCGACTACTGGGACAGGGTACCCTGGTCACTGTCTCT
TCAGGTTCCGCATCCGACCCTTTTCCCCAACCCTTTTCCCCCTCGTCGACATCAGCAGACTCTGACATCAGCAGAACAACTCTGACATCAGCAGAACAACTGTGGTGCAAAGTCCAGCACACCCCAAGACTCCTCCAAAGTGCTGAGCGTCTTCGTCCCA
TTTCTCCTGAAATACAAGAACAACTCTGACATCAGCAGAACAACTGTGGTGCAAAGTCCAGCACACCCCAAGACTCCTCCAAAGTGCTGAGCGTCTTCGTCCCA
TGCAGGGACAGAGACGGCTTCTTCGGCAACCCCGCAAGTCTGGTGTGCAACCCCGCAAGTCTGGCAACCCCGCAAGTCTGGCAACCCCGCAAGTCTGGCAACCCCGCAAGTCTGGCAACCCCGCAAGTCTGGCAACCCCGCAAGTCTGGCAACCCCGCAAGTCTGGCAACCCCGCAAGTCTGGCAACCCCGCAAGTCTGGCAACCCCGCAAGTCTGGCAACCCCGCAAGTCTGGCAACCCCGCAAGTCTGGCAACCCCGCAAGTCTGGCAACCCCGCAAGTCTGGCAACCCCGCAAGTCTGG
CCCCGACGGCTTCTTCGGCAACCCCGCAAGTCTGGCAACCCCGCAAGTCTGGCAACCCCGCAAGTCTGGCAACCCCGCAAGTCTGGCAACCCCGCAAGTCTGGCAACCCCGCAAGTCTGG
CGTCACCACGACCAGGTCAGCCTGCCCCGAGATTCAGCGCCACGACCAGGTCAGCCTGCCCCGAGATTCAGCGCCACGACCAGGTCAGCCTGCCCCGAGATTCAGC
GCGTGGATCACAGGGGCTGACCTTCAGCAGATGCTCCTCCATGTGTCTCCCGATCAGACACAGCCATCCGGCTCTTGCCAGCATCTTCTCACC
AAGTCCACCAAGTTGACCTGCCTGGTCACAGACTGAGGCCAGCTGCCGCGCGAGGTTCAGTCGCCGAGTCGCCCATCACGTGCCTGGTGACGGGCTTC
CCCCAATGCCACTTTCAGCGCCCAAGGGGTGGCCTGCACAGGGCCAGCTGCTGACGTCTACTTGCTGCCCGGAGAAGTATGTGACCAGCGCCCCAATGCCTGAGCCTCGGTACCCGGTACCCGG
CATCTCCCGGACGTCTGTGCAGTGATGCAGAGGGGAGAACCGGGAGACTCTGACATCTGTCCCCAACAGGGTCACCGAGAGGACCGGTGACAAGTCCACCGTAAAC
CTCCCCGGACGTCTGTGCAGTGATGCAGAGGGGAGAACCGGGAGACTCTGACATCTGTCCCCAACAGGGTCACCGAGAGGACCGGTGACAAGTCCACCGTAAAC
CCACCCTGTACAAGTGTCCCTGGTCATGTCCGACACTGGCACCTGCTAC

SEQ ID NO:69
HEAVY CHAIN OF IGM18 AND IGM40
CAGGTGCAGCTCCAGCAGTGGGGAGCAGGACTCTTGAAACCCTCTGAGACTTTGAGCCTCACATGCGCTGTCTATTGGTCCTGGATACGACAGCC
CCCAGGCAAAGACTCGAGTGACTGGAATTGGGAGAATCAACACCACTCTGGTAGCACTACTATAATCCAAGCCTGTGAAGTCCCGTGTAACAATTAGTGTTGATACATCCAAGAACCAATTTCCC
TGAAACTGAGCTCAGTGACTGCCGCCGACACTGCCTCCCCCTCGTCTCCTGTGAGAATAGCCGTCGGATAGCCCGTCGACTACTGGGACAGGGTACCCTGGTCACTGTCTCT
TCAGGTTCCGCATCCGACCCTTTTCCCCAACCCTTTTCCCCCTCGTCGACATCAGCAGACTCTGACATCAGCAGAACAACTGTGGCCAGCACTGTCTCCCCTCGTCTCCTGTGCCGTTGCCGTTGCCGTTGCCGTTGCCGTTGCCGTTGCCGTTGCCGTTGCCGTTGCCGTTGCCGTTGCCGTTGCCGTTGCCGTTGCCGTTGCCGTTGCCGTTGCCGTTGCCGTTGCCGTTGCCGTTGCCGTTGCCGTTGCCGTT
TTTCTCCTGAAATACAAGAACAACTCTGACATCAGCAGAACAACTGTGGTGCAAAGTCCAGCACACCCCAAGACTCCTCCAAAGTGCTGAGCGTCTTCGTCCCA
TGCAGGGACAGAGACGAACACGTGGTTGCAAAGTCCAAACCCCGCAAGTCCAAAGTCCAAGCCAAAGAAAAGAACGTGCCTCTTCCAGTGATTGCTGAGCGTCTTCGTCCCA
CCCCGGACGACGCTTCTTCGGCAACCCCGCCAAGTCCAAAGTCTGGAGGCCAAAGAAAAGAACGTGCCTCTTCCAGTGATTGCTGAGCGTCTTCGTCCCA
CGTCACCACGACGCAGTTCAGCCTGACCTGCCAGGTCACCAAGGTGACCAAAGTCTGCTCCTCCAGCCGTTTCAGTCCCCGGACGATTCAGTGTCCCCGGACGATTCAGTGTCCCCGGACGATTCAGTGTCCCCGGACGATTCAGTGTCCCCGGACGATTCAGTGTCCCCGGACGATTCAG
GCGTGGATCACAGGGGCTGACCTTCAGCAGATGCTCCTCCAGCAGAATCGTTCTGACCAGCGTGTCCCGATCAAGACACAGCCATCCGGCTCTTGCCAGCATCTCCTGAGAGCCA
AAGTCCACCAAGTTGACCTGCCTGGTCACAGACTGAGGCCAGCTGCCGCGCGAGGTTCAGTCGCCGAGTCGCCCATCACGTGCCTGGTGACGGGCTTC
CCCAATGCCACTTTCAGCGCCCAAGGGGTGGCCTGCACAGGGCCAGCTGCTGACGTCTACTTGCTGCCCGGAGAAGTATGTGACCAGCGCCCCAATGCCTGAGCCTCGGTACCCGGTACCCGG
TCTCCCGGACGTCTGTGCAGTGATGCAGAGGGGAGAACCGGGAGACTCTGACATCTGTCCCCAACAGGGTCACCGAGAGGACCGGTGACAAGTCCACCGTAAAC
CATCCTGACCCGGACGTCTGTGCAGTGATGCAGAGGGGAGAACCGGGAGACTCTGACATCTGTCCCCAACAGGGTCACCGAGAGGACCGGTGACAAGTCCACCGTAAAC
CCACCCTGTACAAGTGTCCCTGGTCATGTCCGACACTGGCACCTGCTAC

FIGURE 4J

SEQ ID NO:70
HEAVY CHAIN OF IGM19 AND IGM41
CAGGTGCAGCTCCAGCAGTGGGAGCAGGAGGACTCTTGAAACCCTCTGAGACTTTGAGCCTGCACATGCCTGTCTATGCGGATCTTTCTCCGGCTACTATTGTTCCTGGATACGACAGCC
CCCAGGCAAAGGACTGGAGTGGATTGCCGCCGACACTGACCACTCTGGTAGCACTACTATAATCCAAGCCTGTAAGTCCCGTGTAAGTAGTTGTGATACATCCAAGAACCAATTTTCCC
TGAAACTGAGCTCAGTGACTGCCGCCCAACCCTTTCCCCCTCGTCTCGTGAGAATAGCCCGTCGGATACAGCAGCGTCGGATACAGAGCTCCATCTTCGACTACTGGGACAGGGTACCCTGGTCACTGTCTCT
TCAGGTTCCGCATCCGCCCAACCCTTTCCCCCTCGTCTCGTGAGAATAGCCCGGATACAGCAGCGTGGCCGTTGGCTGCCTCGCACAGGACTTCCTTCCCGACTCCATCAC
TTTCTCCTGGAAATACAAGAACAACTCTGACATCAGCAGACACCCGGGCTTCCCATCAGTCCTGAGAAGAACTGCCTCTTCCAGTGATTGCTGAGCTGCCTCCCAAAGTGAGCGTCTTCGTCCA
TGCAGGGCACAGACGAACACGTGTGTGCAACCCCCGCAAGTCATCTGCCAGGCCACGGGTTTCAGTCCCGCAGATTCAGGTGTCCTGGCTGCGCAGGGAAGCAGGTGGGGTCTGG
CCCGCGACAGGGCTTCTTCGGCACCAGGTGCAGGCTGAGCCGACCAGGTCAGCCTGACCTGACCACCTACAAGGTGACCACACTGAAGCATCAAAGAGAGCGACTGGCTCAGCCAGACGACTGCCATCCCCATCTTTGCCAGCATCTTCCTACC
CGTCACCACGGACAGTTCACGGCCAGGTCCAGCCAGCCAGCCAGGGCCCTGACCTTCGGACTCGACAGAACAGAGCCATCCTCCGATCAAGACACAGCCATCCTCCGATGTGCTCCCGATCAAGACCACACCAGTCTTCGCCAGCTCTTGCCAGCATCTTCCTACC
AGTCCAAGTTGACTGCCACTTCAGCGCCGTGGCTGGGTGCCCGCCCAGAACTCTCCGAGGAGTTACGTGACCTGAACCGCCATGGCCACCATCACGTGCCGCACTGGTGACGGGCTTC
CCCAATGCCACTCCCAAGGTGATCTTGCACGGCCGGCCCTGCACAGGCCCAGCATCTGCGAGGATGTCTACTTGCTCCCCGGAAGTATGTGACCAGCAAGTATGACCCCCATCATGCCCGACCCTACACTGCCGGAGGCGGCCCATGTGCACGCCCGCCCCCATCGCCGAGCCTGTGGCCCAATGCCTGAACGCTTGCCCACCGGAGTCCTGAGCCCCATGCCTGACCCTGACCCTGGTCATGCACAGCGTCCTGCCCCGCCATGTGGCCCAATGCCTGAACGCCCTGCCCAACAGGGTCACCGAGAGGACCGTCACGTCCGCCTGGTGACGCTGCCCCACAG
CATCCTGACCGTGTCCGAAGAGAATGAACACGGGAGGAGACACGGGAGGAGACACGGGAGTATGTGGCCCATGAGCCCATGCTGTGGCCCCAACAGGGTCACCGAGAGGACCGTCACCGAGAGGACCGTCACGTCCGCCTGGTGACGCTGCCCCACAG
CATCCTGACCGTGTCCGAAGAGAATGAACACGGGAGGAGACACGGGAGGAGACACGGGAGTATGTGGCCCATGAGCCCATGCTGTGGCCCCAACAGGGTCACCGAGAGGACCGTGACAAGTCCACCGGTAAAC
CCACCCTGTACAACGTGTCCCTGTCATGTCCGACACAGCTGGCACCTGCTAC

SEQ ID NO:71
HEAVY CHAIN OF IGM20 AND IGM42
CAGGTGCAGCTCCAGCAGTGGGAGCAGTGGGAGCAGGAGGACTCTTGAAACCCTCTGAGACTTTGAGCCTGCACATGCCTGTCTATGCGGATCTTTCTCCGGCTACTATTGTTCCTGGATACGACAGCC
CCCAGGCAAAGGACTCGAGTGGATTGCCGCCGACACTGACCACTCTGGTAGCACTACTATAATCAAGCCTGTGAAGTCCCGTGTGAAGTCCCGTGAGTAGTTGTGATACATCCAAGAACATTTTCCC
TGAAACTGAGCTCAGTGACTGCCGCCGACACTGCCCTACTACTGTGCTCGTCTACTGTGCTCTCTGTGAGAATAGCCCGTCGGATACAGCAGCGTGGCCGTTGGCTGCCTCCCACAGGACTTCCTCCCGACTCACTGTCTCT
TCAGGTTCCGCATCCGCCCAACCCTTTCCCCCTCGTCTCGTGAGAATAGCCCGGATACAGCAGCGTGGCCGTTGGCTGCCTCGCACAGGACTTCCTTCCCGACTCCATCAC
TTTCTCCTGGAAATACAAGAACAACTCTGACATCAGCAGACACCCGGGCTTCCCATCAGTCCTGAGAAGAACTGCCTCTTCCAGTGATTGCTGAGCGTGAGCGTCTTCGTCCA
TGCAGGGCACAGACGAACACGTGTGTGCAACCCCCGCAAGTCATCTGCCAGGCCACGGGTTTCAGTCCCGCAGATTCAGGTGTCCTGGCTGCGCAGGGAAGCAGGTGGGGTCTGG
CCCGCGACAGGGCTTCTTCGGCACCAGGTGCAGGCTGAGCCGACCAGGTCAGCCTGACCTGACCACCTACAAGGTGACCACACTGAAGCATCAAAGAGAGCGACTGGCTCAGCCAGACGACTGCCATCCCCATCTTTGCCAGCATCTTCCTACC
CGTCACCACGGACAGTTCACGGCCAGGTCCAGCCAGCCAGCCAGGGCCCTGACCTTCGGACTCGACAGAACAGAGCCATCCTCCGATCAAGACACAGCCATCCTCCGATGTGCTCCCGATCAAGACCACACCAGTCTTCGCCAGCTCTTGCCAGCATCTTCCTACC
AGTCCAAGTTGACTGCCACTTCAGCGCCGTGGCTGGGTGCCCGCCCAGAACTCTCCGAGGAGTTACGTGACCTGAACCGCCATGGCCACCATCACGTGCCGCACTGGTGACGGGCTTC
CCCAATCTCCCGCGGACGTCTTCGTGAAGAGATGGATGGATGGGAGATGGAATGAACACGGGAGGAGACACGGGAGGAGACACGGGAGTATGTGGCCCATGAGCCCATGCTGTGGCCCCAACAGGGTCACCGAGAGGACCGTCACCGAGAGGACCGTCACGTCCGCCTGGTGACGCTGCCCCACAG
CATCCTGACCGTGTCCGAAGAGAATGAACACGGGAGGAGACACGGGAGGAGACACGGGAGTATGTGGCCCATGAGCCCATGCTGTGGCCCCAACAGGGTCACCGAGAGGACCGTGACAAGTCCACCGGTAAAC
CCACCCTGTACAACGTGTCCCTGTCATGTCCGACACAGCTGGCACCTGCTAC

FIGURE 4K

SEQ ID NO:72
HEAVY CHAIN OF IGM21 AND IGM43

CAGGTGCAGCTGCAGCAGTCGGGAGCAGGACTCTTGAAACCCTCGGCTCTGTCTATGCCGGATCTTTCTCCGGCTACTATTGGTCCTGATACGACAGCC
CCCAGGCAAAGGACTCGAGTGGATTGGGCGACACTGACCTCGTACTACTGTCTCCGTGAGAATAGCCCGTCGGATACGAGCAGCGGCAAGTACGACAGCGTGCCCTCTTCCACATCAGCGACTCCTCCGACTCATCAC
TGAAACTCAGCTCAGTGACTCGCCCCAACCCTTTCCCCCTCGTCTGTCTGTGAGAATAGCCCGTCGGATACGAGCAGCGGCAAGTACGACAGCGTGCCCTCTTCCACATCAGCGACTCCTCCGACTCATCAC
TCAGGTTCCGCATCCGCCCAACCCTTTCCCCCTCGTCTGTCTGTGAGAATAGCCCGTCGGATACGAGCAGCGGCAAGTACGACAGCGTGCCCTCTTCCACATCAGCGACTCCTCCGACTCATCAC
TTTCTCCTGGAAATACAAGAGACAACTGTGACATCTGCAAAGTCCAGCACCCCCAACGCAACAAAGAAAAGAACGTCGCCTCTTCAGTGATTGCTGAGCTGCCTCGCAAAGTGAGCGTCTTCGTCCCA
TGCAGGGCACAGACGAACAGCTGGTCTGCAAGTCCAGGGCCTCATCTGCAGGCCACGGGTTCAGTCCCCGGCAGATTCAGGTGTCCTGGCTGCCCAGAAGACAGGTGGGGTCTGG
CCCCGCGACGGGCTTCTTCGGCAACCCCCCAGGCTGCGAGGCTGCAAAACCCCCAGCTGACCTTACAAGGTGGCCTCAGCGAACCCTACAAGGTGCCAGGCCATCAAAGAGAGCGACTGCTCAGCCAGCATGTTCACCTGCC
GCGTCACCACGGACCAGGTGCAGGCTGAGGCTGCAAAACCCCCAGCTGACCTTACAAGGTGGCCTCAGCGAACCCTACAAGGTGCCAGGCCATCAAAGAGAGCGACTGCTCAGCCAGCATGTTCACCTGCC
AAGTCCACCAAGTTGACCTGCCTGGTCACAGACTGCAAGCCGTGAGGCCAGGCATCTGGACCATCTCCTGGACCCCAGAATGGCGAAGCTGTGAAACCCACACAACATCTCCGAGAGCCA
CCCCAATGCCACTTTCAGCGCCTGGAGCCAGGCCGTGAACTGCGACATCTGCCCACACGCCCCGATGTCTACTTGCTGCCACAGCCCCGATGTCTACTTGCCCACAGCCCCGATGTCTACTTGCCACAGCCCCGATGTCTACTTGCCGAACCTGCAGCACTGAACGCCTCAGCCAGCGCCTGAGCAGGCCGTGACGGGCTTC
TCTCCCGGGACGTCTTCGTGCAGTGGATGCAGAGAGGGCAGCCTTTGTCCCGGAGACCTACACCTGCGTGGTGGCCCATGAGGCCCTGCCCAACAGGGTCACCGAGGAGGACCTGTTCAGCCCACAG
CATCCTGACCGTGTCCGAAGAGGAATGGAACACGGGAGACCCGTCAGCTGCCACACAGCTGGCACCTGCTAC
CCACCCTGTACAACGTGTCCCTGCATGTCCGACACAGCTGGCACCTGCTAC

SEQ ID NO:73
HEAVY CHAIN OF IGM22 AND IGM44

CAGGTGCAGCTGCAGCAGTCGGGAGCAGGACTCTTGAAACCCTCGGCTCTGTCTCATGCGCTCTATGCCGGATCTTTCTCCGGCTACTATTGGTCCTGATACGACAGCC
CCCAGGCAAAGGACTCGAGTGGATTGGGCGACAAATCAACCACTCGGTACTACCTGTCTCCGTGAGAATAGCCCGTCGAAGAGCTTGGGAGAGCTCCATCTTCCGACTACTGGAGCACAGGGTACCCTGGTCACTGTCTCT
TGAAACTCAGCTCAGTGACTCGCCCCAACCCTTTCCCCCTCGTCTGTCTGTGAGAATAGCCCGTCGGATACGAGCAGCGGCAAGTACGACAGCGTGCCCTCTTCCACATCAGCGACTCCTCCGACTCATCAC
TCAGGTTCCGCATCCGCCCAACCCTTTCCCCCTCGTCTGTCTGTGAGAATAGCCCGTCGGATACGAGCAGCGGCAAGTACGACAGCGTGCCCTCTTCCACATCAGCGACTCCTCCGACTCATCAC
TTTCTCCTGGAAATACAAGAGACAACTGTGACATCTGCAAAGTCCAGCACCCCCAACGCAACAAAGAAAAGAACGTCGCCTCTTCAGTGATTGCTGAGCTGCCTCGCAAAGTGAGCGTCTTCGTCCCA
TGCAGGGCACAGACGAACAGCTGGTCTGCAAGTCCAGGGCCTCATCTGCAGGCCACGGGTTCAGTCCCCGGCAGATTCAGGTGTCCTGGCTGCCCAGAAGACAGGTGGGGTCTGG
CCCCGCGACGGGCTTCTTCGGCAACCCCCCAGGCTGCGAGGCTGCAAAACCCCCAGCTGACCTTACAAGGTGGCCTCAGCGAACCCTACAAGGTGCCAGGCCATCAAAGAGAGCGACTGCTCAGCCAGCATGTTCACCTGCC
GCGTCACCACGGACCAGGTGCAGGCTGAGGCTGCAAAACCCCCAGCTGACCTTACAAGGTGGCCTCAGCGAACCCTACAAGGTGCCAGGCCATCAAAGAGAGCGACTGCTCAGCCAGCATGTTCACCTGCC
AAGTCCACCAAGTTGACCTGCCTGGTCACAGACTGCAAGCCGTGAGGCCAGGCATCTGGACCATCTCCTGGACCCCAGAATGGCGAAGCTGTGAAAACCACACAACATCTCCGAGAGCCA
CCCCAATGCCACTTTCAGCGCCTGGAGCCAGGCCGTGAACTGCGACATCTGCCCACACGCCCCGATGTCTACTTGCTGCCACAGCCCCGATGTCTACTTGCCCACAGCCCCGATGTCTACTTGCCACAGCCCCGATGTCTACTTGCCGAACCTGCAGCACTGAACGCCTCAGCCAGCGCCTGAGCAGGCCGTGACGGGCTTC
TCTCCCGGGACGTCTTCGTGCAGTGGATGCAGAGAGGGCAGCCTTTGTCCCGGAGACCTACACCTGCGTGGTGGCCCATGAGGCCCTGCCCAACAGGGTCACCGAGGAGGACCTGTTCAGCCCACAG
CATCCTGACCGTGTCCGAAGAGGAATGGAACACGGGAGACCCGTCAGCTGCCACACAGCTGGCACCTGCTAC
CCACCCTGTACAACGTGTCCCTGCATGTCCGACACAGCTGGCACCTGCTAC

FIGURE 4L

SEQ ID NO:74
LIGHT CHAIN OF IGM1 THROUGH IGM22
GACATACAGATGACCCAGTCCCCAAGCACCCTGTCTGCATCTGTGGGAGATCGCGTGACCATCACCTGCACTGGAACTAGCTCCGACGTAGGAGGCTATAATTATGTTCCTGGTATCA
GCAACATCCTGGAAAGGCTCCAAAGCTGATGATCTACGGTGTTTCCAACCGGTTCAGTGGCTCTAAGAGTGGTAACACCGCATTCTGACATCTCTGACCTGGCAGCCGAAGATGAGG
CCGACTACTACTGCTCCTCCTATACAAGCAGCTCAACCCTCGTGTGTTTGGTGGCGGTACCAAGCTGACCGTCCTAGGTGCAGTGGAAGGTGCCTCACTCTGTTCCACCC
TCCTCTGAGGAGCTTCAAGCCAACAAGGCCACACTGGTGTGTCTCATAAGTGACTTCTACCCGGAGCAGTGCCTGAAGGCAGATAGCAGCCCCGTCAAGGCGGAGTGGA
GACCACCACACCCTCCAAACAAAGCAACAACAAGTACGGGCCAGCAGCTACCTGAGCCTGACGCCTGAGCAGTGGAAGTCCACAGAAGCTACAGCTGCCAGTCACGATGAAGGA
GCACCGTGGAGAAGACAGTGGCCCCTACAGAATGTTCATAG

SEQ ID NO:75
LIGHT CHAIN OF IGM23 THROUGH IGM44
GATATCCAGATGACCCAGTCACCCTCAAGCCTCAGCCTGAGCGCAAGCGTGGGGACCGAGTGACTATTACATGTCGAGCTTCTCAGTCAATCAGCTCCTACCTGAACTGGTATCAGCAGAAACC
TGGAAAGCCCCAAAACTGCTTATCTACGGCCAGTTCCCTGCAAGTGGAGTGCCCTCCAAGTTCAGTGGCTCAGGAAGTGGACTGACTTCACTCTGACTATCAGTAGTCTGCAAC
CAGAAGACTTTGCCACTTACTATTGCCAGCAGAGCTACAGCACCCCTATTACCTTCGGCCGACTAGAGATCAAACGTACTGTGGCTGCCATCTGTCTTCATCTTCCCG
CCATCTGATGAGCAGTTGAAATCTGGAACTGCCTCTGTTGTGTGCCTGCTGAATAACTTCTATCCCAGAGAGGCAAAGTACAGTGGAAGGTGGATAACGCCCTCCAATCGGTAACTC
CCAGGAGAGTGTCACAGAGCAGGACAGCAGGACAAGGACACAGCACCTACAGCCTCAGCAGCCCTGAGCAACAGACTACGAGAAACACAAAGTCTACGCCTGCGAAGTCACCCATC
AGGGCCTGAGCTCGCCCGTCACAAAGAGCTTCAACAGGGGAGAGTGTTAG

FIGURE 5
Non-reducing SDS-PAGE: Panel A showing IGM23 through IGM29 and Panel B showing IGM31 through IGM43.
Panel A
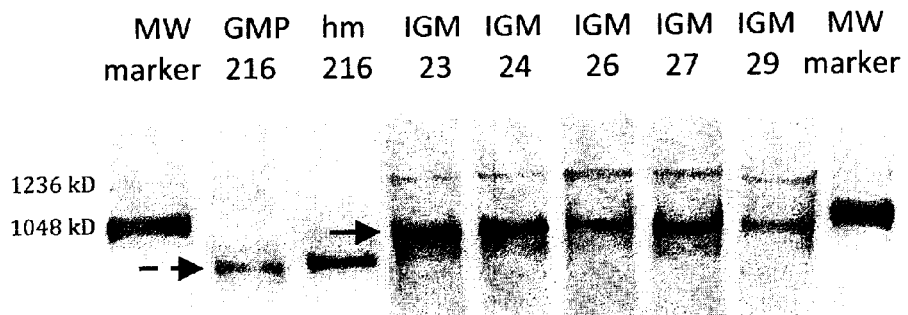
Panel B
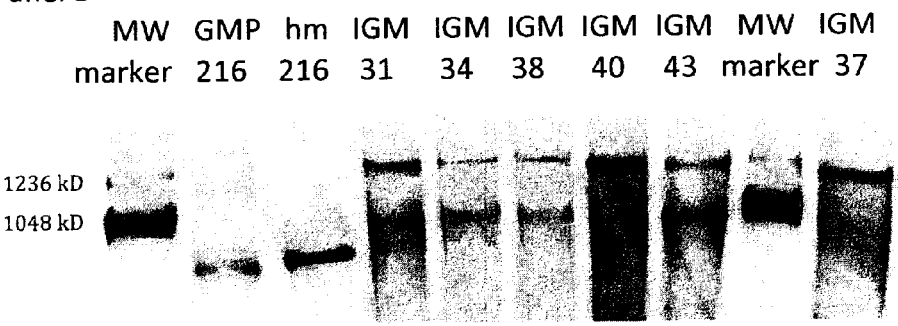

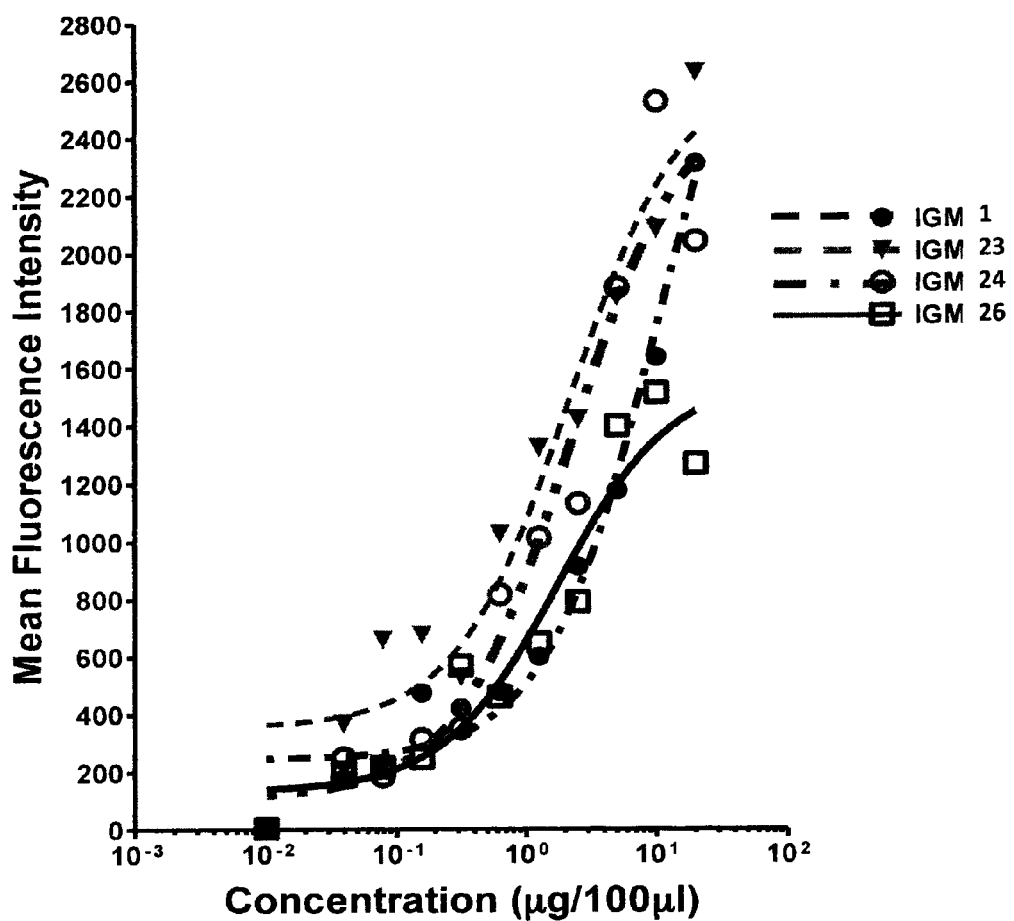

Cytotoxicity on Nalm-6 Cells

Complement Dependent Cytotoxicity:
Samples of IgM on CDIM Expressing Cells (Nalm-6)

FIGURE 8A: Binding to Single Strand DNA
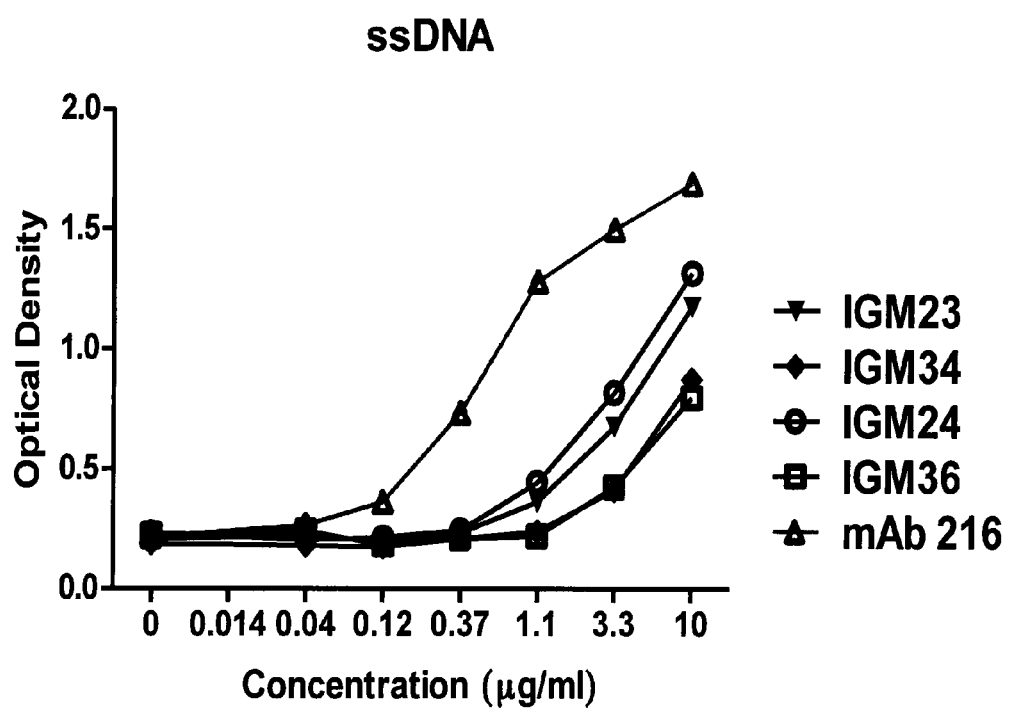

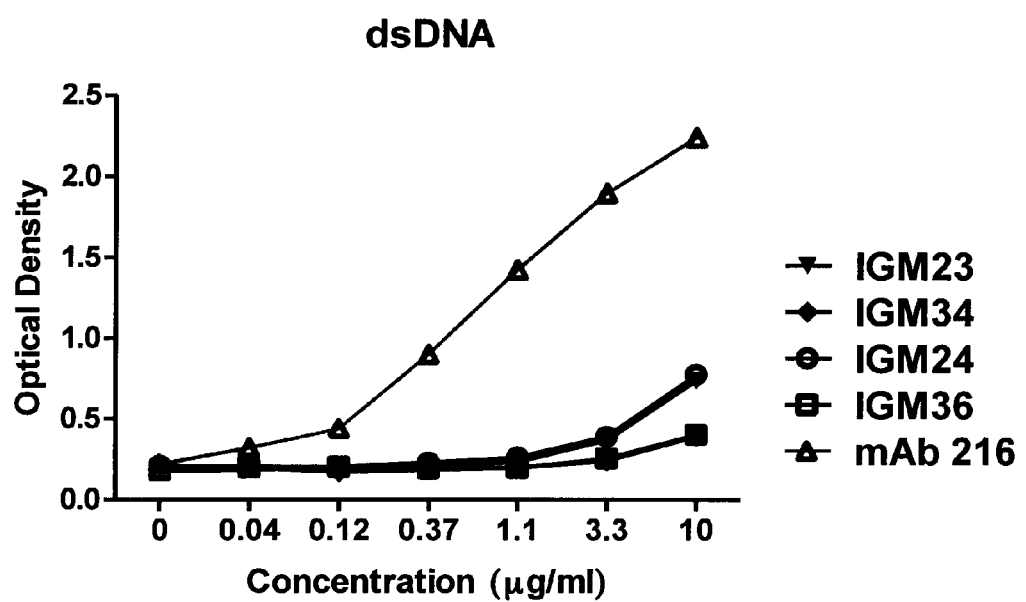
FIGURE 8B: Binding to Double Strand DNA

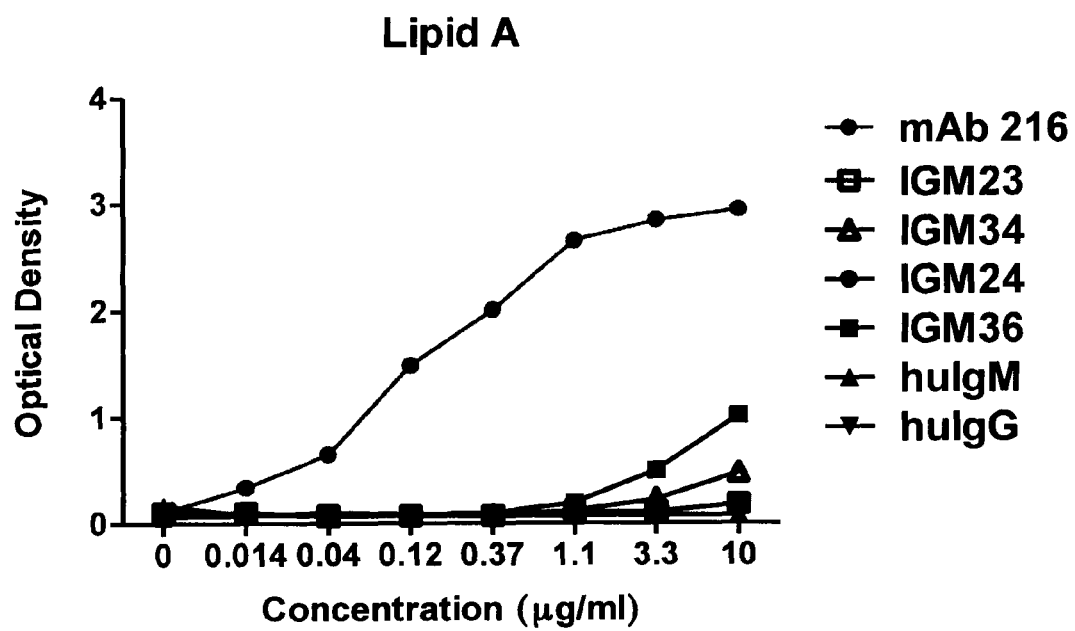
FIGURE 8C: Binding to Bacterial Lipid A

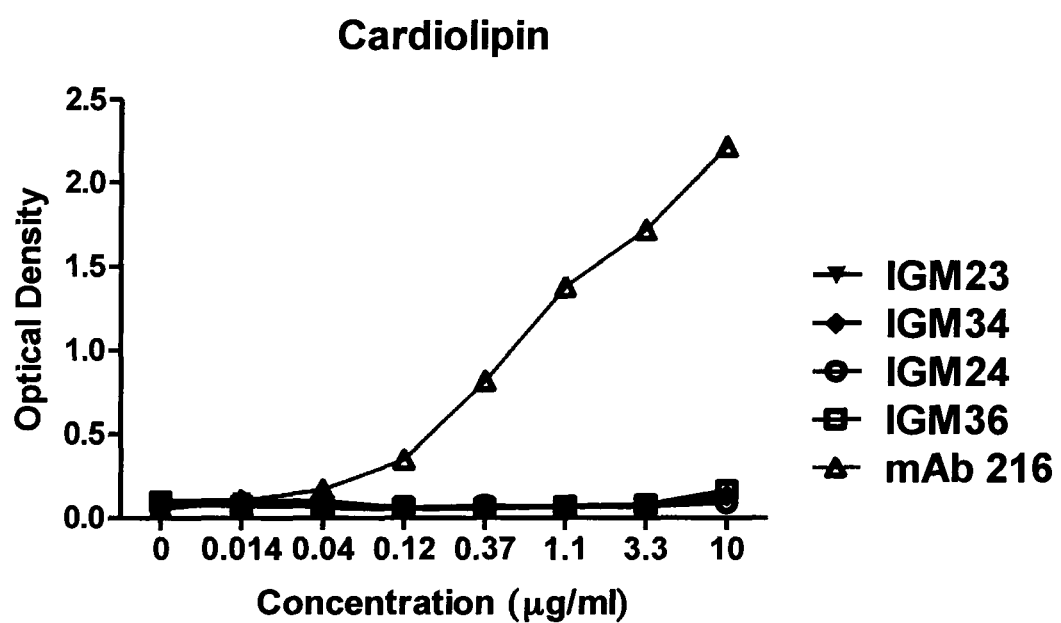
FIGURE 8D: Binding to Cardiolipin

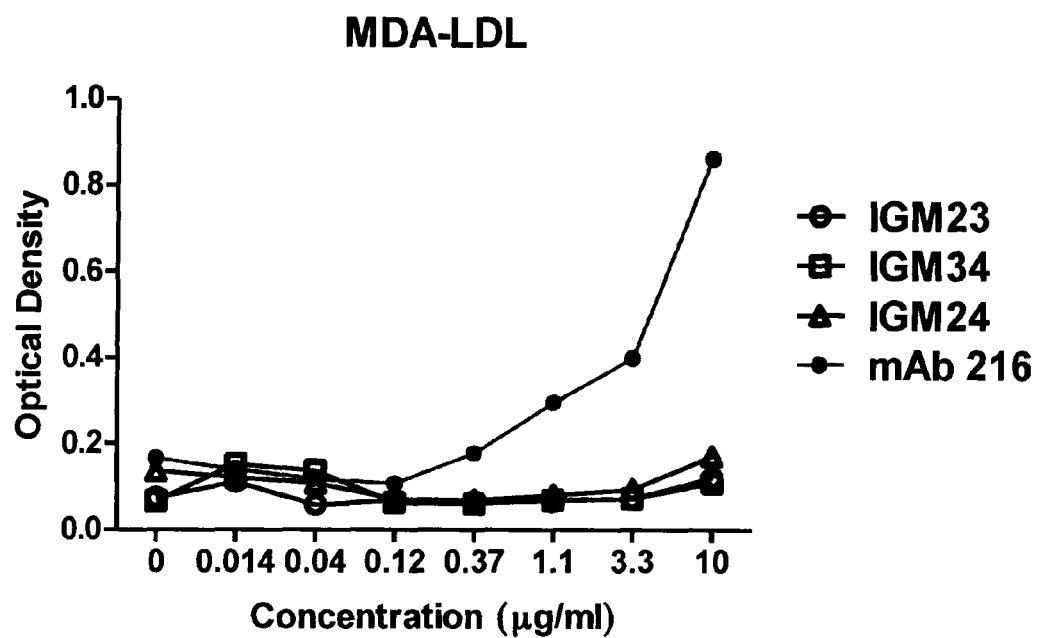
FIGURE 8E: Binding to Malonyl Dialdehyde modified Human Low Density Lipoprotein

FIGURE 9A: Binding to Single Strand DNA
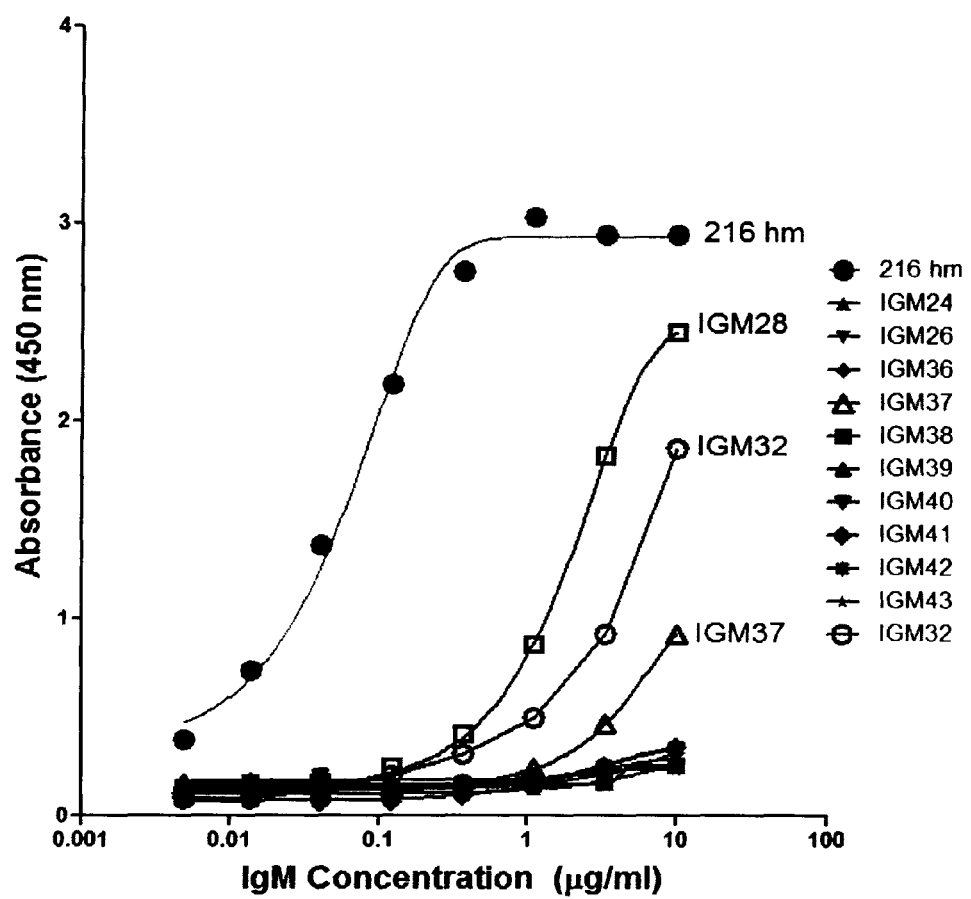

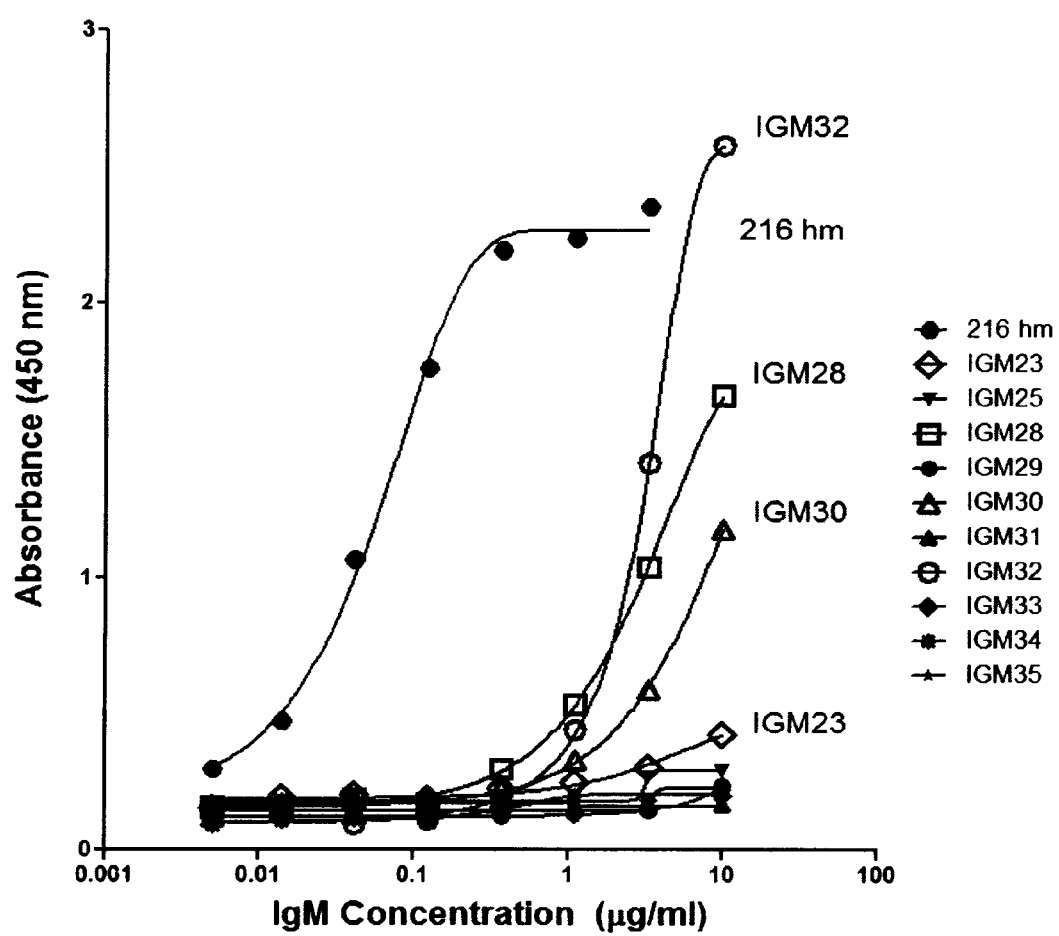
FIGURE 9B: Binding to Double Strand DNA

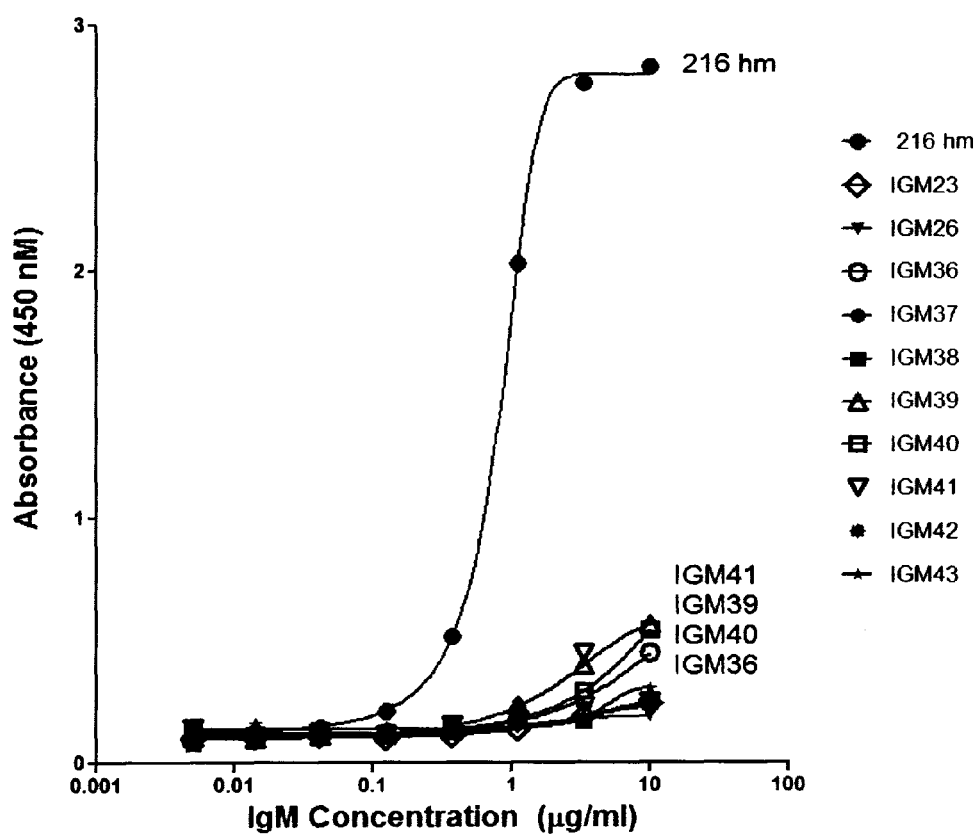
FIGURE 9C: Binding to Lipopolysaccharide (LPS)

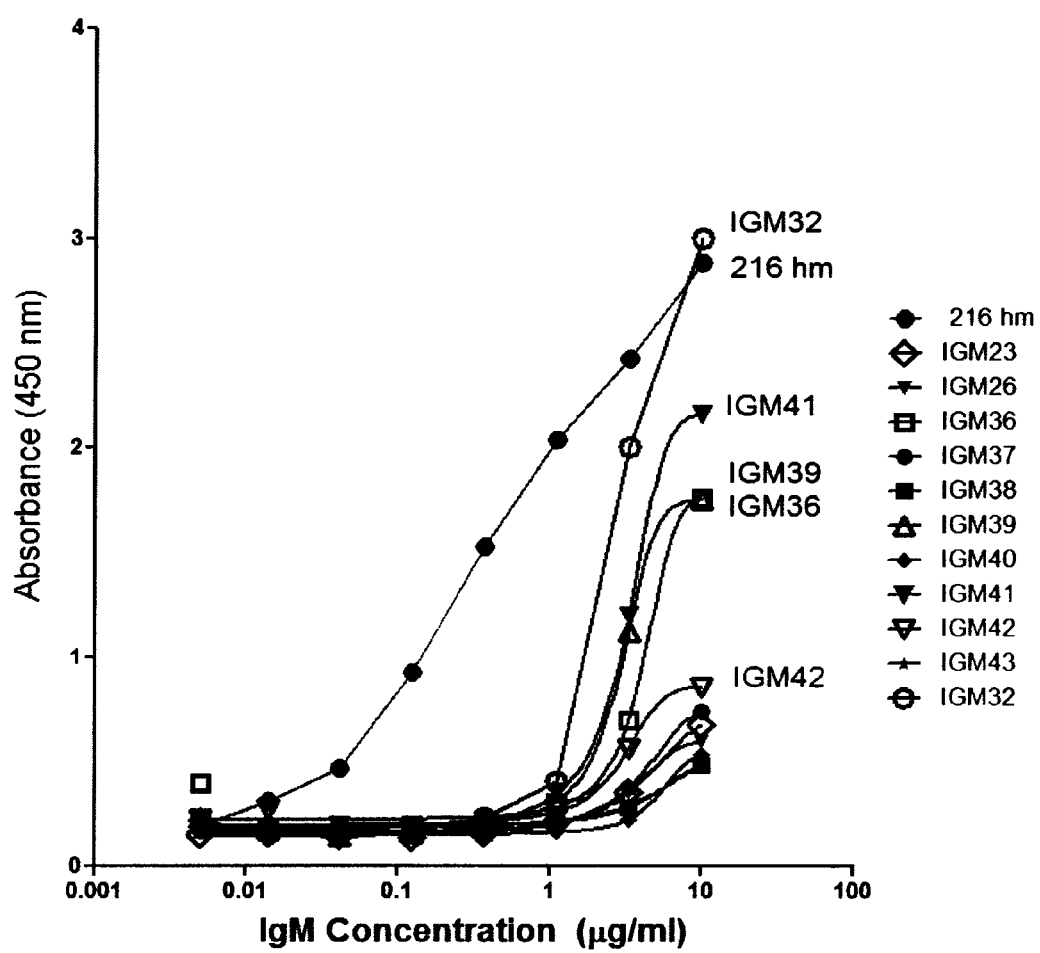
FIGURE 9D: Binding to Cardiolipin

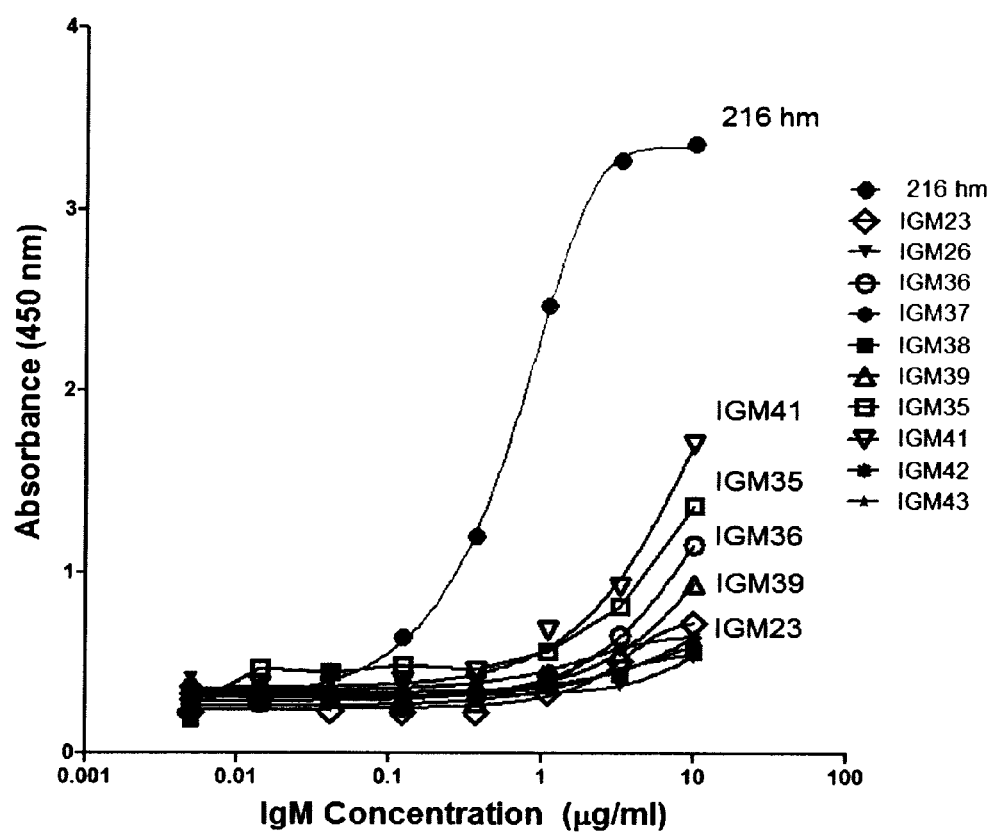
FIGURE 9E: Binding to Chondroitin Sulfate

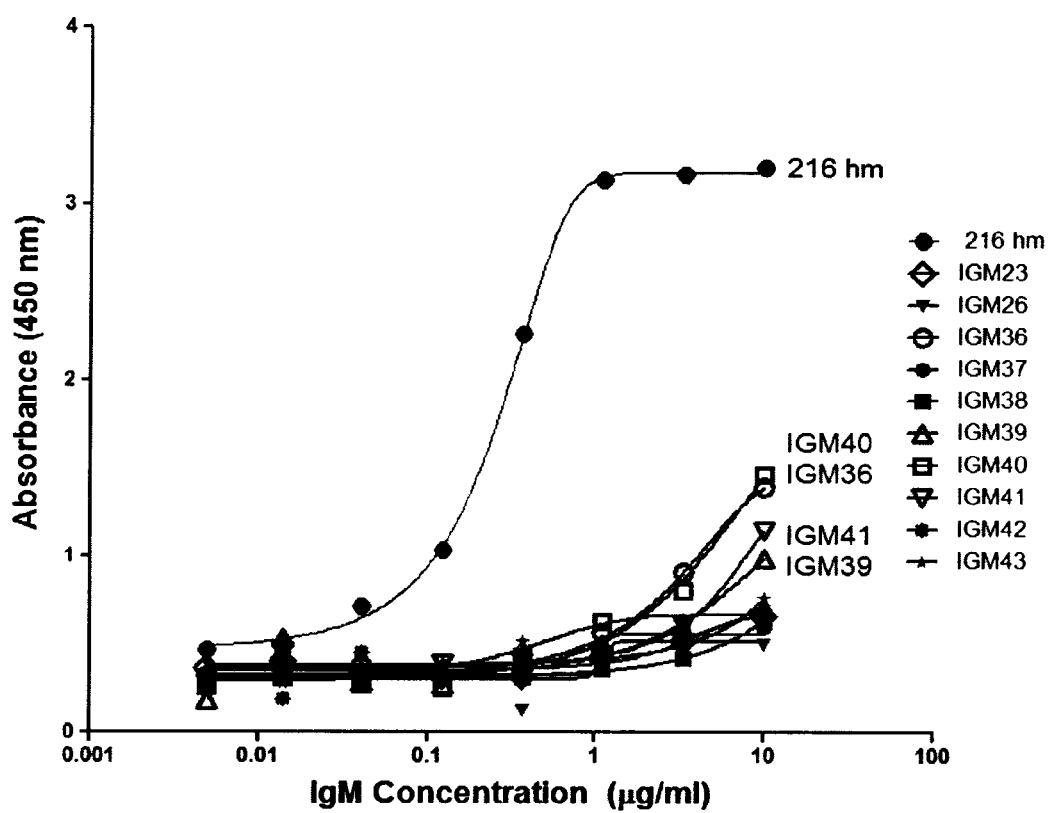
FIGURE 9F: Binding to Heparan Sulfate

CDIM BINDING PROTEINS AND USES THEREOF

This application claims priority to provisional U.S. application Ser. No. 61/633,330, which incorporated herein by reference.

SEQUENCE LISTING

The instant application contains a Sequence Listing which has been submitted in ASCII format via EFS-Web and is hereby incorporated by reference in its entirety. Said ASCII copy, created on Feb. 7, 2013, is named 0155-005WO1_SL.txt and is 225,619 bytes in size.

I. FIELD

The present disclosure relates to Cell Death Inducing Molecule (hereinafter "CDIM") binding proteins and pharmaceutical compositions thereof. Particularly, the disclosure provides CDIM binding proteins that are useful in the selective depleting and killing of B cells, including neoplastic B cells as well as other neoplastic cells that express CDIM or CDIM-like antigens. The disclosure also provides polynucleotides encoding the disclosed CDIM binding proteins, and expression systems for producing the same. Further encompassed in the present disclosure are methods of treating patients with B cell proliferative and B cell mediated diseases by administering the CDIM binding proteins. The disclosure further contemplates diagnostic assays for identifying patient populations that can be treated with the CDIM binding proteins.

II. BACKGROUND

The major responsibility for carrying out the functions of the immune system is born by white blood cells called lymphocytes. Lymphocytes can be categorized into two major classes, i.e., T cells and B cells. T cells (i.e., T-lymphocytes) originate from stem cells in the bone marrow, develop in the thymus gland and secrete lymphokines. B cells (i.e., B-lymphocytes) originate from stem cells in the bone marrow and are the source of antibodies. In fact, B cells generate five different types of antibodies including IgM, IgG, IgA, IgD and IgE. These antibodies can neutralize substances that can trigger an immune response, i.e., antigens, by attaching to specific sites on the antigens in order to block them. IgM is the largest antibody and the primary antibody against A and B antigens on red blood cells. Structurally, IgM forms polymers where multiple immunoglobulins are covalently linked together with disulfide bonds, primarily as a pentamer but also as a hexamer. IgM has a molecular mass of approximately 900 kDa in its pentameric form. Because each monomer has two antigen binding sites, a pentameric IgM has ten (10) binding sites.

Numerous diseases are associated with altered or dysfunctional B cells including, but not limited to, autoimmune diseases and cancer. The proliferation and differentiation of B cells is regulated by receptors localized on the cell surface. The engagement of these receptors induces the activation of intracellular signaling proteins that transmit the receptor signals to specific targets inside the cell that control the cellular responses. Many signaling proteins are the products of oncogenes and many oncogenes are associated with tumorgenesis. The molecular mechanisms of signaling pathways that control the proliferation and differentiation of B cells are still being studied (Jumaa et al. (2005) *Annu. Rev. Immunol.* 23:415-445).

An example of a disease involving neoplastic B lymphocytes is acute lymphoplastic leukemia (ALL). Some progress in combating this disease is due to intensification of chemotherapy, as well as better supportive care for both, pediatric and adult ALL. While the risk of relapse is lower in the pediatric population, both pediatric and adult patients face dire outcomes if the disease recurs. Less than one third of children and few adults with relapsed ALL survive this disease despite the use of aggressive regimens and stem cell transplantation. Novel therapies are therefore needed that reach beyond conventional chemotherapy. For ALL, there is preclinical and early clinical data with a variety of monoclonal antibodies including rituximab, epratuzumab and gemtuzumab, suggesting that the use of monoclonal antibodies alone or in combination with standard chemotherapy is a viable treatment option.

U.S. Pat. No. 5,593,676 describes ways of inducing cell death in neoplastic B cells by using reagents that bind a specific B cell epitope called cell death inducing molecule (CDIM). Herein, the B cell specific oligosaccharide epitope CDIM is used as a neoplastic B cell marker. IgM antibodies specific for this marker are administered to a host in vivo to induce death in neoplastic B cells. The same concept can be applied in ex vivo clinical situations to selectively remove B cells. A human monoclonal antibody (i.e., MAb 216), which recognizes the B cell epitope CDIM is cytotoxic to neoplastic and normal B cells and binds all CD19+ and CD20+ B lymphocytes in human peripheral blood and spleen. Furthermore, MAb 216 does not distinguish B cells by the isotype expressed, binding IgG+ and IgM+ cells with equal intensity. MAb 216 also binds all B cells regardless of their CD5 expression. Hence, MAb 216, is useful in diagnosis and therapy. See, also Bhat et al. (2000), *Scand. J. Immunol.* 51:134-140.

However, there remains a need in the art to identify antibodies that are specific for B cells to selectively kill and/or remove them from the host with reduced off-target binding and/or tissue damaging side effects. Cancer therapy still has a tremendous need for such therapeutic antibodies. The present application addresses this need.

III. BRIEF DESCRIPTION OF THE FIGURES

The present disclosure is best understood when read in conjunction with the accompanying figures, which serve to illustrate the embodiments. It is understood, however, that the disclosure is not limited to the specific embodiments disclosed in the figures.

FIGS. 1A-D depict amino acid sequences of heavy chain variable regions (SEQ ID NOS:1-22) that are representative of the CDIM binding proteins disclosed herein. The three heavy chain complementarity determining regions (CDRH1, CDRH2, and CDRH3) and framework regions of the heavy chain variable region (FR1, FR2, and FR3), and JH (joining region) are shown.

FIG. 1E depicts amino acid sequences of light chain variable regions (SEQ ID NOS:23 and 24) that are representative of the CDIM binding proteins disclosed herein. The three light chain complementarity determining regions (CDRL1, CDRL2, and CDRL3) and framework regions of the light chain variable region (FR1, FR2, and FR3), and IL (joining region) are shown.

FIG. 1F depicts amino acid sequences of a heavy chain constant region (Igμ) (SEQ ID NO:25), and two light chain constant regions (Igλ and Igκ, respectively) (SEQ ID NOS:26 and 27) utilized in representative examples disclosed herein.

FIGS. 2A-2V depict the complete amino acid sequences of the 44 anti-CDIM antibodies disclosed herein, designated IGM1 through IGM44. The 44 disclosed antibodies are formed by combining each of the 22 disclosed heavy chains (SEQ ID NOS:28-49) with each of the two disclosed light chains (SEQ ID NOS:50 and 51).

FIG. 3 depicts the CDR3 sequences of the representative H1 through H22 CDIM binding proteins (SEQ ID NOs:78-99) disclosed herein. The arginine residues of the various sequences are underlined.

FIGS. 4A-K depict exemplary polynucleotide sequences (SEQ ID NOS:52-73) encoding the 22 heavy chains of the antigen binding proteins disclosed herein.

FIG. 4L depicts exemplary polynucleotide sequences (SEQ ID NOS:74 and 75) encoding the two light chains, lambda and kappa, of the antigen binding proteins disclosed herein.

FIG. 5 depict native SDS gels of crude cell extracts from CHO cells expressing H1 through H7 (panel A), and H9 through H21 (panel B), respectively. The band at 1,048 kD represents IgM pentamers, while the band at 1,236 kD represents IgM hexamers.

Figure 6B:
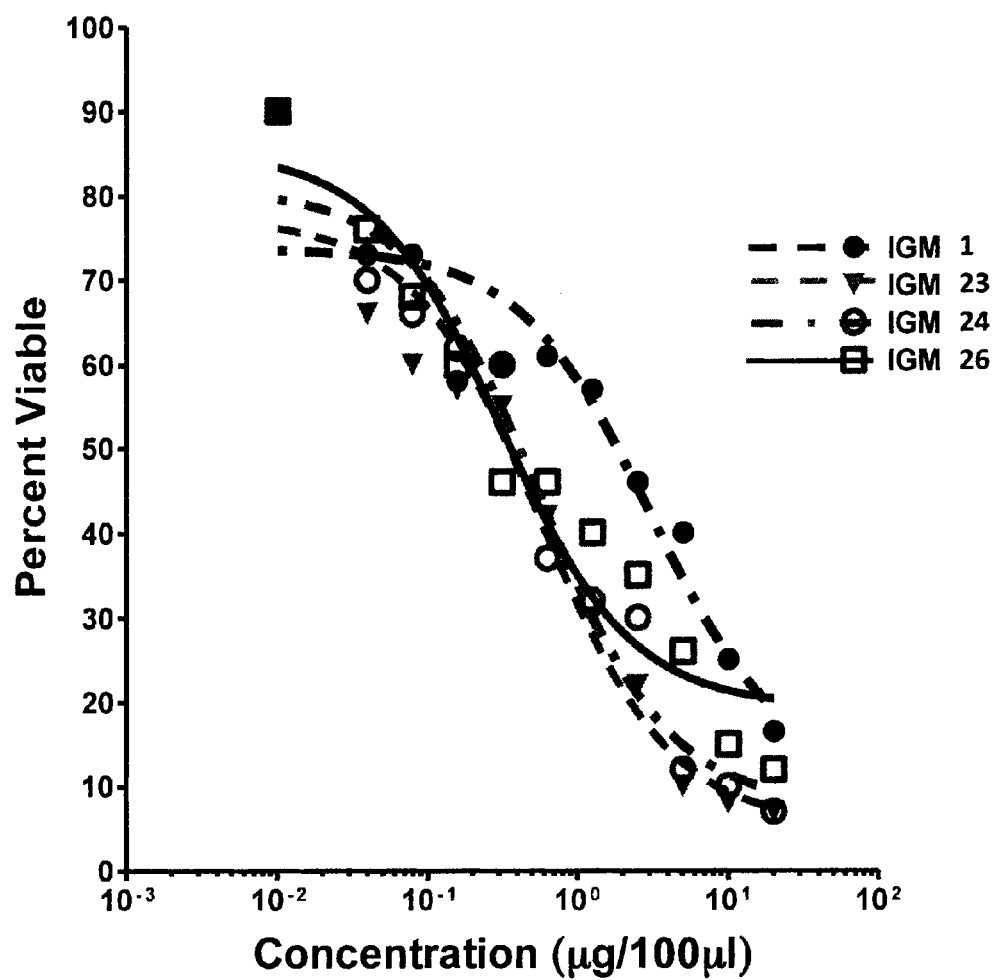

FIG. 6 illustrates the binding of CDIM binding proteins to CDIM expressed on a human B cell line and subsequent cytotoxicity results for the disclosed antibodies. Cell cultures were harvested and analyzed by flow cytometry using (1) mean fluorescence intensity to quantitate binding and (2) propidium iodine uptake to distinguish live from dead cells. As shown in FIG. 6A, all antibodies tested bind to the CDIM expressing human B cell line, NALM-6 across a broad dose range. FIG. 6B shows the cytotoxicity results following binding of the antibodies to the CDIM epitope.

Figure 7:
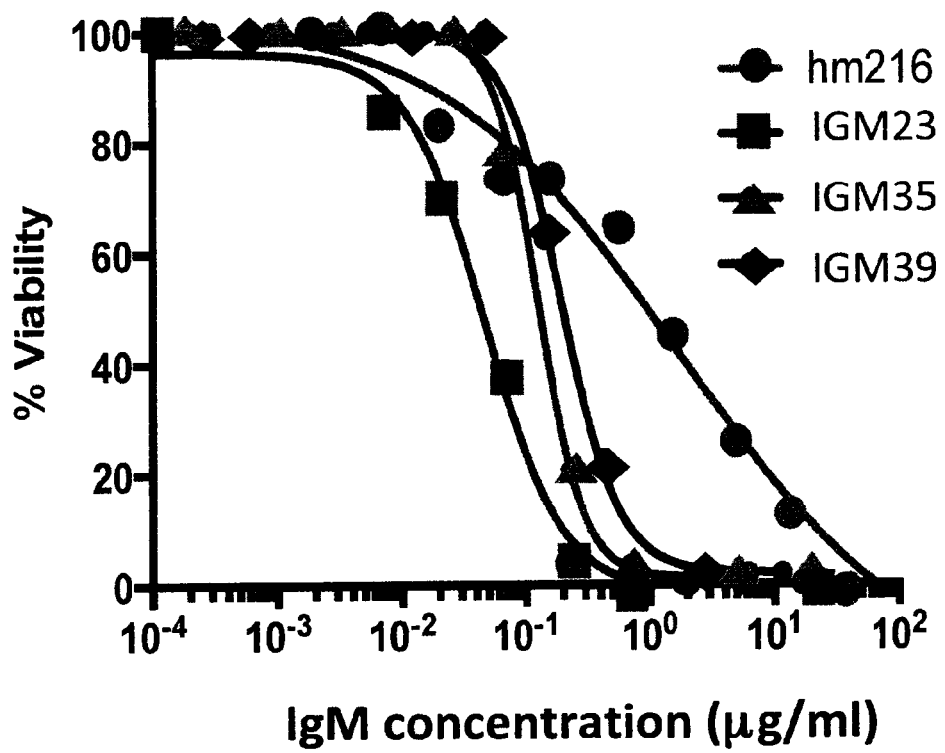

FIG. 7 shows cytotoxicity results following binding of the antibodies to the CDIM epitope.

FIG. 8, panels A-E depict ELISA based binding data that is representative of the CDIM binding proteins to antigens other than CDIM. Results using the antigens single stranded DNA (ssDNA), double stranded DNA (dsDNA), lipid A, cardiolipin, and maleonaldehyde LDL (MDA-LDL) are shown in panels A-E, respectively. As shown, MAb 216 binds to all of the antigens across a broad dose range in comparison with all the disclosed antibodies which demonstrate markedly reduced binding or total lack of binding to these select antigens.

FIG. 9, panels A-F depict ELISA based binding data that is representative of the CDIM binding proteins to antigens other than CDIM. Results using the antigens single stranded DNA (ssDNA), double stranded DNA (dsDNA), lipopolysaccharide, cardiolipin, chondoitrin and heparan, are shown in panels A-F, respectively. As shown, MAb 216 binds to all of the antigens across a broad dose range in comparison with all the disclosed antibodies which demonstrate markedly reduced binding or total lack of binding to these select antigens.

IV. DETAILED DESCRIPTION OF THE EMBODIMENTS

The section headings used herein are for organizational purposes only and are not to be construed as limiting the subject matter described.

Unless otherwise defined herein, scientific and technical terms used in connection with the present application shall have the meanings that are commonly understood by those of ordinary skill in the art. Further, unless otherwise required by context, singular terms shall include pluralities and plural terms shall include the singular.

Generally, nomenclatures used in connection with, and techniques of, cell and tissue culture, molecular biology, immunology, microbiology, genetics and protein and nucleic acid chemistry and hybridization described herein are those well known and commonly used in the art. The methods and techniques of the present application are generally performed according to conventional methods well known in the art and as described in various general and more specific references that are cited and discussed throughout the present specification unless otherwise indicated. See, e.g., Sambrook et al., Molecular Cloning: A Laboratory Manual, 3rd ed., Cold Spring Harbor Laboratory Press, Cold Spring Harbor, N.Y. (2001), Ausubel et al., Current Protocols in Molecular Biology, Greene Publishing Associates (1992), and Harlow and Lane Antibodies: A Laboratory Manual Cold Spring Harbor Laboratory Press, Cold Spring Harbor, N.Y. (1990), which are incorporated herein by reference. Enzymatic reactions and purification techniques are performed according to manufacturer's specifications, as commonly accomplished in the art or as described herein. The terminology used in connection with, and the laboratory procedures and techniques of, analytical chemistry, synthetic organic chemistry, and medicinal and pharmaceutical chemistry described herein are those well known and commonly used in the art. Standard techniques can be used for chemical syntheses, chemical analyses, pharmaceutical preparation, formulation, and delivery, and treatment of patients.

It should be understood that this invention is not limited to the particular methodology, protocols, and reagents, etc., described herein and as such may vary. The terminology used herein is for the purpose of describing particular embodiments only, and is not intended to limit the scope of the disclosed, which is defined solely by the claims.

Other than in the operating examples, or where otherwise indicated, all numbers expressing quantities of ingredients or reaction conditions used herein should be understood as modified in all instances by the term "about." The term "about" when used in connection with percentages may mean+/−1%.

General Overview

The present disclosure provides materials and methods related to treating or diagnosing proliferative diseases involving cells expressing the CDIM antigen. In particular, the disclosure provides CDIM binding proteins with improved ex vivo and in vivo performance that are useful in the selective killing and/or depleting of neoplastic B cells, specifically in patients who are afflicted with a condition characterized by B cell proliferative and B cell mediated diseases. In addition, the CDIM binding proteins are useful for treating solid tumors that express the CDIM antigen. The disclosed CDIM binding proteins may be used alone, or in combination with small molecules chemotherapeutics. As a result of a unique pore inducing effect of the disclosed CDIM binding proteins, i.e., membrane wounding, the targeted cells become more accessible to chemotherapeutic molecules. Therefore, the disclosed binding proteins are particularly suitable to treat cells otherwise resistant to small molecule compounds in combination with the same.

DEFINITIONS

The following terms used herein shall have the meaning as indicated below.

The term "antigen" refers to any substance capable of inducing a specific immune response and of reacting with a specific antibody.

The "antigen binding protein" or "CDIM binding protein," as used herein is a scaffold protein having an antibody like binding activity or an antibody, i.e., an anti-CDIM antibody.

The term "CDIM" ("Cell Death Inducing Molecule"), as used herein, refers to a poly n-acetyl lactosamine glycoform attached to cell surface molecules. The CDIM epitope is found on nearly all peripheral B lymphocytes and splenic B lymphocytes and on certain cultured B cell lymphoma lines. The epitope is also found on primary B cell lymphomas of various histopathologic classifications, and on the cells of some solid tumors.

In more specific terms, the CDIM epitope is a linear B cell lactosamine antigen (i.e., a poly-N-acetyl lactosamine type 2 determinant, with or without a terminal sialic acid) that has a three-dimensional structural conformation and is sensitive to the enzyme endo-beta-galactosidase. The epitope has no branching or substitutions and it can be attached to a glycolipid or a glycoprotein. On glycoproteins, the epitope could branch off a mannose frame work (e.g., enzyme MGAT4), or could be a long chain branching off a "large 1" structure, but is normally at least about four hexose moieties in a straight chain (i.e., type 2) after the branch Gal β1-4 GlcNac β1-3 Gal β1-4 Glc β1; at least about six hexoses for good affinity; and least about twelve hexoses in the longest form. The chain is made by enzymes (e.g., B3GNT1, B4GALT1), which add alternate sugars to the eptitope. Notably, the glycosylated epitope CDIM is present on multiple proteins ranging from molecular weights of about 20 KD to greater than about 200 KD proteins.

The CDIM epitope has been further elucidated in that the glycoform of the antigen is capped with sialic acid, making it a more mature type of glycosylation.

The term "epitope" generally refers to part of an antigen (i.e., the antigenic determinant of a molecule), which is recognized by the immune system. An epitope can be composed of sugars, lipids, and/or amino acids or mixtures thereof. The epitope is recognized by immune cells such as specific T cells, B cells, and/or antibodies produced by B cells. When immune cells recognize and are activated by specific epitopes, they mount an immune response. Alternatively, when antibodies recognize and bind specific epitopes, the cells carrying the epitopes may be depleted, killed, deactivated, wounded, removed, and/or altered.

The term "scaffold protein", or "antigen binding protein," as used herein, means a polypeptide or protein with exposed surface areas in which amino acid insertions, substitutions or deletions are highly tolerable. Examples of scaffold proteins that can be used in accordance with the present invention are protein A from *Staphylococcus aureus*, the bilin binding protein from *Pieris brassicae* or other lipocalins, ankyrin repeat proteins, and human fibronectin (reviewed in Binz and Plückthun (2005) *Curr. Opin. Biotechnol.* 16:459-69). Engineering of a scaffold protein can be regarded as grafting or integrating an affinity function onto or into the structural framework of a stably folded protein. Affinity function means a protein binding affinity according to the present invention. A scaffold can be structurally separable from the amino acid sequences conferring binding specificity. In general, proteins appearing suitable for the development of such artificial affinity reagents may be obtained by rational, or most commonly, combinatorial protein engineering techniques such as panning against CDIM, either purified protein or protein displayed on the cell surface, for binding agents in an artificial scaffold library displayed in vitro, skills which are known in the art (Skerra, A. (2000) *J. Mol. Recog.* 13:167-187; Binz and Plückthun, supra). In addition, a scaffold protein having an antibody like binding activity can be derived from an acceptor polypeptide containing the scaffold domain, which can be grafted with binding domains of a donor polypeptide to confer the binding specificity of the donor polypeptide onto the scaffold domain containing the acceptor polypeptide. Said inserted binding domains may be, for example, the complementarity determining region (CDR) of an antibody, in particular an anti-CDIM antibody. Insertion can be accomplished by various methods known to those skilled in the art including, for example, polypeptide synthesis, nucleic acid synthesis of an encoding amino acid as well by various forms of recombinant methods well known to those skilled in the art. Importantly, the term "heavy chain" or "light chain" is to be understood broadly to be a scaffold protein, embedding one or several of the disclosed CDRs, rather than limited to the traditional meaning of the term in the context of antibody technology.

Moreover, the term "antibody" or "CDIM-binding antibody," as used herein, means a monoclonal antibody, a polyclonal antibody, a recombinant antibody, a humanized antibody (Jones et al. (1986) *Nature* 321:522-525; Riechmann et al. (1988) *Nature* 332:323-329; and Presta (1992) *Curr. Op. Struct. Biol.* 2:593-596), a chimeric antibody (Morrison et al. (1984) *Proc. Natl. Acad. Sci. U.S.A.* 81:6851-6855), a multispecific antibody (e.g., a bispecific antibody) formed from at least two antibodies, or an antibody fragment thereof. The term "antibody fragment" comprises any portion of the aforementioned antibodies, preferably their antigen binding or variable regions. Examples of antibody fragments include Fab fragments, Fab' fragments, F(ab')$_2$ fragments, Fv fragments, diabodies (Hollinger et al. (1993) *Proc. Natl. Acad. Sci. U.S.A.* 90:6444-6448), single chain antibody molecules (Plückthun in: *The Pharmacology of Monoclonal Antibodies* 113, Rosenburg and Moore, EDS, Springer Verlag, N.Y. (1994), 269-315) and other fragments as long as they exhibit the desired capability of binding to CDIM.

In addition, the term "antibody" or "CDIM binding antibody," as used herein, may include antibody-like molecules that contain engineered sub-domains of antibodies or naturally occurring antibody variants. These antibody-like molecules may be single-domain antibodies such as $V_H$-only or $V_L$-only domains derived either from natural sources such as camelids (Muyldermans et al. (2001) *Reviews in Molecular Biotechnology* 74:277-302) or through in vitro display of libraries from humans, camelids or other species (Holt et al. 2003 *Trends Biotechnol.* 21:484-90).

In accordance with the present invention, the "Fv fragment" is the minimum antibody fragment that contains a complete antigen-recognition and -binding site. This region consists of a dimer of one heavy- and one light-chain variable domain in tight, non-covalent association. It is in this configuration that the three CDRs of each variable domain (heavy chain CDRH1, CDRH2, and CDRH3; light chain CDRL1, CDRL2, and CDRL3) interact to define an antigen-binding site on the surface of the $V_H$-$V_L$ dimer. Collectively, the six CDR's confer antigen-binding specificity to the antibody. However, even a single variable domain (or half of an Fv comprising only three CDR's specific for an antigen) has the ability to recognize and bind the antigen. The "Fab fragment" also contains the constant domain of the light chain and the first constant domain (CH1) of the heavy chain. The "Fab fragment" differs from the "Fab' fragment" by the addition of a few residues at the carboxy terminus of the heavy chain CH1 domain including one or more cysteines from the antibody hinge region. The "F(ab')$_2$ fragment" originally is produced as a pair of "Fab' fragments" which have hinge cysteines between them. Methods of preparing such antibody fragments, such as papain or pepsin digestion, are known to those skilled in the art.

In some embodiment of the present invention, the anti-CDIM antibody is of the IgA-, IgD-, IgE, IgG- or IgM-type, preferably of the IgG- or IgM-type including, but not limited to, the IgG1-, IgG2-, IgG3-, IgG4-, IgM1- and IgM2-type. In most embodiments, the antibody is of the IgM type. The light chain may be either a lambda-1, lambda-2, or a kappa. A J chain may be included or omitted.

IgG has several subtypes, including, but not limited to, IgG1, IgG2, IgG3, and IgG4. IgA subtypes include IgA1 and IgA2. In humans, the IgA isotype contain four heavy chains and four light chains; the IgG and IgE isotypes contain two heavy chains and two light chains; and the IgM isotype contains ten or twelve heavy chains and ten or twelve light chains (pentameric or hexameric). In naturally occurring IgM molecules, the J chain stabilizes the pentameric configuration.

The heavy chain C region typically comprises one or more domains that may be responsible for effector function. The number of heavy chain constant region domains will depend on the isotype. In one embodiment, the CDIM binding proteins are of the IgM subtype. In full-length light and heavy chains, the variable and constant regions may be joined by a "J" region of about twelve or more amino acids, with the heavy chain also including a "D" region of about ten more amino acids. (See, e.g., Fundamental Immunology, 2nd ed., Ch. 7 (Paul, W., ed.) (1989) New York: Raven Press).

The CDIM Binding Proteins

A first aspect of the present disclosure relates to an isolated binding protein that binds to the CDIM epitope on human peripheral B lymphocytes, splenic B lymphocytes, neoplastic B lymphocytes, and some solid tumors.

In one embodiment, the antigen binding protein comprises a heavy chain comprising a at least one of a CDRH1, CDRH2, and CDRH3 having a sequence shown in any of SEQ ID NOS:1-22, and/or a light chain comprising at least one of a CDRL1, CDRL2, and CDRL3 shown in SEQ ID NOS:23 or 24. In one embodiment, the antigen binding protein comprises a heavy chain comprising at least a CDRH3 shown in SEQ ID NOS:1-22, and a light chain. In yet another embodiment, the antigen binding protein comprises each a CDRH1, CDRH2, and CDRH3 shown in SEQ ID NOS:1-22, and a light chain. In other embodiments, the antigen binding protein additionally comprises a CDRL1, a CDRL2, and a CDRL3 of SEQ ID NOS:23 or 24, embedded into the light chain. In some embodiments, the antigen binding protein additionally has a FR1 shown in SEQ ID NOS:1-22, embedded in the heavy chain.

In yet another embodiment, the antigen binding protein comprises a heavy chain variable region shown in any of SEQ ID NOS:1-22. Additionally, the disclosure includes an embodiment where the antigen binding protein comprises a light chain variable region that has the sequence shown in SEQ ID NO:23 or 24. Further, the disclosure contemplates an antigen binding protein comprising a heavy chain variable region shown in any of SEQ ID NOS:1-22, and a light chain variable region shown in SEQ ID NO:23 or 24. FIGS. 1A-D illustrate the 22 exemplary unique heavy chain variable regions of the CDIM binding proteins disclosed herein. FIG. 1E depicts two light chain variable regions (SEQ ID NOS:23 and 24). FIG. 1F shows a constant region for the heavy chain (Igμ) (SEQ ID NO:25), as well as constant regions for the light chains (Igλ and Igκ) (SEQ ID NOS:26 and 27). SEQ ID NO: 108 represents MAb 216 (Bhat et al, 2000, supra), a CDIM binding antibody, which was used as experimental reference antibody in assessing potency and specificity. See, Examples, infra.

Each of the heavy chain variable regions may be attached to a heavy chain constant region to form a full heavy chain, and each light chain variable region may be attached to a light chain constant region to form a full light chain, respectively. The amino acid sequences of the exemplary full heavy chains disclosed herein have a sequence shown in SEQ ID NOS:28-49. The amino acid sequences of the exemplary light chains disclosed herein have an amino acid sequence shown in SEQ ID NOS:50 and 51. As explained, supra, two heavy chain and two light chain sequences may form a full antibody tetramer. Disclosed herein are, inter alia, exemplary CDIM binding antibody tetramers, designated IGM1, IGM2, IGM3, IGM4, IGM5, IGM6, IGM7, IGM8, IGM9, IGM10, IGM11, IGM12, IGM13, IGM14, IGM15, IGM16, IGM17, IGM18, IGM19, IGM20, IGM21, IGM22, IGM23, IGM24, IGM25, IGM26, IGM27, IGM28, IGM29, IGM30, IGM31, IGM32, IGM33, IGM34, IGM35, IGM36, IGM37, IGM38, IGM39, IGM40, IGM41, IGM42, IGM43, and IGM44 (collectively also referred to herein as "IGM1-IGM44"). As shown in FIGS. 2A-2V, these 44 disclosed CDIM binding proteins are comprised of the heavy chains of SEQ ID NOS:28-49, each combined with either of the light chains of SEQ ID NOS:50-51. TABLES 3, infra, show the correlation between the various polypeptide and polynucleotide SEQ ID NOS and the IGM1-IGM44 antigen binding proteins.

In one embodiment, the isolated antigen binding protein binds to CDIM, and comprises a heavy chain CDR3 sequence $X_1X_2X_3AX_4GX_5SX_6X_7$, wherein:
$X_1$ is an G, A, or an R;
$X_2$ is an R, a G, or an A;
$X_3$ is an M, an T, or a R;
$X_4$ is an R, a W, or a Y;
$X_5$ is an A, an S or a G;
$X_6$ is an I, a V, or a Y; and
$X_7$ is an N, or no amino acid;
and wherein there is one, and not more than one, Arginine within positions 1 through 3 (relative to heavy chain variable region, positions 98 through 100, position 97 being the invariable Arginine preceding the CDR3 region.

In another embodiment, the isolated antigen binding protein binds to CDIM, and comprises a heavy chain CDR3 sequence $X_1X_2X_3AX_4GX_5SX_6X_7$, wherein:
$X_1$ is an G, A, or an R;
$X_2$ is an R, a G, or an A;
$X_3$ is an M, an T, or a R;
$X_4$ is an R, or a W;
$X_5$ is an A, or an S;
$X_6$ is an I, or a V; and
$X_7$ is an N, or no amino acid;
and wherein there is one, and not more than one, Arginine within positions 1 through 3 (relative to heavy chain variable region, positions 98 through 100, position 97 being the invariable Arginine preceding the CDR3 region.

In accordance with the present invention, it is to be understood, that the amino acid sequence of the binding protein of the invention is not limited to the twenty conventional amino acids (See, Immunology—A Synthesis (2nd Edition, E. S. Golub and D. R. Gren, Eds., Sinauer Associates, Sunderland, Mass. (1991)), which is incorporated herein by reference). For example, the amino acids may include stereoisomers (e.g., D-amino acids) of the twenty conventional amino acids, unnatural amino acids such as α-,α-disubstituted amino acids, N-alkyl amino acids, lactic acid, and other unconventional amino acids. Examples of unconventional amino acids, which may also be suitable components for the binding protein of the invention, include: 4-hydroxyproline, γ-carboxyglutamate, ε-N,N,N-trimethyllysine, ε-N-acetyllysine, O-phosphoserine, N-acetylserine, N-formylmethionine, 3-methylhistidine, 5-hydroxylysine, σ-N-methylarginine, and other similar amino acids and imino acids, e.g., 4-hydroxyproline.

Furthermore, in accordance with the present invention, minor variations in the amino acid sequences shown in SEQ ID NOS:1-51 are contemplated as being encompassed by the present invention, providing that the variations in the amino acid sequence maintain at least 75%, more preferably at least 80%, 90%, 95%, and most preferably 99% of the sequences shown in SEQ ID NOS:1-51. The variations may occur within the framework regions (i.e., outside the CDRs), within the CDRs, or within the framework regions and the CDRs. Preferred variations in the amino acid sequences shown in SEQ ID NOS:1-51, i.e., deletions, insertions and/or replacements of at least one amino acid, occur near boundaries of functional domains. Structural and functional domains can be identified by comparison of the nucleotide and/or amino acid sequence data to public or proprietary sequence databases. Computerized comparison methods can be used to identify sequence motifs or predicted protein conformation domains that occur in other binding proteins of known structure and/or function. Methods to identify protein sequences that fold into a known three-dimensional structure are known. See, e.g., Bowie et al. (1991) *Science* 253:164; Proteins, Structures and Molecular Principles (Creighton, Ed., W.H. Freeman and Company, New York (1984)); Introduction to Protein Structure (C. Branden and J. Tooze, eds., Garland Publishing, New York, N.Y. (1991)); and Thornton et al. 1991 *Nature* 354: 105, which are all incorporated herein by reference. Thus, those of skill in the art can recognize sequence motifs and structural conformations that may be used to define structural and functional domains in accordance with the invention.

Especially preferred variations in the amino acid sequences shown in SEQ ID NOS:1-51, are those that lead to a reduced susceptibility to proteolysis or oxidation, alter glycosylation patterns or alter binding affinities or confer or modify other physicochemical or functional properties of the binding protein. In particular, conservative amino acid replacements are contemplated. Conservative replacements are those that take place within a family of amino acids that are related in their side chains. Preferred amino acid families are the following: acidic family=aspartate, glutamate; basic family=lysine, arginine, histidine; non-polar family=alanine, valine, leucine, isoleucine, proline, phenylalanine, methionine, tryptophan; and uncharged polar family=glycine, asparagine, glutamine, cysteine, serine, threonine, tyrosine. More preferred families are: aliphatic-hydroxy family=serine and threonine; amide-containing family=asparagine and glutamine; aliphatic family=alanine, valine, leucine and isoleucine; and aromatic family=phenylalanine, tryptophan, and tyrosine. For example, it is reasonable to expect that an isolated replacement of a leucine with an isoleucine or valine, an aspartate with a glutamate, a threonine with a serine, or a similar replacement of an amino acid with a structurally related amino acid will not have a major effect on the binding or properties of the resulting binding protein, especially if the replacement does not involve an amino acid within a framework site. Whether an amino acid change results in a functional binding protein, i.e., in an antigen binding protein that binds to CDIM can be readily determined by assaying in ELISA or FACS.

In some embodiments, the CDIM binding protein is a "scaffold protein" having an antibody like binding activity, where one or several CDRs of SEQ ID NOS:1-24 are embedded in a scaffold as defined, supra. In some embodiments at least CDRH3 and CDRL3 are embedded in the scaffold. In some embodiments all six CDRs are embedded in the scaffold. Whether the scaffold protein has CDIM binding activity can be readily determined by assaying in ELISA or FACS competition for binding with MAb 216, which is a naturally occurring CDIM binding antibody, or in vitro or in vivo functional assays.

Furthermore, according to the present invention, it is appreciated that the CDIM binding antibody of the invention is a fully human or humanized antibody. Human antibodies avoid certain of the problems associated with xenogeneic antibodies, for example antibodies that possess murine or rat variable and/or constant regions. The presence of xenogeneic-derived proteins such murine or rat derived proteins can lead to the generation of an immune response against the antibody by a patient, subsequently leading to the rapid clearance of the antibodies, loss of therapeutic utility through neutralization of the antibody and/or severe, even life-threatening, allergic reactions.

The antigen binding proteins described herein may be antibodies or may be derived from antibodies. In certain embodiments, the polypeptide structure of the antigen binding proteins is based on antibodies, including, but not limited to, monoclonal antibodies, bispecific antibodies, minibodies, domain antibodies, synthetic antibodies (sometimes referred to herein as "antibody mimetics"), chimeric antibodies, humanized antibodies, human antibodies, antibody fusions (sometimes referred to herein as "antibody conjugates"), and fragments thereof. The antigen binding proteins provided herein have been shown to bind CDIM epitopes on all B cells, including neoplastic B cells and some solid tumor cells. As demonstrated in the examples, the ability of injured B cells to repair themselves and survive is reduced or inhibited. As a consequence, the disclosed antigen binding proteins are capable of depleting and killing B cells, including tumor cells. The antigen binding proteins that are disclosed herein have a variety of utilities. Some of the antigen binding proteins, are, for example, useful in specific binding assays, affinity purification of CDIM expressing cells, and in screening assays to identify CDIM expressing cells including solid tumor cells, cells of B cell origin. In addition, the disclosed antigen binding proteins may be used for the diagnosis and/or treatment of disease, such as B cell proliferative disorders and autoimmune diseases. To that end, the disclosed antigen binding proteins may be used alone, or in combination with small molecules chemotherapeutics.

In one embodiment, the antigen binding protein is a polyvalent CDIM binding protein (i.e., CDIM binding proteins with two or more binding sites for the CDIM epitope). As such, the binding proteins function as receptors with a specific affinity and avidity for the CDIM epitope, generally at least about $10^{-6}$ M, and more preferably at least about $10^{-7}$ M. The polyvalent nature of the receptor allows the simultaneous binding of at least two CDIM epitopes on the cell membrane surface. Antibodies can be used from any of the immunoglobulin families, such as IgA, IgD, IgE, IgG, and IgM; it is not a requirement that the antibody be associated with various cytotoxic processes associated with particularly Fc-initiated processes. In one embodiment, the antibody will be IgM, since the pentameric or hexameric structure of this molecule allows cross-linking unhindered by steric interference. In some embodiments, the antibody composition is a mixture of IgM pentamers and IgM hexamers, including at least 20% hexamers, or at least 30% hexamers, at least 40% hexamers, at least 50% hexamers, or at least 60% hexamers, or at least 70% hexamers, or at least 80% hexamers. Alternatively, fragments of antibodies may be used or synthetic alternatives thereof that act like antibodies. For example, small synthetic molecules can be devised which will allow for specific binding and cross-linking of the CDIM epitope.

In one embodiment, the antibody has the J chain, in another embodiment the antibody lacks the J chain.

In one aspect, the antigen binding protein is a recombinant antibody constructed based on the VH4-34 germ line sequence. The VH4-34 gene (variable heavy region) is one of the 53 identified human functional antibody germline genes. The VH4-34 gene is present in all haplotypes, and no sequence variation was found in germline DNA that was isolated from unrelated individuals. Anti-B cell VH4-34 antibodies are cytotoxic to B cells (Bhat et al. (1997) *Clin. Exp. Immunol.* 108:151 and Bhat et al. (2001) *Crit. Rev. Oncol. Hematol.* 39:59). As alluded to above, the plasma membrane defects or pores induced by the antibodies are larger than those formed by other well-known pore-forming proteins. By permeabilizing the cells, the disclosed CDIM binding proteins effect significant depletion of the targeted cells (see, also Patent Publication Number 20100322849). B cells that have been permeabilized are more susceptible to the action of additional cytotoxic agents, including, but not limited to, radioactive isotopes, cytotoxic antibodies, immunoconjugates, ligand conjugates, immunosuppressants, cell growth regulator and/or inhibitors, toxins, and/or mixtures thereof. The compromised cell membrane allows entry of cytotoxic agents such as chemotherapeutic agents, thus increasing the efficacy of the chemotherapeutic agents, even in cells that are resistant or impermeable to such agents. Any B cell or cancer cell that expresses the CDIM epitope or CDIM-like epitope, respectively, can be treated with the CDIM binding proteins and is subject to depletion and killing via the disclosed antigen binding proteins.

The CDIM binding proteins of the present disclosure recognize the CDIM epitope on human peripheral B lymphocytes, splenic B lymphocytes and on neoplastic B lymphocytes, and some solid tumors. Many IgM antibodies are polyreactive, i.e., they can bind to a variety of different and structurally unrelated self and non-self foreign antigens. However, the antigen binding proteins disclosed herein were found to have less polyreactivity than some naturally occurring CDIM antibodies. As such, the disclosed antigen binding proteins are subject to less off-target binding, making them better therapeutic and diagnostic candidates for in vivo applications. Their reduced polyreactivity is illustrated in FIGS. 5A-5E, which shows examples of the disclosed antigen binding proteins that have reduced or lost their binding affinity for multiple non-CDIM antigens, specifically ssDNA, dsDNA, lipid A, cardiolipin and MDA-LDL. This suggests that the disclosed CDIM binding proteins are safer for therapeutic applications because the dose required to bind the target cells will be lower since there is no "antigen sink" for the antibody (binding to antigens other than CDIM). The affinity of a polyreactive antibody for different antigens varies by as much as 1000-fold and is generally lower than that of a monoreactive antibody for its antigen. Many of the polyreactive antibodies are usually germline or near germline although some have a small number of substitutions. Polyreactive antibodies may be cleared from the circulation faster than monoreactive antibodies. The rapid clearance of the polyreactive antibodies may be due to the binding of these antibodies to endogenous host antigens (see, also Zhou et al. (2007) *J. Autoimmun.* 29(4):219-228). Many of the natural antibodies are polyreactive antibodies, which have broad antibacterial activity. This partly explains the antibacterial activity in the sera of newborns in the absence of known antigenic stimulation (see, also Zhou et al. (2007), supra). However, for therapeutic purposes, it is generally desirable to employ antibodies that are monospecific and are not cleared too rapidly so as to accomplish binding and killing to B cells and cancer cells that express the CDIM epitope.

In specific therapeutic applications, for example, in treating an autoimmune disease it is desirable that the CDIM binding proteins bind B cells and kill them selectively as B cells contribute to multiple autoimmune diseases by a variety of mechanisms (Browning, J. L. (2006) *Nature* (Reviews) 5:564-576). The rapid depletion of the B cells reduces the activity of the immune system which in turn reduces many associated side-effects such as inflammation and tissue damage. In cancer treatment it is desirable to kill selective cell populations, such as neoplastic B cells or cancer cells in order to stop hyper-proliferation of these cells and the spread of cancer to other organs. Herein, the combination therapy with other agents and cancer drugs can be beneficial in directing the killing of specific cells. Thus, the CDIM binding proteins find therapeutic application in both autoimmune disease and cancer treatment.

As discussed above, binding of the disclosed antigen binding proteins to its linear lactosamine ligand leads to disruption of the plasma membrane and formation of large membrane pores resulting in cell lysis. The combination of vincristine, for example, and the disclosed antigen binding proteins results in an enhanced degree of cytotoxicity to B cells when compared to the additive effect of each single agent alone. Hence, the CDIM binding proteins can be administered to patients alone and in combination with other agent and/or cancer drugs to assess tumor targeting and efficacy. Furthermore, the CDIM binding proteins can be administered to patients alone and in combination with other agents and/or cancer drugs to treat and/or diagnose various diseases including cancer and autoimmune diseases. Examples of other agents that could be used in combination with CDIM binding proteins are shown in TABLE 1 below:

TABLE 1

| COMPOUND | ACTION | EFFECT |
| --- | --- | --- |
| Etoposide (VP-16) | Topoisomerase II Inhibitor | Additive Effect |
| Paclitaxel (Taxol) | Freezes Microtubules | Possible/Undermined Effect |
| Ara-C (Cytarabine) | Analog | Additive Effect |
| Vincristine, Nocodazole, Colchisine | Depolymerize Microtubules | Synergistic Effect |
| Daunorubicin | Anthracyclines | Additive Effect |

In some embodiments, an antigen binding protein of the invention is coupled to a labeling group. Such a binding protein is particularly suitable for diagnostic applications. As used herein, the term "labeling group" refers to a detectable marker, e.g., a radiolabeled amino acid or biotinyl moiety that can be detected by conjugated avidin (e.g., streptavidin bound to a fluorescent marker or enzymatic activity that can be detected by optical or colorimetric methods). Various methods for labeling polypeptides and glycoproteins, such as antibodies, are known in the art and may be used in performing the present invention. Examples of suitable labeling groups include, but are not limited to, the following: radioisotopes or radionuclides (e.g., $^{3}$H, $^{14}$C, $^{15}$N, $^{35}$S, $^{90}$Y, $^{99}$Tc, $^{111}$In, $^{125}$I, $^{131}$I), fluorescent groups (e.g., FITC, rhodamine, lanthanide phosphors), enzymatic groups (e.g., horseradish peroxidase, β-galactosidase, luciferase, alkaline phosphatase), chemiluminescent groups, biotinyl groups, or predetermined polypeptide epitopes recognized by a secondary reporter (e.g., leucine zipper pair sequences, binding sites for secondary antibodies, metal binding domains, epitope tags). In certain respects, it may be desirable that the labeling groups are attached by spacer arms of various lengths to reduce potential steric hindrance.

Alternatively, an antigen binding protein disclosed herein may be coupled to an effector group in another preferred embodiment of the invention. Such a binding protein is especially suitable for therapeutic applications. As used herein, the term "effector group" refers to a cytotoxic group such as a radioisotope or radionuclide, a toxin, a therapeutic group or other effector group known in the art. Examples for suitable effector groups are radioisotopes or radionuclides (e.g., $^{3}H$, $^{14}C$, $^{15}N$, $^{35}S$, $^{90}Y$, $^{99}Tc$, $^{111}In$, $^{125}I$, $^{131}I$), calicheamicin, dolastatin analogs such as auristatins, and chemotherapeutic agents such as geldanamycin and maytansine derivates, including DM1. In certain respects, it may be desirable that the effector groups are attached by spacer arms of various lengths to reduce potential steric hindrance.

Polynucleotides Encoding CDIM Binding Proteins and Expression Systems

Another aspect of the present invention relates to an isolated nucleic acid molecule encoding a binding protein of the invention. Within the context of the present invention, the term "isolated nucleic acid molecule" means a polynucleotide of genomic, cDNA, or synthetic origin or some combination thereof, which by virtue of its origin, the "isolated nucleic acid molecule" (1) is not associated with all or a portion of a polynucleotide in which the "isolated polynucleotide" is found in nature, (2) is operably linked to a polynucleotide which it is not linked to in nature, or (3) does not occur in nature as part of a larger sequence. Further, the term "nucleic acid molecule", as referred to herein, means a polymeric form of nucleotides of at least 10 bases in length, either ribonucleotides or deoxynucleotides or a modified form of either type of nucleotide, such as nucleotides with modified or substituted sugar groups and the like. The term also includes single and double stranded forms of DNA.

Exemplary complete nucleic acid sequences encoding the heavy chain sequences of IGM1-IGM44 (SEQ ID NOS:52-73) are provided in FIGS. 3A-K. Exemplary complete nucleic acid sequences encoding the light chain sequences of IGM1-IGM44 (SEQ ID NOS:74 and 75) are provided in FIG. 3L. Of course, due to the degeneracy of the genetic code, other nucleic acids encoding the CDIM binding proteins described herein can be contemplated.

In a one embodiment of the present invention, a nucleic acid molecule of the invention is operably linked to a control sequence. The term "control sequence", as used herein, refers to polynucleotide sequences that are necessary to effect the expression and processing of coding sequences to which they are ligated. The nature of such control sequences differs depending upon the host organism. In prokaryotes, such control sequences generally include promoters, ribosomal binding sites, and transcription termination sequences. In eukaryotes, generally, such control sequences include promoters and transcription termination sequences. In accordance with the present invention, the term "control sequence" is intended to include, at a minimum, all components whose presence is essential for expression and processing, and can also include additional components whose presence is advantageous, for example, leader sequences and fusion partner sequences. Furthermore, the term "operably linked", as used herein, refers to positions of components so described which are in a relationship permitting them to function in their intended manner.

Moreover, according to the present invention, an expression control sequence operably linked to a coding sequence is ligated in such a way that expression of the coding sequence is achieved under conditions compatible with the expression control sequence.

A further aspect of the present invention is a vector comprising a nucleic acid molecule that encodes a binding protein of the invention. The nucleic acid molecule can be operably linked to a control sequence. Furthermore, the vector may additionally contain a replication origin or a selection marker gene. Examples of vectors that may be used in accordance with the present invention are, e.g., plasmids, cosmids, phages, viruses, etc.

Another aspect of the present invention relates to a host cell transformed with a nucleic acid molecule or vector of the invention. Transformation could be done by any known method for introducing polynucleotides into a host cell, including for example packaging the polynucleotide in a virus (or into a viral vector) and transducing a host cell with the virus (or vector) or by transfection procedures known in the art, as exemplified by U.S. Pat. Nos. 4,399,216, 4,912,040, 4,740,461, and 4,959,455, which patents are hereby incorporated herein by reference. Particularly, methods for introducing heterologous polynucleotides into mammalian cells are well known in the art and include dextran-mediated transfection, calcium phosphate precipitation, polybrene mediated transfection, protoplast fusion, electroporation, encapsulation of the polynucleotide(s) in liposomes, and direct microinjection of the DNA into nuclei. Examples of host cells that may be used according to the present invention are hybridomas eukaryotic cells such as mammalian cells, e.g., hamster, rabbit, rat, pig, mouse or other animal cells; plant cells and fungal cells, e.g., corn, tobacco, *Saccharomyces cerevisiae, Pichia pastoris*; prokaryotic cells such as *E. coli*; and other cells used in the art for the production of antibodies. Especially mammalian cell lines available as hosts for expression are well known in the art and include many immortalized cell lines available from the American Type Culture Collection (ATCC), including but not limited to Chinese hamster ovary (CHO) cells, HeLa cells, baby hamster kidney (BHK) cells, monkey kidney cells (COS), human hepatocellular carcinoma cells (e.g., Hep G2), and a number of others.

Pharmaceutical Compositions of CDIM Binding Proteins and Methods of Treatment and Diagnosis A further aspect of the present disclosure are pharmaceutical compositions and of the CDIM binding proteins. The binding proteins are formulated as pharmaceuticals to be used in the methods of the disclosure. Any composition or compound that can stimulate a biological response associated with the binding of the CDIM binding proteins to the CDIM epitope of B lymphocytes can be used as a pharmaceutical in the disclosure. General details on techniques for formulation and administration are well described in the scientific literature (see, "Remington's Pharmaceutical Sciences", Maack Publishing Co, Easton Pa.). CDIM binding protein pharmaceutical formulations can be prepared according to any method known in the art for the manufacture of pharmaceuticals. The CDIM binding proteins can be formulated for administration in any conventionally acceptable way including via intravenous injection, intramuscular, intraperitoneal, orally, topically or through other routes. Illustrative examples are set forth below.

Pharmaceutical formulations for oral administration can be formulated using pharmaceutically acceptable carriers well known in the art in dosages suitable for oral administration. Such carriers enable the pharmaceutical formulations to be formulated in unit dosage forms as tablets, pills, powder, capsules, liquids, lozenges, gels, syrups, slurries, suspensions, and the like, suitable for ingestion by the patient. Pharmaceutical preparations for oral use can be obtained through combination of the CDIM binding proteins with a solid excipient, optionally grinding a resulting mixture, and processing the mixture of granules, after adding suitable additional compounds, if desired, to obtain tablets or pills. Suitable solid excipients are carbohydrate or protein fillers which include, but are not limited to, sugars, including lactose, sucrose, mannitol, or sorbitol; starch from corn, wheat, rice, potato, or other plants; cellulose such as methyl cellulose, hydroxypropylmethyl-cellulose, or sodium carboxymethylcellulose; and gums including arabic and tragacanth; as well as proteins such as gelatin and collagen. If desired, disintegrating or solubilizing agents may be added, such as the cross-linked polyvinyl pyrrolidone, agar, alginic acid, or a salt thereof, such as sodium alginate. Pharmaceutical preparations of the present disclosure that can also be used orally are, for example, push-fit capsules made of gelatin, as well as soft, sealed capsules made of gelatin and a coating such as glycerol or sorbitol. Push-fit capsules can contain the CDIM binding proteins mixed with a filler or binders such as lactose or starches, lubricants such as talc or magnesium stearate, and, optionally, stabilizers. In soft capsules, the CDIM binding proteins may be dissolved or suspended in suitable liquids, such as fatty oils, liquid paraffin, or liquid polyethylene glycol with or without stabilizers.

Aqueous suspensions of the disclosure contain the CDIM binding proteins in admixture with excipients suitable for the manufacture of aqueous suspensions. Such excipients include a suspending agent, such as sodium carboxymethylcellulose, methylcellulose, hydroxypropylmethylcellulose, sodium alginate, polyvinylpyrrolidone, gum tragacanth and gum acacia, and dispersing or wetting agents such as a naturally occurring phosphatide (e.g., lecithin), a condensation product of an alkylene oxide with a fatty acid (e.g., polyoxyethylene stearate), a condensation product of ethylene oxide with a long chain aliphatic alcohol (e.g., heptadecaethylene oxyethanol), a condensation product of ethylene oxide with a partial ester derived from a fatty acid and a hexitol (e.g., polyoxyethylene sorbitol mono-oleate), or a condensation product of ethylene oxide with a partial ester derived from fatty acid and a hexitol anhydride (e.g., polyoxyethylene sorbitan monooleate). The aqueous suspension can also contain one or more preservatives such as ethyl or n-propyl p-hydroxybenzoate, one or more coloring agents, one or more flavoring agents and one or more sweetening agents, such as sucrose, aspartame or saccharin. Formulations can be adjusted for osmolarity.

Oil suspensions can be formulated by suspending CDIM binding proteins in a vegetable oil, such as arachis oil, olive oil, sesame oil or coconut oil, or in a mineral oil such as liquid paraffin. The oil suspensions can contain a thickening agent, such as beeswax, hard paraffin or cetyl alcohol. Sweetening agents can be added to provide a palatable oral preparation. These formulations can be preserved by the addition of an antioxidant such as ascorbic acid.

Dispersible powders and granules of the disclosure suitable for preparation of an aqueous suspension by the addition of water can be formulated from the CDIM binding proteins in admixture with a dispersing, suspending and/or wetting agent, and one or more preservatives. Suitable dispersing or wetting agents and suspending agents are exemplified by those disclosed above. Additional excipients, for example sweetening, flavoring and coloring agents, can also be present.

The CDIM binding protein pharmaceutical formulations can also be in the form of oil-in-water emulsions. The oily phase can be a vegetable oil, such as olive oil or arachis oil, a mineral oil, such as liquid paraffin, or a mixture of these. Suitable emulsifying agents include naturally-occurring gums, such as gum acacia and gum tragacanth, naturally occurring phosphatides, such as soybean lecithin, esters or partial esters derived from fatty acids and hexitol anhydrides, such as sorbitan mono-oleate, and condensation products of these partial esters with ethylene oxide, such as polyoxyethylene sorbitan mono-oleate. The emulsion can also contain sweetening and flavoring agents. Syrups and elixirs can be formulated with sweetening agents, such as glycerol, sorbitol or sucrose. Such formulations can also contain a demulcent, a preservative, a flavoring or a coloring agent.

When the CDIM binding proteins are delivered by intravenous injection, the pharmaceutical formulations can be in the form of a sterile injectable preparation, such as a sterile injectable aqueous or oleaginous suspension. This suspension can be formulated according to the known art using those suitable dispersing or wetting agents and suspending agents, which have been mentioned above. The sterile injectable preparation can also be a sterile injectable solution or suspension in a nontoxic parenterally-acceptable diluent or solvent. Among the acceptable vehicles and solvents that can be employed are water and Ringer's solution, an isotonic sodium chloride. In addition, sterile fixed oils can conventionally be employed as a solvent or suspending medium. For this purpose any bland fixed oil can be employed including synthetic mono- or diglycerides. In addition, fatty acids such as oleic acid can likewise be used in the preparation of injectables.

The methods of the present disclosure treat human and non-human patients who suffer from lymphoid cancer or leukemia (e.g., B-cell acute lymphoblastic leukemia or ALL), any form of autoimmune disease involving B cells (e.g., rheumatoid arthritis, systemic lupus erythematosus or SLE), any form of B cell hyper-proliferation such as lymphomas and myelomas (e.g., non-Hodgkin's lymphomas), certain forms of solid tumors that express the CDIM antigen, and/or related conditions. The amount of CDIM binding protein that is adequate to accomplish this is considered the therapeutically effective dose. Alternatively, the amount of CDIM binding protein in combination with another agent or another drug that is adequate to accomplish this is also considered a therapeutically effective dose. Other agents are, for example, cytotoxic agents including, but not limited to, a radioactive isotope, a cytotoxic antibody, an immunoconjugate, a ligand conjugate, an immunosuppressant, a cell growth regulator and/or inhibitor, a toxin, or mixtures thereof. A chemotherapeutic agent or compound (see, also TABLE 1) is often an agent that interferes with the polymerization or depolymerization of microtubules such as a taxane, vinca alkaloid or colchicine, or mixtures thereof. The vinca alkaloid includes vinblastine, vincristine, vindesine, or vinorelbine, or mixtures thereof. The taxane includes, but is not limited to, paclitaxel, docetaxel, or mixtures thereof. The cytotoxic antibody that can be administered in combination with the disclosed antigen binding proteins usually has specific binding for a cell surface receptor on a B cell, including CD11a, CD19, CD20, CD21, CD22, CD25, CD34, CD37, CD38, CD40, CD45, CD52, CD80, CD 86, IL-4R, IL-6R, IL-8R, IL-13, IL-13R, $\alpha$-4/$\beta$-1 integrin (VLA4), BLYS receptor, cell surface idiotypic Ig, tumor necrosis factor (TNF), or mixtures thereof. As such, the cytotoxic antibody can be efalizumab (RAPTIVA), rituximab (RITUXAN), daclizumab (ZENAPAX), epratuzumab, basiliximab (SIMULECT), anti-CD52 (CAMPATH), natalizumab, infliximab (REMICADE), and the like. The immunosuppressant includes, but is not limited to, a glucocorticoid, a calcineurin inhibitor, an antiproliferative/antimetabolic agent, or an immunosuppressive antibody. In one embodiment, the agents are etoposide (VP-16), paclitaxel (taxol), ara-C (cytarabine), vincristine, nocodazole, colchisine, daunorubicin, cytochalasin, jasplakinolide, and the like.

In one embodiment of the present invention, at least one binding protein disclosed herein contained in the pharmaceutical composition is coupled to an effector, such as calicheamicin, Auristatin-PE, a radioisotope or a toxic chemotherapeutic agent such as geldanamycin and maytansine. In particular, these binding protein conjugates are useful in targeting cells, e.g., cancer cells, expressing CDIM for elimination.

Moreover, linking the binding proteins disclosed herein to radioisotopes provides advantages to tumor treatments. Unlike chemotherapy and other forms of cancer treatment, radioimmunotherapy or the administration of a radioisotope-binding protein combination directly targets the cancer cells with minimal damage to surrounding normal, healthy tissue. With this "magic bullet", the patient can be treated with much smaller quantities of radioisotopes than other forms of treatment available today. Certain radioisotopes include yttrium$^{90}$ ($^{90}$Y), indium$^{111}$ ($^{111}$In), $^{131}$I, $^{99}$mTc, radiosilver-111, radiogold-199, and Bismuth$^{213}$. The linkage of radioisotopes to binding proteins may e.g., be performed with conventional bifunctional chelates. Since silver and gold can exist in a monovalent state, for radiosilver-111 and radiogold-199 can utilize sulphur-based linkers may be used (Hazra et al. (1994) *Cell Biophys.* 24-25:1-7). Linkage of silver radioisotopes may involve reducing the immunoglobulin with ascorbic acid. Furthermore, tiuxetan is an MX-DTPA linker chelator attached to ibritumomab to form ibritumomab tiuxetan (Zevalin) (Witzig, T. E. (2001) *Cancer Chemother. Pharmacol.* 48 Suppl 1:91-5). Ibritumomab tiuxetan can react with radioisotypes such as indium$^{111}$ ($^{111}$In) or $^{90}$Y to form $^{111}$In-ibritumomab tiuxetan and $^{90}$Y-ibritumomab tiuxetan, respectively.

Furthermore, a binding protein disclosed herein, particularly when used to treat cancer, may be conjugated with toxic chemotherapeutic drugs such as calicheamicin (Hamann et al. (2002) *Bioconjug. Chem.* 13:40-46, geldanamycin (Mandler et al., (2002) *J. Natl. Cancer Inst.*, 92:1549-1951) and maytansine, for example, the maytansinoid drug, DM1 (Liu et al. (1996) *Proc. Natl. Acad. Sci. U.S.A.* 93:8618-8623). Different linkers that release the drugs under acidic or reducing conditions or upon exposure to specific proteases may be employed with this technology. According to the present invention, a binding protein disclosed herein may be conjugated as described in the art.

Auristatin-PE, e.g., is an antimicrotubule agent that is a structural modification of the marine, shell-less mollusk peptide constituent dolastatin 10. Auristatin-PE has both anti-tumor activity and anti-tumor vascular activity (Otani et al. (2000) *Jpn. J. Cancer Res.* 91:837-44). For example, auristatin-PE inhibits cell growth and induces cell cycle arrest and apoptosis in pancreatic cancer cell lines (Li et al. (1999) *Int. J. Mol. Med.* 3:647-653). Accordingly, to specifically target the anti-tumor activity and anti-tumor vascular activities of auristatin-PE to particular tumors, auristatin-PE may be conjugated to the binding protein disclosed herein.

The dosage schedule and amounts effective for this use, i.e., the "dosing regimen," will depend upon a variety of factors, including the stage of the disease or condition, the severity of the disease or condition, the severity of the adverse side effects, the general state of the patient's health, the patient's physical status, age and the like. In calculating the dosage regimen for a patient, the mode of administration is also taken into consideration. The dosage regimen must also take into consideration the pharmacokinetics, i.e., the rate of absorption, bioavailability, metabolism, clearance, and the like (see, for example, Liedtke et al. (2012) *Haematologica* 97(1):30-37).

The state of the art allows the clinician to determine the dosage regimen for each individual patient. CDIM binding proteins can be administered alone or in combination with other compounds. If administered in combination with other compounds, better patient responses and more durable outcomes would be expected. The combined compounds may act synergistically, or additively.

As an illustrative example, the guidelines provided below for CDIM binding proteins can be used as guidance to determine the dosage regimen, i.e., dose schedule and dosage levels, of any CDIM binding protein administered when practicing the methods disclosed herein. The clinical efficacy of CDIM binding proteins may be enhanced by the co-administration of a second compound such as vincristine or similar agent. Likewise, the efficacy of a small molecule chemotherapeutic may be enhanced by the co-administration with the CDIM antigen binding protein. CDIM binding proteins are effective in a dose range of about between 0.25 mg/kg to 100 mg/kg. Single or multiple administrations of CDIM binding protein formulations may be administered depending on the dosage and frequency as required and tolerated by the patient who suffers from lymphoid cancer or leukemia (e.g., B-cell acute lymphoblastic leukemia or ALL), any form of autoimmune disease involving B cells (e.g., rheumatoid arthritis, systemic lupus erythematosus or SLE), or any form of B cell hyperproliferation such as lymphomas and myelomas (e.g., non-Hodgkin's lymphomas) and/or related conditions. The formulations should provide a sufficient quantity of CDIM binding protein to effectively ameliorate the condition. For example, any one of the 44 antigen binding proteins disclosed herein may be administered to a patient through monotherapy (i.e., with no other medications) or in combination therapy with, for example, vincristine or other agents, see, supra). The antigen binding proteins having specific binding for the CDIM epitope on a B cell can be administered at a dose of from about 2.5 to about 3000 mg/m$^2$, or more preferably, from about 25 to 1000 mg/m$^2$, or in particular, about 75, 150, 300 or 600 mg/m$^2$. In additional aspects, the antibody is administered at a dose of from about 0.25 mg/kg to about 100 mg/kg, and more preferably, at about 1.25, 2.5, 5, 10, or 20 mg/kg. The anti-CDIM antibody is typically administered on a weekly basis, and in some embodiments, more frequently than once per week, as often as once per day. Additional cytotoxic antibodies can be administered in an amount of 10-375 mg/m$^2$ per week for four weeks, or 0.4-20 mg/kg per week for 2 to 10 weeks in form of a combination therapy. In one embodiment, CDIM binding proteins are currently administered to a patient daily as monotherapy in an amount from about 0.25 mg/kg to about 100 mg/kg. In another embodiment, CDIM binding proteins are administered to a patient daily in combination therapy with a second agent selected from the group consisting of vinblastine, vincristine, vindesine, vinorelbine, or mixtures thereof in an amount from about from about 0.15 mg/kg to about 50 mg/kg.

Notably, the dosages of selective CDIM binding proteins administered to a patient may vary depending on age, degree of illness, drug tolerance, and concomitant medications and conditions. The CDIM binding proteins may be administered to the patient in combination with another drug in order to potentiate the effect of the CDIM binding proteins and in order to reduce adverse side effects. Using a second drug, the activity of co-administration of CDIM binding proteins may be enhanced by between 10% and 90% and the combination therapy will continue until the combination treatment is no longer deemed beneficial or necessary. The CDIM binding proteins may be administered to a patient simultaneously or within specific time frames of one another. Different CDIM binding proteins can be administered to the patient simultaneously in separate pills or tablets or in the form of a combination pill.

Disorders and Diseases

The CDIM binding proteins of the present disclosure can be used to treat patients who suffer from lymphoid cancer or leukemia, any form of autoimmune disease involving B, or any form of B cell hyperproliferation such as acute or chronic leukemia, lymphomas and myelomas, and/or related disorders. Any condition that is characterized by a hyperproliferation of B cells including lymphoid cancer, viral infection, immunodeficiency, or autoimmune disease can be treated with the CDIM binding proteins. Similarly, any tumor cell or cancer cell that expresses the CDIM epitope or a CDIM-like antigen can be treated with the CDIM binding proteins.

The disclosure provides improved CDIM binding proteins for selective B cell killing and depleting in disorders related to autoimmunity including, but not limited to, multiple sclerosis, rheumatoid arthritis, systemic lupus erythematosus (SLE), Myasthenia gravis, Pemphigus vulgaris, Grave's disease and autoimmune thrombocytopaenia. Autoreactive B cells secrete autoantibodies directed against self-proteins. B lymphocytes not only produce autoantibodies but also play an important regulatory role independent of their function as antibody-producing cells. This is relevant with respect to autoimmunity, since autoreactive B cells have the ability to activate pathogenic T cells to produce pro-inflammatory cytokines. Myasthenia gravis, Pemphigus vulgaris, Grave's disease and autoimmune thrombocytopaenia are good examples of conditions in which pathogenic antibodies drive the clinical phenotype (see, Browning, J. F, supra). In addition, autoimmune disorders lead to overactive and increased numbers of B cells that should be removed in order to prevent massive inflammation and tissue damage. Thus, the depletion of B lymphocytes is useful in the treatment of such autoimmune diseases. Since the treatment of many rheumatic autoimmune diseases such as rheumatoid arthritis relies primarily on the use of cytotoxic immunosuppressants and corticosteroids patients often suffer additional severe side effects. In addition, patient relapse rates remain high. There is a need for safer and more effective drugs such as the CDIM binding proteins of the present disclosure.

A lymphoid cancer is any acute or chronic leukemia or lymphoma of B cell origin, including, but not limited to, acute lymphocytic leukemia (ALL), non-Hodgkins lymphoma (NHL), Burkitt's lymphoma, B progenitor ALL, adult ALL, chronic lymphocytic leukemia (CLL), and Waldenstrom's macroglobulinaemia. The CDIM binding proteins bind to the epitope CDIM, which is found on cancerous B cells.

In order to allow prediction of patients who will respond to treatment with the disclosed CDIM antigen binding proteins, in vitro or in vivo analysis may be performed. In vivo imaging may be performed prior to treatment by administering CDIM antigen binding proteins as a conjugate which allows visualization of the CDIM antigen on the tissue of interest. A particular level of reactivity may be established that would allow prediction of patient response to therapy. Alternatively, this type of analysis may help in establishing dosing parameters based on tumor load. In vitro analysis may be performed on samples of patient's lymphoid cells (peripheral blood, bone marrow or other) prior to treatment. Cells will be stained with CDIM antigen binding proteins using standard flow cytometric analysis. A cut-off will be established that allows prediction of positive outcome following therapy. For example, a minimal mean fluorescence intensity may be established which predicts positive outcome.

V. EXAMPLES

The following specific examples are intended to illustrate the disclosure and should not be construed as limiting the scope of the claims.

Example 1

Generation and Sequence Determination of Exemplary CDIM Binding Proteins

Plasmid DNA Construction.

All the H series mu chain constructs variable heavy regions (designated H1-H22) were synthesized by Genscript with XbaI-KpnI sites on the 5' and 3' ends respectively. All the H series Mu chain constructs were assembled by isolating each of heavy chain variable regions as XbaI-KpnI fragments and joining them in a three-part ligation with a KpnI-BamH1 fragment spanning the constant mu region together with the expression vector AB11 that had been digested with XbaI and BamH1. The ligated plasmids were transformed into competent bacteria. The resulting cloned plasmids were confirmed by direct sequencing. Plasmid midi-preps were generated using Qiagen, to provide adequate amounts of DNA for transfection into CHO-S cells.

The light chain plasmid were constructed in a similar fashion. The lambda insert was cloned in a three part ligation; the variable lambda region was designed as a XbaI-EcoRI fragment, which was mixed with the EcoRI-BamHI lambda constant region fragment and ligated into the AB2 vector between XbaI and BamHI sites. The L2 kappa insert was isolated as a XbaI-BamHI fragment and ligated into the AB2-Kappa vector.

Transfection of CHO-S Cells with the H1-H22/L2 Plasmid DNA.

DNA corresponding to heavy and light chains, was prepared for co-transfection (equal amounts of L2 and of H1-22) using the PEI technique. CHO-S cells ($1E^8$ of log phase growth) used for transfection were grown in RPMI1640 media. DNA:PEI was mixed 1:2 and this DNA:PEI mixture was added to CHO-S cells in CD OptiCHO supplemented with 0.5× Pen/Strep, Glutamax and HT. After overnight incubation in shaker flask, the media was exchanged into CD OptiCHO with 0.5×P/S, Glu. On day 7 post-transfection, the cell culture supernatant (100 ml) was harvested by centrifugation of the cells. For characterization of these IgM examples, 15 ml of cell culture supernatant was concentrated 10× by Centricon.

The amino acid sequences of the 22 distinct heavy chain variable regions are depicted in FIGS. 1A-D. The amino acid sequences of the 2 distinct light chain variable regions are depicted in FIG. 1E. The amino acid sequences of the constant regions of the heavy and light chains are shown in FIG. 1F. It is understood that either kappa or lambda constant regions can be utilized. The amino acid sequences that are representative of the identified and isolated CDIM binding proteins, IGM1-IGM44, shown in FIGS. 2A-2V. The CDR3 sequences of H1 through H22 are depicted in FIG. 3.

Examples of polynucleotide sequences that could be used to encode the 44 disclosed CDIM binding proteins are depicted in FIGS. 4A-L. It is understood that due to degeneracy in the genetic code, other sequences could be utilized to encode the exact amino acid sequence. The sequences of the various complementarity determining regions (CDRHs) and framework (FR) regions of the heavy chain variable region of the antibodies were determined include framework 1 (FR1), complementarity determining region 1 (CDRH1), framework 2 (FR2), complementarity determining region 2 (CDRH2), framework 3 (FR3) and complementarity determining region 3 (CDRH3).

Example 2

Making of CDIM Binding Proteins

This example describes how some of the disclosed binding proteins were made. Sequences consisted of heavy and light chain variable region variants (both kappa and lambda constant regions were encoded). Specific combinations of heavy and light chain variants were transfected into CHO cells, i.e., DG44 CHO cells and transient transfections were made. Expression levels of 10-100 µg/ml were obtained from the initial transfections. IgM antibodies were purified by affinity chromatography, evaluated by gel electrophoresis and tested for bioactivity by cell binding, cytotoxicity assays and ELISA testing for binding to multiple biomolecules. Results obtained from the functional assays were used to guide lead candidate selection. Once selected, the lead candidates were stably transfected into CHO cells and sub-cloned into 20 plates (approximately 2000 wells) and screened by ELISA for highest level of secretion. The top 50 clones were expanded to T75 flasks followed expansion of the best 24 clones being transferred into shaker flasks. IgM from these 24 clones were purified and quantified and the top six clones (selected by IgM antibody secretion levels) were grown under further selection in methotrexate (50 nM, 100 nM, 200 nM, 400 nM) to facilitate outgrowth of high secreting cell lines.

Example 3

Evaluation of IgM Expression Using Non-Reduced SDS-PAGE

Non-reducing gel electrophoresis is a separation method typically used in proteomics and resolves proteins based on molecular mass and oligomeric structures. Under non-reducing conditions, protein disulfide bonds are left intact and so the IgM oligomer can be resolved as pentameric or hexameric structures.

To confirm IgM antibody expression by transient transfection of CHO-S cell supernatant, we performed non-reducing SDS polyacrylamide gel electrophoresis as described in Vorauer-Uhl, et al, J. Immunol. Methods 359 (2010): 21-27. This example describes how transiently transfected IgM mAbs were investigated for purity and multimeric structure. Protein sample of interest is incubated with NuPage SDS sample buffer for 5 minutes at room temperature. After incubation, the molecular weight standards and test samples are loaded onto the gel and run at 100V constant voltage for approximately 2 hours until dye front reaches the bottom of the gel. After electrophoresis, the gel is removed from XCell Mini-Cell apparatus, fixed and stained with Colloidal Blue dye.

To demonstrate pentamer and hexamer formation, non-reducing SDS PAGE of concentrated supernatant of CHO cells, transfected with the various CDIM binding protein samples (L1-L7, and L9-L21, respectively), was performed using SDS PAGE, Life Technologies' (Carlsbad, Calif.) Native Page Novex 3-12% Bis-Tris gels.

FIG. 5 shows the SDS gel stained according to the Colloidal Blue Staining protocol (Life Technologies, Carlsbad, Calif.), with a prominent band at 1,048 kD, which represents the IgM pentamers, and a prominent band at 1,236 kD, which represents the IgM hexamers. As can be seen in the figure, pentamer formation for the IgM examples (solid arrow) is more dominant compared with hexamer formation. Similarly, the isolated human IgM 216 is predominately of pentameric form (dashed arrow), however, it appears as a lower molecular weight due to the smaller lambda light chains included in this IgM format.

Example 4

Binding of CDIM Binding Proteins to CDIM Antigen

This example describes how the binding properties of the disclosed antibodies were investigated. The antibodies were prepared by affinity chromatography. In FIG. 6A, the human pro-B cell line, NALM-6, which expresses the CDIM antigen on the cell surface was stained with the series of recombinant IgM antibodies. The antibodies were used to determine the dose response beginning at 20 µg/tube diluted stepwise by 2, to a final concentration at 0.039 µg. Cells were stained in a 100 µl volume in 3% FBS/PBS on ice for 1 hour followed by a subsequent staining with DyLight-488 conjugated anti-human IgM (Jackson Immuno), 1 µg/ml for 20 minutes at 4 C.

Analysis of CDIM binding was performed on FACScan flow cytometer using CellQuest analysis software. Results are shown as raw data points with Mean Fluorescence Intensity (MFI) on Y-axis and concentration of primary antibody (µg/100 µl) on X-axis.

The data were re-analyzed using GraphPad analysis program to fit the results using non-linear regression curve fit. $EC_{50}$ (µg/100 µl) for each antibody was (a) 10.6 for IGM1, (b) 2.2 for IGM23, (c) 2.2 for IGM34, and (d) 1.7 for IGM36.

Example 5

Cytotoxicity Resulting from Cellular Binding of CDIM Binding Proteins

This example describes how the cytotoxicity of the CDIM binding proteins was investigated. The human pro-B cell line NALM-6 was stained identically as described in FIG. 6A above. In FIG. 6B, cell killing was evaluated by measuring cell viability after 1 hour of staining. By quantifying the proportion of cells that did not uptake propidium iodine, the percentage of viable cells was calculated. Results are shown as raw data with % viability on Y-axis and concentration (µg/100 µl) on X-axis.

Identical results were graphed using GraphPad analysis program and data fit using non-linear regression curve fitting. The $EC_{50}$ was calculated for each antibody using the same approach described above. $EC_{50}$ (µg/100 µl) for each antibody was (a) 3.0 for IGM1, (b) 0.6 for IGM 23, (c) 0.6 for IGM34, and (d) 0.3 for IGM36.

Results from FIGS. 6A and 6B show that the disclosed antibodies bind human B cells across a broad dose range and that these antibodies are cytotoxic for B cells resulting in cellular death.

Example 6

Cytotoxicity Resulting from Human Complement Dependent Cytotoxicity Assay of CDIM Binding Proteins "Complement-dependent cytotoxicity" or "CDC" refers to the lysis of a target cell in the presence of complement. Activation of the classical complement pathway is initiated by the binding of the first component of the complement system (CIq) to antibodies, which are bound to their cognate antigen. To assess complement activation, a CDC assay, as described in Hinton et al, J. Immunol. 2006 Jan. 1; 176(1): 346-56, may be performed. Briefly, this example describes how the cytotoxicity of the CDIM binding proteins was investigated. Human pro-B NALM-6 cells (50,000) were plated in a 96-well flat bottom microtiter plate. Human complement is added at the optimal tested dilution with or without a serial dilution of supernatant containing expressed antibody of interest. After 24 hours, a colorimetric substrate CCK8 was added for 3 hours and then the optical density (OD) was measured at 450 nm wavelength on a Microtiter Plate Reader. Quantification of the increase in OD is directly proportional to viable proliferating NALM-6 cells. The OD of untreated Nalm6 without supernatant is then used to calculate 100%, with supernatant OD values normalized accordingly to obtain viability percentages. In FIG. 8, the results are shown as percent viability on plotted on the Y-axis versus antibody containing concentration of supernatant (ug/ml) on X-axis. These results were analyzed using the GraphPad program and data were modeled using four parameter, non-linear regression curve fitting. The IC50 was calculated for each antibody using the same approach as described above.

Example 7

Binding of CDIM Binding Proteins to Non-CDIM Antigens

This example describes the binding specificity of the CDIM binding proteins for antigens other than CDIM. The antibodies were purified by affinity chromatography. Antibodies were tested across a broad dose range against a panel of antigens available in commercially available ELISA kits. ELISA plates pre-coated with the antigens, ssDNA (Inova Diagnostics, Inc, San Diego, Calif.), dsDNA (Inova Diagnostics, Inc., San Diego, Calif.), cardiolipin (Inova Diagnostics, Inc., San Diego, Calif.) MDA-LDL (malondialdehyde modified low density lipoprotein) (Rocky Mountain Diagnostics, Colorado Springs, Colo.) were purchased from various vendors. Lipid A (Avanti Polar Lipids, Alabaster, Ala.) was purchased as an antigen, dissolved in ethanol and diluted in 100 mM Na carbonate buffer at pH 9.5 prior to coating onto ELISA plates. Anti-CDIM antibodies were used at concentrations indicated and ELISA was performed according to manufacturers recommendations. Briefly, plates were blocked with BSA-milk powder for 1 hour, followed by washing. The disclosed antibodies were added at the concentrations indicated. The antibodies were allowed to bind for 1.5 hours at room temperature followed by a wash step. The HRP-conjugated anti-human IgM antibody was added, followed by substrate addition. Results were quantified using absorbance at 450 nm (Bio-Tek Synergy HT). As shown in FIGS. 8 and 9, MAb 216 binds to all the antigens tested while each of the disclosed antibodies show either decreased binding (i.e., ssDNA) or complete elimination of specificity for the antigen (i.e., cardiolipin). These results demonstrate that the disclosed antibodies have more restricted antigen binding specificities than MAb 216.

TABLE 2 summarizes the potency and specificity characteristics of the various CDIM binding proteins disclosed herein.

TABLE 2

Summary of Name and Characteristics of the Various Samples

| Example | ELISA (µg/ml) | Cytotoxicity IC50 (ng/ml) | LPS | ss DNA | ds DNA | Cardio-lipin | Chondroitin Sulfate | Heparan Sulfate |
|---|---|---|---|---|---|---|---|---|
| hm216 | 71 | 1762 | ++++ | ++++ | ++++ | +++ | ++++ | ++++ |
| H1 | 66 | 47 | + | + | + | + | + | + |
| H2 | 61 | 49 | − | − | − | − | + | + |
| H3 | 27 | 1762 | − | − | − | − | + | ++ |
| H4 | 44 | 66 | − | − | − | − | + | − |
| H5 | 82 | 190 | − | − | − | − | + | + |
| H7 | 88 | 60 | − | + | − | − | + | + |
| H8 | 50 | 150 | − | + | ++ | ++ | ++ | ++ |
| H9 | 201 | 29 | + | + | − | + | + | ++ |
| H12 | 223 | 46 | − | + | − | + | − | + |
| H13 | 74 | 128 | − | + | − | +++ | ++ | +++ |
| H14 | 72 | 184 | + | + | − | ++ | + | ++ |
| H16 | 79 | 30 | − | − | − | + | − | − |
| H17 | 46 | 194 | + | − | + | ++ | + | + |
| H18 | 185 | 33 | + | + | − | + | + | ++ |
| H21 | 136 | 42 | − | − | − | + | − | + |

TABLE 2 summarizes the data shown in FIG. 6 and FIGS. 7A-7F for the CDIM binding proteins comprising variable heavy chains H1, H2, H3, H4, H5, H6, H7, H9, H10, H11, H12, H13, H14, H15, H16, H17, H18, H19, H20, and H21, respectively. The ELISA value refers to the concentration of IgM determined in the conditioned media following transient transfection of IgM heavy and light chains. The cytotoxicity $IC_{50}$ is the half-maximal concentration of IgM antibody that results in 50% cell death upon incubation of antibodies, with human complement and Nalm-6 cells (see, also FIG. 6). The $IC_{50}$ value represents the potency of the various CDIM binding proteins disclosed herein.

The additional binding to other antigens (LPS, ssDNA, dsDNA, etc.) is the binding observed in ELISA format (see, also, FIGS. 9A-9F). The relative reactivity of IgM samples to various antigens is based on the maximal reaction ($OD_{450}$ nm) when the IgM is at 10 µg/ml. The values shown represent the values of non-specificity of the various CDIM binding proteins. The scoring of relative reactivity is as follows: $OD_{450}$ is 0 to 0.3, the score is given as (−) minus. The (+), (++), (+++) and (++++) scores are given for maximal ELISA values of 0.3 to 1, 1 to 2, 2 to 3 and above 3, respectively.

Various modifications and variations of the present disclosure will be apparent to those skilled in the art without departing from the scope and spirit of the disclosure. Although the disclosure has been described in connection with specific embodiments, it should be understood that the claims should not be unduly limited to such specific embodiments. Indeed, various modifications of the described modes for carrying out the disclosure, which are understood by those skilled in the art are intended to be within the scope of the claims.

TABLE 3A

| | CDIM BINDING PROTEIN: POLYPEPTIDES | | | | | |
|---|---|---|---|---|---|---|
| Name of Antibody | Heavy Chain Variable Region Polypeptide Sequence ID Number (SEQ ID NO) | Light Chain Variable Region Polypeptide Sequence ID Number (SEQ ID NO) | Heavy Chain Constant Region Polypeptide Sequence ID Number (SEQ ID NO) | Light Chain Constant Region Polypeptide Sequence ID Number (SEQ ID NO) | Complete Heavy Chain Polypeptide Sequence ID Number (SEQ ID NO) | Complete Light Chain Polypeptide Sequence ID Number (SEQ ID NO) |
| IGM1 | 1 | 23 | 25 | 26 (lambda) | 28 | 50 |
| IGM2 | 2 | 23 | 25 | 26 (lambda) | 29 | 50 |
| IGM3 | 3 | 23 | 25 | 26 (lambda) | 30 | 50 |
| IGM4 | 4 | 23 | 25 | 26 (lambda) | 31 | 50 |
| IGM5 | 5 | 23 | 25 | 26 (lambda) | 32 | 50 |
| IGM6 | 6 | 23 | 25 | 26 (lambda) | 33 | 50 |
| IGM7 | 7 | 23 | 25 | 26 (lambda) | 34 | 50 |
| IGM8 | 8 | 23 | 25 | 26 (lambda) | 35 | 50 |
| IGM9 | 9 | 23 | 25 | 26 (lambda) | 36 | 50 |
| IGM10 | 10 | 23 | 25 | 26 (lambda) | 37 | 50 |
| IGM11 | 11 | 23 | 25 | 26 (lambda) | 38 | 50 |
| IGM12 | 12 | 23 | 25 | 26 (lambda) | 39 | 50 |
| IGM13 | 13 | 23 | 25 | 26 (lambda) | 40 | 50 |
| IGM14 | 14 | 23 | 25 | 26 (lambda) | 41 | 50 |
| IGM15 | 15 | 23 | 25 | 26 (lambda) | 42 | 50 |
| IGM16 | 16 | 23 | 25 | 26 (lambda) | 43 | 50 |
| IGM17 | 17 | 23 | 25 | 26 (lambda) | 44 | 50 |
| IGM18 | 18 | 23 | 25 | 26 (lambda) | 45 | 50 |
| IGM19 | 19 | 23 | 25 | 26 (lambda) | 46 | 50 |
| IGM20 | 20 | 23 | 25 | 26 (lambda) | 47 | 50 |
| IGM21 | 21 | 23 | 25 | 26 (lambda) | 48 | 50 |
| IGM22 | 22 | 23 | 25 | 26 (lambda) | 49 | 50 |
| IGM23 | 1 | 24 | 25 | 27 (kappa) | 28 | 51 |
| IGM24 | 2 | 24 | 25 | 27 (kappa) | 29 | 51 |
| IGM25 | 3 | 24 | 25 | 27 (kappa) | 30 | 51 |
| IGM26 | 4 | 24 | 25 | 27 (kappa) | 31 | 51 |
| IGM27 | 5 | 24 | 25 | 27 (kappa) | 32 | 51 |
| IGM28 | 6 | 24 | 25 | 27 (kappa) | 33 | 51 |
| IGM29 | 7 | 24 | 25 | 27 (kappa) | 34 | 51 |
| IGM30 | 8 | 24 | 25 | 27 (kappa) | 35 | 51 |
| IGM31 | 9 | 24 | 25 | 27 (kappa) | 36 | 51 |
| IGM32 | 10 | 24 | 25 | 27 (kappa) | 37 | 51 |
| IGM33 | 11 | 24 | 25 | 27 (kappa) | 38 | 51 |
| IGM34 | 12 | 24 | 25 | 27 (kappa) | 39 | 51 |
| IGM35 | 13 | 24 | 25 | 27 (kappa) | 40 | 51 |
| IGM36 | 14 | 24 | 25 | 27 (kappa) | 41 | 51 |
| IGM37 | 15 | 24 | 25 | 27 (kappa) | 42 | 51 |
| IGM38 | 16 | 24 | 25 | 27 (kappa) | 43 | 51 |
| IGM39 | 17 | 24 | 25 | 27 (kappa) | 44 | 51 |
| IGM40 | 18 | 24 | 25 | 27 (kappa) | 45 | 51 |
| IGM41 | 19 | 24 | 25 | 27 (kappa) | 46 | 51 |
| IGM42 | 20 | 24 | 25 | 27 (kappa) | 47 | 51 |
| IGM43 | 21 | 24 | 25 | 27 (kappa) | 48 | 51 |
| IGM44 | 22 | 24 | 25 | 27 (kappa) | 49 | 51 |

TABLE 3B

HEAVY CHAIN CDR SEQUENCES

| Antibody/ Heavy Chain Designation | Heavy Chain CDR1 Sequence | Heavy Chain CDR1 SEQ ID NO) | Heavy Chain CDR2 Sequence | Heavy Chain CDR2 SEQ ID NO | Heavy Chain CDR3 Sequence | Heavy Chain CDR3 SEQ ID NO |
|---|---|---|---|---|---|---|
| IGM1 (H1) | FSGYYWS | 76 | EINHSGSTNYNPSLKS | 77 | GRMAWGASVN | 78 |
| IGM2 (H2) | FSGYYWS | 76 | EINHSGSTNYNPSLKS | 77 | GRRAWGASVN | 79 |
| IGM3 (H3) | FSGYYWS | 76 | EINHSGSTNYNPSLKS | 77 | GRMARGASVN | 80 |
| IGM4 (H4) | FSGYYWS | 76 | EINHSGSTNYNPSLKS | 77 | GRRARGASVN | 81 |
| IGM5 (H5) | FSGYYWS | 76 | EINHSGSTNYNPSLKS | 77 | RGMAWGASVN | 82 |
| IGM6 (H6) | FSGYYWS | 76 | EINHSGSTNYNPSLKS | 77 | RRMAWGASVN | 83 |
| IGM7 (H7) | FSGYYWS | 76 | EINHSGSTNYNPSLKS | 77 | RGMARGASVN | 84 |
| IGM8 (H8) | FSGYYWS | 76 | EINHSGSTNYNPSLKS | 77 | RGRARGASVN | 85 |
| IGM9 (H9) | FSGYYWS | 76 | EINHSGSTNYNPSLKS | 77 | RRGARGASVN | 86 |
| IGM10 (H10) | FSGYYWS | 76 | EINHSGSTNYNPSLKS | 77 | AGRAWGASVN | 87 |
| IGM11 (H11) | FSGYYWS | 76 | EINHSGSTNYNPSLKS | 77 | RGRAWGASVN | 88 |
| IGM12 (H12) | FSGYYWS | 76 | EINHSGSTNYNPSLKS | 77 | ARTAWGSSI | 89 |
| IGM13 (H13) | FSGYYWS | 76 | EINHSGSTNYNPSLKS | 77 | ARRAWGSSI | 90 |
| IGM14 (H14) | FSGYYWS | 76 | EINHSGSTNYNPSLKS | 77 | ARTARGSSI | 91 |
| IGM15 (H15) | FSGYYWS | 76 | EINHSGSTNYNPSLKS | 77 | ARRARGSSI | 92 |
| IGM16 (H16) | FSGYYWS | 76 | EINHSGSTNYNPSLKS | 77 | RATAWGSSI | 93 |
| IGM17 (H17) | FSGYYWS | 76 | EINHSGSTNYNPSLKS | 77 | RRTAWGSSI | 94 |
| IGM18 (H18) | FSGYYWS | 76 | EINHSGSTNYNPSLKS | 77 | RATARGSSI | 94 |
| IGM19 (H19) | FSGYYWS | 76 | EINHSGSTNYNPSLKS | 77 | RARARGSSI | 95 |
| IGM20 (H20) | FSGYYWS | 76 | EINHSGSTNYNPSLKS | 77 | RRTARGSSI | 97 |
| IGM21 (H21) | FSGYYWS | 76 | EINHSGSTNYNPSLKS | 77 | GARAWGSSI | 98 |
| IGM22 (H22) | FSGYYWS | 76 | EINHSGSTNYNPSLKS | 77 | RARAWGSSI | 99 |
| IGM23 (H1) | FSGYYWS | 76 | EINHSGSTNYNPSLKS | 77 | GRMAWGASVN | 78 |
| IGM24 (H2) | FSGYYWS | 76 | EINHSGSTNYNPSLKS | 77 | GRRAWGASVN | 79 |
| IGM25 (H3) | FSGYYWS | 76 | EINHSGSTNYNPSLKS | 77 | GRMARGASVN | 80 |
| IGM26 (H4) | FSGYYWS | 76 | EINHSGSTNYNPSLKS | 77 | GRRARGASVN | 81 |
| IGM27 (H5) | FSGYYWS | 76 | EINHSGSTNYNPSLKS | 77 | RGMAWGASVN | 82 |
| IGM28 (H6) | FSGYYWS | 76 | EINHSGSTNYNPSLKS | 77 | RRMAWGASVN | 83 |
| IGM29 (H7) | FSGYYWS | 76 | EINHSGSTNYNPSLKS | 77 | RGMARGASVN | 84 |
| IGM30 (H8) | FSGYYWS | 76 | EINHSGSTNYNPSLKS | 77 | RGRARGASVN | 85 |
| IGM31 (H9) | FSGYYWS | 76 | EINHSGSTNYNPSLKS | 77 | RRGARGASVN | 86 |
| IGM32 (H10) | FSGYYWS | 76 | EINHSGSTNYNPSLKS | 77 | AGRAWGASVN | 87 |
| IGM33 (H11) | FSGYYWS | 76 | EINHSGSTNYNPSLKS | 77 | RGRAWGASVN | 88 |
| IGM34 (H12) | FSGYYWS | 76 | EINHSGSTNYNPSLKS | 77 | ARTAWGSSI | 89 |
| IGM35 (H13) | FSGYYWS | 76 | EINHSGSTNYNPSLKS | 77 | ARRAWGSSI | 90 |
| IGM36 (H15) | FSGYYWS | 76 | EINHSGSTNYNPSLKS | 77 | ARTARGSSI | 91 |

TABLE 3B-continued

HEAVY CHAIN CDR SEQUENCES

| Antibody/ Heavy Chain Designation | Heavy Chain CDR1 Sequence | Heavy Chain CDR1 SEQ ID NO) | Heavy Chain CDR2 Sequence | Heavy Chain CDR2 SEQ ID NO | Heavy Chain CDR3 Sequence | Heavy Chain CDR3 SEQ ID NO |
|---|---|---|---|---|---|---|
| IGM37 (H15) | FSGYYWS | 76 | EINHSGSTNYNPSLKS | 77 | ARRARGSSI | 92 |
| IGM38 (H16) | FSGYYWS | 76 | EINHSGSTNYNPSLKS | 77 | RATAWGSSI | 93 |
| IGM39 (H17) | FSGYYWS | 76 | EINHSGSTNYNPSLKS | 77 | RRTAWGSSI | 94 |
| IGM40 (H18) | FSGYYWS | 76 | EINHSGSTNYNPSLKS | 77 | RATARGSSI | 94 |
| IGM41 (H19) | FSGYYWS | 76 | EINHSGSTNYNPSLKS | 77 | RARARGSSI | 95 |
| IGM42 (H20) | FSGYYWS | 76 | EINHSGSTNYNPSLKS | 77 | RRTARGSSI | 97 |
| IGM43 (H21) | FSGYYWS | 76 | EINHSGSTNYNPSLKS | 77 | GARAWGSSI | 98 |
| IGM44 (H22) | FSGYYWS | 76 | EINHSGSTNYNPSLKS | 77 | RARAWGSSI | 99 |

TABLE 3C

LIGHT CHAIN CDR SEQUENCES

| Light Chain SEQ IG NO. | Light Chain CDR1 Sequence | Light Chain CDR1 SEQ ID NO | Light Chain CDR2 Sequence | Light Chain CDR2 SEQ ID NO | Light Chain CDR3 Sequence | Light Chain CDR3 SEQ ID NO |
|---|---|---|---|---|---|---|
| 23 (Used with lambda light chain constant region) | TGTSSDVGGYNYVS | 100 | GVSNRFS | 102 | SSYTSSSTL | 104 |
| 24 (Used with kappa light chain region) | RASQSISSYLN | 101 | AASSLQS | 103 | QQSYSTP | 105 |

TABLE 4

POLYNUCLEOTIDES

| Name of Antibody | Heavy Chain Variable Region Polynucleotide Sequence ID Number (SEQ ID NO) | Light Chain Variable Region Polynucleotide Sequence ID Number (SEQ ID NO) |
|---|---|---|
| IGM1 | 52 | 74 |
| IGM2 | 53 | 74 |
| IGM3 | 54 | 74 |
| IGM4 | 55 | 74 |
| IGM5 | 56 | 74 |
| IGM6 | 57 | 74 |
| IGM7 | 58 | 74 |
| IGM8 | 59 | 74 |
| IGM9 | 60 | 74 |
| IGM10 | 61 | 74 |
| IGM11 | 62 | 74 |
| IGM12 | 63 | 74 |
| IGM13 | 64 | 74 |
| IGM14 | 65 | 74 |
| IGM15 | 66 | 74 |
| IGM16 | 67 | 74 |
| IGM17 | 68 | 74 |
| IGM18 | 69 | 74 |
| IGM19 | 70 | 74 |
| IGM20 | 71 | 74 |
| IGM21 | 72 | 74 |
| IGM22 | 73 | 74 |
| IGM23 | 52 | 75 |
| IGM24 | 53 | 75 |
| IGM25 | 54 | 75 |
| IGM26 | 55 | 75 |
| IGM27 | 56 | 75 |
| IGM28 | 57 | 75 |
| IGM29 | 58 | 75 |
| IGM30 | 59 | 75 |
| IGM31 | 60 | 75 |
| IGM32 | 61 | 75 |
| IGM33 | 62 | 75 |
| IGM34 | 63 | 75 |
| IGM35 | 64 | 75 |
| IGM36 | 65 | 75 |
| IGM37 | 66 | 75 |
| IGM38 | 67 | 75 |
| IGM39 | 68 | 75 |
| IGM40 | 69 | 75 |

TABLE 4-continued

POLYNUCLEOTIDES

| Name of Antibody | Heavy Chain Variable Region Polynucleotide Sequence ID Number (SEQ ID NO) | Light Chain Variable Region Polynucleotide Sequence ID Number (SEQ ID NO) |
|---|---|---|
| IGM41 | 70 | 75 |
| IGM42 | 71 | 75 |
| IGM43 | 72 | 75 |
| IGM44 | 73 | 75 |

What is claimed is:

1. An isolated antibody or antigen-binding fragment thereof that binds to the linear B cell lactosamine antigen CDIM, comprising:
   (a) a heavy chain comprising a CDRH1 having the sequence shown in SEQ ID NO:76, a CDRH2 having the sequence shown in SEQ ID NO:77, and a CDRH3 having the sequence shown in any one of SEQ ID NOS: 78-90, 92-98, or 99; and
   (b) a light chain comprising (i) a CDRL1 having the sequence shown in SEQ ID NO:100, a CDRL2 having the sequence shown in SEQ ID NO: 102 and a CDRL3 having the sequence shown in SEQ ID NO: 104, or (ii) a CDRL1 having the sequence shown in SEQ ID NO:101, a CDRL2 having the sequence shown in SEQ ID NO:103, and a CDRL3 having the sequence shown in SEQ ID NO: 105.

2. The isolated antibody or an antigen-binding fragment thereof of claim 1, which does not cross-react with single stranded DNA (ssDNA), double stranded DNA (dsDNA), lipopolysaccharide, cardiolipin, chondroitin, and heparan.

3. The isolated antibody or an antigen-binding fragment thereof of claim 1, further comprising: a heavy chain comprising a framework 1 (FR1) shown in any of SEQ ID NOS: 1-22.

4. An isolated antigen binding protein that binds to the linear B cell lactosamine antigen CDIM, comprising a heavy chain variable region sequence selected from the group consisting of SEQ ID NOS: 1, 2, 3, 4, 5, 6, 7, 8, 9, 10, 11, 12, 13, 15, 16, 17, 18, 19, 20, 21, and 22, and a light chain variable region sequence selected from the group consisting of SEQ ID NOS:23 and 24.

5. An isolated antigen binding protein that binds to the linear B cell lactosamine antigen CDIM, comprising: (a) a heavy chain variable region selected from the group consisting of SEQ ID NO:1, SEQ ID NO:2, and SEQ ID NO:12; and (b) a light chain variable region selected from the group consisting of SEQ ID NO:23 and SEQ ID NO:24.

6. The isolated antibody or an antigen-binding fragment thereof of claim 1, wherein the antibody is a monoclonal antibody, a polyclonal antibody, a recombinant antibody, a human antibody, a humanized antibody, a chimeric antibody, or a multi-specific antibody.

7. The isolated antibody or an antigen-binding fragment thereof of claim 1, wherein the antigen-binding fragment is a Fab fragment, a Fab' fragment, a F(ab)2 fragment, a Fv fragment, a diabody, or a single chain antibody molecule.

8. The isolated antibody or an antigen-binding fragment thereof of claim 6, wherein the antibody is a human antibody.

9. The isolated antibody or an antigen-binding fragment thereof of claim 6, wherein the antibody is a monoclonal antibody.

10. The isolated antibody or an antigen-binding fragment thereof of claim 6, wherein the antibody has an isotype selected from the group consisting of IgA, IgD, IgM, IgG, and IgE.

11. The isolated antibody or an antigen-binding fragment thereof of claim 10, wherein the antibody is an IgM.

12. The isolated antibody or an antigen-binding fragment thereof of claim 1, wherein said antibody or an antigen-binding fragment thereof is coupled to a labeling group.

13. The isolated antibody or an antigen-binding fragment thereof of claim 12, wherein said labeling group is a radioisotope, a radionuclide, a fluorescent group, an enzymatic group, a chemiluminescent group, a biotinyl group, or a predetermined polypeptide group.

14. The isolated antibody or an antigen-binding fragment thereof of claim 1, wherein said antibody or an antigen-binding fragment thereof is coupled to an effector group.

15. The isolated antibody or an antigen-binding fragment thereof claim 14, wherein said effector group is a radioisotope, a radionucleotide, a toxin, a therapeutic group, or a chemotherapeutic group.

16. The isolated antibody or an antigen-binding fragment thereof of claim 15, wherein the therapeutic or chemotherapeutic group is selected from the group consisting of calicheamicin, auristatin-PE, geldanamycin, and maytansine.

17. The isolated antibody or an antigen-binding fragment thereof of claim 6, wherein said antibody or an antigen-binding fragment thereof is characterized by (a) the presence of a J chain; or (b) the absence of a J chain.

18. A mixture of the antibody or an antigen-binding fragment thereof according to claim 11, wherein said mixture is a mixture comprising pentamers and hexamers.

19. A pharmaceutical composition comprising as an active agent at least one antibody or an antigen-binding fragment thereof of claim 1 and a pharmaceutically acceptable carrier, diluent or adjuvant.

20. A kit comprising the isolated antibody or an antigen-binding fragment thereof of claim 1.

21. The kit of claim 20, comprising a further therapeutic agent.

22. The kit of claim 21, wherein the further therapeutic agent is an antineoplastic agent.

23. The kit of claim 22, wherein the anti-neoplastic agent is an anti-tumor antibody or a chemotherapeutic agent.

* * * * *

SEQUENCE LISTING

```
<160> NUMBER OF SEQ ID NOS: 108

<210> SEQ ID NO 1
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 1

Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Gly Tyr
            20                  25                  30

Tyr Trp Ser Trp Ile Arg Gln Pro Pro Gly Lys Gly Leu Glu Trp Ile
        35                  40                  45

Gly Glu Ile Asn His Ser Gly Ser Thr Asn Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Gly Arg Met Ala Trp Gly Ala Ser Val Asn Phe Asp Tyr Trp Gly
            100                 105                 110

Gln Gly Thr Leu Val Thr Val Ser Ser
        115                 120

<210> SEQ ID NO 2
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 2

Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Gly Tyr
            20                  25                  30

Tyr Trp Ser Trp Ile Arg Gln Pro Pro Gly Lys Gly Leu Glu Trp Ile
        35                  40                  45

Gly Glu Ile Asn His Ser Gly Ser Thr Asn Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95
```

```
Arg Gly Arg Arg Ala Trp Gly Ala Ser Val Asn Phe Asp Tyr Trp Gly
            100                 105                 110

Gln Gly Thr Leu Val Thr Val Ser Ser
        115                 120

<210> SEQ ID NO 3
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 3

Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Gly Tyr
            20                  25                  30

Tyr Trp Ser Trp Ile Arg Gln Pro Pro Gly Lys Gly Leu Glu Trp Ile
        35                  40                  45

Gly Glu Ile Asn His Ser Gly Ser Thr Asn Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Gly Arg Met Ala Arg Gly Ala Ser Val Asn Phe Asp Tyr Trp Gly
            100                 105                 110

Gln Gly Thr Leu Val Thr Val Ser Ser
        115                 120

<210> SEQ ID NO 4
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 4

Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Gly Tyr
            20                  25                  30

Tyr Trp Ser Trp Ile Arg Gln Pro Pro Gly Lys Gly Leu Glu Trp Ile
        35                  40                  45

Gly Glu Ile Asn His Ser Gly Ser Thr Asn Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Gly Arg Arg Ala Arg Gly Ala Ser Val Asn Phe Asp Tyr Trp Gly
            100                 105                 110

Gln Gly Thr Leu Val Thr Val Ser Ser
        115                 120

<210> SEQ ID NO 5
```

```
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 5

Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Gly Tyr
            20                  25                  30

Tyr Trp Ser Trp Ile Arg Gln Pro Pro Gly Lys Gly Leu Glu Trp Ile
        35                  40                  45

Gly Glu Ile Asn His Ser Gly Ser Thr Asn Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Arg Gly Met Ala Trp Gly Ala Ser Val Asn Phe Asp Tyr Trp Gly
            100                 105                 110

Gln Gly Thr Leu Val Thr Val Ser Ser
        115                 120

<210> SEQ ID NO 6
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 6

Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Gly Tyr
            20                  25                  30

Tyr Trp Ser Trp Ile Arg Gln Pro Pro Gly Lys Gly Leu Glu Trp Ile
        35                  40                  45

Gly Glu Ile Asn His Ser Gly Ser Thr Asn Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Arg Arg Met Ala Trp Gly Ala Ser Val Asn Phe Asp Tyr Trp Gly
            100                 105                 110

Gln Gly Thr Leu Val Thr Val Ser Ser
        115                 120

<210> SEQ ID NO 7
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 7
```

```
Gln Val Gln Leu Gln Gln Trp Gly Ala Gly Leu Leu Lys Pro Ser Glu
  1               5                  10                  15

Thr Leu Ser Leu Thr Cys Ala Val Tyr Gly Gly Ser Phe Ser Gly Tyr
             20                  25                  30

Tyr Trp Ser Trp Ile Arg Gln Pro Pro Gly Lys Gly Leu Glu Trp Ile
         35                  40                  45

Gly Glu Ile Asn His Ser Gly Ser Thr Asn Tyr Asn Pro Ser Leu Lys
     50                  55                  60

Ser Arg Val Thr Ile Ser Val Asp Thr Ser Lys Asn Gln Phe Ser Leu
 65                  70                  75                  80

Lys Leu Ser Ser Val Thr Ala Ala Asp Thr Ala Val Tyr Tyr Cys Ala
                 85                  90                  95

Arg Arg Gly Met Ala Arg Gly Ala Ser Val Asn Phe Asp Tyr Trp Gly
             100                 105                 110

Gln Gly Thr Leu Val Thr Val Ser Ser
             115                 120
```

```
<210> SEQ ID NO 8
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 8
```

```
Gln Val Gln Leu Gln Gln Trp Gly Ala Gly Leu Leu Lys Pro Ser Glu
  1               5                  10                  15

Thr Leu Ser Leu Thr Cys Ala Val Tyr Gly Gly Ser Phe Ser Gly Tyr
             20                  25                  30

Tyr Trp Ser Trp Ile Arg Gln Pro Pro Gly Lys Gly Leu Glu Trp Ile
         35                  40                  45

Gly Glu Ile Asn His Ser Gly Ser Thr Asn Tyr Asn Pro Ser Leu Lys
     50                  55                  60

Ser Arg Val Thr Ile Ser Val Asp Thr Ser Lys Asn Gln Phe Ser Leu
 65                  70                  75                  80

Lys Leu Ser Ser Val Thr Ala Ala Asp Thr Ala Val Tyr Tyr Cys Ala
                 85                  90                  95

Arg Arg Gly Arg Ala Arg Gly Ala Ser Val Asn Phe Asp Tyr Trp Gly
             100                 105                 110

Gln Gly Thr Leu Val Thr Val Ser Ser
             115                 120
```

```
<210> SEQ ID NO 9
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 9
```

```
Gln Val Gln Leu Gln Gln Trp Gly Ala Gly Leu Leu Lys Pro Ser Glu
  1               5                  10                  15

Thr Leu Ser Leu Thr Cys Ala Val Tyr Gly Gly Ser Phe Ser Gly Tyr
             20                  25                  30

Tyr Trp Ser Trp Ile Arg Gln Pro Pro Gly Lys Gly Leu Glu Trp Ile
         35                  40                  45
```

Gly Glu Ile Asn His Ser Gly Ser Thr Asn Tyr Asn Pro Ser Leu Lys
            50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Arg Arg Gly Ala Arg Gly Ala Ser Val Asn Phe Asp Tyr Trp Gly
            100                 105                 110

Gln Gly Thr Leu Val Thr Val Ser Ser
        115                 120

<210> SEQ ID NO 10
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 10

Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Gly Tyr
            20                  25                  30

Tyr Trp Ser Trp Ile Arg Gln Pro Pro Gly Lys Gly Leu Glu Trp Ile
        35                  40                  45

Gly Glu Ile Asn His Ser Gly Ser Thr Asn Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Ala Gly Arg Ala Trp Gly Ala Ser Val Asn Phe Asp Tyr Trp Gly
            100                 105                 110

Gln Gly Thr Leu Val Thr Val Ser Ser
        115                 120

<210> SEQ ID NO 11
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 11

Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Gly Tyr
            20                  25                  30

Tyr Trp Ser Trp Ile Arg Gln Pro Pro Gly Lys Gly Leu Glu Trp Ile
        35                  40                  45

Gly Glu Ile Asn His Ser Gly Ser Thr Asn Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Arg Gly Arg Ala Trp Gly Ala Ser Val Asn Phe Asp Tyr Trp Gly
            100                 105                 110

Gln Gly Thr Leu Val Thr Val Ser Ser
        115                 120

<210> SEQ ID NO 12
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 12

Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Gly Tyr
            20                  25                  30

Tyr Trp Ser Trp Ile Arg Gln Pro Pro Gly Lys Gly Leu Glu Trp Ile
        35                  40                  45

Gly Glu Ile Asn His Ser Gly Ser Thr Asn Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Ala Arg Thr Ala Trp Gly Ser Ser Ile Phe Asp Tyr Trp Gly Gln
            100                 105                 110

Gly Thr Leu Val Thr Val Ser Ser
        115                 120

<210> SEQ ID NO 13
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 13

Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Gly Tyr
            20                  25                  30

Tyr Trp Ser Trp Ile Arg Gln Pro Pro Gly Lys Gly Leu Glu Trp Ile
        35                  40                  45

Gly Glu Ile Asn His Ser Gly Ser Thr Asn Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Ala Arg Arg Ala Trp Gly Ser Ser Ile Phe Asp Tyr Trp Gly Gln
            100                 105                 110

Gly Thr Leu Val Thr Val Ser Ser
        115                 120

<210> SEQ ID NO 14
<211> LENGTH: 120

<212> TYPE: PRT
<213> ORGANISM: Artificial Sequence
<220> FEATURE:
<223> OTHER INFORMATION: Description of Artificial Sequence: Synthetic
       polypeptide

<400> SEQUENCE: 14

Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Gly Tyr
            20                  25                  30

Tyr Trp Ser Trp Ile Arg Gln Pro Pro Gly Lys Gly Leu Glu Trp Ile
        35                  40                  45

Gly Glu Ile Asn His Ser Gly Ser Thr Asn Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Ala Arg Thr Ala Arg Gly Ser Ser Ile Phe Asp Tyr Trp Gly Gln
            100                 105                 110

Gly Thr Leu Val Thr Val Ser Ser
        115                 120

<210> SEQ ID NO 15
<211> LENGTH: 120
<212> TYPE: PRT
<213> ORGANISM: Artificial Sequence
<220> FEATURE:
<223> OTHER INFORMATION: Description of Artificial Sequence: Synthetic
       polypeptide

<400> SEQUENCE: 15

Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Gly Tyr
            20                  25                  30

Tyr Trp Ser Trp Ile Arg Gln Pro Pro Gly Lys Gly Leu Glu Trp Ile
        35                  40                  45

Gly Glu Ile Asn His Ser Gly Ser Thr Asn Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Ala Arg Arg Ala Arg Gly Ser Ser Ile Phe Asp Tyr Trp Gly Gln
            100                 105                 110

Gly Thr Leu Val Thr Val Ser Ser
        115                 120

<210> SEQ ID NO 16
<211> LENGTH: 120
<212> TYPE: PRT
<213> ORGANISM: Artificial Sequence
<220> FEATURE:
<223> OTHER INFORMATION: Description of Artificial Sequence: Synthetic
       polypeptide

<400> SEQUENCE: 16

Gln Val Gln Leu Gln Gln Trp Gly Ala Gly Leu Leu Lys Pro Ser Glu

-continued

```
               1               5                  10                 15
           Thr Leu Ser Leu Thr Cys Ala Val Tyr Gly Gly Ser Phe Ser Gly Tyr
                            20                 25                 30

Tyr Trp Ser Trp Ile Arg Gln Pro Pro Gly Lys Gly Leu Glu Trp Ile
                        35                 40                 45

Gly Glu Ile Asn His Ser Gly Ser Thr Asn Tyr Asn Pro Ser Leu Lys
                    50                 55                 60

Ser Arg Val Thr Ile Ser Val Asp Thr Ser Lys Asn Gln Phe Ser Leu
           65                 70                 75                 80

Lys Leu Ser Ser Val Thr Ala Ala Asp Thr Ala Val Tyr Tyr Cys Ala
                            85                 90                 95

Arg Arg Ala Thr Ala Trp Gly Ser Ser Ile Phe Asp Tyr Trp Gly Gln
                        100                105                110

Gly Thr Leu Val Thr Val Ser Ser
                    115                120

<210> SEQ ID NO 17
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 17

Gln Val Gln Leu Gln Gln Trp Gly Ala Gly Leu Leu Lys Pro Ser Glu
1               5                  10                 15

Thr Leu Ser Leu Thr Cys Ala Val Tyr Gly Gly Ser Phe Ser Gly Tyr
            20                 25                 30

Tyr Trp Ser Trp Ile Arg Gln Pro Pro Gly Lys Gly Leu Glu Trp Ile
        35                 40                 45

Gly Glu Ile Asn His Ser Gly Ser Thr Asn Tyr Asn Pro Ser Leu Lys
    50                 55                 60

Ser Arg Val Thr Ile Ser Val Asp Thr Ser Lys Asn Gln Phe Ser Leu
65                 70                 75                 80

Lys Leu Ser Ser Val Thr Ala Ala Asp Thr Ala Val Tyr Tyr Cys Ala
            85                 90                 95

Arg Arg Arg Thr Ala Trp Gly Ser Ser Ile Phe Asp Tyr Trp Gly Gln
        100                105                110

Gly Thr Leu Val Thr Val Ser Ser
    115                120

<210> SEQ ID NO 18
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 18

Gln Val Gln Leu Gln Gln Trp Gly Ala Gly Leu Leu Lys Pro Ser Glu
1               5                  10                 15

Thr Leu Ser Leu Thr Cys Ala Val Tyr Gly Gly Ser Phe Ser Gly Tyr
            20                 25                 30

Tyr Trp Ser Trp Ile Arg Gln Pro Pro Gly Lys Gly Leu Glu Trp Ile
        35                 40                 45

Gly Glu Ile Asn His Ser Gly Ser Thr Asn Tyr Asn Pro Ser Leu Lys
```

```
                50                  55                  60
Ser Arg Val Thr Ile Ser Val Asp Thr Ser Lys Asn Gln Phe Ser Leu
 65                  70                  75                  80

Lys Leu Ser Ser Val Thr Ala Ala Asp Thr Ala Val Tyr Tyr Cys Ala
                 85                  90                  95

Arg Arg Ala Thr Ala Arg Gly Ser Ser Ile Phe Asp Tyr Trp Gly Gln
            100                 105                 110

Gly Thr Leu Val Thr Val Ser Ser
        115                 120

<210> SEQ ID NO 19
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 19

Gln Val Gln Leu Gln Gln Trp Gly Ala Gly Leu Leu Lys Pro Ser Glu
 1               5                  10                  15

Thr Leu Ser Leu Thr Cys Ala Val Tyr Gly Gly Ser Phe Ser Gly Tyr
                20                  25                  30

Tyr Trp Ser Trp Ile Arg Gln Pro Pro Gly Lys Gly Leu Glu Trp Ile
            35                  40                  45

Gly Glu Ile Asn His Ser Gly Ser Thr Asn Tyr Asn Pro Ser Leu Lys
     50                  55                  60

Ser Arg Val Thr Ile Ser Val Asp Thr Ser Lys Asn Gln Phe Ser Leu
 65                  70                  75                  80

Lys Leu Ser Ser Val Thr Ala Ala Asp Thr Ala Val Tyr Tyr Cys Ala
                 85                  90                  95

Arg Arg Ala Arg Ala Arg Gly Ser Ser Ile Phe Asp Tyr Trp Gly Gln
            100                 105                 110

Gly Thr Leu Val Thr Val Ser Ser
        115                 120

<210> SEQ ID NO 20
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 20

Gln Val Gln Leu Gln Gln Trp Gly Ala Gly Leu Leu Lys Pro Ser Glu
 1               5                  10                  15

Thr Leu Ser Leu Thr Cys Ala Val Tyr Gly Gly Ser Phe Ser Gly Tyr
                20                  25                  30

Tyr Trp Ser Trp Ile Arg Gln Pro Pro Gly Lys Gly Leu Glu Trp Ile
            35                  40                  45

Gly Glu Ile Asn His Ser Gly Ser Thr Asn Tyr Asn Pro Ser Leu Lys
     50                  55                  60

Ser Arg Val Thr Ile Ser Val Asp Thr Ser Lys Asn Gln Phe Ser Leu
 65                  70                  75                  80

Lys Leu Ser Ser Val Thr Ala Ala Asp Thr Ala Val Tyr Tyr Cys Ala
                 85                  90                  95

Arg Arg Arg Thr Ala Arg Gly Ser Ser Ile Phe Asp Tyr Trp Gly Gln
```

```
                100                 105                 110
Gly Thr Leu Val Thr Val Ser Ser
        115                 120

<210> SEQ ID NO 21
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 21

Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Gly Tyr
            20                  25                  30

Tyr Trp Ser Trp Ile Arg Gln Pro Pro Gly Lys Gly Leu Glu Trp Ile
        35                  40                  45

Gly Glu Ile Asn His Ser Gly Ser Thr Asn Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Gly Ala Arg Ala Trp Gly Ser Ser Ile Phe Asp Tyr Trp Gly Gln
            100                 105                 110

Gly Thr Leu Val Thr Val Ser Ser
        115                 120

<210> SEQ ID NO 22
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 22

Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Gly Tyr
            20                  25                  30

Tyr Trp Ser Trp Ile Arg Gln Pro Pro Gly Lys Gly Leu Glu Trp Ile
        35                  40                  45

Gly Glu Ile Asn His Ser Gly Ser Thr Asn Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Arg Ala Arg Ala Trp Gly Ser Ser Ile Phe Asp Tyr Trp Gly Gln
            100                 105                 110

Gly Thr Leu Val Thr Val Ser Ser
        115                 120

<210> SEQ ID NO 23
<211> LENGTH: 106
<212> TYPE: PRT
```

<213> ORGANISM: Artificial Sequence
<220> FEATURE:
<223> OTHER INFORMATION: Description of Artificial Sequence: Synthetic
      polypeptide

<400> SEQUENCE: 23

Asp Ile Gln Met Thr Gln Ser Pro Ser Thr Leu Ser Ala Ser Val Gly
1               5                   10                  15

Asp Arg Val Thr Ile Thr Cys Thr Gly Thr Ser Ser Asp Val Gly Gly
            20                  25                  30

Tyr Asn Tyr Val Ser Trp Tyr Gln Gln His Pro Gly Lys Ala Pro Lys
        35                  40                  45

Leu Met Ile Tyr Gly Val Ser Asn Arg Phe Ser Gly Ser Lys Ser Gly
    50                  55                  60

Asn Thr Ala Ser Leu Thr Ile Ser Gly Leu Ala Ala Glu Asp Glu Ala
65                  70                  75                  80

Asp Tyr Tyr Cys Ser Ser Tyr Thr Ser Ser Ser Thr Leu Val Val Phe
                85                  90                  95

Gly Gly Gly Thr Lys Leu Thr Val Leu Gly
            100                 105

<210> SEQ ID NO 24
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 24

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Ile
                85                  90                  95

Thr Phe Gly Gln Gly Thr Arg Leu Glu Ile Lys Arg
            100                 105

<210> SEQ ID NO 25
<211> LENGTH: 452
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 25

Gly Ser Ala Ser Ala Pro Thr Leu Phe Pro Leu Val Ser Cys Glu Asn
1               5                   10                  15

Ser Pro Ser Asp Thr Ser Ser Val Ala Val Gly Cys Leu Ala Gln Asp
            20                  25                  30

Phe Leu Pro Asp Ser Ile Thr Phe Ser Trp Lys Tyr Lys Asn Asn Ser
        35                  40                  45

```
Asp Ile Ser Ser Thr Arg Gly Phe Pro Ser Val Leu Arg Gly Gly Lys
 50                  55                  60

Tyr Ala Ala Thr Ser Gln Val Leu Leu Pro Ser Lys Asp Val Met Gln
 65                  70                  75                  80

Gly Thr Asp Glu His Val Val Cys Lys Val Gln His Pro Asn Gly Asn
                 85                  90                  95

Lys Glu Lys Asn Val Pro Leu Pro Val Ile Ala Glu Leu Pro Pro Lys
            100                 105                 110

Val Ser Val Phe Val Pro Pro Arg Asp Gly Phe Phe Gly Asn Pro Arg
        115                 120                 125

Lys Ser Lys Leu Ile Cys Gln Ala Thr Gly Phe Ser Pro Arg Gln Ile
130                 135                 140

Gln Val Ser Trp Leu Arg Glu Gly Lys Gln Val Gly Ser Gly Val Thr
145                 150                 155                 160

Thr Asp Gln Val Gln Ala Glu Ala Lys Glu Ser Gly Pro Thr Thr Tyr
                165                 170                 175

Lys Val Thr Ser Thr Leu Thr Ile Lys Glu Ser Asp Trp Leu Gly Gln
            180                 185                 190

Ser Met Phe Thr Cys Arg Val Asp His Arg Gly Leu Thr Phe Gln Gln
        195                 200                 205

Asn Ala Ser Ser Met Cys Val Pro Asp Gln Asp Thr Ala Ile Arg Val
210                 215                 220

Phe Ala Ile Pro Pro Ser Phe Ala Ser Ile Phe Leu Thr Lys Ser Thr
225                 230                 235                 240

Lys Leu Thr Cys Leu Val Thr Asp Leu Thr Thr Tyr Asp Ser Val Thr
                245                 250                 255

Ile Ser Trp Thr Arg Gln Asn Gly Glu Ala Val Lys Thr His Thr Asn
            260                 265                 270

Ile Ser Glu Ser His Pro Asn Ala Thr Phe Ser Ala Val Gly Glu Ala
        275                 280                 285

Ser Ile Cys Glu Asp Asp Trp Asn Ser Gly Glu Arg Phe Thr Cys Thr
290                 295                 300

Val Thr His Thr Asp Leu Pro Ser Pro Leu Lys Gln Thr Ile Ser Arg
305                 310                 315                 320

Pro Lys Gly Val Ala Leu His Arg Pro Asp Val Tyr Leu Leu Pro Pro
                325                 330                 335

Ala Arg Glu Gln Leu Asn Leu Arg Glu Ser Ala Thr Ile Thr Cys Leu
            340                 345                 350

Val Thr Gly Phe Ser Pro Ala Asp Val Phe Val Gln Trp Met Gln Arg
        355                 360                 365

Gly Gln Pro Leu Ser Pro Glu Lys Tyr Val Thr Ser Ala Pro Met Pro
370                 375                 380

Glu Pro Gln Ala Pro Gly Arg Tyr Phe Ala His Ser Ile Leu Thr Val
385                 390                 395                 400

Ser Glu Glu Glu Trp Asn Thr Gly Glu Thr Tyr Thr Cys Val Ala His
                405                 410                 415

Asp Ala Leu Pro Asn Arg Val Thr Glu Arg Thr Val Asp Lys Ser Thr
            420                 425                 430

Gly Lys Pro Thr Leu Tyr Asn Val Ser Leu Val Met Ser Asp Thr Ala
        435                 440                 445

Gly Thr Cys Tyr
450
```

```
<210> SEQ ID NO 26
<211> LENGTH: 105
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 26

Gln Pro Lys Ala Ala Pro Ser Val Thr Leu Phe Pro Pro Ser Ser Glu
1               5                   10                  15

Glu Leu Gln Ala Asn Lys Ala Thr Leu Val Cys Leu Ile Ser Asp Phe
                20                  25                  30

Tyr Pro Gly Ala Val Thr Val Ala Trp Lys Ala Asp Ser Ser Pro Val
            35                  40                  45

Lys Ala Gly Val Glu Thr Thr Pro Ser Lys Gln Ser Asn Asn Lys
    50                  55                  60

Tyr Ala Ala Ser Ser Tyr Leu Ser Leu Thr Pro Glu Gln Trp Lys Ser
65                  70                  75                  80

His Arg Ser Tyr Ser Cys Gln Val Thr His Glu Gly Ser Thr Val Glu
                85                  90                  95

Lys Thr Val Ala Pro Thr Glu Cys Ser
            100                 105

<210> SEQ ID NO 27
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 27

Thr Val Ala Ala Pro Ser Val Phe Ile Phe Pro Pro Ser Asp Glu Gln
1               5                   10                  15

Leu Lys Ser Gly Thr Ala Ser Val Val Cys Leu Leu Asn Asn Phe Tyr
                20                  25                  30

Pro Arg Glu Ala Lys Val Gln Trp Lys Val Asp Asn Ala Leu Gln Ser
            35                  40                  45

Gly Asn Ser Gln Glu Ser Val Thr Glu Gln Asp Ser Lys Asp Ser Thr
    50                  55                  60

Tyr Ser Leu Ser Ser Thr Leu Thr Leu Ser Lys Ala Asp Tyr Glu Lys
65                  70                  75                  80

His Lys Val Tyr Ala Cys Glu Val Thr His Gln Gly Leu Ser Ser Pro
                85                  90                  95

Val Thr Lys Ser Phe Asn Arg Gly Glu Cys
            100                 105

<210> SEQ ID NO 28
<211> LENGTH: 574
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 28

Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Gly Tyr
```

```
                 20                  25                  30
Tyr Trp Ser Trp Ile Arg Gln Pro Pro Gly Lys Gly Leu Glu Trp Ile
             35                  40                  45
Gly Glu Ile Asn His Ser Gly Ser Thr Asn Tyr Asn Pro Ser Leu Lys
         50                  55                  60
Ser Arg Val Thr Ile Ser Val Asp Thr Ser Lys Asn Gln Phe Ser Leu
65                  70                  75                  80
Lys Leu Ser Ser Val Thr Ala Ala Asp Thr Ala Val Tyr Tyr Cys Ala
                 85                  90                  95
Arg Gly Arg Met Ala Trp Gly Ala Ser Val Asn Phe Asp Tyr Trp Gly
             100                 105                 110
Gln Gly Thr Leu Val Thr Val Ser Ser Gly Ser Ala Ser Ala Pro Thr
         115                 120                 125
Leu Phe Pro Leu Val Ser Cys Glu Asn Ser Pro Ser Asp Thr Ser Ser
         130                 135                 140
Val Ala Val Gly Cys Leu Ala Gln Asp Phe Leu Pro Asp Ser Ile Thr
145                 150                 155                 160
Phe Ser Trp Lys Tyr Lys Asn Asn Ser Asp Ile Ser Ser Thr Arg Gly
                 165                 170                 175
Phe Pro Ser Val Leu Arg Gly Gly Lys Tyr Ala Ala Thr Ser Gln Val
             180                 185                 190
Leu Leu Pro Ser Lys Asp Val Met Gln Gly Thr Asp Glu His Val Val
         195                 200                 205
Cys Lys Val Gln His Pro Asn Gly Asn Lys Glu Lys Asn Val Pro Leu
     210                 215                 220
Pro Val Ile Ala Glu Leu Pro Pro Lys Val Ser Val Phe Val Pro Pro
225                 230                 235                 240
Arg Asp Gly Phe Phe Gly Asn Pro Arg Lys Ser Lys Leu Ile Cys Gln
                 245                 250                 255
Ala Thr Gly Phe Ser Pro Arg Gln Ile Gln Val Ser Trp Leu Arg Glu
             260                 265                 270
Gly Lys Gln Val Gly Ser Gly Val Thr Thr Asp Gln Val Gln Ala Glu
         275                 280                 285
Ala Lys Glu Ser Gly Pro Thr Thr Tyr Lys Val Thr Ser Thr Leu Thr
     290                 295                 300
Ile Lys Glu Ser Asp Trp Leu Ser Gln Ser Met Phe Thr Cys Arg Val
305                 310                 315                 320
Asp His Arg Gly Leu Thr Phe Gln Gln Asn Ala Ser Ser Met Cys Val
                 325                 330                 335
Pro Asp Gln Asp Thr Ala Ile Arg Val Phe Ala Ile Pro Pro Ser Phe
             340                 345                 350
Ala Ser Ile Phe Leu Thr Lys Ser Thr Lys Leu Thr Cys Leu Val Thr
         355                 360                 365
Asp Leu Thr Thr Tyr Asp Ser Val Thr Ile Ser Trp Thr Arg Gln Asn
     370                 375                 380
Gly Glu Ala Val Lys Thr His Thr Asn Ile Ser Glu Ser His Pro Asn
385                 390                 395                 400
Ala Thr Phe Ser Ala Val Gly Glu Ala Ser Ile Cys Glu Asp Asp Trp
                 405                 410                 415
Asn Ser Gly Glu Arg Phe Thr Cys Thr Val Thr His Thr Asp Leu Pro
             420                 425                 430
Ser Pro Leu Lys Gln Thr Ile Ser Arg Pro Lys Gly Val Ala Leu His
         435                 440                 445
```

Arg Pro Asp Val Tyr Leu Leu Pro Pro Ala Arg Glu Gln Leu Asn Leu
            450                 455                 460

Arg Glu Ser Ala Thr Ile Thr Cys Leu Val Thr Gly Phe Ser Pro Ala
465                 470                 475                 480

Asp Val Phe Val Gln Trp Met Gln Arg Gly Gln Pro Leu Ser Pro Glu
                    485                 490                 495

Lys Tyr Val Thr Ser Ala Pro Met Pro Glu Pro Gln Ala Pro Gly Arg
                500                 505                 510

Tyr Phe Ala His Ser Ile Leu Thr Val Ser Glu Glu Trp Asn Thr
                515                 520                 525

Gly Glu Thr Tyr Thr Cys Val Val Ala His Glu Ala Leu Pro Asn Arg
530                 535                 540

Val Thr Glu Arg Thr Val Asp Lys Ser Thr Gly Lys Pro Thr Leu Tyr
545                 550                 555                 560

Asn Val Ser Leu Val Met Ser Asp Thr Ala Gly Thr Cys Tyr
                    565                 570

<210> SEQ ID NO 29
<211> LENGTH: 574
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 29

Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Gly Tyr
            20                  25                  30

Tyr Trp Ser Trp Ile Arg Gln Pro Pro Gly Lys Gly Leu Glu Trp Ile
        35                  40                  45

Gly Glu Ile Asn His Ser Gly Ser Thr Asn Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Gly Arg Arg Ala Trp Gly Ala Ser Val Asn Phe Asp Tyr Trp Gly
            100                 105                 110

Gln Gly Thr Leu Val Thr Val Ser Ser Gly Ser Ala Ser Ala Pro Thr
        115                 120                 125

Leu Phe Pro Leu Val Ser Cys Glu Asn Ser Pro Ser Asp Thr Ser Ser
    130                 135                 140

Val Ala Val Gly Cys Leu Ala Gln Asp Phe Leu Pro Asp Ser Ile Thr
145                 150                 155                 160

Phe Ser Trp Lys Tyr Lys Asn Asn Ser Asp Ile Ser Ser Thr Arg Gly
                165                 170                 175

Phe Pro Ser Val Leu Arg Gly Gly Lys Tyr Ala Ala Thr Ser Gln Val
            180                 185                 190

Leu Leu Pro Ser Lys Asp Val Met Gln Gly Thr Asp Glu His Val Val
        195                 200                 205

Cys Lys Val Gln His Pro Asn Gly Asn Lys Glu Lys Asn Val Pro Leu
    210                 215                 220

Pro Val Ile Ala Glu Leu Pro Pro Lys Val Ser Val Phe Val Pro Pro

```
                225                 230                 235                 240
Arg Asp Gly Phe Phe Gly Asn Pro Arg Lys Ser Lys Leu Ile Cys Gln
                245                 250                 255

Ala Thr Gly Phe Ser Pro Arg Gln Ile Gln Val Ser Trp Leu Arg Glu
                260                 265                 270

Gly Lys Gln Val Gly Ser Gly Val Thr Thr Asp Gln Val Gln Ala Glu
                275                 280                 285

Ala Lys Glu Ser Gly Pro Thr Thr Tyr Lys Val Thr Ser Thr Leu Thr
                290                 295                 300

Ile Lys Glu Ser Asp Trp Leu Ser Gln Ser Met Phe Thr Cys Arg Val
305                 310                 315                 320

Asp His Arg Gly Leu Thr Phe Gln Gln Asn Ala Ser Ser Met Cys Val
                325                 330                 335

Pro Asp Gln Asp Thr Ala Ile Arg Val Phe Ala Ile Pro Pro Ser Phe
                340                 345                 350

Ala Ser Ile Phe Leu Thr Lys Ser Thr Lys Leu Thr Cys Leu Val Thr
                355                 360                 365

Asp Leu Thr Thr Tyr Asp Ser Val Thr Ile Ser Trp Thr Arg Gln Asn
                370                 375                 380

Gly Glu Ala Val Lys Thr His Thr Asn Ile Ser Glu Ser His Pro Asn
385                 390                 395                 400

Ala Thr Phe Ser Ala Val Gly Glu Ala Ser Ile Cys Glu Asp Asp Trp
                405                 410                 415

Asn Ser Gly Glu Arg Phe Thr Cys Thr Val Thr His Thr Asp Leu Pro
                420                 425                 430

Ser Pro Leu Lys Gln Thr Ile Ser Arg Pro Lys Gly Val Ala Leu His
                435                 440                 445

Arg Pro Asp Val Tyr Leu Leu Pro Pro Ala Arg Glu Gln Leu Asn Leu
                450                 455                 460

Arg Glu Ser Ala Thr Ile Thr Cys Leu Val Thr Gly Phe Ser Pro Ala
465                 470                 475                 480

Asp Val Phe Val Gln Trp Met Gln Arg Gly Gln Pro Leu Ser Pro Glu
                485                 490                 495

Lys Tyr Val Thr Ser Ala Pro Met Pro Glu Pro Gln Ala Pro Gly Arg
                500                 505                 510

Tyr Phe Ala His Ser Ile Leu Thr Val Ser Glu Glu Glu Trp Asn Thr
                515                 520                 525

Gly Glu Thr Tyr Thr Cys Val Val Ala His Glu Ala Leu Pro Asn Arg
                530                 535                 540

Val Thr Glu Arg Thr Val Asp Lys Ser Thr Gly Lys Pro Thr Leu Tyr
545                 550                 555                 560

Asn Val Ser Leu Val Met Ser Asp Thr Ala Gly Thr Cys Tyr
                565                 570

<210> SEQ ID NO 30
<211> LENGTH: 574
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 30

Gln Val Gln Leu Gln Gln Trp Gly Ala Gly Leu Leu Lys Pro Ser Glu
1               5                   10                  15
```

Thr Leu Ser Leu Thr Cys Ala Val Tyr Gly Gly Ser Phe Gly Tyr
         20                  25                  30

Tyr Trp Ser Trp Ile Arg Gln Pro Pro Gly Lys Gly Leu Glu Trp Ile
     35                  40                  45

Gly Glu Ile Asn His Ser Gly Ser Thr Asn Tyr Asn Pro Ser Leu Lys
 50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                 85                  90                  95

Arg Gly Arg Met Ala Arg Gly Ala Ser Val Asn Phe Asp Tyr Trp Gly
             100                 105                 110

Gln Gly Thr Leu Val Thr Val Ser Ser Gly Ser Ala Ser Ala Pro Thr
         115                 120                 125

Leu Phe Pro Leu Val Ser Cys Glu Asn Ser Pro Ser Asp Thr Ser Ser
     130                 135                 140

Val Ala Val Gly Cys Leu Ala Gln Asp Phe Leu Pro Asp Ser Ile Thr
145                 150                 155                 160

Phe Ser Trp Lys Tyr Lys Asn Asn Ser Asp Ile Ser Ser Thr Arg Gly
                 165                 170                 175

Phe Pro Ser Val Leu Arg Gly Gly Lys Tyr Ala Ala Thr Ser Gln Val
             180                 185                 190

Leu Leu Pro Ser Lys Asp Val Met Gln Gly Thr Asp Glu His Val Val
         195                 200                 205

Cys Lys Val Gln His Pro Asn Gly Asn Lys Glu Lys Asn Val Pro Leu
     210                 215                 220

Pro Val Ile Ala Glu Leu Pro Pro Lys Val Ser Val Phe Val Pro Pro
225                 230                 235                 240

Arg Asp Gly Phe Phe Gly Asn Pro Arg Lys Ser Lys Leu Ile Cys Gln
                 245                 250                 255

Ala Thr Gly Phe Ser Pro Arg Gln Ile Gln Val Ser Trp Leu Arg Glu
             260                 265                 270

Gly Lys Gln Val Gly Ser Gly Val Thr Thr Asp Gln Val Gln Ala Glu
         275                 280                 285

Ala Lys Glu Ser Gly Pro Thr Thr Tyr Lys Val Thr Ser Thr Leu Thr
     290                 295                 300

Ile Lys Glu Ser Asp Trp Leu Ser Gln Ser Met Phe Thr Cys Arg Val
305                 310                 315                 320

Asp His Arg Gly Leu Thr Phe Gln Gln Asn Ala Ser Ser Met Cys Val
                 325                 330                 335

Pro Asp Gln Asp Thr Ala Ile Arg Val Phe Ala Ile Pro Pro Ser Phe
             340                 345                 350

Ala Ser Ile Phe Leu Thr Lys Ser Thr Lys Leu Thr Cys Leu Val Thr
     355                 360                 365

Asp Leu Thr Thr Tyr Asp Ser Val Thr Ile Ser Trp Thr Arg Gln Asn
         370                 375                 380

Gly Glu Ala Val Lys Thr His Thr Asn Ile Ser Glu Ser His Pro Asn
385                 390                 395                 400

Ala Thr Phe Ser Ala Val Gly Glu Ala Ser Ile Cys Glu Asp Asp Trp
                 405                 410                 415

Asn Ser Gly Glu Arg Phe Thr Cys Thr Val Thr His Thr Asp Leu Pro
             420                 425                 430

Ser Pro Leu Lys Gln Thr Ile Ser Arg Pro Lys Gly Val Ala Leu His

```
                435                 440                 445
Arg Pro Asp Val Tyr Leu Leu Pro Pro Ala Arg Glu Gln Leu Asn Leu
450                 455                 460

Arg Glu Ser Ala Thr Ile Thr Cys Leu Val Thr Gly Phe Ser Pro Ala
465                 470                 475                 480

Asp Val Phe Val Gln Trp Met Gln Arg Gly Gln Pro Leu Ser Pro Glu
                485                 490                 495

Lys Tyr Val Thr Ser Ala Pro Met Pro Glu Pro Gln Ala Pro Gly Arg
                500                 505                 510

Tyr Phe Ala His Ser Ile Leu Thr Val Ser Glu Glu Trp Asn Thr
                515                 520                 525

Gly Glu Thr Tyr Thr Cys Val Val Ala His Glu Ala Leu Pro Asn Arg
530                 535                 540

Val Thr Glu Arg Thr Val Asp Lys Ser Thr Gly Lys Pro Thr Leu Tyr
545                 550                 555                 560

Asn Val Ser Leu Val Met Ser Asp Thr Ala Gly Thr Cys Tyr
                565                 570
```

<210> SEQ ID NO 31
<211> LENGTH: 574
<212> TYPE: PRT
<213> ORGANISM: Artificial Sequence
<220> FEATURE:
<223> OTHER INFORMATION: Description of Artificial Sequence: Synthetic
    polypeptide

<400> SEQUENCE: 31

```
Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Gly Tyr
            20                  25                  30

Tyr Trp Ser Trp Ile Arg Gln Pro Pro Gly Lys Gly Leu Glu Trp Ile
        35                  40                  45

Gly Glu Ile Asn His Ser Gly Ser Thr Asn Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Gly Arg Arg Ala Arg Gly Ala Ser Val Asn Phe Asp Tyr Trp Gly
            100                 105                 110

Gln Gly Thr Leu Val Thr Val Ser Ser Gly Ser Ala Ser Ala Pro Thr
        115                 120                 125

Leu Phe Pro Leu Val Ser Cys Glu Asn Ser Pro Ser Asp Thr Ser Ser
    130                 135                 140

Val Ala Val Gly Cys Leu Ala Gln Asp Phe Leu Pro Asp Ser Ile Thr
145                 150                 155                 160

Phe Ser Trp Lys Tyr Lys Asn Asn Ser Asp Ile Ser Ser Thr Arg Gly
                165                 170                 175

Phe Pro Ser Val Leu Arg Gly Gly Lys Tyr Ala Ala Thr Ser Gln Val
            180                 185                 190

Leu Leu Pro Ser Lys Asp Val Met Gln Gly Thr Asp Glu His Val Val
        195                 200                 205

Cys Lys Val Gln His Pro Asn Gly Asn Lys Glu Lys Asn Val Pro Leu
    210                 215                 220
```

-continued

```
Pro Val Ile Ala Glu Leu Pro Pro Lys Val Ser Val Phe Val Pro Pro
225                 230                 235                 240

Arg Asp Gly Phe Phe Gly Asn Pro Arg Lys Ser Lys Leu Ile Cys Gln
            245                 250                 255

Ala Thr Gly Phe Ser Pro Arg Gln Ile Gln Val Ser Trp Leu Arg Glu
            260                 265                 270

Gly Lys Gln Val Gly Ser Gly Val Thr Thr Asp Gln Val Gln Ala Glu
        275                 280                 285

Ala Lys Glu Ser Gly Pro Thr Thr Tyr Lys Val Thr Ser Thr Leu Thr
    290                 295                 300

Ile Lys Glu Ser Asp Trp Leu Ser Gln Ser Met Phe Thr Cys Arg Val
305                 310                 315                 320

Asp His Arg Gly Leu Thr Phe Gln Gln Asn Ala Ser Ser Met Cys Val
            325                 330                 335

Pro Asp Gln Asp Thr Ala Ile Arg Val Phe Ala Ile Pro Pro Ser Phe
            340                 345                 350

Ala Ser Ile Phe Leu Thr Lys Ser Thr Lys Leu Thr Cys Leu Val Thr
        355                 360                 365

Asp Leu Thr Thr Tyr Asp Ser Val Thr Ile Ser Trp Thr Arg Gln Asn
    370                 375                 380

Gly Glu Ala Val Lys Thr His Thr Asn Ile Ser Glu Ser His Pro Asn
385                 390                 395                 400

Ala Thr Phe Ser Ala Val Gly Glu Ala Ser Ile Cys Glu Asp Asp Trp
            405                 410                 415

Asn Ser Gly Glu Arg Phe Thr Cys Thr Val Thr His Thr Asp Leu Pro
            420                 425                 430

Ser Pro Leu Lys Gln Thr Ile Ser Arg Pro Lys Gly Val Ala Leu His
        435                 440                 445

Arg Pro Asp Val Tyr Leu Leu Pro Pro Ala Arg Glu Gln Leu Asn Leu
    450                 455                 460

Arg Glu Ser Ala Thr Ile Thr Cys Leu Val Thr Gly Phe Ser Pro Ala
465                 470                 475                 480

Asp Val Phe Val Gln Trp Met Gln Arg Gly Gln Pro Leu Ser Pro Glu
            485                 490                 495

Lys Tyr Val Thr Ser Ala Pro Met Pro Glu Pro Gln Ala Pro Gly Arg
            500                 505                 510

Tyr Phe Ala His Ser Ile Leu Thr Val Ser Glu Glu Trp Asn Thr
        515                 520                 525

Gly Glu Thr Tyr Thr Cys Val Val Ala His Glu Ala Leu Pro Asn Arg
    530                 535                 540

Val Thr Glu Arg Thr Val Asp Lys Ser Thr Gly Lys Pro Thr Leu Tyr
545                 550                 555                 560

Asn Val Ser Leu Val Met Ser Asp Thr Ala Gly Thr Cys Tyr
            565                 570
```

<210> SEQ ID NO 32
<211> LENGTH: 574
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 32

```
Gln Val Gln Leu Gln Gln Trp Gly Ala Gly Leu Leu Lys Pro Ser Glu
1               5                   10                  15
```

```
Thr Leu Ser Leu Thr Cys Ala Val Tyr Gly Gly Ser Phe Ser Gly Tyr
            20                  25                  30

Tyr Trp Ser Trp Ile Arg Gln Pro Pro Gly Lys Gly Leu Glu Trp Ile
        35                  40                  45

Gly Glu Ile Asn His Ser Gly Ser Thr Asn Tyr Asn Pro Ser Leu Lys
50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Arg Gly Met Ala Trp Gly Ala Ser Val Asn Phe Asp Tyr Trp Gly
            100                 105                 110

Gln Gly Thr Leu Val Thr Val Ser Ser Gly Ser Ala Ser Ala Pro Thr
        115                 120                 125

Leu Phe Pro Leu Val Ser Cys Glu Asn Ser Pro Ser Asp Thr Ser Ser
130                 135                 140

Val Ala Val Gly Cys Leu Ala Gln Asp Phe Leu Pro Asp Ser Ile Thr
145                 150                 155                 160

Phe Ser Trp Lys Tyr Lys Asn Asn Ser Asp Ile Ser Ser Thr Arg Gly
                165                 170                 175

Phe Pro Ser Val Leu Arg Gly Gly Lys Tyr Ala Ala Thr Ser Gln Val
            180                 185                 190

Leu Leu Pro Ser Lys Asp Val Met Gln Gly Thr Asp Glu His Val Val
        195                 200                 205

Cys Lys Val Gln His Pro Asn Gly Asn Lys Glu Lys Asn Val Pro Leu
210                 215                 220

Pro Val Ile Ala Glu Leu Pro Pro Lys Val Ser Val Phe Val Pro Pro
225                 230                 235                 240

Arg Asp Gly Phe Phe Gly Asn Pro Arg Lys Ser Lys Leu Ile Cys Gln
                245                 250                 255

Ala Thr Gly Phe Ser Pro Arg Gln Ile Gln Val Ser Trp Leu Arg Glu
            260                 265                 270

Gly Lys Gln Val Gly Ser Gly Val Thr Thr Asp Gln Val Gln Ala Glu
        275                 280                 285

Ala Lys Glu Ser Gly Pro Thr Thr Tyr Lys Val Thr Ser Thr Leu Thr
290                 295                 300

Ile Lys Glu Ser Asp Trp Leu Ser Gln Ser Met Phe Thr Cys Arg Val
305                 310                 315                 320

Asp His Arg Gly Leu Thr Phe Gln Gln Asn Ala Ser Ser Met Cys Val
                325                 330                 335

Pro Asp Gln Asp Thr Ala Ile Arg Val Phe Ala Ile Pro Pro Ser Phe
            340                 345                 350

Ala Ser Ile Phe Leu Thr Lys Ser Thr Lys Leu Thr Cys Leu Val Thr
        355                 360                 365

Asp Leu Thr Thr Tyr Asp Ser Val Thr Ile Ser Trp Thr Arg Gln Asn
370                 375                 380

Gly Glu Ala Val Lys Thr His Thr Asn Ile Ser Glu Ser His Pro Asn
385                 390                 395                 400

Ala Thr Phe Ser Ala Val Gly Glu Ala Ser Ile Cys Glu Asp Asp Trp
                405                 410                 415

Asn Ser Gly Glu Arg Phe Thr Cys Thr Val Thr His Thr Asp Leu Pro
            420                 425                 430
```

```
Ser Pro Leu Lys Gln Thr Ile Ser Arg Pro Lys Gly Val Ala Leu His
            435                 440                 445

Arg Pro Asp Val Tyr Leu Leu Pro Pro Ala Arg Glu Gln Leu Asn Leu
450                 455                 460

Arg Glu Ser Ala Thr Ile Thr Cys Leu Val Thr Gly Phe Ser Pro Ala
465                 470                 475                 480

Asp Val Phe Val Gln Trp Met Gln Arg Gly Gln Pro Leu Ser Pro Glu
                485                 490                 495

Lys Tyr Val Thr Ser Ala Pro Met Pro Glu Pro Gln Ala Pro Gly Arg
            500                 505                 510

Tyr Phe Ala His Ser Ile Leu Thr Val Ser Glu Glu Trp Asn Thr
            515                 520                 525

Gly Glu Thr Tyr Thr Cys Val Val Ala His Glu Ala Leu Pro Asn Arg
530                 535                 540

Val Thr Glu Arg Thr Val Asp Lys Ser Thr Gly Lys Pro Thr Leu Tyr
545                 550                 555                 560

Asn Val Ser Leu Val Met Ser Asp Thr Ala Gly Thr Cys Tyr
                565                 570
```

<210> SEQ ID NO 33
<211> LENGTH: 574
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 33

```
Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Gly Tyr
            20                  25                  30

Tyr Trp Ser Trp Ile Arg Gln Pro Pro Gly Lys Gly Leu Glu Trp Ile
        35                  40                  45

Gly Glu Ile Asn His Ser Gly Ser Thr Asn Tyr Asn Pro Ser Leu Lys
50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Arg Arg Met Ala Trp Gly Ala Ser Val Asn Phe Asp Tyr Trp Gly
            100                 105                 110

Gln Gly Thr Leu Val Thr Val Ser Ser Gly Ser Ala Ser Ala Pro Thr
        115                 120                 125

Leu Phe Pro Leu Val Ser Cys Glu Asn Ser Pro Ser Asp Thr Ser Ser
130                 135                 140

Val Ala Val Gly Cys Leu Ala Gln Asp Phe Leu Pro Asp Ser Ile Thr
145                 150                 155                 160

Phe Ser Trp Lys Tyr Lys Asn Asn Ser Asp Ile Ser Ser Thr Arg Gly
                165                 170                 175

Phe Pro Ser Val Leu Arg Gly Gly Lys Tyr Ala Ala Thr Ser Gln Val
            180                 185                 190

Leu Leu Pro Ser Lys Asp Val Met Gln Gly Thr Asp Glu His Val Val
        195                 200                 205

Cys Lys Val Gln His Pro Asn Gly Asn Lys Glu Lys Asn Val Pro Leu
210                 215                 220
```

Pro Val Ile Ala Glu Leu Pro Pro Lys Val Ser Val Phe Val Pro Pro
225                 230                 235                 240

Arg Asp Gly Phe Phe Gly Asn Pro Arg Lys Ser Lys Leu Ile Cys Gln
            245                 250                 255

Ala Thr Gly Phe Ser Pro Arg Gln Ile Gln Val Ser Trp Leu Arg Glu
            260                 265                 270

Gly Lys Gln Val Gly Ser Gly Val Thr Thr Asp Gln Val Gln Ala Glu
            275                 280                 285

Ala Lys Glu Ser Gly Pro Thr Thr Tyr Lys Val Thr Ser Thr Leu Thr
290                 295                 300

Ile Lys Glu Ser Asp Trp Leu Ser Gln Ser Met Phe Thr Cys Arg Val
305                 310                 315                 320

Asp His Arg Gly Leu Thr Phe Gln Gln Asn Ala Ser Ser Met Cys Val
            325                 330                 335

Pro Asp Gln Asp Thr Ala Ile Arg Val Phe Ala Ile Pro Pro Ser Phe
            340                 345                 350

Ala Ser Ile Phe Leu Thr Lys Ser Thr Lys Leu Thr Cys Leu Val Thr
            355                 360                 365

Asp Leu Thr Thr Tyr Asp Ser Val Thr Ile Ser Trp Thr Arg Gln Asn
370                 375                 380

Gly Glu Ala Val Lys Thr His Thr Asn Ile Ser Glu Ser His Pro Asn
385                 390                 395                 400

Ala Thr Phe Ser Ala Val Gly Glu Ala Ser Ile Cys Glu Asp Asp Trp
            405                 410                 415

Asn Ser Gly Glu Arg Phe Thr Cys Thr Val Thr His Thr Asp Leu Pro
            420                 425                 430

Ser Pro Leu Lys Gln Thr Ile Ser Arg Pro Lys Gly Val Ala Leu His
            435                 440                 445

Arg Pro Asp Val Tyr Leu Leu Pro Pro Ala Arg Glu Gln Leu Asn Leu
450                 455                 460

Arg Glu Ser Ala Thr Ile Thr Cys Leu Val Thr Gly Phe Ser Pro Ala
465                 470                 475                 480

Asp Val Phe Val Gln Trp Met Gln Arg Gly Gln Pro Leu Ser Pro Glu
            485                 490                 495

Lys Tyr Val Thr Ser Ala Pro Met Pro Glu Pro Gln Ala Pro Gly Arg
            500                 505                 510

Tyr Phe Ala His Ser Ile Leu Thr Val Ser Glu Glu Trp Asn Thr
            515                 520                 525

Gly Glu Thr Tyr Thr Cys Val Val Ala His Glu Ala Leu Pro Asn Arg
530                 535                 540

Val Thr Glu Arg Thr Val Asp Lys Ser Thr Gly Lys Pro Thr Leu Tyr
545                 550                 555                 560

Asn Val Ser Leu Val Met Ser Asp Thr Ala Gly Thr Cys Tyr
            565                 570

<210> SEQ ID NO 34
<211> LENGTH: 574
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 34

Gln Val Gln Leu Gln Gln Trp Gly Ala Gly Leu Leu Lys Pro Ser Glu

```
1               5                   10                  15
Thr Leu Ser Leu Thr Cys Ala Val Tyr Gly Gly Ser Phe Ser Gly Tyr
            20                  25                  30

Tyr Trp Ser Trp Ile Arg Gln Pro Pro Gly Lys Gly Leu Glu Trp Ile
            35                  40                  45

Gly Glu Ile Asn His Ser Gly Ser Thr Asn Tyr Asn Pro Ser Leu Lys
            50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Arg Gly Met Ala Arg Gly Ala Ser Val Asn Phe Asp Tyr Trp Gly
                100                 105                 110

Gln Gly Thr Leu Val Thr Val Ser Ser Gly Ser Ala Ser Ala Pro Thr
                115                 120                 125

Leu Phe Pro Leu Val Ser Cys Glu Asn Ser Pro Ser Asp Thr Ser Ser
            130                 135                 140

Val Ala Val Gly Cys Leu Ala Gln Asp Phe Leu Pro Asp Ser Ile Thr
145                 150                 155                 160

Phe Ser Trp Lys Tyr Lys Asn Asn Ser Asp Ile Ser Ser Thr Arg Gly
                165                 170                 175

Phe Pro Ser Val Leu Arg Gly Gly Lys Tyr Ala Ala Thr Ser Gln Val
                180                 185                 190

Leu Leu Pro Ser Lys Asp Val Met Gln Gly Thr Asp Glu His Val Val
                195                 200                 205

Cys Lys Val Gln His Pro Asn Gly Asn Lys Glu Lys Asn Val Pro Leu
            210                 215                 220

Pro Val Ile Ala Glu Leu Pro Pro Lys Val Ser Val Phe Val Pro Pro
225                 230                 235                 240

Arg Asp Gly Phe Phe Gly Asn Pro Arg Lys Ser Lys Leu Ile Cys Gln
                245                 250                 255

Ala Thr Gly Phe Ser Pro Arg Gln Ile Gln Val Ser Trp Leu Arg Glu
                260                 265                 270

Gly Lys Gln Val Gly Ser Gly Val Thr Thr Asp Gln Val Gln Ala Glu
                275                 280                 285

Ala Lys Glu Ser Gly Pro Thr Thr Tyr Lys Val Thr Ser Thr Leu Thr
                290                 295                 300

Ile Lys Glu Ser Asp Trp Leu Ser Gln Ser Met Phe Thr Cys Arg Val
305                 310                 315                 320

Asp His Arg Gly Leu Thr Phe Gln Gln Asn Ala Ser Ser Met Cys Val
                325                 330                 335

Pro Asp Gln Asp Thr Ala Ile Arg Val Phe Ala Ile Pro Pro Ser Phe
                340                 345                 350

Ala Ser Ile Phe Leu Thr Lys Ser Thr Lys Leu Thr Cys Leu Val Thr
                355                 360                 365

Asp Leu Thr Thr Tyr Asp Ser Val Thr Ile Ser Trp Thr Arg Gln Asn
            370                 375                 380

Gly Glu Ala Val Lys Thr His Thr Asn Ile Ser Glu Ser His Pro Asn
385                 390                 395                 400

Ala Thr Phe Ser Ala Val Gly Glu Ala Ser Ile Cys Glu Asp Asp Trp
                405                 410                 415

Asn Ser Gly Glu Arg Phe Thr Cys Thr Val Thr His Thr Asp Leu Pro
            420                 425                 430
```

Ser Pro Leu Lys Gln Thr Ile Ser Arg Pro Lys Gly Val Ala Leu His
        435                 440                 445

Arg Pro Asp Val Tyr Leu Leu Pro Pro Ala Arg Glu Gln Leu Asn Leu
    450                 455                 460

Arg Glu Ser Ala Thr Ile Thr Cys Leu Val Thr Gly Phe Ser Pro Ala
465                 470                 475                 480

Asp Val Phe Val Gln Trp Met Gln Arg Gly Gln Pro Leu Ser Pro Glu
                485                 490                 495

Lys Tyr Val Thr Ser Ala Pro Met Pro Glu Pro Gln Ala Pro Gly Arg
            500                 505                 510

Tyr Phe Ala His Ser Ile Leu Thr Val Ser Glu Glu Trp Asn Thr
                515                 520                 525

Gly Glu Thr Tyr Thr Cys Val Val Ala His Glu Ala Leu Pro Asn Arg
            530                 535                 540

Val Thr Glu Arg Thr Val Asp Lys Ser Thr Gly Lys Pro Thr Leu Tyr
545                 550                 555                 560

Asn Val Ser Leu Val Met Ser Asp Thr Ala Gly Thr Cys Tyr
                565                 570

<210> SEQ ID NO 35
<211> LENGTH: 574
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 35

Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Gly Tyr
            20                  25                  30

Tyr Trp Ser Trp Ile Arg Gln Pro Pro Gly Lys Gly Leu Glu Trp Ile
        35                  40                  45

Gly Glu Ile Asn His Ser Gly Ser Thr Asn Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Arg Gly Arg Ala Arg Gly Ala Ser Val Asn Phe Asp Tyr Trp Gly
            100                 105                 110

Gln Gly Thr Leu Val Thr Val Ser Ser Gly Ser Ala Ser Ala Pro Thr
        115                 120                 125

Leu Phe Pro Leu Val Ser Cys Glu Asn Ser Pro Ser Asp Thr Ser Ser
    130                 135                 140

Val Ala Val Gly Cys Leu Ala Gln Asp Phe Leu Pro Asp Ser Ile Thr
145                 150                 155                 160

Phe Ser Trp Lys Tyr Lys Asn Asn Ser Asp Ile Ser Ser Thr Arg Gly
                165                 170                 175

Phe Pro Ser Val Leu Arg Gly Gly Lys Tyr Ala Ala Thr Ser Gln Val
            180                 185                 190

Leu Leu Pro Ser Lys Asp Val Met Gln Gly Thr Asp Glu His Val Val
        195                 200                 205

Cys Lys Val Gln His Pro Asn Gly Asn Lys Glu Lys Asn Val Pro Leu

```
            210                 215                 220
Pro Val Ile Ala Glu Leu Pro Lys Val Ser Val Phe Val Pro Pro
225                 230                 235                 240

Arg Asp Gly Phe Phe Gly Asn Pro Arg Lys Ser Lys Leu Ile Cys Gln
                245                 250                 255

Ala Thr Gly Phe Ser Pro Arg Gln Ile Gln Val Ser Trp Leu Arg Glu
                260                 265                 270

Gly Lys Gln Val Gly Ser Gly Val Thr Thr Asp Gln Val Gln Ala Glu
                275                 280                 285

Ala Lys Glu Ser Gly Pro Thr Thr Tyr Lys Val Thr Ser Thr Leu Thr
290                 295                 300

Ile Lys Glu Ser Asp Trp Leu Ser Gln Ser Met Phe Thr Cys Arg Val
305                 310                 315                 320

Asp His Arg Gly Leu Thr Phe Gln Gln Asn Ala Ser Ser Met Cys Val
                325                 330                 335

Pro Asp Gln Asp Thr Ala Ile Arg Val Phe Ala Ile Pro Pro Ser Phe
                340                 345                 350

Ala Ser Ile Phe Leu Thr Lys Ser Thr Lys Leu Thr Cys Leu Val Thr
                355                 360                 365

Asp Leu Thr Thr Tyr Asp Ser Val Thr Ile Ser Trp Thr Arg Gln Asn
                370                 375                 380

Gly Glu Ala Val Lys Thr His Thr Asn Ile Ser Glu Ser His Pro Asn
385                 390                 395                 400

Ala Thr Phe Ser Ala Val Gly Glu Ala Ser Ile Cys Glu Asp Asp Trp
                405                 410                 415

Asn Ser Gly Glu Arg Phe Thr Cys Thr Val Thr His Thr Asp Leu Pro
                420                 425                 430

Ser Pro Leu Lys Gln Thr Ile Ser Arg Pro Lys Gly Val Ala Leu His
                435                 440                 445

Arg Pro Asp Val Tyr Leu Leu Pro Pro Ala Arg Glu Gln Leu Asn Leu
450                 455                 460

Arg Glu Ser Ala Thr Ile Thr Cys Leu Val Thr Gly Phe Ser Pro Ala
465                 470                 475                 480

Asp Val Phe Val Gln Trp Met Gln Arg Gly Gln Pro Leu Ser Pro Glu
                485                 490                 495

Lys Tyr Val Thr Ser Ala Pro Met Pro Glu Pro Gln Ala Pro Gly Arg
                500                 505                 510

Tyr Phe Ala His Ser Ile Leu Thr Val Ser Glu Glu Trp Asn Thr
                515                 520                 525

Gly Glu Thr Tyr Thr Cys Val Val Ala His Glu Ala Leu Pro Asn Arg
530                 535                 540

Val Thr Glu Arg Thr Val Asp Lys Ser Thr Gly Lys Pro Thr Leu Tyr
545                 550                 555                 560

Asn Val Ser Leu Val Met Ser Asp Thr Ala Gly Thr Cys Tyr
                565                 570
```

<210> SEQ ID NO 36
<211> LENGTH: 574
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 36

-continued

```
Gln Val Gln Leu Gln Gln Trp Gly Ala Gly Leu Leu Lys Pro Ser Glu
  1               5                  10                  15

Thr Leu Ser Leu Thr Cys Ala Val Tyr Gly Gly Ser Phe Ser Gly Tyr
             20                  25                  30

Tyr Trp Ser Trp Ile Arg Gln Pro Pro Gly Lys Gly Leu Glu Trp Ile
         35                  40                  45

Gly Glu Ile Asn His Ser Gly Ser Thr Asn Tyr Asn Pro Ser Leu Lys
 50                  55                  60

Ser Arg Val Thr Ile Ser Val Asp Thr Ser Lys Asn Gln Phe Ser Leu
 65                  70                  75                  80

Lys Leu Ser Ser Val Thr Ala Ala Asp Thr Ala Val Tyr Tyr Cys Ala
                 85                  90                  95

Arg Arg Arg Gly Ala Arg Gly Ala Ser Val Asn Phe Asp Tyr Trp Gly
             100                 105                 110

Gln Gly Thr Leu Val Thr Val Ser Ser Gly Ser Ala Ser Ala Pro Thr
             115                 120                 125

Leu Phe Pro Leu Val Ser Cys Glu Asn Ser Pro Ser Asp Thr Ser Ser
         130                 135                 140

Val Ala Val Gly Cys Leu Ala Gln Asp Phe Leu Pro Asp Ser Ile Thr
145                 150                 155                 160

Phe Ser Trp Lys Tyr Lys Asn Asn Ser Asp Ile Ser Ser Thr Arg Gly
                 165                 170                 175

Phe Pro Ser Val Leu Arg Gly Gly Lys Tyr Ala Ala Thr Ser Gln Val
             180                 185                 190

Leu Leu Pro Ser Lys Asp Val Met Gln Gly Thr Asp Glu His Val Val
         195                 200                 205

Cys Lys Val Gln His Pro Asn Gly Asn Lys Glu Lys Asn Val Pro Leu
 210                 215                 220

Pro Val Ile Ala Glu Leu Pro Pro Lys Val Ser Val Phe Val Pro Pro
225                 230                 235                 240

Arg Asp Gly Phe Phe Gly Asn Pro Arg Lys Ser Lys Leu Ile Cys Gln
                 245                 250                 255

Ala Thr Gly Phe Ser Pro Arg Gln Ile Gln Val Ser Trp Leu Arg Glu
             260                 265                 270

Gly Lys Gln Val Gly Ser Gly Val Thr Thr Asp Gln Val Gln Ala Glu
         275                 280                 285

Ala Lys Glu Ser Gly Pro Thr Thr Tyr Lys Val Thr Ser Thr Leu Thr
 290                 295                 300

Ile Lys Glu Ser Asp Trp Leu Ser Gln Ser Met Phe Thr Cys Arg Val
305                 310                 315                 320

Asp His Arg Gly Leu Thr Phe Gln Gln Asn Ala Ser Ser Met Cys Val
                 325                 330                 335

Pro Asp Gln Asp Thr Ala Ile Arg Val Phe Ala Ile Pro Pro Ser Phe
             340                 345                 350

Ala Ser Ile Phe Leu Thr Lys Ser Thr Lys Leu Thr Cys Leu Val Thr
         355                 360                 365

Asp Leu Thr Thr Tyr Asp Ser Val Thr Ile Ser Trp Thr Arg Gln Asn
 370                 375                 380

Gly Glu Ala Val Lys Thr His Thr Asn Ile Ser Glu Ser His Pro Asn
385                 390                 395                 400

Ala Thr Phe Ser Ala Val Gly Glu Ala Ser Ile Cys Glu Asp Asp Trp
                 405                 410                 415

Asn Ser Gly Glu Arg Phe Thr Cys Thr Val Thr His Thr Asp Leu Pro
```

```
                420             425             430
Ser Pro Leu Lys Gln Thr Ile Ser Arg Pro Lys Gly Val Ala Leu His
            435                 440                 445

Arg Pro Asp Val Tyr Leu Leu Pro Ala Arg Glu Gln Leu Asn Leu
        450                 455                 460

Arg Glu Ser Ala Thr Ile Thr Cys Leu Val Thr Gly Phe Ser Pro Ala
465                 470                 475                 480

Asp Val Phe Val Gln Trp Met Gln Arg Gly Gln Pro Leu Ser Pro Glu
                485                 490                 495

Lys Tyr Val Thr Ser Ala Pro Met Pro Glu Pro Gln Ala Pro Gly Arg
            500                 505                 510

Tyr Phe Ala His Ser Ile Leu Thr Val Ser Glu Glu Glu Trp Asn Thr
        515                 520                 525

Gly Glu Thr Tyr Thr Cys Val Val Ala His Glu Ala Leu Pro Asn Arg
530                 535                 540

Val Thr Glu Arg Thr Val Asp Lys Ser Thr Gly Lys Pro Thr Leu Tyr
545                 550                 555                 560

Asn Val Ser Leu Val Met Ser Asp Thr Ala Gly Thr Cys Tyr
                565                 570

<210> SEQ ID NO 37
<211> LENGTH: 574
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 37

Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Gly Tyr
            20                  25                  30

Tyr Trp Ser Trp Ile Arg Gln Pro Pro Gly Lys Gly Leu Glu Trp Ile
        35                  40                  45

Gly Glu Ile Asn His Ser Gly Ser Thr Asn Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Ala Gly Arg Ala Trp Gly Ala Ser Val Asn Phe Asp Tyr Trp Gly
            100                 105                 110

Gln Gly Thr Leu Val Thr Val Ser Ser Gly Ser Ala Ser Ala Pro Thr
        115                 120                 125

Leu Phe Pro Leu Val Ser Cys Glu Asn Ser Pro Ser Asp Thr Ser Ser
    130                 135                 140

Val Ala Val Gly Cys Leu Ala Gln Asp Phe Leu Pro Asp Ser Ile Thr
145                 150                 155                 160

Phe Ser Trp Lys Tyr Lys Asn Asn Ser Asp Ile Ser Ser Thr Arg Gly
                165                 170                 175

Phe Pro Ser Val Leu Arg Gly Gly Lys Tyr Ala Ala Thr Ser Gln Val
            180                 185                 190

Leu Leu Pro Ser Lys Asp Val Met Gln Gly Thr Asp Glu His Val Val
        195                 200                 205
```

```
Cys Lys Val Gln His Pro Asn Gly Asn Lys Glu Lys Asn Val Pro Leu
210                 215                 220

Pro Val Ile Ala Glu Leu Pro Pro Lys Val Ser Val Phe Val Pro Pro
225                 230                 235                 240

Arg Asp Gly Phe Phe Gly Asn Pro Arg Lys Ser Lys Leu Ile Cys Gln
            245                 250                 255

Ala Thr Gly Phe Ser Pro Arg Gln Ile Gln Val Ser Trp Leu Arg Glu
            260                 265                 270

Gly Lys Gln Val Gly Ser Gly Val Thr Thr Asp Gln Val Gln Ala Glu
        275                 280                 285

Ala Lys Glu Ser Gly Pro Thr Thr Tyr Lys Val Thr Ser Thr Leu Thr
290                 295                 300

Ile Lys Glu Ser Asp Trp Leu Ser Gln Ser Met Phe Thr Cys Arg Val
305                 310                 315                 320

Asp His Arg Gly Leu Thr Phe Gln Gln Asn Ala Ser Ser Met Cys Val
                325                 330                 335

Pro Asp Gln Asp Thr Ala Ile Arg Val Phe Ala Ile Pro Pro Ser Phe
            340                 345                 350

Ala Ser Ile Phe Leu Thr Lys Ser Thr Lys Leu Thr Cys Leu Val Thr
            355                 360                 365

Asp Leu Thr Thr Tyr Asp Ser Val Thr Ile Ser Trp Thr Arg Gln Asn
370                 375                 380

Gly Glu Ala Val Lys Thr His Thr Asn Ile Ser Glu Ser His Pro Asn
385                 390                 395                 400

Ala Thr Phe Ser Ala Val Gly Glu Ala Ser Ile Cys Glu Asp Asp Trp
                405                 410                 415

Asn Ser Gly Glu Arg Phe Thr Cys Thr Val Thr His Thr Asp Leu Pro
            420                 425                 430

Ser Pro Leu Lys Gln Thr Ile Ser Arg Pro Lys Gly Val Ala Leu His
            435                 440                 445

Arg Pro Asp Val Tyr Leu Leu Pro Pro Ala Arg Glu Gln Leu Asn Leu
450                 455                 460

Arg Glu Ser Ala Thr Ile Thr Cys Leu Val Thr Gly Phe Ser Pro Ala
465                 470                 475                 480

Asp Val Phe Val Gln Trp Met Gln Arg Gly Gln Pro Leu Ser Pro Glu
                485                 490                 495

Lys Tyr Val Thr Ser Ala Pro Met Pro Glu Pro Gln Ala Pro Gly Arg
            500                 505                 510

Tyr Phe Ala His Ser Ile Leu Thr Val Ser Glu Glu Glu Trp Asn Thr
            515                 520                 525

Gly Glu Thr Tyr Thr Cys Val Val Ala His Glu Ala Leu Pro Asn Arg
530                 535                 540

Val Thr Glu Arg Thr Val Asp Lys Ser Thr Gly Lys Pro Thr Leu Tyr
545                 550                 555                 560

Asn Val Ser Leu Val Met Ser Asp Thr Ala Gly Thr Cys Tyr
                565                 570

<210> SEQ ID NO 38
<211> LENGTH: 574
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 38
```

-continued

```
Gln Val Gln Leu Gln Gln Trp Gly Ala Gly Leu Leu Lys Pro Ser Glu
1               5                   10                  15
Thr Leu Ser Leu Thr Cys Ala Val Tyr Gly Gly Ser Phe Ser Gly Tyr
            20                  25                  30
Tyr Trp Ser Trp Ile Arg Gln Pro Pro Gly Lys Gly Leu Glu Trp Ile
        35                  40                  45
Gly Glu Ile Asn His Ser Gly Ser Thr Asn Tyr Asn Pro Ser Leu Lys
    50                  55                  60
Ser Arg Val Thr Ile Ser Val Asp Thr Ser Lys Asn Gln Phe Ser Leu
65                  70                  75                  80
Lys Leu Ser Ser Val Thr Ala Ala Asp Thr Ala Val Tyr Tyr Cys Ala
                85                  90                  95
Arg Arg Gly Arg Ala Trp Gly Ala Ser Val Asn Phe Asp Tyr Trp Gly
            100                 105                 110
Gln Gly Thr Leu Val Thr Val Ser Ser Gly Ser Ala Ser Ala Pro Thr
        115                 120                 125
Leu Phe Pro Leu Val Ser Cys Glu Asn Ser Pro Ser Asp Thr Ser Ser
    130                 135                 140
Val Ala Val Gly Cys Leu Ala Gln Asp Phe Leu Pro Asp Ser Ile Thr
145                 150                 155                 160
Phe Ser Trp Lys Tyr Lys Asn Asn Ser Asp Ile Ser Ser Thr Arg Gly
                165                 170                 175
Phe Pro Ser Val Leu Arg Gly Gly Lys Tyr Ala Ala Thr Ser Gln Val
            180                 185                 190
Leu Leu Pro Ser Lys Asp Val Met Gln Gly Thr Asp Glu His Val Val
        195                 200                 205
Cys Lys Val Gln His Pro Asn Gly Asn Lys Glu Lys Asn Val Pro Leu
    210                 215                 220
Pro Val Ile Ala Glu Leu Pro Pro Lys Val Ser Val Phe Val Pro Pro
225                 230                 235                 240
Arg Asp Gly Phe Phe Gly Asn Pro Arg Lys Ser Lys Leu Ile Cys Gln
                245                 250                 255
Ala Thr Gly Phe Ser Pro Arg Gln Ile Gln Val Ser Trp Leu Arg Glu
            260                 265                 270
Gly Lys Gln Val Gly Ser Gly Val Thr Thr Asp Gln Val Gln Ala Glu
        275                 280                 285
Ala Lys Glu Ser Gly Pro Thr Thr Tyr Lys Val Thr Ser Thr Leu Thr
    290                 295                 300
Ile Lys Glu Ser Asp Trp Leu Ser Gln Ser Met Phe Thr Cys Arg Val
305                 310                 315                 320
Asp His Arg Gly Leu Thr Phe Gln Gln Asn Ala Ser Ser Met Cys Val
                325                 330                 335
Pro Asp Gln Asp Thr Ala Ile Arg Val Phe Ala Ile Pro Pro Ser Phe
            340                 345                 350
Ala Ser Ile Phe Leu Thr Lys Ser Thr Lys Leu Thr Cys Leu Val Thr
        355                 360                 365
Asp Leu Thr Thr Tyr Asp Ser Val Thr Ile Ser Trp Thr Arg Gln Asn
    370                 375                 380
Gly Glu Ala Val Lys Thr His Thr Asn Ile Ser Glu Ser His Pro Asn
385                 390                 395                 400
Ala Thr Phe Ser Ala Val Gly Glu Ala Ser Ile Cys Glu Asp Asp Trp
                405                 410                 415
```

Asn Ser Gly Glu Arg Phe Thr Cys Thr Val Thr His Thr Asp Leu Pro
              420                 425                 430

Ser Pro Leu Lys Gln Thr Ile Ser Arg Pro Lys Gly Val Ala Leu His
        435                 440                 445

Arg Pro Asp Val Tyr Leu Leu Pro Pro Ala Arg Glu Gln Leu Asn Leu
450                 455                 460

Arg Glu Ser Ala Thr Ile Thr Cys Leu Val Thr Gly Phe Ser Pro Ala
465                 470                 475                 480

Asp Val Phe Val Gln Trp Met Gln Arg Gly Gln Pro Leu Ser Pro Glu
                485                 490                 495

Lys Tyr Val Thr Ser Ala Pro Met Pro Glu Pro Gln Ala Pro Gly Arg
            500                 505                 510

Tyr Phe Ala His Ser Ile Leu Thr Val Ser Glu Glu Trp Asn Thr
            515                 520                 525

Gly Glu Thr Tyr Thr Cys Val Val Ala His Glu Ala Leu Pro Asn Arg
            530                 535                 540

Val Thr Glu Arg Thr Val Asp Lys Ser Thr Gly Lys Pro Thr Leu Tyr
545                 550                 555                 560

Asn Val Ser Leu Val Met Ser Asp Thr Ala Gly Thr Cys Tyr
                565                 570

<210> SEQ ID NO 39
<211> LENGTH: 573
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 39

Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Gly Tyr
            20                  25                  30

Tyr Trp Ser Trp Ile Arg Gln Pro Pro Gly Lys Gly Leu Glu Trp Ile
        35                  40                  45

Gly Glu Ile Asn His Ser Gly Ser Thr Asn Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Ala Arg Thr Ala Trp Gly Ser Ser Ile Phe Asp Tyr Trp Gly Gln
            100                 105                 110

Gly Thr Leu Val Thr Val Ser Ser Gly Ser Ala Ser Ala Pro Thr Leu
        115                 120                 125

Phe Pro Leu Val Ser Cys Glu Asn Ser Pro Ser Asp Thr Ser Ser Val
    130                 135                 140

Ala Val Gly Cys Leu Ala Gln Asp Phe Leu Pro Asp Ser Ile Thr Phe
145                 150                 155                 160

Ser Trp Lys Tyr Lys Asn Asn Ser Asp Ile Ser Ser Thr Arg Gly Phe
                165                 170                 175

Pro Ser Val Leu Arg Gly Gly Lys Tyr Ala Ala Thr Ser Gln Val Leu
            180                 185                 190

Leu Pro Ser Lys Asp Val Met Gln Gly Thr Asp Glu His Val Val Cys
        195                 200                 205

Lys Val Gln His Pro Asn Gly Asn Lys Glu Lys Asn Val Pro Leu Pro
210                 215                 220

Val Ile Ala Glu Leu Pro Pro Lys Val Ser Val Phe Val Pro Pro Arg
225                 230                 235                 240

Asp Gly Phe Phe Gly Asn Pro Arg Lys Ser Lys Leu Ile Cys Gln Ala
            245                 250                 255

Thr Gly Phe Ser Pro Arg Gln Ile Gln Val Ser Trp Leu Arg Glu Gly
            260                 265                 270

Lys Gln Val Gly Ser Gly Val Thr Thr Asp Gln Val Gln Ala Glu Ala
            275                 280                 285

Lys Glu Ser Gly Pro Thr Thr Tyr Lys Val Thr Ser Thr Leu Thr Ile
290                 295                 300

Lys Glu Ser Asp Trp Leu Ser Gln Ser Met Phe Thr Cys Arg Val Asp
305                 310                 315                 320

His Arg Gly Leu Thr Phe Gln Gln Asn Ala Ser Ser Met Cys Val Pro
            325                 330                 335

Asp Gln Asp Thr Ala Ile Arg Val Phe Ala Ile Pro Pro Ser Phe Ala
            340                 345                 350

Ser Ile Phe Leu Thr Lys Ser Thr Lys Leu Thr Cys Leu Val Thr Asp
            355                 360                 365

Leu Thr Thr Tyr Asp Ser Val Thr Ile Ser Trp Thr Arg Gln Asn Gly
370                 375                 380

Glu Ala Val Lys Thr His Thr Asn Ile Ser Glu Ser His Pro Asn Ala
385                 390                 395                 400

Thr Phe Ser Ala Val Gly Glu Ala Ser Ile Cys Glu Asp Asp Trp Asn
            405                 410                 415

Ser Gly Glu Arg Phe Thr Cys Thr Val Thr His Thr Asp Leu Pro Ser
            420                 425                 430

Pro Leu Lys Gln Thr Ile Ser Arg Pro Lys Gly Val Ala Leu His Arg
            435                 440                 445

Pro Asp Val Tyr Leu Leu Pro Pro Ala Arg Glu Gln Leu Asn Leu Arg
450                 455                 460

Glu Ser Ala Thr Ile Thr Cys Leu Val Thr Gly Phe Ser Pro Ala Asp
465                 470                 475                 480

Val Phe Val Gln Trp Met Gln Arg Gly Gln Pro Leu Ser Pro Glu Lys
            485                 490                 495

Tyr Val Thr Ser Ala Pro Met Pro Glu Pro Gln Ala Pro Gly Arg Tyr
            500                 505                 510

Phe Ala His Ser Ile Leu Thr Val Ser Glu Glu Glu Trp Asn Thr Gly
            515                 520                 525

Glu Thr Tyr Thr Cys Val Val Ala His Glu Ala Leu Pro Asn Arg Val
530                 535                 540

Thr Glu Arg Thr Val Asp Lys Ser Thr Gly Lys Pro Thr Leu Tyr Asn
545                 550                 555                 560

Val Ser Leu Val Met Ser Asp Thr Ala Gly Thr Cys Tyr
                565                 570

<210> SEQ ID NO 40
<211> LENGTH: 573
<212> TYPE: PRT
<213> ORGANISM: Artificial Sequence
<220> FEATURE:
<223> OTHER INFORMATION: Description of Artificial Sequence: Synthetic
      polypeptide -continued

```
<400> SEQUENCE: 40

Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Gly Tyr
            20                  25                  30

Tyr Trp Ser Trp Ile Arg Gln Pro Pro Gly Lys Gly Leu Glu Trp Ile
        35                  40                  45

Gly Glu Ile Asn His Ser Gly Ser Thr Asn Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Ala Arg Arg Ala Trp Gly Ser Ser Ile Phe Asp Tyr Trp Gly Gln
            100                 105                 110

Gly Thr Leu Val Thr Val Ser Ser Gly Ser Ala Ser Ala Pro Thr Leu
        115                 120                 125

Phe Pro Leu Val Ser Cys Glu Asn Ser Pro Ser Asp Thr Ser Ser Val
    130                 135                 140

Ala Val Gly Cys Leu Ala Gln Asp Phe Leu Pro Asp Ser Ile Thr Phe
145                 150                 155                 160

Ser Trp Lys Tyr Lys Asn Asn Ser Asp Ile Ser Ser Thr Arg Gly Phe
                165                 170                 175

Pro Ser Val Leu Arg Gly Gly Lys Tyr Ala Ala Thr Ser Gln Val Leu
            180                 185                 190

Leu Pro Ser Lys Asp Val Met Gln Gly Thr Asp Glu His Val Val Cys
        195                 200                 205

Lys Val Gln His Pro Asn Gly Asn Lys Glu Lys Asn Val Pro Leu Pro
    210                 215                 220

Val Ile Ala Glu Leu Pro Pro Lys Val Ser Val Phe Val Pro Pro Arg
225                 230                 235                 240

Asp Gly Phe Phe Gly Asn Pro Arg Lys Ser Lys Leu Ile Cys Gln Ala
                245                 250                 255

Thr Gly Phe Ser Pro Arg Gln Ile Gln Val Ser Trp Leu Arg Glu Gly
            260                 265                 270

Lys Gln Val Gly Ser Gly Val Thr Thr Asp Gln Val Gln Ala Glu Ala
        275                 280                 285

Lys Glu Ser Gly Pro Thr Thr Tyr Lys Val Thr Ser Thr Leu Thr Ile
    290                 295                 300

Lys Glu Ser Asp Trp Leu Ser Gln Ser Met Phe Thr Cys Arg Val Asp
305                 310                 315                 320

His Arg Gly Leu Thr Phe Gln Gln Asn Ala Ser Ser Met Cys Val Pro
                325                 330                 335

Asp Gln Asp Thr Ala Ile Arg Val Phe Ala Ile Pro Pro Ser Phe Ala
            340                 345                 350

Ser Ile Phe Leu Thr Lys Ser Thr Lys Leu Thr Cys Leu Val Thr Asp
        355                 360                 365

Leu Thr Thr Tyr Asp Ser Val Thr Ile Ser Trp Thr Arg Gln Asn Gly
    370                 375                 380

Glu Ala Val Lys Thr His Thr Asn Ile Ser Glu Ser His Pro Asn Ala
385                 390                 395                 400

Thr Phe Ser Ala Val Gly Glu Ala Ser Ile Cys Glu Asp Asp Trp Asn
                405                 410                 415
```

```
Ser Gly Glu Arg Phe Thr Cys Thr Val Thr His Thr Asp Leu Pro Ser
            420                 425                 430

Pro Leu Lys Gln Thr Ile Ser Arg Pro Lys Gly Val Ala Leu His Arg
        435                 440                 445

Pro Asp Val Tyr Leu Leu Pro Pro Ala Arg Glu Gln Leu Asn Leu Arg
450                 455                 460

Glu Ser Ala Thr Ile Thr Cys Leu Val Thr Gly Phe Ser Pro Ala Asp
465                 470                 475                 480

Val Phe Val Gln Trp Met Gln Arg Gly Gln Pro Leu Ser Pro Glu Lys
                485                 490                 495

Tyr Val Thr Ser Ala Pro Met Pro Glu Pro Gln Ala Pro Gly Arg Tyr
                500                 505                 510

Phe Ala His Ser Ile Leu Thr Val Ser Glu Glu Glu Trp Asn Thr Gly
            515                 520                 525

Glu Thr Tyr Thr Cys Val Val Ala His Glu Ala Leu Pro Asn Arg Val
        530                 535                 540

Thr Glu Arg Thr Val Asp Lys Ser Thr Gly Lys Pro Thr Leu Tyr Asn
545                 550                 555                 560

Val Ser Leu Val Met Ser Asp Thr Ala Gly Thr Cys Tyr
                565                 570

<210> SEQ ID NO 41
<211> LENGTH: 573
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 41

Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Gly Tyr
            20                  25                  30

Tyr Trp Ser Trp Ile Arg Gln Pro Pro Gly Lys Gly Leu Glu Trp Ile
        35                  40                  45

Gly Glu Ile Asn His Ser Gly Ser Thr Asn Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Ala Arg Arg Ala Trp Gly Ser Ser Ile Phe Asp Tyr Trp Gly Gln
            100                 105                 110

Gly Thr Leu Val Thr Val Ser Ser Gly Ser Ala Ser Ala Pro Thr Leu
        115                 120                 125

Phe Pro Leu Val Ser Cys Glu Asn Ser Pro Ser Asp Thr Ser Ser Val
130                 135                 140

Ala Val Gly Cys Leu Ala Gln Asp Phe Leu Pro Asp Ser Ile Thr Phe
145                 150                 155                 160

Ser Trp Lys Tyr Lys Asn Asn Ser Asp Ile Ser Ser Thr Arg Gly Phe
                165                 170                 175

Pro Ser Val Leu Arg Gly Gly Lys Tyr Ala Ala Thr Ser Gln Val Leu
            180                 185                 190

Leu Pro Ser Lys Asp Val Met Gln Gly Thr Asp Glu His Val Val Cys
```

195                 200                 205
Lys Val Gln His Pro Asn Gly Asn Lys Glu Lys Asn Val Pro Leu Pro
210                 215                 220

Val Ile Ala Glu Leu Pro Pro Lys Val Ser Val Phe Val Pro Pro Arg
225                 230                 235                 240

Asp Gly Phe Phe Gly Asn Pro Arg Lys Ser Lys Leu Ile Cys Gln Ala
                245                 250                 255

Thr Gly Phe Ser Pro Arg Gln Ile Gln Val Ser Trp Leu Arg Glu Gly
            260                 265                 270

Lys Gln Val Gly Ser Gly Val Thr Thr Asp Gln Val Gln Ala Glu Ala
        275                 280                 285

Lys Glu Ser Gly Pro Thr Thr Tyr Lys Val Thr Ser Thr Leu Thr Ile
290                 295                 300

Lys Glu Ser Asp Trp Leu Ser Gln Ser Met Phe Thr Cys Arg Val Asp
305                 310                 315                 320

His Arg Gly Leu Thr Phe Gln Gln Asn Ala Ser Ser Met Cys Val Pro
                325                 330                 335

Asp Gln Asp Thr Ala Ile Arg Val Phe Ala Ile Pro Pro Ser Phe Ala
            340                 345                 350

Ser Ile Phe Leu Thr Lys Ser Thr Lys Leu Thr Cys Leu Val Thr Asp
        355                 360                 365

Leu Thr Thr Tyr Asp Ser Val Thr Ile Ser Trp Thr Arg Gln Asn Gly
370                 375                 380

Glu Ala Val Lys Thr His Thr Asn Ile Ser Glu Ser His Pro Asn Ala
385                 390                 395                 400

Thr Phe Ser Ala Val Gly Glu Ala Ser Ile Cys Glu Asp Asp Trp Asn
                405                 410                 415

Ser Gly Glu Arg Phe Thr Cys Thr Val Thr His Thr Asp Leu Pro Ser
            420                 425                 430

Pro Leu Lys Gln Thr Ile Ser Arg Pro Lys Gly Val Ala Leu His Arg
        435                 440                 445

Pro Asp Val Tyr Leu Leu Pro Pro Ala Arg Glu Gln Leu Asn Leu Arg
450                 455                 460

Glu Ser Ala Thr Ile Thr Cys Leu Val Thr Gly Phe Ser Pro Ala Asp
465                 470                 475                 480

Val Phe Val Gln Trp Met Gln Arg Gly Gln Pro Leu Ser Pro Glu Lys
                485                 490                 495

Tyr Val Thr Ser Ala Pro Met Pro Glu Pro Gln Ala Pro Gly Arg Tyr
            500                 505                 510

Phe Ala His Ser Ile Leu Thr Val Ser Glu Glu Glu Trp Asn Thr Gly
        515                 520                 525

Glu Thr Tyr Thr Cys Val Val Ala His Glu Ala Leu Pro Asn Arg Val
530                 535                 540

Thr Glu Arg Thr Val Asp Lys Ser Thr Gly Lys Pro Thr Leu Tyr Asn
545                 550                 555                 560

Val Ser Leu Val Met Ser Asp Thr Ala Gly Thr Cys Tyr
                565                 570

<210> SEQ ID NO 42
<211> LENGTH: 573
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 42

```
Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Gly Tyr
            20                  25                  30

Tyr Trp Ser Trp Ile Arg Gln Pro Pro Gly Lys Gly Leu Glu Trp Ile
        35                  40                  45

Gly Glu Ile Asn His Ser Gly Ser Thr Asn Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Ala Arg Arg Ala Arg Gly Ser Ser Ile Phe Asp Tyr Trp Gly Gln
            100                 105                 110

Gly Thr Leu Val Thr Val Ser Ser Gly Ser Ala Ser Ala Pro Thr Leu
        115                 120                 125

Phe Pro Leu Val Ser Cys Glu Asn Ser Pro Ser Asp Thr Ser Ser Val
130                 135                 140

Ala Val Gly Cys Leu Ala Gln Asp Phe Leu Pro Asp Ser Ile Thr Phe
145                 150                 155                 160

Ser Trp Lys Tyr Lys Asn Asn Ser Asp Ile Ser Ser Thr Arg Gly Phe
                165                 170                 175

Pro Ser Val Leu Arg Gly Gly Lys Tyr Ala Ala Thr Ser Gln Val Leu
            180                 185                 190

Leu Pro Ser Lys Asp Val Met Gln Gly Thr Asp Glu His Val Val Cys
        195                 200                 205

Lys Val Gln His Pro Asn Gly Asn Lys Glu Lys Asn Val Pro Leu Pro
    210                 215                 220

Val Ile Ala Glu Leu Pro Pro Lys Val Ser Val Phe Val Pro Pro Arg
225                 230                 235                 240

Asp Gly Phe Phe Gly Asn Pro Arg Lys Ser Lys Leu Ile Cys Gln Ala
                245                 250                 255

Thr Gly Phe Ser Pro Arg Gln Ile Gln Val Ser Trp Leu Arg Glu Gly
            260                 265                 270

Lys Gln Val Gly Ser Gly Val Thr Thr Asp Gln Val Gln Ala Glu Ala
        275                 280                 285

Lys Glu Ser Gly Pro Thr Thr Tyr Lys Val Thr Ser Thr Leu Thr Ile
    290                 295                 300

Lys Glu Ser Asp Trp Leu Ser Gln Ser Met Phe Thr Cys Arg Val Asp
305                 310                 315                 320

His Arg Gly Leu Thr Phe Gln Gln Asn Ala Ser Ser Met Cys Val Pro
                325                 330                 335

Asp Gln Asp Thr Ala Ile Arg Val Phe Ala Ile Pro Pro Ser Phe Ala
            340                 345                 350

Ser Ile Phe Leu Thr Lys Ser Thr Lys Leu Thr Cys Leu Val Thr Asp
        355                 360                 365

Leu Thr Thr Tyr Asp Ser Val Thr Ile Ser Trp Thr Arg Gln Asn Gly
    370                 375                 380

Glu Ala Val Lys Thr His Thr Asn Ile Ser Glu Ser His Pro Asn Ala
385                 390                 395                 400

Thr Phe Ser Ala Val Gly Glu Ala Ser Ile Cys Glu Asp Asp Trp Asn
```

-continued

```
                405                 410                 415
Ser Gly Glu Arg Phe Thr Cys Thr Val Thr His Thr Asp Leu Pro Ser
                420                 425                 430

Pro Leu Lys Gln Thr Ile Ser Arg Pro Lys Gly Val Ala Leu His Arg
            435                 440                 445

Pro Asp Val Tyr Leu Leu Pro Pro Ala Arg Glu Gln Leu Asn Leu Arg
        450                 455                 460

Glu Ser Ala Thr Ile Thr Cys Leu Val Thr Gly Phe Ser Pro Ala Asp
465                 470                 475                 480

Val Phe Val Gln Trp Met Gln Arg Gly Gln Pro Leu Ser Pro Glu Lys
                485                 490                 495

Tyr Val Thr Ser Ala Pro Met Pro Glu Pro Gln Ala Pro Gly Arg Tyr
            500                 505                 510

Phe Ala His Ser Ile Leu Thr Val Ser Glu Glu Glu Trp Asn Thr Gly
        515                 520                 525

Glu Thr Tyr Thr Cys Val Val Ala His Glu Ala Leu Pro Asn Arg Val
530                 535                 540

Thr Glu Arg Thr Val Asp Lys Ser Thr Gly Lys Pro Thr Leu Tyr Asn
545                 550                 555                 560

Val Ser Leu Val Met Ser Asp Thr Ala Gly Thr Cys Tyr
                565                 570
```

<210> SEQ ID NO 43
<211> LENGTH: 573
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 43

```
Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Gly Tyr
            20                  25                  30

Tyr Trp Ser Trp Ile Arg Gln Pro Pro Gly Lys Gly Leu Glu Trp Ile
        35                  40                  45

Gly Glu Ile Asn His Ser Gly Ser Thr Asn Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Arg Ala Thr Ala Trp Gly Ser Ser Ile Phe Asp Tyr Trp Gly Gln
            100                 105                 110

Gly Thr Leu Val Thr Val Ser Ser Gly Ser Ala Ser Ala Pro Thr Leu
        115                 120                 125

Phe Pro Leu Val Ser Cys Glu Asn Ser Pro Ser Asp Thr Ser Ser Val
    130                 135                 140

Ala Val Gly Cys Leu Ala Gln Asp Phe Leu Pro Asp Ser Ile Thr Phe
145                 150                 155                 160

Ser Trp Lys Tyr Lys Asn Asn Ser Asp Ile Ser Ser Thr Arg Gly Phe
                165                 170                 175

Pro Ser Val Leu Arg Gly Gly Lys Tyr Ala Ala Thr Ser Gln Val Leu
            180                 185                 190
```

Leu Pro Ser Lys Asp Val Met Gln Gly Thr Asp Glu His Val Val Cys
            195                 200                 205

Lys Val Gln His Pro Asn Gly Asn Lys Glu Lys Asn Val Pro Leu Pro
210                 215                 220

Val Ile Ala Glu Leu Pro Pro Lys Val Ser Val Phe Val Pro Pro Arg
225                 230                 235                 240

Asp Gly Phe Phe Gly Asn Pro Arg Lys Ser Lys Leu Ile Cys Gln Ala
            245                 250                 255

Thr Gly Phe Ser Pro Arg Gln Ile Gln Val Ser Trp Leu Arg Glu Gly
            260                 265                 270

Lys Gln Val Gly Ser Gly Val Thr Thr Asp Gln Val Gln Ala Glu Ala
        275                 280                 285

Lys Glu Ser Gly Pro Thr Thr Tyr Lys Val Thr Ser Thr Leu Thr Ile
        290                 295                 300

Lys Glu Ser Asp Trp Leu Ser Gln Ser Met Phe Thr Cys Arg Val Asp
305                 310                 315                 320

His Arg Gly Leu Thr Phe Gln Gln Asn Ala Ser Ser Met Cys Val Pro
            325                 330                 335

Asp Gln Asp Thr Ala Ile Arg Val Phe Ala Ile Pro Pro Ser Phe Ala
            340                 345                 350

Ser Ile Phe Leu Thr Lys Ser Thr Lys Leu Thr Cys Leu Val Thr Asp
        355                 360                 365

Leu Thr Thr Tyr Asp Ser Val Thr Ile Ser Trp Thr Arg Gln Asn Gly
        370                 375                 380

Glu Ala Val Lys Thr His Thr Asn Ile Ser Glu Ser His Pro Asn Ala
385                 390                 395                 400

Thr Phe Ser Ala Val Gly Glu Ala Ser Ile Cys Glu Asp Asp Trp Asn
            405                 410                 415

Ser Gly Glu Arg Phe Thr Cys Thr Val Thr His Thr Asp Leu Pro Ser
            420                 425                 430

Pro Leu Lys Gln Thr Ile Ser Arg Pro Lys Gly Val Ala Leu His Arg
        435                 440                 445

Pro Asp Val Tyr Leu Leu Pro Pro Ala Arg Glu Gln Leu Asn Leu Arg
450                 455                 460

Glu Ser Ala Thr Ile Thr Cys Leu Val Thr Gly Phe Ser Pro Ala Asp
465                 470                 475                 480

Val Phe Val Gln Trp Met Gln Arg Gly Gln Pro Leu Ser Pro Glu Lys
            485                 490                 495

Tyr Val Thr Ser Ala Pro Met Pro Glu Pro Gln Ala Pro Gly Arg Tyr
            500                 505                 510

Phe Ala His Ser Ile Leu Thr Val Ser Glu Glu Glu Trp Asn Thr Gly
        515                 520                 525

Glu Thr Tyr Thr Cys Val Val Ala His Glu Ala Leu Pro Asn Arg Val
        530                 535                 540

Thr Glu Arg Thr Val Asp Lys Ser Thr Gly Lys Pro Thr Leu Tyr Asn
545                 550                 555                 560

Val Ser Leu Val Met Ser Asp Thr Ala Gly Thr Cys Tyr
            565                 570

<210> SEQ ID NO 44
<211> LENGTH: 573
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 44

Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Gly Tyr
            20                  25                  30

Tyr Trp Ser Trp Ile Arg Gln Pro Pro Gly Lys Gly Leu Glu Trp Ile
        35                  40                  45

Gly Glu Ile Asn His Ser Gly Ser Thr Asn Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Arg Arg Thr Ala Trp Gly Ser Ser Ile Phe Asp Tyr Trp Gly Gln
            100                 105                 110

Gly Thr Leu Val Thr Val Ser Ser Gly Ser Ala Ser Ala Pro Thr Leu
        115                 120                 125

Phe Pro Leu Val Ser Cys Glu Asn Ser Pro Ser Asp Thr Ser Ser Val
130                 135                 140

Ala Val Gly Cys Leu Ala Gln Asp Phe Leu Pro Asp Ser Ile Thr Phe
145                 150                 155                 160

Ser Trp Lys Tyr Lys Asn Asn Ser Asp Ile Ser Ser Thr Arg Gly Phe
                165                 170                 175

Pro Ser Val Leu Arg Gly Gly Lys Tyr Ala Ala Thr Ser Gln Val Leu
            180                 185                 190

Leu Pro Ser Lys Asp Val Met Gln Gly Thr Asp Glu His Val Val Cys
        195                 200                 205

Lys Val Gln His Pro Asn Gly Asn Lys Glu Lys Asn Val Pro Leu Pro
    210                 215                 220

Val Ile Ala Glu Leu Pro Pro Lys Val Ser Val Phe Val Pro Pro Arg
225                 230                 235                 240

Asp Gly Phe Phe Gly Asn Pro Arg Lys Ser Lys Leu Ile Cys Gln Ala
                245                 250                 255

Thr Gly Phe Ser Pro Arg Gln Ile Gln Val Ser Trp Leu Arg Glu Gly
            260                 265                 270

Lys Gln Val Gly Ser Gly Val Thr Thr Asp Gln Val Gln Ala Glu Ala
        275                 280                 285

Lys Glu Ser Gly Pro Thr Thr Tyr Lys Val Thr Ser Thr Leu Thr Ile
    290                 295                 300

Lys Glu Ser Asp Trp Leu Ser Gln Ser Met Phe Thr Cys Arg Val Asp
305                 310                 315                 320

His Arg Gly Leu Thr Phe Gln Gln Asn Ala Ser Ser Met Cys Val Pro
                325                 330                 335

Asp Gln Asp Thr Ala Ile Arg Val Phe Ala Ile Pro Pro Ser Phe Ala
            340                 345                 350

Ser Ile Phe Leu Thr Lys Ser Thr Lys Leu Thr Cys Leu Val Thr Asp
        355                 360                 365

Leu Thr Thr Tyr Asp Ser Val Thr Ile Ser Trp Thr Arg Gln Asn Gly
    370                 375                 380

Glu Ala Val Lys Thr His Thr Asn Ile Ser Glu Ser His Pro Asn Ala
385                 390                 395                 400

```
Thr Phe Ser Ala Val Gly Glu Ala Ser Ile Cys Glu Asp Asp Trp Asn
                405                 410                 415

Ser Gly Glu Arg Phe Thr Cys Thr Val Thr His Thr Asp Leu Pro Ser
            420                 425                 430

Pro Leu Lys Gln Thr Ile Ser Arg Pro Lys Gly Val Ala Leu His Arg
        435                 440                 445

Pro Asp Val Tyr Leu Leu Pro Pro Ala Arg Glu Gln Leu Asn Leu Arg
    450                 455                 460

Glu Ser Ala Thr Ile Thr Cys Leu Val Thr Gly Phe Ser Pro Ala Asp
465                 470                 475                 480

Val Phe Val Gln Trp Met Gln Arg Gly Gln Pro Leu Ser Pro Glu Lys
                485                 490                 495

Tyr Val Thr Ser Ala Pro Met Pro Glu Pro Gln Ala Pro Gly Arg Tyr
            500                 505                 510

Phe Ala His Ser Ile Leu Thr Val Ser Glu Glu Glu Trp Asn Thr Gly
        515                 520                 525

Glu Thr Tyr Thr Cys Val Val Ala His Glu Ala Leu Pro Asn Arg Val
    530                 535                 540

Thr Glu Arg Thr Val Asp Lys Ser Thr Gly Lys Pro Thr Leu Tyr Asn
545                 550                 555                 560

Val Ser Leu Val Met Ser Asp Thr Ala Gly Thr Cys Tyr
                565                 570

<210> SEQ ID NO 45
<211> LENGTH: 573
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 45

Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Gly Tyr
            20                  25                  30

Tyr Trp Ser Trp Ile Arg Gln Pro Pro Gly Lys Gly Leu Glu Trp Ile
        35                  40                  45

Gly Glu Ile Asn His Ser Gly Ser Thr Asn Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Arg Ala Thr Ala Arg Gly Ser Ser Ile Phe Asp Tyr Trp Gly Gln
            100                 105                 110

Gly Thr Leu Val Thr Val Ser Ser Gly Ser Ala Ser Ala Pro Thr Leu
        115                 120                 125

Phe Pro Leu Val Ser Cys Glu Asn Ser Pro Ser Asp Thr Ser Ser Val
    130                 135                 140

Ala Val Gly Cys Leu Ala Gln Asp Phe Leu Pro Asp Ser Ile Thr Phe
145                 150                 155                 160

Ser Trp Lys Tyr Lys Asn Asn Ser Asp Ile Ser Ser Thr Arg Gly Phe
                165                 170                 175

Pro Ser Val Leu Arg Gly Gly Lys Tyr Ala Ala Thr Ser Gln Val Leu
            180                 185                 190
```

Leu Pro Ser Lys Asp Val Met Gln Gly Thr Asp Glu His Val Val Cys
                195                 200                 205

Lys Val Gln His Pro Asn Gly Asn Lys Glu Lys Asn Val Pro Leu Pro
        210                 215                 220

Val Ile Ala Glu Leu Pro Pro Lys Val Ser Val Phe Val Pro Pro Arg
225                 230                 235                 240

Asp Gly Phe Phe Gly Asn Pro Arg Lys Ser Lys Leu Ile Cys Gln Ala
                245                 250                 255

Thr Gly Phe Ser Pro Arg Gln Ile Gln Val Ser Trp Leu Arg Glu Gly
                260                 265                 270

Lys Gln Val Gly Ser Gly Val Thr Thr Asp Gln Val Gln Ala Glu Ala
        275                 280                 285

Lys Glu Ser Gly Pro Thr Thr Tyr Lys Val Thr Ser Thr Leu Thr Ile
        290                 295                 300

Lys Glu Ser Asp Trp Leu Ser Gln Ser Met Phe Thr Cys Arg Val Asp
305                 310                 315                 320

His Arg Gly Leu Thr Phe Gln Gln Asn Ala Ser Ser Met Cys Val Pro
                325                 330                 335

Asp Gln Asp Thr Ala Ile Arg Val Phe Ala Ile Pro Pro Ser Phe Ala
                340                 345                 350

Ser Ile Phe Leu Thr Lys Ser Thr Lys Leu Thr Cys Leu Val Thr Asp
                355                 360                 365

Leu Thr Thr Tyr Asp Ser Val Thr Ile Ser Trp Thr Arg Gln Asn Gly
        370                 375                 380

Glu Ala Val Lys Thr His Thr Asn Ile Ser Glu Ser His Pro Asn Ala
385                 390                 395                 400

Thr Phe Ser Ala Val Gly Glu Ala Ser Ile Cys Glu Asp Asp Trp Asn
                405                 410                 415

Ser Gly Glu Arg Phe Thr Cys Thr Val Thr His Thr Asp Leu Pro Ser
                420                 425                 430

Pro Leu Lys Gln Thr Ile Ser Arg Pro Lys Gly Val Ala Leu His Arg
        435                 440                 445

Pro Asp Val Tyr Leu Leu Pro Pro Ala Arg Glu Gln Leu Asn Leu Arg
        450                 455                 460

Glu Ser Ala Thr Ile Thr Cys Leu Val Thr Gly Phe Ser Pro Ala Asp
465                 470                 475                 480

Val Phe Val Gln Trp Met Gln Arg Gly Gln Pro Leu Ser Pro Glu Lys
                485                 490                 495

Tyr Val Thr Ser Ala Pro Met Pro Glu Pro Gln Ala Pro Gly Arg Tyr
                500                 505                 510

Phe Ala His Ser Ile Leu Thr Val Ser Glu Glu Glu Trp Asn Thr Gly
        515                 520                 525

Glu Thr Tyr Thr Cys Val Val Ala His Glu Ala Leu Pro Asn Arg Val
        530                 535                 540

Thr Glu Arg Thr Val Asp Lys Ser Thr Gly Lys Pro Thr Leu Tyr Asn
545                 550                 555                 560

Val Ser Leu Val Met Ser Asp Thr Ala Gly Thr Cys Tyr
                565                 570

<210> SEQ ID NO 46
<211> LENGTH: 573
<212> TYPE: PRT
<213> ORGANISM: Artificial Sequence
<220> FEATURE:

-continued

<223> OTHER INFORMATION: Description of Artificial Sequence: Synthetic
      polypeptide

<400> SEQUENCE: 46

Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Gly Tyr
            20                  25                  30

Tyr Trp Ser Trp Ile Arg Gln Pro Pro Gly Lys Gly Leu Glu Trp Ile
        35                  40                  45

Gly Glu Ile Asn His Ser Gly Ser Thr Asn Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Arg Ala Arg Ala Arg Gly Ser Ser Ile Phe Asp Tyr Trp Gly Gln
            100                 105                 110

Gly Thr Leu Val Thr Val Ser Ser Gly Ser Ala Ser Ala Pro Thr Leu
        115                 120                 125

Phe Pro Leu Val Ser Cys Glu Asn Ser Pro Ser Asp Thr Ser Ser Val
    130                 135                 140

Ala Val Gly Cys Leu Ala Gln Asp Phe Leu Pro Asp Ser Ile Thr Phe
145                 150                 155                 160

Ser Trp Lys Tyr Lys Asn Asn Ser Asp Ile Ser Ser Thr Arg Gly Phe
                165                 170                 175

Pro Ser Val Leu Arg Gly Gly Lys Tyr Ala Ala Thr Ser Gln Val Leu
            180                 185                 190

Leu Pro Ser Lys Asp Val Met Gln Gly Thr Asp Glu His Val Val Cys
        195                 200                 205

Lys Val Gln His Pro Asn Gly Asn Lys Glu Lys Asn Val Pro Leu Pro
    210                 215                 220

Val Ile Ala Glu Leu Pro Pro Lys Val Ser Val Phe Val Pro Pro Arg
225                 230                 235                 240

Asp Gly Phe Phe Gly Asn Pro Arg Lys Ser Lys Leu Ile Cys Gln Ala
                245                 250                 255

Thr Gly Phe Ser Pro Arg Gln Ile Gln Val Ser Trp Leu Arg Glu Gly
            260                 265                 270

Lys Gln Val Gly Ser Gly Val Thr Thr Asp Gln Val Gln Ala Glu Ala
        275                 280                 285

Lys Glu Ser Gly Pro Thr Thr Tyr Lys Val Thr Ser Thr Leu Thr Ile
    290                 295                 300

Lys Glu Ser Asp Trp Leu Ser Gln Ser Met Phe Thr Cys Arg Val Asp
305                 310                 315                 320

His Arg Gly Leu Thr Phe Gln Gln Asn Ala Ser Ser Met Cys Val Pro
                325                 330                 335

Asp Gln Asp Thr Ala Ile Arg Val Phe Ala Ile Pro Pro Ser Phe Ala
            340                 345                 350

Ser Ile Phe Leu Thr Lys Ser Thr Lys Leu Thr Cys Leu Val Thr Asp
        355                 360                 365

Leu Thr Thr Tyr Asp Ser Val Thr Ile Ser Trp Thr Arg Gln Asn Gly
    370                 375                 380

Glu Ala Val Lys Thr His Thr Asn Ile Ser Glu Ser His Pro Asn Ala
385                 390                 395                 400

```
Thr Phe Ser Ala Val Gly Glu Ala Ser Ile Cys Asp Asp Trp Asn
                405                 410                 415

Ser Gly Glu Arg Phe Thr Cys Thr Val Thr His Thr Asp Leu Pro Ser
            420                 425                 430

Pro Leu Lys Gln Thr Ile Ser Arg Pro Lys Gly Val Ala Leu His Arg
            435                 440                 445

Pro Asp Val Tyr Leu Leu Pro Pro Ala Arg Glu Gln Leu Asn Leu Arg
    450                 455                 460

Glu Ser Ala Thr Ile Thr Cys Leu Val Thr Gly Phe Ser Pro Ala Asp
465                 470                 475                 480

Val Phe Val Gln Trp Met Gln Arg Gly Gln Pro Leu Ser Pro Glu Lys
                485                 490                 495

Tyr Val Thr Ser Ala Pro Met Pro Glu Pro Gln Ala Pro Gly Arg Tyr
            500                 505                 510

Phe Ala His Ser Ile Leu Thr Val Ser Glu Glu Trp Asn Thr Gly
            515                 520                 525

Glu Thr Tyr Thr Cys Val Val Ala His Glu Ala Leu Pro Asn Arg Val
        530                 535                 540

Thr Glu Arg Thr Val Asp Lys Ser Thr Gly Lys Pro Thr Leu Tyr Asn
545                 550                 555                 560

Val Ser Leu Val Met Ser Asp Thr Ala Gly Thr Cys Tyr
                565                 570
```

<210> SEQ ID NO 47
<211> LENGTH: 573
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 47

```
Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Gly Tyr
            20                  25                  30

Tyr Trp Ser Trp Ile Arg Gln Pro Pro Gly Lys Gly Leu Glu Trp Ile
        35                  40                  45

Gly Glu Ile Asn His Ser Gly Ser Thr Asn Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Arg Arg Thr Ala Arg Gly Ser Ser Ile Phe Asp Tyr Trp Gly Gln
            100                 105                 110

Gly Thr Leu Val Thr Val Ser Ser Gly Ser Ala Ser Ala Pro Thr Leu
        115                 120                 125

Phe Pro Leu Val Ser Cys Glu Asn Ser Pro Ser Asp Thr Ser Ser Val
    130                 135                 140

Ala Val Gly Cys Leu Ala Gln Asp Phe Leu Pro Asp Ser Ile Thr Phe
145                 150                 155                 160

Ser Trp Lys Tyr Lys Asn Asn Ser Asp Ile Ser Ser Thr Arg Gly Phe
                165                 170                 175

Pro Ser Val Leu Arg Gly Gly Lys Tyr Ala Ala Thr Ser Gln Val Leu
```

```
            180                 185                 190
Leu Pro Ser Lys Asp Val Met Gln Gly Thr Asp Glu His Val Val Cys
            195                 200                 205

Lys Val Gln His Pro Asn Gly Asn Lys Glu Lys Asn Val Pro Leu Pro
            210                 215                 220

Val Ile Ala Glu Leu Pro Pro Lys Val Ser Val Phe Val Pro Pro Arg
225                 230                 235                 240

Asp Gly Phe Phe Gly Asn Pro Arg Lys Ser Lys Leu Ile Cys Gln Ala
                    245                 250                 255

Thr Gly Phe Ser Pro Arg Gln Ile Gln Val Ser Trp Leu Arg Glu Gly
                260                 265                 270

Lys Gln Val Gly Ser Gly Val Thr Thr Asp Gln Val Gln Ala Glu Ala
            275                 280                 285

Lys Glu Ser Gly Pro Thr Thr Tyr Lys Val Thr Ser Thr Leu Thr Ile
            290                 295                 300

Lys Glu Ser Asp Trp Leu Ser Gln Ser Met Phe Thr Cys Arg Val Asp
305                 310                 315                 320

His Arg Gly Leu Thr Phe Gln Gln Asn Ala Ser Ser Met Cys Val Pro
                325                 330                 335

Asp Gln Asp Thr Ala Ile Arg Val Phe Ala Ile Pro Pro Ser Phe Ala
                340                 345                 350

Ser Ile Phe Leu Thr Lys Ser Thr Lys Leu Thr Cys Leu Val Thr Asp
                355                 360                 365

Leu Thr Thr Tyr Asp Ser Val Thr Ile Ser Trp Thr Arg Gln Asn Gly
370                 375                 380

Glu Ala Val Lys Thr His Thr Asn Ile Ser Glu Ser His Pro Asn Ala
385                 390                 395                 400

Thr Phe Ser Ala Val Gly Glu Ala Ser Ile Cys Glu Asp Asp Trp Asn
                405                 410                 415

Ser Gly Glu Arg Phe Thr Cys Thr Val Thr His Thr Asp Leu Pro Ser
                420                 425                 430

Pro Leu Lys Gln Thr Ile Ser Arg Pro Lys Gly Val Ala Leu His Arg
                435                 440                 445

Pro Asp Val Tyr Leu Leu Pro Pro Ala Arg Glu Gln Leu Asn Leu Arg
            450                 455                 460

Glu Ser Ala Thr Ile Thr Cys Leu Val Thr Gly Phe Ser Pro Ala Asp
465                 470                 475                 480

Val Phe Val Gln Trp Met Gln Arg Gly Gln Pro Leu Ser Pro Glu Lys
                    485                 490                 495

Tyr Val Thr Ser Ala Pro Met Pro Glu Pro Gln Ala Pro Gly Arg Tyr
                500                 505                 510

Phe Ala His Ser Ile Leu Thr Val Ser Glu Glu Glu Trp Asn Thr Gly
                515                 520                 525

Glu Thr Tyr Thr Cys Val Val Ala His Glu Ala Leu Pro Asn Arg Val
            530                 535                 540

Thr Glu Arg Thr Val Asp Lys Ser Thr Gly Lys Pro Thr Leu Tyr Asn
545                 550                 555                 560

Val Ser Leu Val Met Ser Asp Thr Ala Gly Thr Cys Tyr
                    565                 570

<210> SEQ ID NO 48
<211> LENGTH: 573
<212> TYPE: PRT
<213> ORGANISM: Artificial Sequence
```

<220> FEATURE:
<223> OTHER INFORMATION: Description of Artificial Sequence: Synthetic
      polypeptide

<400> SEQUENCE: 48

```
Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Gly Tyr
            20                  25                  30

Tyr Trp Ser Trp Ile Arg Gln Pro Pro Gly Lys Gly Leu Glu Trp Ile
        35                  40                  45

Gly Glu Ile Asn His Ser Gly Ser Thr Asn Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Gly Ala Arg Ala Trp Gly Ser Ser Ile Phe Asp Tyr Trp Gly Gln
            100                 105                 110

Gly Thr Leu Val Thr Val Ser Ser Gly Ser Ala Ser Ala Pro Thr Leu
        115                 120                 125

Phe Pro Leu Val Ser Cys Glu Asn Ser Pro Ser Asp Thr Ser Ser Val
    130                 135                 140

Ala Val Gly Cys Leu Ala Gln Asp Phe Leu Pro Asp Ser Ile Thr Phe
145                 150                 155                 160

Ser Trp Lys Tyr Lys Asn Asn Ser Asp Ile Ser Ser Thr Arg Gly Phe
                165                 170                 175

Pro Ser Val Leu Arg Gly Gly Lys Tyr Ala Ala Thr Ser Gln Val Leu
            180                 185                 190

Leu Pro Ser Lys Asp Val Met Gln Gly Thr Asp Glu His Val Val Cys
        195                 200                 205

Lys Val Gln His Pro Asn Gly Asn Lys Glu Lys Asn Val Pro Leu Pro
    210                 215                 220

Val Ile Ala Glu Leu Pro Pro Lys Val Ser Val Phe Val Pro Pro Arg
225                 230                 235                 240

Asp Gly Phe Phe Gly Asn Pro Arg Lys Ser Lys Leu Ile Cys Gln Ala
                245                 250                 255

Thr Gly Phe Ser Pro Arg Gln Ile Gln Val Ser Trp Leu Arg Glu Gly
            260                 265                 270

Lys Gln Val Gly Ser Gly Val Thr Thr Asp Gln Val Gln Ala Glu Ala
        275                 280                 285

Lys Glu Ser Gly Pro Thr Thr Tyr Lys Val Thr Ser Thr Leu Thr Ile
    290                 295                 300

Lys Glu Ser Asp Trp Leu Ser Gln Ser Met Phe Thr Cys Arg Val Asp
305                 310                 315                 320

His Arg Gly Leu Thr Phe Gln Gln Asn Ala Ser Ser Met Cys Val Pro
                325                 330                 335

Asp Gln Asp Thr Ala Ile Arg Val Phe Ala Ile Pro Pro Ser Phe Ala
            340                 345                 350

Ser Ile Phe Leu Thr Lys Ser Thr Lys Leu Thr Cys Leu Val Thr Asp
        355                 360                 365

Leu Thr Thr Tyr Asp Ser Val Thr Ile Ser Trp Thr Arg Gln Asn Gly
    370                 375                 380

Glu Ala Val Lys Thr His Thr Asn Ile Ser Glu Ser His Pro Asn Ala
```

```
                385                 390                 395                 400
        Thr Phe Ser Ala Val Gly Glu Ala Ser Ile Cys Glu Asp Asp Trp Asn
                        405                 410                 415

Ser Gly Glu Arg Phe Thr Cys Thr Val Thr His Thr Asp Leu Pro Ser
                        420                 425                 430

Pro Leu Lys Gln Thr Ile Ser Arg Pro Lys Gly Val Ala Leu His Arg
                        435                 440                 445

Pro Asp Val Tyr Leu Leu Pro Pro Ala Arg Glu Gln Leu Asn Leu Arg
                        450                 455                 460

Glu Ser Ala Thr Ile Thr Cys Leu Val Thr Gly Phe Ser Pro Ala Asp
        465                 470                 475                 480

Val Phe Val Gln Trp Met Gln Arg Gly Gln Pro Leu Ser Pro Glu Lys
                        485                 490                 495

Tyr Val Thr Ser Ala Pro Met Pro Glu Pro Gln Ala Pro Gly Arg Tyr
                        500                 505                 510

Phe Ala His Ser Ile Leu Thr Val Ser Glu Glu Glu Trp Asn Thr Gly
                        515                 520                 525

Glu Thr Tyr Thr Cys Val Val Ala His Glu Ala Leu Pro Asn Arg Val
                        530                 535                 540

Thr Glu Arg Thr Val Asp Lys Ser Thr Gly Lys Pro Thr Leu Tyr Asn
        545                 550                 555                 560

Val Ser Leu Val Met Ser Asp Thr Ala Gly Thr Cys Tyr
                        565                 570

<210> SEQ ID NO 49
<211> LENGTH: 573
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 49

Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Gly Tyr
                20                  25                  30

Tyr Trp Ser Trp Ile Arg Gln Pro Pro Gly Lys Gly Leu Glu Trp Ile
            35                  40                  45

Gly Glu Ile Asn His Ser Gly Ser Thr Asn Tyr Asn Pro Ser Leu Lys
        50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Arg Ala Arg Ala Trp Gly Ser Ser Ile Phe Asp Tyr Trp Gly Gln
                100                 105                 110

Gly Thr Leu Val Thr Val Ser Ser Gly Ser Ala Ser Ala Pro Thr Leu
            115                 120                 125

Phe Pro Leu Val Ser Cys Glu Asn Ser Pro Ser Asp Thr Ser Ser Val
        130                 135                 140

Ala Val Gly Cys Leu Ala Gln Asp Phe Leu Pro Asp Ser Ile Thr Phe
145                 150                 155                 160

Ser Trp Lys Tyr Lys Asn Asn Ser Asp Ile Ser Ser Thr Arg Gly Phe
                165                 170                 175
```

Pro Ser Val Leu Arg Gly Gly Lys Tyr Ala Ala Thr Ser Gln Val Leu
            180                 185                 190

Leu Pro Ser Lys Asp Val Met Gln Gly Thr Asp Glu His Val Val Cys
        195                 200                 205

Lys Val Gln His Pro Asn Gly Asn Lys Glu Lys Asn Val Pro Leu Pro
    210                 215                 220

Val Ile Ala Glu Leu Pro Pro Lys Val Ser Val Phe Val Pro Pro Arg
225                 230                 235                 240

Asp Gly Phe Phe Gly Asn Pro Arg Lys Ser Lys Leu Ile Cys Gln Ala
                245                 250                 255

Thr Gly Phe Ser Pro Arg Gln Ile Gln Val Ser Trp Leu Arg Glu Gly
            260                 265                 270

Lys Gln Val Gly Ser Gly Val Thr Thr Asp Gln Val Gln Ala Glu Ala
    275                 280                 285

Lys Glu Ser Gly Pro Thr Thr Tyr Lys Val Thr Ser Thr Leu Thr Ile
290                 295                 300

Lys Glu Ser Asp Trp Leu Ser Gln Ser Met Phe Thr Cys Arg Val Asp
305                 310                 315                 320

His Arg Gly Leu Thr Phe Gln Gln Asn Ala Ser Ser Met Cys Val Pro
                325                 330                 335

Asp Gln Asp Thr Ala Ile Arg Val Phe Ala Ile Pro Pro Ser Phe Ala
            340                 345                 350

Ser Ile Phe Leu Thr Lys Ser Thr Lys Leu Thr Cys Leu Val Thr Asp
    355                 360                 365

Leu Thr Thr Tyr Asp Ser Val Thr Ile Ser Trp Thr Arg Gln Asn Gly
370                 375                 380

Glu Ala Val Lys Thr His Thr Asn Ile Ser Glu Ser His Pro Asn Ala
385                 390                 395                 400

Thr Phe Ser Ala Val Gly Glu Ala Ser Ile Cys Glu Asp Asp Trp Asn
                405                 410                 415

Ser Gly Glu Arg Phe Thr Cys Thr Val Thr His Thr Asp Leu Pro Ser
            420                 425                 430

Pro Leu Lys Gln Thr Ile Ser Arg Pro Lys Gly Val Ala Leu His Arg
    435                 440                 445

Pro Asp Val Tyr Leu Leu Pro Pro Ala Arg Glu Gln Leu Asn Leu Arg
450                 455                 460

Glu Ser Ala Thr Ile Thr Cys Leu Val Thr Gly Phe Ser Pro Ala Asp
465                 470                 475                 480

Val Phe Val Gln Trp Met Gln Arg Gly Gln Pro Leu Ser Pro Glu Lys
                485                 490                 495

Tyr Val Thr Ser Ala Pro Met Pro Glu Pro Gln Ala Pro Gly Arg Tyr
            500                 505                 510

Phe Ala His Ser Ile Leu Thr Val Ser Glu Glu Glu Trp Asn Thr Gly
    515                 520                 525

Glu Thr Tyr Thr Cys Val Val Ala His Glu Ala Leu Pro Asn Arg Val
530                 535                 540

Thr Glu Arg Thr Val Asp Lys Ser Thr Gly Lys Pro Thr Leu Tyr Asn
545                 550                 555                 560

Val Ser Leu Val Met Ser Asp Thr Ala Gly Thr Cys Tyr
                565                 570

<210> SEQ ID NO 50
<211> LENGTH: 211
<212> TYPE: PRT

<400> SEQUENCE: 50

Asp Ile Gln Met Thr Gln Ser Pro Ser Thr Leu Ser Ala Ser Val Gly
1               5                   10                  15

Asp Arg Val Thr Ile Thr Cys Thr Gly Thr Ser Ser Asp Val Gly Gly
            20                  25                  30

Tyr Asn Tyr Val Ser Trp Tyr Gln Gln His Pro Gly Lys Ala Pro Lys
        35                  40                  45

Leu Met Ile Tyr Gly Val Ser Asn Arg Phe Ser Gly Ser Lys Ser Gly
    50                  55                  60

Asn Thr Ala Ser Leu Thr Ile Ser Gly Leu Ala Ala Glu Asp Glu Ala
65                  70                  75                  80

Asp Tyr Tyr Cys Ser Ser Tyr Thr Ser Ser Thr Leu Val Val Phe
                85                  90                  95

Gly Gly Gly Thr Lys Leu Thr Val Leu Gly Gln Pro Lys Ala Ala Pro
            100                 105                 110

Ser Val Thr Leu Phe Pro Pro Ser Ser Glu Glu Leu Gln Ala Asn Lys
        115                 120                 125

Ala Thr Leu Val Cys Leu Ile Ser Asp Phe Tyr Pro Gly Ala Val Thr
130                 135                 140

Val Ala Trp Lys Ala Asp Ser Ser Pro Val Lys Ala Gly Val Glu Thr
145                 150                 155                 160

Thr Thr Pro Ser Lys Gln Ser Asn Asn Lys Tyr Ala Ala Ser Ser Tyr
            165                 170                 175

Leu Ser Leu Thr Pro Glu Gln Trp Lys Ser His Arg Ser Tyr Ser Cys
        180                 185                 190

Gln Val Thr His Glu Gly Ser Thr Val Glu Lys Thr Val Ala Pro Thr
    195                 200                 205

Glu Cys Ser
    210

<210> SEQ ID NO 51
<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 51

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Ile
                85                  90                  95

Thr Phe Gly Gln Gly Thr Arg Leu Glu Ile Lys Arg Thr Val Ala Ala

```
            100                 105                 110
Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
        210
```

<210> SEQ ID NO 52
<211> LENGTH: 1722
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 52

```
caggtgcagc tccagcagtg gggagcagga ctcttgaaac cctctgagac tttgagcctc      60
acatgcgctg tctatggcgg atctttctcc ggctactatt ggtcctggat acgacagccc     120
ccaggcaaag gactcgagtg gattgggaa atcaaccact ctggtagcac taactataat     180
ccaagcctga gtcccgtgt aacaattagt gttgatacat ccaagaacca attttccctg     240
aaactgagct cagtgactgc cgccgacact gccgtctact actgtgctcg tggtagaatg     300
gcctggggcg cttccgtgaa tttcgactac tggggacagg gtaccctggt cactgtctct     360
tcaggttccg catccgcccc aaccctttc ccctcgtct cctgtgagaa tagcccgtcg     420
gatacgagca gcgtggccgt tggctgcctc gcacaggact ccttcccga ctccatcact     480
ttctcctgga atacaagaa caactctgac atcagcagca cccggggctt cccatcagtc     540
ctgagagggg gcaagtacgc agccacctca caggtgctgc tgccttccaa ggacgtcatg     600
cagggcacag acgaacacgt ggtgtgcaaa gtccagcacc caacggcaa caagaaaaag     660
aacgtgcctc ttccagtgat tgctgagctg cctcccaaag tgagcgtctt cgtcccaccc     720
cgcgacggct tcttcggcaa ccccgcaag tccaagctca tctgccaggc cacgggtttc     780
agtccccggc agattcaggt gtcctggctg cgcgagggga agcaggtggg gtctggcgtc     840
accacggacc aggtgcaggc tgaggccaaa gagtctgggc ccacgaccta aaggtgacc     900
agcacactga ccatcaaaga gagcgactgg ctcagccaga gcatgttcac ctgccgcgtg     960
gatcacaggg gcctgacctt ccagcagaat gcgtcctcca tgtgtgtccc cgatcaagac    1020
acagccatcc gggtcttcgc catcccccca tcctttgcca gcatcttcct caccaagtcc    1080
accaagttga cctgcctggt cacagacctg accacctatg acagcgtgac catctcctgg    1140
acccgccaga atggcgaagc tgtgaaaacc cacaccaaca tctccgagag ccaccccaat    1200
gccactttca gcgccgtggg tgaggccagc atctgcgagg atgactggaa tagcggggag    1260
aggttcacgt gcaccgtgac ccacacagac ctgcctcgc cactgaagca gaccatctcc    1320
cggcccaagg gggtggccct gcacaggccc gatgtctact gctgccacc agcccgggag    1380
```

```
cagctgaacc tgcgggagtc ggccaccatc acgtgcctgg tgacgggctt ctctcccgcg   1440
gacgtcttcg tgcagtggat gcagaggggg cagcccttgt ccccggagaa gtatgtgacc   1500
agcgccccaa tgcctgagcc ccaggcccca ggccggtact cgcccacag catcctgacc    1560 gtgtccgaag aggaatggaa cacggggag acctacacct gcgtggtggc ccatgaggcc    1620
ctgcccaaca gggtcaccga gaggaccgtg acaagtcca ccggtaaacc caccctgtac    1680
aacgtgtccc tggtcatgtc cgacacagct ggcacctgct ac                     1722
```

<210> SEQ ID NO 53
<211> LENGTH: 1722
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 53

```
caggtgcagc tccagcagtg gggagcagga ctcttgaaac cctctgagac tttgagcctc     60
acatgcgctg tctatggcgg atctttctcc ggctactatt ggtcctggat acgacagccc    120
ccaggcaaag gactcgagtg gattgggaa atcaaccact ctggtagcac taactataat     180
ccaagcctga gtcccgtgt aacaattagt gttgatacat ccaagaacca attttccctg     240
aaactgagct cagtgactgc cgccgacact gccgtctact actgtgctcg tggtagaagg     300
gcctggggcg cttccgtgaa tttcgactac tggggacagg gtaccctggt cactgtctct     360
tcaggttccg catccgcccc aacccttttc ccctcgtct cctgtgagaa tagcccgtcg     420
gatacgagca gcgtggccgt tggctgcctc gcacaggact tccttcccga ctccatcact     480
ttctcctgga aatacaagaa caactctgac atcagcagca cccggggctt cccatcagtc     540
ctgagagggg gcaagtacgc agccacctca caggtgctgc tgccttccaa ggacgtcatg     600
cagggcacag acgaacacgt ggtgtgcaaa gtccagcacc caacggcaa caaagaaaag     660 aacgtgcctc ttccagtgat tgctgagctg cctcccaaag tgagcgtctt cgtcccaccc     720
cgcgacggct tcttcggcaa cccccgcaag tccaagctca tctgccaggc cacgggtttc    780
agtccccggc agattcaggt gtcctggctg cgcgagggga agcaggtggg gtctggcgtc    840
accacggacc aggtgcaggc tgaggccaaa gagtctgggc ccacgaccta caaggtgacc    900
agcacactga ccatcaaaga gagcgactgg ctcagccaga gcatgttcac ctgccgcgtg    960
gatcacaggg gcctgacctt ccagcagaat gcgtcctcca tgtgtgtccc cgatcaagac   1020
acagccatcc gggtcttcgc catcccccca tcctttgcca gcatcttcct caccaagtcc   1080
accaagttga cctgcctggt cacagacctg accacctatg acagcgtgac catctcctgg   1140
acccgccaga atggcgaagc tgtgaaaacc cacaccaaca tctccgagag ccaccccaat   1200
gccactttca gcgccgtggg tgaggccagc atctgcgagg atgactggaa tagcggggag   1260
aggttcacgt gcaccgtgac ccacacagac ctgccctcgc cactgaagca gaccatctcc   1320
cggcccaagg gggtggccct gcacaggccc gatgtctact tgctgccacc agcccgggag   1380
cagctgaacc tgcgggagtc ggccaccatc acgtgcctgg tgacgggctt ctctcccgcg   1440
gacgtcttcg tgcagtggat gcagaggggg cagcccttgt ccccggagaa gtatgtgacc   1500
agcgccccaa tgcctgagcc ccaggcccca ggccggtact cgcccacag catcctgacc    1560 gtgtccgaag aggaatggaa cacggggag acctacacct gcgtggtggc ccatgaggcc    1620
ctgcccaaca gggtcaccga gaggaccgtg acaagtcca ccggtaaacc caccctgtac    1680
```

```
aacgtgtccc tggtcatgtc cgacacagct ggcacctgct ac                  1722
```

<210> SEQ ID NO 54
<211> LENGTH: 1722
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 54

```
caggtgcagc tccagcagtg gggagcagga ctcttgaaac cctctgagac tttgagcctc    60
acatgcgctg tctatggcgg atctttctcc ggctactatt ggtcctggat acgacagccc   120
ccaggcaaag gactcgagtg gattggggaa atcaaccact ctggtagcac taactataat   180
ccaagcctga gtcccgtgt aacaattagt gttgatacat ccaagaacca attttccctg    240
aaactgagct cagtgactgc cgccgacact gccgtctact actgtgctcg tggtagaatg   300
gccaggggcg cttccgtgaa tttcgactac tggggacagg gtaccctggt cactgtctct   360
tcaggttccg catccgcccc aacccttttc cccctcgtct cctgtgagaa tagcccgtcg   420
gatacgagca gcgtggccgt tggctgcctc gcacaggact ccttcccga ctccatcact    480
ttctcctgga atacaagaa caactctgac atcagcagca cccggggctt cccatcagtc    540
ctgagagggg gcaagtacgc agccacctca caggtgctgc tgccttccaa ggacgtcatg   600
cagggcacag acgaacacgt ggtgtgcaaa gtccagcacc caacggcaa caaagaaaag    660
aacgtgcctc ttccagtgat tgctgagctg cctcccaaag tgagcgtctt cgtcccaccc   720
cgcgacggct tcttcggcaa cccccgcaag tccaagctca tctgccaggc cacgggtttc   780
agtccccggc agattcaggt gtcctggctg cgcgagggga agcaggtggg gtctggcgtc   840
accacggacc aggtgcaggc tgaggccaaa gagtctgggc cacgacctaa caggtgacc    900
agcacactga ccatcaaaga gagcgactgg ctcagccaga gcatgttcac ctgccgcgtg   960
gatcacaggg gcctgacctt ccagcagaat gcgtcctcca tgtgtgtccc cgatcaagac  1020
acagccatcc gggtcttcgc catcccccca tcctttgcca gcatcttcct caccaagtcc  1080
accaagttga cctgcctggt cacagacctg accacctatg acagcgtgac catctcctgg  1140
acccgccaga tggcgaagc tgtgaaaacc cacaccaaca tctccgagag ccaccccaat  1200
gccactttca gcgccgtggg tgaggccagc atctgcgagg atgactggaa tagcggggag  1260
aggttcacgt gcaccgtgac ccacacagac ctgccctcgc cactgaagca gaccatctcc  1320
cggcccaagg gggtggccct gcacaggccc gatgtctact tgctgccacc agcccgggag  1380
cagctgaacc tgcgggagtc ggccaccatc acgtgcctgg tgacgggctt ctctcccgcg  1440
gacgtcttcg tgcagtggat gcagaggggg cagcccttgt ccccggagaa gtatgtgacc  1500
agcgccccaa tgcctgagcc ccaggcccca ggccggtact cgcccacag catcctgacc  1560
gtgtccgaag aggaatggaa cacggggag acctacacct gcgtggtggc ccatgaggcc  1620
ctgcccaaca gggtcaccga ggaccgtg acaagtcca ccggtaaacc caccctgtac    1680
aacgtgtccc tggtcatgtc cgacacagct ggcacctgct ac                    1722
```

<210> SEQ ID NO 55
<211> LENGTH: 1722
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 55

```
caggtgcagc tccagcagtg gggagcagga ctcttgaaac cctctgagac tttgagcctc      60
acatgcgctg tctatggcgg atctttctcc ggctactatt ggtcctggat acgacagccc     120
ccaggcaaag gactcgagtg gattggggaa atcaaccact ctggtagcac taactataat     180
ccaagcctga gtcccgtgt aacaattagt gttgatacat ccaagaacca attttccctg     240
aaactgagct cagtgactgc cgccgacact gccgtctact actgtgctcg tggtagaagg     300
gccaggggcg cttccgtgaa tttcgactac tggggacagg gtaccctggt cactgtctct     360
tcaggttccg catccgcccc aacccttttc cccctcgtct cctgtgagaa tagcccgtcg     420
gatacgagca gcgtggccgt tggctgcctc gcacaggact ccttcccga ctccatcact     480
ttctcctgga atacaagaa caactctgac atcagcagca cccggggctt cccatcagtc     540
ctgagagggg gcaagtacgc agccacctca caggtgctgc tgccttccaa ggacgtcatg     600
cagggcacag acgaacacgt ggtgtgcaaa gtccagcacc caacggcaa caaagaaaag     660
aacgtgcctc ttccagtgat tgctgagctg cctcccaaag tgagcgtctt cgtcccaccc     720
cgcgacggct tcttcggcaa ccccgcaag tccaagctca tctgccaggc cacgggttc      780
agtccccggc agattcaggt gtcctggctg cgcgagggga agcaggtggg gtctggcgtc     840
accacggacc aggtgcaggc tgaggccaaa gagtctgggc ccacgaccta caaggtgacc     900
agcacactga ccatcaaaga gagcgactgg ctcagccaga gcatgttcac ctgccgcgtg     960
gatcacaggg gcctgacctt ccagcagaat gcgtcctcca tgtgtgtccc cgatcaagac    1020
acagccatcc gggtcttcgc catcccccca tcctttgcca gcatcttcct caccaagtcc    1080
accaagttga cctgcctggt cacagacctg accacctatg acagcgtgac catctcctgg    1140
acccgccaga tggcgaagc tgtgaaaacc cacaccaaca tctccgagag ccaccccaat    1200
gccactttca gcgccgtggg tgaggccagc atctgcgagg atgactggaa tagcggggag    1260
aggttcacgt gcaccgtgac ccacacagac ctgccctcgc cactgaagca gaccatctcc    1320
cggcccaagg gggtggccct gcacaggccc gatgtgtact gctgccacc agcccgggag    1380
cagctgaacc tgcgggagtc ggccaccatc acgtgcctgg tgacgggctt ctctcccgcg    1440
gacgtcttcg tgcagtggat gcagaggggg cagcccttgt ccccggagaa gtatgtgacc    1500
agcgccccaa tgcctgagcc ccaggcccca ggccggtact cgcccacag catcctgacc    1560
gtgtccgaag aggaatggaa cacggggag acctacacct gcgtggtggc ccatgaggcc    1620
ctgcccaaca gggtcaccga gaggaccgtg acaagtcca ccggtaaacc caccctgtac    1680
aacgtgtccc tggtcatgtc cgacacagct ggcacctgct ac                      1722
```

<210> SEQ ID NO 56
<211> LENGTH: 1722
<212> TYPE: DNA
<213> ORGANISM: Artificial Sequence
<220> FEATURE:
<223> OTHER INFORMATION: Description of Artificial Sequence: Synthetic
    polynucleotide

<400> SEQUENCE: 56

```
caggtgcagc tccagcagtg gggagcagga ctcttgaaac cctctgagac tttgagcctc      60
acatgcgctg tctatggcgg atctttctcc ggctactatt ggtcctggat acgacagccc     120
ccaggcaaag gactcgagtg gattggggaa atcaaccact ctggtagcac taactataat     180
```

```
ccaagcctga agtcccgtgt aacaattagt gttgatacat ccaagaacca atttccctg      240
aaactgagct cagtgactgc cgccgacact gccgtctact actgtgctcg tcggggaatg      300
gcctggggcg cttccgtgaa tttcgactac tggggacagg gtaccctggt cactgtctct      360
tcaggttccg catccgcccc aacccttttc cccctcgtct cctgtgagaa tagcccgtcg      420
gatacgagca gcgtggccgt tggctgcctc gcacaggact tccttcccga ctccatcact      480
ttctcctgga atacaagaa caactctgac atcagcagca cccggggctt cccatcagtc       540
ctgagagggg gcaagtacgc agccacctca caggtgctgc tgccttccaa ggacgtcatg      600
cagggcacag acgaacacgt ggtgtgcaaa gtccagcacc ccaacggcaa caaagaaaag      660
aacgtgcctc ttccagtgat tgctgagctg cctcccaaag tgagcgtctt cgtcccaccc      720
cgcgacggct tcttcggcaa ccccgcaag tccaagctca tctgccaggc cacgggtttc       780
agtccccggc agattcaggt gtcctggctg cgcgagggga gcaggtggg gtctggcgtc       840
accacggacc aggtgcaggc tgaggccaaa gagtctgggc ccacgaccta caaggtgacc      900
agcacactga ccatcaaaga gagcgactgg ctcagccaga gcatgttcac ctgccgcgtg      960
gatcacaggg gcctgacctt ccagcagaat gcgtcctcca tgtgtgtccc cgatcaagac     1020
acagccatcc gggtcttcgc catccccca tcctttgcca gcatcttcct caccaagtcc      1080
accaagttga cctgcctggt cacagacctg accacctatg acagcgtgac catctcctgg     1140
acccgccaga tggcgaagc tgtgaaaacc cacaccaaca tctccgagag ccaccccaat      1200
gccactttca gcgccgtggg tgaggccagc atctgcgagg atgactggaa tagcggggag     1260
aggttcacgt gcaccgtgac ccacacagac ctgcctcgc cactgaagca gaccatctcc      1320
cggcccaagg gggtggccct gcacaggccc gatgtctact gctgccacc agcccgggag     1380
cagctgaacc tgcgggagtc ggccaccatc acgtgcctgg tgacgggctt ctctcccgcg     1440
gacgtcttcg tgcagtggat gcagaggggg cagcccttgt ccccggagaa gtatgtgacc     1500
agcgccccaa tgcctgagcc ccaggcccca ggccggtact cgcccacag catcctgacc      1560
gtgtccgaag aggaatggaa cacggggag acctacacct gcgtggtggc ccatgaggcc      1620
ctgcccaaca gggtcaccga gaggaccgtg acaagtcca ccggtaaacc caccctgtac      1680
aacgtgtccc tggtcatgtc cgacacagct ggcacctgct ac                        1722
```

<210> SEQ ID NO 57
<211> LENGTH: 1722
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 57

```
caggtgcagc tccagcagtg gggagcagga ctcttgaaac cctctgagac tttgagcctc       60
acatgcgctg tctatggcgg atctttctcc ggctactatt ggtcctggat acgacagccc      120
ccaggcaaag gactcgagtg gattggggaa atcaaccact ctggtagcac taactataat      180
ccaagcctga agtcccgtgt aacaattagt gttgatacat ccaagaacca atttccctg      240
aaactgagct cagtgactgc cgccgacact gccgtctact actgtgctcg tcggagaatg      300
gcctggggcg cttccgtgaa tttcgactac tggggacagg gtaccctggt cactgtctct      360
tcaggttccg catccgcccc aacccttttc cccctcgtct cctgtgagaa tagcccgtcg      420
gatacgagca gcgtggccgt tggctgcctc gcacaggact tccttcccga ctccatcact      480
```

| ttctcctgga aatacaagaa caactctgac atcagcagca cccgggggctt cccatcagtc | 540 |
| ctgagagggg gcaagtacgc agccacctca caggtgctgc tgccttccaa ggacgtcatg | 600 |
| cagggcacag acgaacacgt ggtgtgcaaa gtccagcacc caacggcaa caaagaaaag | 660 |
| aacgtgcctc ttccagtgat tgctgagctg cctcccaaag tgagcgtctt cgtcccaccc | 720 |
| cgcgacggct tcttcggcaa ccccgcaag tccaagctca tctgccaggc cacgggtttc | 780 |
| agtccccggc agattcaggt gtcctggctg cgcgagggga agcaggtggg gtctggcgtc | 840 |
| accacggacc aggtgcaggc tgaggccaaa gagtctgggc ccacgaccta caaggtgacc | 900 |
| agcacactga ccatcaaaga gagcgactgg ctcagccaga gcatgttcac ctgccgcgtg | 960 |
| gatcacaggg gcctgacctt ccagcagaat gcgtcctcca tgtgtgtccc cgatcaagac | 1020 |
| acagccatcc gggtcttcgc catcccccca tcctttgcca gcatcttcct caccaagtcc | 1080 |
| accaagttga cctgcctggt cacagacctg accacctatg acagcgtgac catctcctgg | 1140 |
| acccgccaga tggcgaagc tgtgaaaacc cacaccaaca tctccgagag ccaccccaat | 1200 |
| gccactttca gcgccgtggg tgaggccagc atctgcgagg atgactggaa tagcggggag | 1260 |
| aggttcacgt gcaccgtgac ccacacagac ctgccctcgc cactgaagca gaccatctcc | 1320 |
| cggcccaagg ggtggccct gcacaggccc gatgtctact tgctgccacc agcccgggag | 1380 |
| cagctgaacc tgcgggagtc ggccaccatc acgtgcctgg tgacgggctt ctctcccgcg | 1440 |
| gacgtcttcg tgcagtggat gcagaggggg cagcccttgt ccccggagaa gtatgtgacc | 1500 |
| agcgccccaa tgcctgagcc ccaggcccca ggccggtact cgcccacag catcctgacc | 1560 |
| gtgtccgaag aggaatggaa cacgggggag acctacacct gcgtggtggc ccatgaggcc | 1620 |
| ctgcccaaca gggtcaccga gaggaccgtg gacaagtcca ccggtaaacc caccctgtac | 1680 |
| aacgtgtccc tggtcatgtc cgacacagct ggcacctgct ac | 1722 |

<210> SEQ ID NO 58
<211> LENGTH: 1722
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 58

| caggtgcagc tccagcagtg gggagcagga ctcttgaaac cctctgagac tttgagcctc | 60 |
| acatgcgctg tctatggcgg atctttctcc ggctactatt ggtcctggat acgacagccc | 120 |
| ccaggcaaag gactcgagtg gattggggaa atcaaccact ctggtagcac taactataat | 180 |
| ccaagcctga gtcccgtgt aacaattagt gttgatacat ccaagaacca attttccctg | 240 |
| aaactgagct cagtgactgc cgccgacact gccgtctact actgtgctcg tcggggaatg | 300 |
| gccaggggcg cttccgtgaa tttcgactac tggggacagg gtaccctggt cactgtctct | 360 |
| tcaggttccg catccgcccc aacccttttc ccctcgtct cctgtgagaa tagcccgtcg | 420 |
| gatacgagca gcgtggccgt tggctgcctc gcacaggact tccttcccga ctccatcact | 480 |
| ttctcctgga aatacaagaa caactctgac atcagcagca cccgggggctt cccatcagtc | 540 |
| ctgagagggg gcaagtacgc agccacctca caggtgctgc tgccttccaa ggacgtcatg | 600 |
| cagggcacag acgaacacgt ggtgtgcaaa gtccagcacc caacggcaa caaagaaaag | 660 |
| aacgtgcctc ttccagtgat tgctgagctg cctcccaaag tgagcgtctt cgtcccaccc | 720 |
| cgcgacggct tcttcggcaa ccccgcaag tccaagctca tctgccaggc cacgggtttc | 780 |

| | |
|---|---|
| agtccccggc agattcaggt gtcctggctg cgcgagggga agcaggtggg gtctggcgtc | 840 |
| accacggacc aggtgcaggc tgaggccaaa gagtctgggc ccacgaccta caaggtgacc | 900 |
| agcacactga ccatcaaaga gagcgactgg ctcagccaga gcatgttcac ctgccgcgtg | 960 |
| gatcacaggg gcctgacctt ccagcagaat gcgtcctcca tgtgtgtccc cgatcaagac | 1020 |
| acagccatcc gggtcttcgc catcccccca tcctttgcca gcatcttcct caccaagtcc | 1080 |
| accaagttga cctgcctggt cacagacctg accacctatg acagcgtgac catctcctgg | 1140 |
| acccgccaga atggcgaagc tgtgaaaacc cacaccaaca tctccgagag ccaccccaat | 1200 |
| gccactttca cgccgtgggt gaggccagc atctgcgagg atgactggaa tagcggggag | 1260 |
| aggttcacgt gcaccgtgac ccacacagac ctgccctcgc cactgaagca gaccatctcc | 1320 |
| cggcccaagg gggtggccct gcacaggccc gatgtctact tgctgccacc agcccgggag | 1380 |
| cagctgaacc tgcgggagtc ggccaccatc acgtgcctgg tgacgggctt ctctcccgcg | 1440 |
| gacgtcttcg tgcagtggat gcagaggggg cagcccttgt ccccggagaa gtatgtgacc | 1500 |
| agcgccccaa tgcctgagcc ccaggcccca ggccggtact tcgcccacag catcctgacc | 1560 |
| gtgtccgaag aggaatggaa cacgggggag acctacacct gcgtggtggc ccatgaggcc | 1620 |
| ctgcccaaca gggtcaccga gaggaccgtg acaagtcca ccggtaaacc caccctgtac | 1680 |
| aacgtgtccc tggtcatgtc cgacacagct ggcacctgct ac | 1722 |

<210> SEQ ID NO 59
<211> LENGTH: 1722
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 59

| | |
|---|---|
| caggtgcagc tccagcagtg gggagcagga ctcttgaaac cctctgagac tttgagcctc | 60 |
| acatgcgctg tctatggcgg atctttctcc ggctactatt ggtcctggat acgacagccc | 120 |
| ccaggcaaag gactcgagtg gattggggaa atcaaccact ctggtagcac taactataat | 180 |
| ccaagcctga gtcccgtgt aacaattagt gttgatacat ccaagaacca attttccctg | 240 |
| aaactgagct cagtgactgc cgccgacact gccgtctact actgtgctcg tcggggaagg | 300 |
| gccaggggcg cttccgtgaa tttcgactac tggggacagg gtaccctggt cactgtctct | 360 |
| tcaggttccg catccgcccc aaccctttc cccctcgtct cctgtgagaa tagcccgtcg | 420 |
| gatacgagca gcgtggccgt tggctgcctc gcacaggact ccttcccga ctccatcact | 480 |
| ttctcctgga atacaagaa caactctgac atcagcagca cccggggctt cccatcagtc | 540 |
| ctgagagggg gcaagtacgc agccacctca caggtgctgc tgccttccaa ggacgtcatg | 600 |
| cagggcacag acgaacacgt ggtgtgcaaa gtccagcacc caacggcaa caaagaaaag | 660 |
| aacgtgcctc ttccagtgat tgctgagctg cctcccaaag tgagcgtctt cgtcccaccc | 720 |
| cgcgacggct tcttcggcaa ccccgcaag tccaagctca tctgccaggc cacgggtttc | 780 |
| agtccccggc agattcaggt gtcctggctg cgcgagggga agcaggtggg gtctggcgtc | 840 |
| accacggacc aggtgcaggc tgaggccaaa gagtctgggc ccacgaccta caaggtgacc | 900 |
| agcacactga ccatcaaaga gagcgactgg ctcagccaga gcatgttcac ctgccgcgtg | 960 |
| gatcacaggg gcctgacctt ccagcagaat gcgtcctcca tgtgtgtccc cgatcaagac | 1020 |
| acagccatcc gggtcttcgc catcccccca tcctttgcca gcatcttcct caccaagtcc | 1080 |

```
accaagttga cctgcctggt cacagacctg accacctatg acagcgtgac catctcctgg    1140
acccgccaga atggcgaagc tgtgaaaacc cacaccaaca tctccgagag ccaccccaat    1200
gccactttca gcgccgtggg tgaggccagc atctgcgagg atgactggaa tagcggggag    1260
aggttcacgt gcaccgtgac ccacacagac ctgccctcgc cactgaagca gaccatctcc    1320
cggcccaagg gggtggccct gcacaggccc gatgtctact tgctgccacc agcccgggag    1380
cagctgaacc tgcgggagtc ggccaccatc acgtgcctgg tgacgggctt ctctcccgcg    1440
gacgtcttcg tgcagtggat gcagagggg cagcccttgt ccccggagaa gtatgtgacc    1500
agcgccccaa tgcctgagcc ccaggcccca ggccggtact cgcccacag catcctgacc     1560 gtgtccgaag aggaatggaa cacgggggag acctacacct gcgtggtggc ccatgaggcc    1620
ctgcccaaca gggtcaccga gaggaccgtg acaagtcca ccggtaaacc caccctgtac     1680
aacgtgtccc tggtcatgtc cgacacagct ggcacctgct ac                      1722

<210> SEQ ID NO 60
<211> LENGTH: 1722
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 60
caggtgcagc tccagcagtg gggagcagga ctcttgaaac cctctgagac tttgagcctc      60
acatgcgctg tctatggcgg atctttctcc ggctactatt ggtcctggat acgacagccc    120
ccaggcaaag gactcgagtg gattgggaa atcaaccact ctggtagcac taactataat      180
ccaagcctga gtcccgtgt aacaattagt gttgatacat ccaagaacca attttccctg      240
aaactgagct cagtgactgc cgccgacact gccgtctact actgtgctcg tcggagaggg    300
gccaggggcg cttccgtgaa tttcgactac tggggacagg gtaccctggt cactgtctct    360
tcaggttccg catccgcccc aacccttttc cccctcgtct cctgtgagaa tagcccgtcg    420
gatacgagca gcgtggccgt tggctgcctc gcacaggact ccttcccga ctccatcact     480 ttctcctgga aatacaagaa caactctgac atcagcagca cccggggctt cccatcagtc    540
ctgagagggg gcaagtacgc agccacctca caggtgctgc tgccttccaa ggacgtcatg    600
cagggcacag acgaacacgt ggtgtgcaaa gtccagcacc caacggcaa caaagaaaag     660 aacgtgcctc ttccagtgat tgctgagctg cctcccaaag tgagcgtctt cgtcccaccc    720
cgcgacggct tcttcggcaa cccccgcaag tccaagctca tctgccaggc cacggggttc    780
agtccccggc agattcaggt gtcctggctg cgcgaggga agcaggtggg gtctggcgtc      840
accacggacc aggtgcaggc tgaggccaaa gagtctgggc cacgacctaa caaggtgacc     900
agcacactga ccatcaaaga gagcgactgg ctcagccaga gcatgttcac ctgccgcgtg    960
gatcacaggg gcctgacctt ccagcagaat cgtcctcca tgtgtgtccc cgatcaagac     1020
acagccatcc gggtcttcgc catcccccca tcctttgcca gcatcttcct caccaagtcc    1080
accaagttga cctgcctggt cacagacctg accacctatg acagcgtgac catctcctgg    1140
acccgccaga atggcgaagc tgtgaaaacc cacaccaaca tctccgagag ccaccccaat    1200
gccactttca gcgccgtggg tgaggccagc atctgcgagg atgactggaa tagcggggag    1260
aggttcacgt gcaccgtgac ccacacagac ctgccctcgc cactgaagca gaccatctcc    1320
cggcccaagg gggtggccct gcacaggccc gatgtctact tgctgccacc agcccgggag    1380
```

```
cagctgaacc tgcgggagtc ggccaccatc acgtgcctgg tgacgggctt ctctcccgcg    1440
gacgtcttcg tgcagtggat gcagaggggg cagcccttgt ccccggagaa gtatgtgacc    1500
agcgccccaa tgcctgagcc ccaggcccca ggccggtact tcgcccacag catcctgacc    1560
gtgtccgaag aggaatggaa cacggggag acctacacct gcgtggtggc ccatgaggcc     1620
ctgcccaaca gggtcaccga gaggaccgtg acaagtcca ccggtaaacc caccctgtac    1680
aacgtgtccc tggtcatgtc cgacacagct ggcacctgct ac                      1722
```

<210> SEQ ID NO 61
<211> LENGTH: 1722
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 61

```
caggtgcagc tccagcagtg gggagcagga ctcttgaaac cctctgagac tttgagcctc      60
acatgcgctg tctatggcgg atctttctcc ggctactatt ggtcctggat acgacagccc     120
ccaggcaaag gactcgagtg gattggggaa atcaaccact ctggtagcac taactataat     180
ccaagcctga agtcccgtgt aacaattagt gttgatacat ccaagaacca atttccctg      240 aaactgagct cagtgactgc cgccgacact gccgtctact actgtgctcg tgctggcaga     300
gcctggggcg cttccgtgaa tttcgactac tggggacagg gtaccctggt cactgtctct     360
tcaggttccg catccgcccc aacccttttc cccctcgtct cctgtgagaa tagcccgtcg     420
gatacgagca gcgtggccgt tggctgcctc gcacaggact ccttcccga ctccatcact      480 ttctcctgga atacaagaa caactctgac atcagcagca cccggggctt cccatcagtc     540
ctgagagggg gcaagtacgc agccacctca caggtgctgc tgccttccaa ggacgtcatg     600
cagggcacag acgaacacgt ggtgtgcaaa gtccagcacc caacggcaa caaagaaaag      660 aacgtgcctc ttccagtgat tgctgagctg cctcccaaag tgagcgtctt cgtcccaccc    720
cgcgacggct tcttcggcaa ccccccgcaag tccaagctca tctgccaggc cacgggttc     780 agtccccggc agattcaggt gtcctggctg cgcgagggga gcaggtggg gtctggcgtc     840 accacggacc aggtgcaggc tgaggccaaa gagtctgggc ccacgaccta caaggtgacc     900
agcacactga ccatcaaaga gagcgactgg ctcagccaga gcatgttcac ctgccgcgtg    960
gatcacaggg gcctgacctt ccagcagaat gcgtcctcca tgtgtgtccc cgatcaagac    1020
acagccatcc gggtcttcgc catccccca tcctttgcca gcatcttcct caccaagtcc    1080
accaagttga cctgcctggt cacagacctg accacctatg acagcgtgac catctcctgg    1140
acccgccaga tgcgaagc tgtgaaaacc cacaccaaca tctccgagag ccaccccaat      1200
gccactttca cgccgtggg tgaggccagc atctgcgagg atgactggaa tagcggggag    1260
aggttcacgt gcaccgtgac ccacacagac ctgccctcgc cactgaagca gaccatctcc    1320
cggcccaagg ggtggccct gcacaggccc gatgtctact tgctgccacc agccgggag      1380 cagctgaacc tgcgggagtc ggccaccatc acgtgcctgg tgacgggctt ctctcccgcg    1440
gacgtcttcg tgcagtggat gcagaggggg cagcccttgt ccccggagaa gtatgtgacc    1500
agcgccccaa tgcctgagcc ccaggcccca ggccggtact tcgcccacag catcctgacc    1560
gtgtccgaag aggaatggaa cacggggag acctacacct gcgtggtggc ccatgaggcc     1620
ctgcccaaca gggtcaccga gaggaccgtg acaagtcca ccggtaaacc caccctgtac    1680
```

| | |
|---|---|
| aacgtgtccc tggtcatgtc cgacacagct ggcacctgct ac | 1722 |

<210> SEQ ID NO 62
<211> LENGTH: 1722
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 62

| | |
|---|---|
| caggtgcagc tccagcagtg gggagcagga ctcttgaaac cctctgagac tttgagcctc | 60 |
| acatgcgctg tctatggcgg atctttctcc ggctactatt ggtcctggat acgacagccc | 120 |
| ccaggcaaag gactcgagtg gattgggaa atcaaccact ctggtagcac taactataat | 180 |
| ccaagcctga gtcccgtgt aacaattagt gttgatacat ccaagaacca attttccctg | 240 |
| aaactgagct cagtgactgc cgccgacact gccgtctact actgtgctcg tagaggacgg | 300 |
| gcctggggcg cttccgtgaa tttcgactac tggggacagg gtaccctggt cactgtctct | 360 |
| tcaggttccg catccgcccc aacccttttc cccctcgtct cctgtgagaa tagcccgtcg | 420 |
| gatacgagca gcgtggccgt tggctgcctc gcacaggact ccttcccga ctccatcact | 480 |
| ttctcctgga aatacaagaa caactctgac atcagcagca cccgggggctt cccatcagtc | 540 |
| ctgagagggg gcaagtacgc agccacctca caggtgctgc tgccttccaa ggacgtcatg | 600 |
| cagggcacag acgaacacgt ggtgtgcaaa gtccagcacc caacggcaa caaagaaaag | 660 |
| aacgtgcctc ttccagtgat tgctgagctg cctcccaaag tgagcgtctt cgtcccaccc | 720 |
| cgcgacggct tcttcggcaa ccccgcaag tccaagctca tctgccaggc cacgggtttc | 780 |
| agtccccggc agattcaggt gtcctggctg cgcgagggga agcaggtggg gtctggcgtc | 840 |
| accacggacc aggtgcaggc tgaggccaaa gagtctgggc ccacgaccta caaggtgacc | 900 |
| agcacactga ccatcaaaga gagcgactgg ctcagccaga gcatgttcac ctgccgcgtg | 960 |
| gatcacaggg gcctgacctt ccagcagaat gcgtcctcca tgtgtgtccc cgatcaagac | 1020 |
| acagccatcc gggtcttcgc catcccccca tcctttgcca gcatcttcct caccaagtcc | 1080 |
| accaagttga cctgcctggt cacagacctg accacctatg acagcgtgac catctcctgg | 1140 |
| acccgccaga atggcgaagc tgtgaaaacc cacaccaaca tctccgagag ccaccccaat | 1200 |
| gccactttca gcgccgtggg tgaggccagc atctgcgagg atgactggaa tagcggggag | 1260 |
| aggttcacgt gcaccgtgac ccacacagac ctgccctcgc cactgaagca gaccatctcc | 1320 |
| cggcccaagg gggtggccct gcacaggccc gatgtctact tgctgccacc agcccgggag | 1380 |
| cagctgaacc tgcgggagtc ggccaccatc acgtgcctgg tgacgggctt ctctcccgcg | 1440 |
| gacgtcttcg tgcagtggat gcagaggggg cagcccttgt ccccggagaa gtatgtgacc | 1500 |
| agcgccccaa tgcctgagcc ccaggcccca ggccggtact cgcccacag catcctgacc | 1560 |
| gtgtccgaag aggaatggaa cacgggggag acctacacct gcgtggtggc ccatgaggcc | 1620 |
| ctgcccaaca gggtcaccga gaggaccgtg gacaagtcca ccggtaaacc caccctgtac | 1680 |
| aacgtgtccc tggtcatgtc cgacacagct ggcacctgct ac | 1722 |

<210> SEQ ID NO 63
<211> LENGTH: 1719
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 63

```
caggtgcagc tccagcagtg gggagcagga ctcttgaaac cctctgagac tttgagcctc      60
acatgcgctg tctatggcgg atctttctcc ggctactatt ggtcctggat acgacagccc     120
ccaggcaaag gactcgagtg gattggggaa atcaaccact ctggtagcac taactataat     180
ccaagcctga agtcccgtgt aacaattagt gttgatacat ccaagaacca attttccctg     240
aaactgagct cagtgactgc cgccgacact gccgtctact actgtgctcg tgctagaacc     300
gcttggggaa gctccatctt cgactactgg ggacagggta ccctggtcac tgtctcttca     360
ggttccgcat ccgccccaac ccttttcccc ctcgtctcct gtgagaatag cccgtcggat     420
acgagcagcg tggccgttgg ctgcctcgca caggacttcc ttcccgactc catcactttc     480
tcctggaaat acaagaacaa ctctgacatc agcagcaccc ggggcttccc atcagtcctg     540
agaggggca agtacgcagc cacctcacag gtgctgctgc cttccaagga cgtcatgcag     600
ggcacagacg aacacgtggt gtgcaaagtc agcaccccca cggcaacaaa gaaaagaac     660
gtgcctcttc cagtgattgc tgagctgcct cccaaagtga gcgtcttcgt cccaccccgc     720
gacggcttct tcggcaaccc ccgcaagtcc aagctcatct gccaggccac gggtttcagt     780
ccccggcaga ttcaggtgtc ctggctgcgc gaggggaagc aggtggggtc tggcgtcacc     840
acggaccagg tgcaggctga ggccaaagag tctgggccca cgacctacaa ggtgaccagc     900
acactgacca tcaaagagag cgactggctc agccagagca tgttcacctg ccgcgtggat     960
cacagggcc tgaccttcca gcagaatgcg tcctccatgt gtgtccccga tcaagacaca    1020
gccatccggg tcttcgccat ccccccatcc tttgccagca tcttcctcac caagtccacc    1080
aagttgacct gcctggtcac agacctgacc acctatgaca gcgtgaccat ctcctggacc    1140
cgccagaatg gcgaagctgt gaaaacccac accaacatct ccgagagcca ccccaatgcc    1200
actttcagcg ccgtgggtga ggccagcatc tgcgaggatg actggaatag cggggagagg    1260
ttcacgtgca ccgtgaccca cacagacctg ccctcgccac tgaagcagac catctcccgg    1320
cccaaggggg tggccctgca caggcccgat gtctacttgc tgccaccagc ccgggagcag    1380
ctgaacctgc gggagtcggc caccatcacg tgcctggtga cgggcttctc tcccgcggac    1440
gtcttcgtgc agtggatgca gagggggcag cccttgtccc cggagaagta tgtgaccagc    1500
gccccaatgc ctgagcccca ggccccaggc cggtacttcg cccacagcat cctgaccgtg    1560
tccgaagagg aatggaacac gggggagacc tacacctgcg tggtgcccca tgaggcctg    1620
cccaacaggg tcaccgagag gaccgtggac aagtccaccg gtaaacccac cctgtacaac    1680
gtgtccctgg tcatgtccga cacagctggc acctgctac                          1719
```

<210> SEQ ID NO 64
<211> LENGTH: 1719
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 64

```
caggtgcagc tccagcagtg gggagcagga ctcttgaaac cctctgagac tttgagcctc      60
acatgcgctg tctatggcgg atctttctcc ggctactatt ggtcctggat acgacagccc     120
ccaggcaaag gactcgagtg gattggggaa atcaaccact ctggtagcac taactataat     180
ccaagcctga agtcccgtgt aacaattagt gttgatacat ccaagaacca attttccctg     240
```

```
aaactgagct cagtgactgc cgccgacact gccgtctact actgtgctcg tgctagaagg    300
gcttggggaa gctccatctt cgactactgg ggacagggta ccctggtcac tgtctcttca    360
ggttccgcat ccgccccaac ccttttcccc ctcgtctcct gtgagaatag cccgtcggat    420
acgagcagcg tggccgttgg ctgcctcgca caggacttcc ttcccgactc catcactttc    480
tcctggaaat acaagaacaa ctctgacatc agcagcaccc ggggcttccc atcagtcctg    540 agaggggca gtacgcagc cacctcacag gtgctgctgc cttccaagga cgtcatgcag    600
ggcacagacg aacacgtggt gtgcaaagtc cagcacccca cggcaacaa agaaaagaac    660 gtgcctcttc cagtgattgc tgagctgcct cccaaagtga gcgtcttcgt cccacccgc    720 gacggcttct tcggcaaccc ccgcaagtcc aagctcatct gccaggccac gggtttcagt    780
ccccggcaga ttcaggtgtc ctggctgcgc gagggcaagc aggtggggtc tggcgtcacc    840
acggaccagg tgcaggctga ggccaaagag tctgggccca cgacctacaa ggtgaccagc    900
acactgacca tcaaagagag cgactggctc agccagagca tgttcacctg ccgcgtggat    960 cacagggggcc tgaccttcca gcagaatgcg tcctccatgt gtgtccccga tcaagacaca    1020
gccatccggg tcttcgccat cccccccatcc tttgccagca tcttcctcac caagtccacc    1080
aagttgacct gcctggtcac agacctgacc acctatgaca gcgtgaccat ctcctggacc    1140
cgccagaatg gcgaagctgt gaaaacccac accaacatct ccgagagcca ccccaatgcc    1200
actttcagcg ccgtgggtga ggccagcatc tgcgaggatg actggaatag cggggagagg    1260
ttcacgtgca ccgtgaccca cacagacctg ccctcgccac tgaagcagac catctcccgg    1320 cccaagggg tggccctgca caggcccgat gtctacttgc tgccaccagc ccgggagcag    1380
ctgaacctgc gggagtcggc caccatcacg tgcctggtga cgggcttctc tcccgcggac    1440
gtcttcgtgc agtggatgca gaggggggcag cccttgtccc cggagaagta tgtgaccagc    1500
gccccaatgc ctgagcccca ggccccaggc cggtacttcg cccacagcat cctgaccgtg    1560
tccgaagagg aatggaacac gggggagacc tacacctgcg tggtggccca tgaggccctg    1620
cccaacaggg tcaccgagag gaccgtggac aagtccaccg gtaaacccac cctgtacaac    1680
gtgtccctgg tcatgtccga cacagctggc acctgctac                          1719

<210> SEQ ID NO 65
<211> LENGTH: 1719
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 65
caggtgcagc tccagcagtg gggagcagga ctcttgaaac cctctgagac tttgagcctc    60
acatgcgctg tctatggcgg atctttctcc ggctactatt ggtcctggat acgacagccc    120
ccaggcaaag gactcgagtg gattggggaa atcaaccact ctggtagcac taactataat    180
ccaagcctga agtcccgtgt aacaattagt gttgatacat ccaagaacca attttccctg    240
aaactgagct cagtgactgc cgccgacact gccgtctact actgtgctcg tgctagaacc    300
gctaggggaa gctccatctt cgactactgg ggacagggta ccctggtcac tgtctcttca    360
ggttccgcat ccgccccaac ccttttcccc ctcgtctcct gtgagaatag cccgtcggat    420
acgagcagcg tggccgttgg ctgcctcgca caggacttcc ttcccgactc catcactttc    480
tcctggaaat acaagaacaa ctctgacatc agcagcaccc ggggcttccc atcagtcctg    540
```

```
agaggggca   agtacgcagc   cacctcacag   gtgctgctgc   cttccaagga   cgtcatgcag      600
ggcacagacg   aacacgtggt   gtgcaaagtc   cagcacccca   acggcaacaa   agaaaagaac      660
gtgcctcttc   cagtgattgc   tgagctgcct   cccaaagtga   gcgtcttcgt   cccaccccgc      720
gacggcttct   tcggcaaccc   ccgcaagtcc   aagctcatct   gccaggccac   gggtttcagt      780
ccccggcaga   ttcaggtgtc   ctggctgcgc   gaggggaagc   aggtggggtc   tggcgtcacc      840
acggaccagg   tgcaggctga   ggccaaagag   tctgggccca   cgacctacaa   ggtgaccagc      900
acactgacca   tcaaagagag   cgactggctc   agccagcagca   tgttcacctg   ccgcgtggat      960
cacagggggc   tgaccttcca   gcagaatgcg   tcctccatgt   gtgtccccga   tcaagacaca     1020
gccatccggg   tcttcgccat   cccccatcc   tttgccagca   tcttcctcac   caagtccacc     1080
aagttgacct   gcctggtcac   agacctgacc   acctatgaca   gcgtgaccat   ctcctggacc     1140
cgccagaatg   gcgaagctgt   gaaaaccac   accaacatct   ccgagagcca   ccccaatgcc     1200
actttcagcg   ccgtgggtga   ggccagcatc   tgcgaggatg   actggaatag   cggggagagg     1260
ttcacgtgca   ccgtgaccca   cacagacctg   ccctcgccac   tgaagcagac   catctcccgg     1320 cccaagggg   tggccctgca   caggcccgat   gtctacttgc   tgccaccagc   ccgggagcag     1380
ctgaacctgc   gggagtcggc   caccatcacg   tgcctggtga   cgggcttctc   tcccgcggac     1440
gtcttcgtgc   agtggatgca   gagggggcag   cccttgtccc   cggagaagta   tgtgaccagc     1500
gccccaatgc   ctgagcccca   ggcccaggc   cggtacttcg   cccacagcat   cctgaccgtg     1560
tccgaagagg   aatggaacac   gggggagacc   tacacctgcg   tggtggccca   tgaggccctg     1620
cccaacaggg   tcaccgagag   gaccgtggac   aagtccaccg   gtaaacccac   cctgtacaac     1680
gtgtccctgg   tcatgtccga   cacagctggc   acctgctac                                1719
```

<210> SEQ ID NO 66
<211> LENGTH: 1719
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 66

```
caggtgcagc   tccagcagtg   gggagcagga   ctcttgaaac   cctctgagac   tttgagcctc       60
acatgcgctg   tctatggcgg   atctttctcc   ggctactatt   ggtcctggat   acgacagccc      120
ccaggcaaag   gactcgagtg   gattggggaa   atcaaccact   ctggtagcac   taactataat      180
ccaagcctga   agtcccgtgt   aacaattagt   gttgatacat   ccaagaacca   attttccctg      240
aaactgagct   cagtgactgc   cgccgacact   gccgtctact   actgtgctcg   tgctagaaga      300
gctaggggaa   gctccatctt   cgactactgg   ggacaggta   ccctggtcac   tgtctcttca      360
ggttccgcat   ccgcccaac   cctttttccc   ctcgtctcct   gtgagaatag   cccgtcggat      420
acgagcagcg   tggccgttgg   ctgcctcgca   caggacttcc   ttcccgactc   catcactttc      480
tcctggaaat   acaagaacaa   ctctgacatc   agcagcaccc   ggggcttccc   atcagtcctg      540 agaggggca   agtacgcagc   cacctcacag   gtgctgctgc   cttccaagga   cgtcatgcag      600
ggcacagacg   aacacgtggt   gtgcaaagtc   cagcacccca   acggcaacaa   agaaaagaac      660
gtgcctcttc   cagtgattgc   tgagctgcct   cccaaagtga   gcgtcttcgt   cccaccccgc      720
gacggcttct   tcggcaaccc   ccgcaagtcc   aagctcatct   gccaggccac   gggtttcagt      780
ccccggcaga   ttcaggtgtc   ctggctgcgc   gaggggaagc   aggtggggtc   tggcgtcacc      840
```

```
acggaccagg tgcaggctga ggccaaagag tctgggccca cgacctacaa ggtgaccagc      900
acactgacca tcaaagagag cgactggctc agccagagca tgttcacctg ccgcgtggat      960
cacaggggcc tgaccttcca gcagaatgcg tcctccatgt gtgtccccga tcaagacaca     1020
gccatccggg tcttcgccat ccccccatcc tttgccagca tcttcctcac caagtccacc     1080
aagttgacct gcctggtcac agacctgacc acctatgaca gcgtgaccat ctcctggacc     1140
cgccagaatg gcgaagctgt gaaaacccac accaacatct ccgagagcca ccccaatgcc     1200
actttcagcg ccgtgggtga ggccagcatc tgcgaggatg actggaatag cggggagagg     1260
ttcacgtgca ccgtgaccca cacagacctg ccctcgccac tgaagcagac catctcccgg     1320 cccaagggg tggccctgca caggcccgat gtctacttgc tgccaccagc ccgggagcag     1380
ctgaacctgc gggagtcggc caccatcacg tgcctggtga cgggcttctc tcccgcggac     1440
gtcttcgtgc agtggatgca gaggggcag cccttgtccc cggagaagta tgtgaccagc     1500
gccccaatgc ctgagcccca ggccccaggc cggtacttcg cccacagcat cctgaccgtg     1560
tccgaagagg aatggaacac gggggagacc tacacctgcg tggtggccca tgaggccctg     1620
cccaacaggt tcaccgagag gaccgtggac aagtccaccg gtaaacccac cctgtacaac     1680
gtgtccctgg tcatgtccga cacagctggc acctgctac                            1719

<210> SEQ ID NO 67
<211> LENGTH: 1719
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 67
caggtgcagc tccagcagtg gggagcagga ctcttgaaac cctctgagac tttgagcctc       60
acatgcgctg tctatggcgg atctttctcc ggctactatt ggtcctggat acgacagccc      120
ccaggcaaag gactcgagtg gattgggaa atcaaccact ctggtagcac taactataat      180
ccaagcctga gtcccgtgt aacaattagt gttgatacat ccaagaacca attttccctg      240
aaactgagct cagtgactgc cgccgacact gccgtctact actgtgctcg tagagcaacc      300
gcttggggaa gctccatctt cgactactgg ggacagggta ccctggtcac tgtctcttca      360
ggttccgcat ccgccccaac ccttttcccc ctcgtctcct gtgagaatag cccgtcggat      420
acgagcagcg tggccgttgg ctgcctcgca caggacttcc ttcccgactc catcactttc      480
tcctggaaat acaagaacaa ctctgacatc agcagcaccc ggggcttccc atcagtcctg      540 agaggggca agtacgcagc cacctcacag gtgctgctgc cttccaagga cgtcatgcag      600
ggcacagacg aacacgtggt gtgcaaagtc cagcacccca cggcaacaa agaaaagaac      660 gtgcctcttc cagtgattgc tgagctgcct cccaaagtga cgtcttcgt cccaccccgc      720 gacggcttct tcggcaaccc ccgcaagtcc aagctcatct gccaggccac gggtttcagt     780
ccccggcaga ttcaggtgtc ctggctgcgc gaggggaagc aggtggggtc tggcgtcacc      840
acggaccagg tgcaggctga ggccaaagag tctgggccca cgacctacaa ggtgaccagc      900
acactgacca tcaaagagag cgactggctc agccagagca tgttcacctg ccgcgtggat      960
cacaggggcc tgaccttcca gcagaatgcg tcctccatgt gtgtccccga tcaagacaca     1020
gccatccggg tcttcgccat ccccccatcc tttgccagca tcttcctcac caagtccacc     1080
aagttgacct gcctggtcac agacctgacc acctatgaca gcgtgaccat ctcctggacc     1140
```

```
cgccagaatg gcgaagctgt gaaaacccac accaacatct ccgagagcca ccccaatgcc   1200
actttcagcg ccgtgggtga ggccagcatc tgcgaggatg actggaatag cggggagagg   1260
ttcacgtgca ccgtgaccca cacagacctg ccctcgccac tgaagcagac catctcccgg   1320 cccaggggg tggccctgca caggcccgat gtctacttgc tgccaccagc ccgggagcag   1380
ctgaacctgc gggagtcggc caccatcacg tgcctggtga cgggcttctc tcccgcggac   1440
gtcttcgtgc agtggatgca gaggggggcag cccttgtccc cggagaagta tgtgaccagc   1500
gccccaatgc ctgagcccca ggccccaggc cggtacttcg cccacagcat cctgaccgtg   1560
tccgaagagg aatggaacac gggggagacc tacacctgcg tggtggccca tgaggccctg   1620
cccaacaggg tcaccgagag gaccgtggac aagtccaccg gtaaacccac cctgtacaac   1680
gtgtccctgg tcatgtccga cacagctggc acctgctac                         1719
```

<210> SEQ ID NO 68
<211> LENGTH: 1719
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 68

```
caggtgcagc tccagcagtg gggagcagga ctcttgaaac cctctgagac tttgagcctc   60
acatgcgctg tctatggcgg atctttctcc ggctactatt ggtcctggat acgacagccc   120
ccaggcaaag gactcgagtg gattggggaa atcaaccact ctggtagcac taactataat   180
ccaagcctga agtcccgtgt aacaattagt gttgatacat ccaagaacca atttccctg   240 aaactgagct cagtgactgc cgccgacact gccgtctact actgtgctcg tagaagaacc   300
gcttggggaa gctccatctt cgactactgg ggacagggta ccctggtcac tgtctcttca   360
ggttccgcat ccgccccaac ccttttcccc ctcgtctcct gtgagaatag cccgtcggat   420
acgagcagcg tggccgttgg ctgcctcgca caggacttcc ttcccgactc catcactttc   480
tcctggaaat acaagaacaa ctctgacatc agcagcaccc ggggcttccc atcagtcctg   540
agagggggca agtacgcagc cacctcacag gtgctgctgc cttccaagga cgtcatgcag   600
ggcacagacg aacacgtggt gtgcaaagtc cagcaccccca acggcaacaa agaaaagaac   660
gtgcctcttc cagtgattgc tgagctgcct cccaaagtga gcgtcttcgt cccacccgc   720 gacggcttct tcggcaaccc ccgcaagtcc aagctcatct gccaggccac gggtttcagt   780
ccccggcaga ttcaggtgtc ctggctgcgc gaggggaagc aggtggggtc tggcgtcacc   840
acggaccagg tgcaggctga ggccaaagag tctgggccca cgacctacaa ggtgaccagc   900
acactgacca tcaaagagag cgactggctc agccagagca tgttcacctg ccgcgtggat   960 cacagggggcc tgaccttcca gcagaatgcg tcctccatgt gtgtcccga tcaagacaca   1020 gccatccggg tcttcgccat cccccatcc tttgccagca tcttcctcac caagtccacc   1080
aagttgacct gcctggtcac agacctgacc acctatgaca cgtgaccat ctcctggacc   1140 cgccagaatg cgaagctgt gaaaacccac accaacatct ccgagagcca ccccaatgcc   1200
actttcagcg ccgtgggtga ggccagcatc tgcgaggatg actggaatag cggggagagg   1260
ttcacgtgca ccgtgaccca cacagacctg ccctcgccac tgaagcagac catctcccgg   1320 cccaggggg tggccctgca caggcccgat gtctacttgc tgccaccagc ccgggagcag   1380
ctgaacctgc gggagtcggc caccatcacg tgcctggtga cgggcttctc tcccgcggac   1440
```

| | |
|---|---|
| gtcttcgtgc agtggatgca gaggggcag cccttgtccc ggagaagta tgtgaccagc | 1500 |
| gccccaatgc ctgagcccca ggccccaggc cggtacttcg cccacagcat cctgaccgtg | 1560 |
| tccgaagagg aatggaacac gggggagacc tacacctgcg tggtggccca tgaggcctg | 1620 |
| cccaacaggg tcaccgagag gaccgtggac aagtccaccg gtaaacccac cctgtacaac | 1680 |
| gtgtccctgg tcatgtccga cacagctggc acctgctac | 1719 |

<210> SEQ ID NO 69
<211> LENGTH: 1719
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 69

| | |
|---|---|
| caggtgcagc tccagcagtg gggagcagga ctcttgaaac cctctgagac tttgagcctc | 60 |
| acatgcgctg tctatggcgg atctttctcc ggctactatt ggtcctggat cgacagccc | 120 |
| ccaggcaaag gactcgagtg gattgggaa atcaaccact ctggtagcac taactataat | 180 |
| ccaagcctga gtcccgtgt aacaattagt gttgatacat ccaagaacca atttccctg | 240 |
| aaactgagct cagtgactgc cgccgacact gccgtctact actgtgctcg tagagcaacc | 300 |
| gctaggggaa gctccatctt cgactactgg ggacaggta ccctggtcac tgtctcttca | 360 |
| ggttccgcat ccgccccaac ccttttcccc ctcgtctcct gtgagaatag cccgtcggat | 420 |
| acgagcagcg tggccgttgg ctgcctcgca caggacttcc ttcccgactc catcactttc | 480 |
| tcctggaaat acaagaacaa ctctgacatc agcagcaccc ggggcttccc atcagtcctg | 540 |
| agaggggca gtacgcagc cacctcacag gtgctgctgc cttccaagga cgtcatgcag | 600 |
| ggcacagacg aacacgtggt gtgcaaagtc cagcacccca acggcaacaa agaaaagaac | 660 |
| gtgcctcttc cagtgattgc tgagctgcct cccaaagtga gcgtcttcgt cccaccccgc | 720 |
| gacggcttct tcggcaaccc ccgcaagtcc aagctcatct gccaggccac gggtttcagt | 780 |
| cccggcaga ttcaggtgtc ctggctgcgc gaggggaagc aggtggggtc tggcgtcacc | 840 |
| acggaccagg tgcaggctga ggccaaagag tctgggccca cgacctacaa ggtgaccagc | 900 |
| acactgacca tcaaagagag cgactggctc agccagagca tgttcacctg ccgcgtggat | 960 |
| cacaggggcc tgaccttcca gcagaatgcg tcctccatgt gtgtccccga tcaagacaca | 1020 |
| gccatccggg tcttcgccat ccccccatcc tttgccagca tcttcctcac caagtccacc | 1080 |
| aagttgacct gcctggtcac agacctgacc acctatgaca gcgtgaccat ctcctggacc | 1140 |
| cgccagaatg gcgaagctgt gaaaacccac accaacatct ccgagagcca ccccaatgcc | 1200 |
| actttcagcg ccgtgggtga ggccagcatc tgcgaggatg actggaatag cggggagagg | 1260 |
| ttcacgtgca ccgtgaccca cacagacctg ccctcgccac tgaagcagac catctcccgg | 1320 |
| cccaaggggg tggccctgca caggcccgat gtctacttgc tgccaccagc ccgggagcag | 1380 |
| ctgaacctgc gggagtcggc caccatcacg tgcctggtga cgggcttctc tccgcggac | 1440 |
| gtcttcgtgc agtggatgca gagggggcag cccttgtccc ggagaagta tgtgaccagc | 1500 |
| gccccaatgc ctgagcccca ggccccaggc cggtacttcg cccacagcat cctgaccgtg | 1560 |
| tccgaagagg aatggaacac gggggagacc tacacctgcg tggtggccca tgaggcctg | 1620 |
| cccaacaggg tcaccgagag gaccgtggac aagtccaccg gtaaacccac cctgtacaac | 1680 |
| gtgtccctgg tcatgtccga cacagctggc acctgctac | 1719 |

<210> SEQ ID NO 70
<211> LENGTH: 1719
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 70

| | | | | | |
|---|---|---|---|---|---|
| caggtgcagc | tccagcagtg | gggagcagga | ctcttgaaac | cctctgagac | tttgagcctc | 60 |
| acatgcgctg | tctatggcgg | atctttctcc | ggctactatt | ggtcctggat | acgacagccc | 120 |
| ccaggcaaag | gactcgagtg | gattggggaa | atcaaccact | ctggtagcac | taactataat | 180 |
| ccaagcctga | agtcccgtgt | aacaattagt | gttgatacat | ccaagaacca | atttccctg | 240 |
| aaactgagct | cagtgactgc | cgccgacact | gccgtctact | actgtgctcg | tagagcaaga | 300 |
| gctaggggaa | gctccatctt | cgactactgg | ggacaggggta | ccctggtcac | tgtctcttca | 360 |
| ggttccgcat | ccgccccaac | cctttctccc | ctcgtctcct | gtgagaatag | cccgtcggat | 420 |
| acgagcagcg | tggccgttgg | ctgcctcgca | caggacttcc | ttcccgactc | catcactttc | 480 |
| tcctggaaat | acaagaacaa | ctctgacatc | agcagcaccc | ggggcttccc | atcagtcctg | 540 |
| agaggggca | agtacgcagc | cacctcacag | gtgctgctgc | cttccaagga | cgtcatgcag | 600 |
| ggcacagacg | aacacgtggt | gtgcaaagtc | agcaccccca | acggcaacaa | agaaaagaac | 660 |
| gtgcctcttc | cagtgattgc | tgagctgcct | cccaaagtga | gcgtcttcgt | cccaccccgc | 720 |
| gacggcttct | tcggcaaccc | ccgcaagtcc | aagctcatct | gccaggccac | gggtttcagt | 780 |
| ccccggcaga | ttcaggtgtc | ctggctgcgc | gaggggaagc | aggtggggtc | tggcgtcacc | 840 |
| acggaccagg | tgcaggctga | ggccaaagag | tctgggccca | cgacctacaa | ggtgaccagc | 900 |
| acactgacca | tcaaagagag | cgactggctc | agccagagca | tgttcacctg | ccgcgtggat | 960 |
| cacaggggcc | tgaccttcca | gcagaatgcg | tcctccatgt | gtgtcccga | tcaagacaca | 1020 |
| gccatccggg | tcttcgccat | cccccccatcc | tttgccagca | tcttcctcac | caagtccacc | 1080 |
| aagttgacct | gcctggtcac | agacctgacc | acctatgaca | gcgtgaccat | ctcctggacc | 1140 |
| cgccagaatg | gcgaagctgt | gaaaacccac | accaacatct | ccgagagcca | ccccaatgcc | 1200 |
| actttcagcg | ccgtgggtga | ggccagcatc | tgcgaggatg | actggaatag | cggggagagg | 1260 |
| ttcacgtgca | ccgtgaccca | cacagacctg | ccctcgccac | tgaagcagac | catctcccgg | 1320 |
| cccaagggg | tggccctgca | caggcccgat | gtctacttgc | tgccaccagc | ccgggagcag | 1380 |
| ctgaacctgc | gggagtcggc | caccatcacg | tgcctggtga | cgggcttctc | tcccgcggac | 1440 |
| gtcttcgtgc | agtggatgca | gaggggggcag | cccttgtccc | cggagaagta | tgtgaccagc | 1500 |
| gccccaatgc | ctgagcccca | ggcccaggc | cggtacttcg | cccacagcat | cctgaccgtg | 1560 |
| tccgaagagg | aatggaacac | gggggagacc | tacacctgcg | tggtggccca | tgaggccctg | 1620 |
| cccaacaggg | tcaccgagag | gaccgtggac | aagtccaccg | gtaaacccac | cctgtacaac | 1680 |
| gtgtccctgg | tcatgtccga | cacagctggc | acctgctac | | | 1719 |

<210> SEQ ID NO 71
<211> LENGTH: 1719
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 71

```
caggtgcagc tccagcagtg gggagcagga ctcttgaaac cctctgagac tttgagcctc      60
acatgcgctg tctatggcgg atctttctcc ggctactatt ggtcctggat acgacagccc     120
ccaggcaaag gactcgagtg gattggggaa atcaaccact ctggtagcac taactataat     180
ccaagcctga agtcccgtgt aacaattagt gttgatacat ccaagaacca attttccctg     240
aaactgagct cagtgactgc cgccgacact gccgtctact actgtgctcg tagaagaaca     300
gctaggggaa gctccatctt cgactactgg ggacagggta ccctggtcac tgtctcttca     360
ggttccgcat ccgccccaac cctttttccc ctcgtctcct gtgagaatag cccgtcggat     420
acgagcagcg tggccgttgg ctgcctcgca caggacttcc ttcccgactc catcactttc     480
tcctggaaat acaagaacaa ctctgacatc agcagcaccc ggggcttccc atcagtcctg     540
agaggggcaa gtacgcagc cacctcacag gtgctgctgc cttccaagga cgtcatgcag     600
ggcacagacg aacacgtggt gtgcaaagtc cagcaccca acggcaacaa agaaaagaac     660
gtgcctcttc cagtgattgc tgagctgcct cccaaagtga gcgtcttcgt cccacccgc      720
gacggcttct tcggcaaccc ccgcaagtcc aagctcatct gccaggccac gggtttcagt     780
ccccggcaga ttcaggtgtc ctggctgcgc gaggggaagc aggtggggtc tggcgtcacc     840
acggaccagg tgcaggctga ggccaaagag tctgggccca cgacctacaa ggtgaccagc     900
acactgacca tcaagagag cgactggctc agccagcagc tgttcacctg ccgcgtggat     960
cacagggcc tgaccttcca gcagaatgcg tcctccatgt gtgtcccga tcaagacaca    1020
gccatccggg tcttcgccat ccccccatcc tttgccagca tcttcctcac caagtccacc    1080
aagttgacct gcctggtcac agacctgacc acctatgaca gcgtgaccat ctcctggacc    1140
cgccagaatg gcgaagctgt gaaaacccac accaacatct ccgagagcca ccccaatgcc    1200
actttcagcg ccgtgggtga ggccagcatc tgcgaggatg actggaatag cggggagagg    1260
ttcacgtgca ccgtgaccca cacagacctg ccctcgccac tgaagcagac catctcccgg    1320
cccaaggggg tggccctgca caggcccgat gtctacttgc tgccaccagc ccgggagcag    1380
ctgaacctgc gggagtcggc caccatcacg tgcctggtga cgggcttctc tcccgcggac    1440
gtcttcgtgc agtggatgca gagggggcag cccttgtccc cggagaagta tgtgaccagc    1500
gccccaatgc ctgagcccca ggccccaggc cggtacttcg cccacagcat cctgaccgtg    1560
tccgaagagg aatggaacac ggggagacc tacacctgcg tggtggccca tgaggccctg    1620
cccaacaggg tcaccgagag gaccgtggac aagtccaccg gtaaacccac cctgtacaac    1680
gtgtccctgg tcatgtccga cacagctggc acctgctac                           1719
```

<210> SEQ ID NO 72
<211> LENGTH: 1719
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 72

```
caggtgcagc tccagcagtg gggagcagga ctcttgaaac cctctgagac tttgagcctc      60
acatgcgctg tctatggcgg atctttctcc ggctactatt ggtcctggat acgacagccc     120
ccaggcaaag gactcgagtg gattggggaa atcaaccact ctggtagcac taactataat     180
ccaagcctga agtcccgtgt aacaattagt gttgatacat ccaagaacca attttccctg     240
```

| | |
|---|---|
| aaactgagct cagtgactgc cgccgacact gccgtctact actgtgctcg tggagcaaga | 300 |
| gcttggggaa gctccatctt cgactactgg ggacagggta ccctggtcac tgtctcttca | 360 |
| ggttccgcat ccgccccaac ccttttcccc ctcgtctcct gtgagaatag cccgtcggat | 420 |
| acgagcagcg tggccgttgg ctgcctcgca caggacttcc ttcccgactc catcactttc | 480 |
| tcctggaaat acaagaacaa ctctgacatc agcagcaccc ggggcttccc atcagtcctg | 540 |
| agagggggca agtacgcagc cacctcacag gtgctgctgc cttccaagga cgtcatgcag | 600 |
| ggcacagacg aacacgtggt gtgcaaagtc agcaccccca cggcaacaa agaaaagaac | 660 |
| gtgcctcttc cagtgattgc tgagctgcct cccaaagtga gcgtcttcgt cccaccccgc | 720 |
| gacggcttct tcggcaaccc ccgcaagtcc aagctcatct gccaggccac gggtttcagt | 780 |
| ccccggcaga ttcaggtgtc ctggctgcgc gaggggaagc aggtggggtc tggcgtcacc | 840 |
| acggaccagg tgcaggctga ggccaaagag tctgggccca cgacctacaa ggtgaccagc | 900 |
| acactgacca tcaaagagag cgactggctc agccagagca tgttcacctg ccgcgtggat | 960 |
| cacagggggcc tgaccttcca gcagaatgcg tcctccatgt gtgtccccga tcaagacaca | 1020 |
| gccatccggg tcttcgccat cccccccatcc tttgccagca tcttcctcac caagtccacc | 1080 |
| aagttgacct gcctggtcac agacctgacc acctatgaca gcgtgaccat ctcctggacc | 1140 |
| cgccagaatg gcgaagctgt gaaaacccac accaacatct ccgagagcca ccccaatgcc | 1200 |
| actttcagcg ccgtgggtga ggccagcatc tgcgaggatg actggaatag cggggagagg | 1260 |
| ttcacgtgca ccgtgacccca cacagacctg ccctcgccac tgaagcagac catctcccgg | 1320 |
| cccaagggg tggccctgca caggcccgat gtctacttgc tgccaccagc ccgggagcag | 1380 |
| ctgaacctgc gggagtcggc caccatcacg tgcctggtga cgggcttctc tcccgcggac | 1440 |
| gtcttcgtgc agtggatgca gagggggcag cccttgtccc cggagaagta tgtgaccagc | 1500 |
| gccccaatgc ctgagcccca ggcccaggc cggtacttcg cccacagcat cctgaccgtg | 1560 |
| tccgaagagg aatggaacac gggggagacc tacacctgcg tggtggccca tgaggccctg | 1620 |
| cccaacaggg tcaccgagag gaccgtggac aagtccaccg gtaaacccac cctgtacaac | 1680 |
| gtgtccctgg tcatgtccga cacagctggc acctgctac | 1719 |

<210> SEQ ID NO 73
<211> LENGTH: 1719
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 73

| | |
|---|---|
| caggtgcagc tccagcagtg gggagcagga ctcttgaaac cctctgagac tttgagcctc | 60 |
| acatgcgctg tctatggcgg atctttctcc ggctactatt ggtcctggat acgacagccc | 120 |
| ccaggcaaag gactcgagtg gattggggaa atcaaccact ctggtagcac taactataat | 180 |
| ccaagcctga gtcccgtgt aacaattagt gttgatacat ccaagaacca attttccctg | 240 |
| aaactgagct cagtgactgc cgccgacact gccgtctact actgtgctcg tagagcaaga | 300 |
| gcttggggaa gctccatctt cgactactgg ggacagggta ccctggtcac tgtctcttca | 360 |
| ggttccgcat ccgccccaac ccttttcccc ctcgtctcct gtgagaatag cccgtcggat | 420 |
| acgagcagcg tggccgttgg ctgcctcgca caggacttcc ttcccgactc catcactttc | 480 |
| tcctggaaat acaagaacaa ctctgacatc agcagcaccc ggggcttccc atcagtcctg | 540 |

```
agaggggca agtacgcagc cacctcacag gtgctgctgc cttccaagga cgtcatgcag    600
ggcacagacg aacacgtggt gtgcaaagtc cagcacccca acggcaacaa agaaaagaac    660
gtgcctcttc cagtgattgc tgagctgcct cccaaagtga gcgtcttcgt cccacccgc    720 gacggcttct tcggcaaccc ccgcaagtcc aagctcatct gccaggccac gggtttcagt    780
ccccggcaga ttcaggtgtc ctggctgcgc gaggggaagc aggtggggtc tggcgtcacc    840
acggaccagg tgcaggctga ggccaaagag tctgggccca cgacctacaa ggtgaccagc    900
acactgacca tcaaagagag cgactggctc agccagagca tgttcacctg ccgcgtggat    960
cacaggggcc tgaccttcca gcagaatgcg tcctccatgt gtgtccccga tcaagacaca   1020
gccatccggg tcttcgccat ccccccatcc tttgccagca tcttcctcac caagtccacc   1080
aagttgacct gcctggtcac agacctgacc acctatgaca gcgtgaccat ctcctggacc   1140
cgccagaatg gcgaagctgt gaaaacccac accaacatct ccgagagcca ccccaatgcc   1200
actttcagcg ccgtgggtga ggccagcatc tgcgaggatg actggaatag cggggagagg   1260
ttcacgtgca ccgtgaccca cacagacctg ccctcgccac tgaagcagac catctcccgg   1320 cccaagggg tggccctgca caggcccgat gtctacttgc tgccaccagc ccgggagcag   1380
ctgaacctgc gggagtcggc caccatcacg tgcctggtga cgggcttctc tcccgcggac   1440
gtcttcgtgc agtggatgca gaggggcag cccttgtccc cggagaagta tgtgaccagc   1500
gccccaatgc ctgagcccca ggccccaggc cggtacttcg cccacagcat cctgaccgtg   1560
tccgaagagg aatggaacac gggggagacc tacacctgcg tggtggccca tgaggccctg   1620
cccaacaggg tcaccgagag gaccgtggac aagtccaccg gtaaacccac cctgtacaac   1680
gtgtccctgg tcatgtccga cacagctggc acctgctac                         1719
```

<210> SEQ ID NO 74
<211> LENGTH: 636
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 74

```
gacatacaga tgacccagtc cccaagcacc ctgtctgcat ctgtgggaga tcgcgtgacc     60
atcacctgca ctggaactag ctccgacgta ggaggctata attatgtttc ctggtatcag    120
caacatcctg gaaaggctcc aaagctgatg atctacggtg tttccaaccg gttcagtggc    180
tctaagagtg gtaacaccgc atctctgacc attagtggcc tggcagccga agatgaggcc    240
gactactact gctcctccta tacaagcagc tcaaccctcg tggtgtttgg tggcggtacc    300
aagctgaccg tcctaggtca gcccaaggct gccccctcgg tcactctgtt cccaccctcc    360
tctgaggagc ttcaagccaa caaggccaca ctggtgtgtc tcataagtga cttctacccg    420
ggagccgtga cagtggcctg gaaggcagat agcagccccg tcaaggcggg agtggagacc    480
accacaccct ccaaacaaag caacaacaag tacgcggcca gcagctacct gagcctgacg    540
cctgagcagt ggaagtccca cagaagctac agctgccagg tcacgcatga agggagcacc    600
gtggagaaga cagtggcccc tacagaatgt tcatag                              636
```

<210> SEQ ID NO 75
<211> LENGTH: 645
<212> TYPE: DNA
<213> ORGANISM: Artificial Sequence
<220> FEATURE:

-continued

<223> OTHER INFORMATION: Description of Artificial Sequence: Synthetic
      polynucleotide

<400> SEQUENCE: 75

```
gatatccaga tgacccagtc accctcaagc ctgagcgcaa gcgtggggga ccgagtgact    60
attacatgtc gagcttctca gtcaatcagc tcctacctga actggtatca gcagaaacct   120
ggaaaagccc caaaactgct tatctacgca gccagttccc tgcaaagtgg agtgccctcc   180
cgattcagtg gctcaggaag tgggactgac ttcactctga ctatcagtag tctgcaacca   240
gaagactttg ccacctacta ttgccagcag agctacagca ccctattac cttcggccag    300
ggtacccgac tagagatcaa acgtactgtg gctgcaccat ctgtcttcat cttcccgcca   360
tctgatgagc agttgaaatc tggaactgcc tctgttgtgt gcctgctgaa taacttctat   420
cccagagagg ccaaagtaca gtggaaggtg gataacgccc tccaatcggg taactcccag   480
gagagtgtca cagagcagga cagcaaggac agcacctaca gcctcagcag cacccctgacg 540
ctgagcaaag cagactacga gaaacacaaa gtctacgcct gcgaagtcac ccatcagggc   600
ctgagctcgc ccgtcacaaa gagcttcaac aggggagagt gttag                   645
```

<210> SEQ ID NO 76
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 76

Phe Ser Gly Tyr Tyr Trp Ser
1               5

<210> SEQ ID NO 77
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 77

Glu Ile Asn His Ser Gly Ser Thr Asn Tyr Asn Pro Ser Leu Lys Ser
1               5                   10                  15

<210> SEQ ID NO 78
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 78

Gly Arg Met Ala Trp Gly Ala Ser Val Asn
1               5                   10

<210> SEQ ID NO 79
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 79

```
Gly Arg Arg Ala Trp Gly Ala Ser Val Asn
1               5                   10

<210> SEQ ID NO 80
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 80

Gly Arg Met Ala Arg Gly Ala Ser Val Asn
1               5                   10

<210> SEQ ID NO 81
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 81

Gly Arg Arg Ala Arg Gly Ala Ser Val Asn
1               5                   10

<210> SEQ ID NO 82
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 82

Arg Gly Met Ala Trp Gly Ala Ser Val Asn
1               5                   10

<210> SEQ ID NO 83
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 83

Arg Arg Met Ala Trp Gly Ala Ser Val Asn
1               5                   10

<210> SEQ ID NO 84
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 84

Arg Gly Met Ala Arg Gly Ala Ser Val Asn
1               5                   10

<210> SEQ ID NO 85
<211> LENGTH: 10
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 85

Arg Gly Arg Ala Arg Gly Ala Ser Val Asn
1               5                   10

<210> SEQ ID NO 86
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 86

Arg Arg Gly Ala Arg Gly Ala Ser Val Asn
1               5                   10

<210> SEQ ID NO 87
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 87

Ala Gly Arg Ala Trp Gly Ala Ser Val Asn
1               5                   10

<210> SEQ ID NO 88
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 88

Arg Gly Arg Ala Trp Gly Ala Ser Val Asn
1               5                   10

<210> SEQ ID NO 89
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 89

Ala Arg Thr Ala Trp Gly Ser Ser Ile
1               5

<210> SEQ ID NO 90
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 90

Ala Arg Arg Ala Trp Gly Ser Ser Ile
1               5
```

<210> SEQ ID NO 91
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 91

Ala Arg Thr Ala Arg Gly Ser Ser Ile
1               5

<210> SEQ ID NO 92
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 92

Ala Arg Arg Ala Arg Gly Ser Ser Ile
1               5

<210> SEQ ID NO 93
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 93

Arg Ala Thr Ala Trp Gly Ser Ser Ile
1               5

<210> SEQ ID NO 94
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 94

Arg Arg Thr Ala Trp Gly Ser Ser Ile
1               5

<210> SEQ ID NO 95
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 95

Arg Ala Thr Ala Arg Gly Ser Ser Ile
1               5

<210> SEQ ID NO 96
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 96

Arg Ala Arg Ala Arg Gly Ser Ser Ile
1               5

<210> SEQ ID NO 97
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 97

Arg Arg Thr Ala Arg Gly Ser Ser Ile
1               5

<210> SEQ ID NO 98
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 98

Gly Ala Arg Ala Trp Gly Ser Ser Ile
1               5

<210> SEQ ID NO 99
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 99

Arg Ala Arg Ala Trp Gly Ser Ser Ile
1               5

<210> SEQ ID NO 100
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 100

Thr Gly Thr Ser Ser Asp Val Gly Gly Tyr Asn Tyr Val Ser
1               5                   10

<210> SEQ ID NO 101
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 101

Arg Ala Ser Gln Ser Ile Ser Ser Tyr Leu Asn
1               5                   10

<210> SEQ ID NO 102
<211> LENGTH: 7
<212> TYPE: PRT
```

```
<213> ORGANISM: Artificial Sequence
<220> FEATURE:
<223> OTHER INFORMATION: Description of Artificial Sequence: Synthetic
      peptide

<400> SEQUENCE: 102

Gly Val Ser Asn Arg Phe Ser
1               5

<210> SEQ ID NO 103
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 103

Ala Ala Ser Ser Leu Gln Ser
1               5

<210> SEQ ID NO 104
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 104

Ser Ser Tyr Thr Ser Ser Ser Thr Leu
1               5

<210> SEQ ID NO 105
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 105

Gln Gln Ser Tyr Ser Thr Pro
1               5

<210> SEQ ID NO 106
<211> LENGTH: 575
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 106

Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Gly Tyr
            20                  25                  30

Tyr Trp Ser Trp Ile Arg Gln Pro Pro Gly Lys Gly Leu Glu Trp Ile
        35                  40                  45

Gly Glu Ile Asn His Ser Gly Ser Thr Asn Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
```

-continued

```
                85                  90                  95
Arg Gly Arg Met Val Arg Gly Ala Lys Tyr Asn Trp Phe Asp Pro Trp
            100                 105                 110
Gly Gln Gly Thr Leu Val Thr Val Ser Ser Gly Ser Ala Ser Ala Pro
            115                 120                 125
Thr Leu Phe Pro Leu Val Ser Cys Glu Asn Ser Pro Ser Asp Thr Ser
130                 135                 140
Ser Val Ala Val Gly Cys Leu Ala Gln Asp Phe Leu Pro Asp Ser Ile
145                 150                 155                 160
Thr Phe Ser Trp Lys Tyr Lys Asn Asn Ser Asp Ile Ser Ser Thr Arg
                165                 170                 175
Gly Phe Pro Ser Val Leu Arg Gly Gly Lys Tyr Ala Ala Thr Ser Gln
                180                 185                 190
Val Leu Leu Pro Ser Lys Asp Val Met Gln Gly Thr Asp Glu His Val
                195                 200                 205
Val Cys Lys Val Gln His Pro Asn Gly Asn Lys Glu Lys Asn Val Pro
            210                 215                 220
Leu Pro Val Ile Ala Glu Leu Pro Pro Lys Val Ser Val Phe Val Pro
225                 230                 235                 240
Pro Arg Asp Gly Phe Phe Gly Asn Pro Arg Lys Ser Lys Leu Ile Cys
                245                 250                 255
Gln Ala Thr Gly Phe Ser Pro Arg Gln Ile Gln Val Ser Trp Leu Arg
            260                 265                 270
Glu Gly Lys Gln Val Gly Ser Gly Val Thr Thr Asp Gln Val Gln Ala
            275                 280                 285
Glu Ala Lys Glu Ser Gly Pro Thr Thr Tyr Lys Val Thr Ser Thr Leu
            290                 295                 300
Thr Ile Lys Glu Ser Asp Trp Leu Ser Gln Ser Met Phe Thr Cys Arg
305                 310                 315                 320
Val Asp His Arg Gly Leu Thr Phe Gln Gln Asn Ala Ser Ser Met Cys
                325                 330                 335
Val Pro Asp Gln Asp Thr Ala Ile Arg Val Phe Ala Ile Pro Pro Ser
            340                 345                 350
Phe Ala Ser Ile Phe Leu Thr Lys Ser Thr Lys Leu Thr Cys Leu Val
            355                 360                 365
Thr Asp Leu Thr Thr Tyr Asp Ser Val Thr Ile Ser Trp Thr Arg Gln
            370                 375                 380
Asn Gly Glu Ala Val Lys Thr His Thr Asn Ile Ser Glu Ser His Pro
385                 390                 395                 400
Asn Ala Thr Phe Ser Ala Val Gly Glu Ala Ser Ile Cys Glu Asp Asp
                405                 410                 415
Trp Asn Ser Gly Glu Arg Phe Thr Cys Thr Val Thr His Thr Asp Leu
            420                 425                 430
Pro Ser Pro Leu Lys Gln Thr Ile Ser Arg Pro Lys Gly Val Ala Leu
            435                 440                 445
His Arg Pro Asp Val Tyr Leu Leu Pro Pro Ala Arg Glu Gln Leu Asn
            450                 455                 460
Leu Arg Glu Ser Ala Thr Ile Thr Cys Leu Val Thr Gly Phe Ser Pro
465                 470                 475                 480
Ala Asp Val Phe Val Gln Trp Met Gln Arg Gly Gln Pro Leu Ser Pro
                485                 490                 495
Glu Lys Tyr Val Thr Ser Ala Pro Met Pro Glu Pro Gln Ala Pro Gly
            500                 505                 510
```

Arg Tyr Phe Ala His Ser Ile Leu Thr Val Ser Glu Glu Trp Asn
            515                 520                 525

Thr Gly Glu Thr Tyr Thr Cys Val Val Ala His Glu Ala Leu Pro Asn
530                 535                 540

Arg Val Thr Glu Arg Thr Val Asp Lys Ser Thr Gly Lys Pro Thr Leu
545                 550                 555                 560

Tyr Asn Val Ser Leu Val Met Ser Asp Thr Ala Gly Thr Cys Tyr
            565                 570                 575

<210> SEQ ID NO 107
<211> LENGTH: 216
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 107

Gln Ser Ala Leu Thr Gln Pro Arg Ser Val Ser Gly Ala Pro Gly Gln
1               5                   10                  15

Ser Val Thr Ile Ser Cys Thr Gly Thr Ser Ser Asp Val Gly Gly Tyr
            20                  25                  30

Asn Tyr Val Ser Trp Tyr Gln Gln His Pro Gly Lys Ala Pro Lys Leu
        35                  40                  45

Met Ile Tyr Asp Val Ser Lys Arg Pro Gly Val Pro Asp Arg Phe Ser
    50                  55                  60

Gly Ser Lys Ser Gly Asn Thr Ala Ser Leu Thr Ile Ser Gly Leu Gln
65                  70                  75                  80

Ala Glu Asp Glu Ala Asp Tyr Tyr Cys Cys Ser Tyr Ala Gly Ser Tyr
                85                  90                  95

Thr Pro Val Val Phe Gly Gly Gly Thr Lys Leu Thr Val Leu Gly Gln
            100                 105                 110

Pro Lys Ala Ala Pro Ser Val Thr Leu Phe Pro Pro Ser Ser Glu Glu
        115                 120                 125

Leu Gln Ala Asn Lys Ala Thr Leu Val Cys Leu Ile Ser Asp Phe Tyr
    130                 135                 140

Pro Gly Ala Val Thr Val Ala Trp Lys Ala Asp Ser Ser Pro Val Lys
145                 150                 155                 160

Ala Gly Val Glu Thr Thr Thr Pro Ser Lys Gln Ser Asn Asn Lys Tyr
                165                 170                 175

Ala Ala Ser Ser Tyr Leu Ser Leu Thr Pro Glu Gln Trp Lys Ser His
            180                 185                 190

Arg Ser Tyr Ser Cys Gln Val Thr His Glu Gly Ser Thr Val Glu Lys
        195                 200                 205

Thr Val Ala Pro Thr Glu Cys Ser
    210                 215

<210> SEQ ID NO 108
<211> LENGTH: 573
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 108

Gln Val Gln Leu Gln Gln Trp Gly Ala Gly Leu Leu Lys Pro Ser Glu
1               5                   10                  15

-continued

Thr Leu Ser Leu Thr Cys Ala Val Tyr Gly Gly Ser Phe Ser Gly Tyr
            20                  25                  30

Tyr Trp Ser Trp Ile Arg Gln Pro Pro Gly Lys Gly Leu Glu Trp Ile
        35                  40                  45

Gly Glu Ile Asn His Ser Gly Ser Thr Asn Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Ala Arg Thr Ala Arg Gly Ser Ser Ile Phe Asp Tyr Trp Gly Gln
            100                 105                 110

Gly Thr Leu Val Thr Val Ser Ser Gly Ser Ala Ser Ala Pro Thr Leu
        115                 120                 125

Phe Pro Leu Val Ser Cys Glu Asn Ser Pro Ser Asp Thr Ser Ser Val
    130                 135                 140

Ala Val Gly Cys Leu Ala Gln Asp Phe Leu Pro Asp Ser Ile Thr Phe
145                 150                 155                 160

Ser Trp Lys Tyr Lys Asn Asn Ser Asp Ile Ser Ser Thr Arg Gly Phe
                165                 170                 175

Pro Ser Val Leu Arg Gly Gly Lys Tyr Ala Ala Thr Ser Gln Val Leu
            180                 185                 190

Leu Pro Ser Lys Asp Val Met Gln Gly Thr Asp Glu His Val Val Cys
        195                 200                 205

Lys Val Gln His Pro Asn Gly Asn Lys Glu Lys Asn Val Pro Leu Pro
    210                 215                 220

Val Ile Ala Glu Leu Pro Pro Lys Val Ser Val Phe Val Pro Pro Arg
225                 230                 235                 240

Asp Gly Phe Phe Gly Asn Pro Arg Lys Ser Lys Leu Ile Cys Gln Ala
                245                 250                 255

Thr Gly Phe Ser Pro Arg Gln Ile Gln Val Ser Trp Leu Arg Glu Gly
            260                 265                 270

Lys Gln Val Gly Ser Gly Val Thr Thr Asp Gln Val Gln Ala Glu Ala
        275                 280                 285

Lys Glu Ser Gly Pro Thr Thr Tyr Lys Val Thr Ser Thr Leu Thr Ile
    290                 295                 300

Lys Glu Ser Asp Trp Leu Ser Gln Ser Met Phe Thr Cys Arg Val Asp
305                 310                 315                 320

His Arg Gly Leu Thr Phe Gln Gln Asn Ala Ser Ser Met Cys Val Pro
                325                 330                 335

Asp Gln Asp Thr Ala Ile Arg Val Phe Ala Ile Pro Pro Ser Phe Ala
            340                 345                 350

Ser Ile Phe Leu Thr Lys Ser Thr Lys Leu Thr Cys Leu Val Thr Asp
        355                 360                 365

Leu Thr Thr Tyr Asp Ser Val Thr Ile Ser Trp Thr Arg Gln Asn Gly
    370                 375                 380

Glu Ala Val Lys Thr His Thr Asn Ile Ser Glu Ser His Pro Asn Ala
385                 390                 395                 400

Thr Phe Ser Ala Val Gly Glu Ala Ser Ile Cys Glu Asp Asp Trp Asn
                405                 410                 415

Ser Gly Glu Arg Phe Thr Cys Thr Val Thr His Thr Asp Leu Pro Ser
            420                 425                 430

-continued

```
Pro Leu Lys Gln Thr Ile Ser Arg Pro Lys Gly Val Ala Leu His Arg
        435                 440                 445

Pro Asp Val Tyr Leu Leu Pro Pro Ala Arg Glu Gln Leu Asn Leu Arg
    450                 455                 460

Glu Ser Ala Thr Ile Thr Cys Leu Val Thr Gly Phe Ser Pro Ala Asp
465                 470                 475                 480

Val Phe Val Gln Trp Met Gln Arg Gly Gln Pro Leu Ser Pro Glu Lys
                485                 490                 495

Tyr Val Thr Ser Ala Pro Met Pro Glu Pro Gln Ala Pro Gly Arg Tyr
            500                 505                 510

Phe Ala His Ser Ile Leu Thr Val Ser Glu Glu Glu Trp Asn Thr Gly
        515                 520                 525

Glu Thr Tyr Thr Cys Val Val Ala His Glu Ala Leu Pro Asn Arg Val
530                 535                 540

Thr Glu Arg Thr Val Asp Lys Ser Thr Gly Lys Pro Thr Leu Tyr Asn
545                 550                 555                 560

Val Ser Leu Val Met Ser Asp Thr Ala Gly Thr Cys Tyr
                565                 570
```